United States Patent
Newton et al.

(10) Patent No.: US 9,433,622 B2
(45) Date of Patent: Sep. 6, 2016

(54) PYRIMIDINE COMPOUNDS USEFUL IN THE TREATMENT OF DISEASES MEDIATED BY IKKE AND/OR TBK1 MECHANISMS

(71) Applicant: DOMAINEX LIMITED, Cambridgeshire (GB)

(72) Inventors: Gary Karl Newton, Cambridgeshire (GB); Mark Richard Stewart, Cambridgeshire (GB); Trevor Robert Perrior, Cambridgeshire (GB); Stuart Richard Crosby, Cambridgeshire (GB); Anna Hopkins, Cambridgeshire (GB); Gabriel Negoita-Giras, Cambridgeshire (GB); Kerry Jenkins, Cambridgeshire (GB)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 14/769,421

(22) PCT Filed: Feb. 21, 2014

(86) PCT No.: PCT/GB2014/050521
§ 371 (c)(1),
(2) Date: Aug. 20, 2015

(87) PCT Pub. No.: WO2014/128486
PCT Pub. Date: Aug. 28, 2014

(65) Prior Publication Data
US 2016/0000784 A1 Jan. 7, 2016

(30) Foreign Application Priority Data
Feb. 21, 2013 (GB) .................................. 1303109.1

(51) Int. Cl.
| | |
|---|---|
| *A61K 31/506* | (2006.01) |
| *C07D 401/14* | (2006.01) |
| *C07D 401/04* | (2006.01) |
| *C07D 405/14* | (2006.01) |
| *C07D 413/14* | (2006.01) |
| *C07D 451/06* | (2006.01) |
| *C07D 471/04* | (2006.01) |
| *C07D 491/10* | (2006.01) |
| *C07D 498/08* | (2006.01) |
| *A61K 45/06* | (2006.01) |
| *A61K 31/5377* | (2006.01) |
| *A61K 31/551* | (2006.01) |

(Continued)

(52) U.S. Cl.
CPC ......... *A61K 31/506* (2013.01); *A61K 31/5377* (2013.01); *A61K 31/551* (2013.01); *A61K 31/553* (2013.01); *A61K 45/06* (2013.01); *C07D 401/04* (2013.01); *C07D 401/14* (2013.01); *C07D 405/14* (2013.01); *C07D 413/14* (2013.01); *C07D 451/06* (2013.01); *C07D 471/04* (2013.01); *C07D 491/10* (2013.01); *C07D 491/107* (2013.01); *C07D 498/08* (2013.01)

(58) Field of Classification Search
CPC ........... A61K 31/506; A61K 31/5377; A61K 31/551; A61K 31/553; A61K 45/06; C07D 401/04; C07D 401/14; C07D 405/14; C07D 413/14; C07D 451/06; C07D 471/04; C07D 491/10; C07D 491/107; C07D 498/08
See application file for complete search history.

(56) References Cited

U.S. PATENT DOCUMENTS

| | | | | |
|---|---|---|---|---|
| 8,563,549 | B2 * | 10/2013 | Burger | C07D 401/04 514/232.2 |
| 2013/0267491 | A1 * | 10/2013 | Perrior | C07D 239/42 514/210.2 |
| 2013/0289017 | A1 | 10/2013 | Dorsch et al. | |

(Continued)

FOREIGN PATENT DOCUMENTS

| | | |
|---|---|---|
| WO | 2005/012262 A1 | 2/2005 |
| WO | 2006/021458 A2 | 3/2006 |

(Continued)

OTHER PUBLICATIONS

J.S. Boehm et al., 129 Cell, 1065-1079 (2007).*

(Continued)

*Primary Examiner* — Alexander R Pagano
(74) *Attorney, Agent, or Firm* — Hahn Loeser & Parks LLP

(57) ABSTRACT

Compounds of the general formula (I) and salts thereof are useful in the treatment of diseases associated with aberrant activity of the protein kinases IKKε and/or TBK-1 in which one of V and W is N, and the other of V and W is C—H; and $R^1$, $R^2$, $R^3$ and $R^4$ are as defined in the specification. The invention also provides uses of the compounds and compositions containing them.

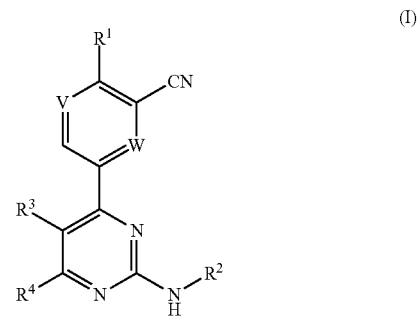

22 Claims, No Drawings

(51) Int. Cl.
*A61K 31/553* (2006.01)
*C07D 491/107* (2006.01)

(56) References Cited

U.S. PATENT DOCUMENTS

| | | |
|---|---|---|
| 2014/0228340 A1 | 8/2014 | Hoelzemann et al. |
| 2014/0323481 A1 | 10/2014 | Dorsch et al. |
| 2015/0152104 A1 | 6/2015 | Dorsch et al. |

FOREIGN PATENT DOCUMENTS

| | | |
|---|---|---|
| WO | 2009/032861 A1 | 3/2009 |
| WO | 2009/103032 A1 | 8/2009 |
| WO | 2011/046970 A1 | 4/2011 |
| WO | 2012/010826 A1 | 1/2012 |
| WO | 2012/095142 A1 | 7/2012 |
| WO | 2012/104007 A2 | 8/2012 |
| WO | 2012/142329 A1 | 10/2012 |
| WO | 2012161877 A2 | 11/2012 |
| WO | 2013024282 A2 | 2/2013 |
| WO | 2013/034238 A1 | 3/2013 |
| WO | 2013/075785 A1 | 5/2013 |
| WO | 2013/117285 A1 | 8/2013 |

OTHER PUBLICATIONS

J. Guo et al., 32 Oncogene, 151-159 (2013).*
J.P. Guo et al., 175 The American Journal of Pathology, 324-333 (2009).*
S.M. Reilly et al., 19 Nature Medicine, 313-321 (2013).*
H-H Lee et al., 106 PNAS, 6363-6368 (2009).*
K-W Zeng et al., 692 European Journal of Pharmacology, 29-37 (2012).*

* cited by examiner

PYRIMIDINE COMPOUNDS USEFUL IN THE TREATMENT OF DISEASES MEDIATED BY IKKE AND/OR TBK1 MECHANISMS

The present invention relates to novel pyrimidine compounds and compositions containing them, and to processes for preparing them. The compounds are useful in the treatment of diseases associated with aberrant activity of the protein kinases IKKε and/or TBK-1.

An important large family of enzymes is the protein kinase family. There are approximately 500 different known protein kinases. Protein kinases serve to catalyze the phosphorylation of an amino acid side chain in various substrate proteins. I-kappa-B-kinase epsilon, IKKε, (also known as I-kappa-B-kinase-3 (IKK3) or inducible I-kappa-B-kinase (IKKi)), and TANK Binding Kinase-1, TBK-1 (also known as T2K or NF-kappa B-activating kinase), are serine-threonine kinases. Studies have shown that protein kinases play a key role in many cell functions, including signal transduction, transcriptional regulation, cell motility, and cell division. Aberrant or inappropriate protein kinase activity can contribute to the development and maintenance of certain disease states. Several oncogenes have also been shown to encode protein kinases, suggesting that kinases play a role in oncogenesis.

IKKε and TBK1 have a high degree of sequence homology and as a result they share a number of key biological functions. In the innate immune system IKKε and TBK1 are activated in response to lipopolysaccharide (from bacterial cell wall) engagement with Toll-like receptor 4 (TLR4) or double-stranded RNA (from double stranded RNA viruses) engagement of TLR3. They may also be activated in response to pro-inflammatory cytokines such as TNF and interleukin-1 (IL-1). Once activated these kinases phosphorylate and activate IRF3, a transcription factor that triggers the production of interferon-beta and chemokines, such as RANTES. These substances play a key role in mediating host defence against infection by bacteria and viruses. Mice that do not express IRF3 are resistant to LPS-induced septic shock. These observations suggest that an inhibitor of IKKε and TBK1 may have efficacy for the treatment/prevention of septic shock and/or the treatment of inflammatory disease.

IKKε is not believed to be a component of the "classical" IKK pathway for the activation of transcription factors such as the NF-κB family in which its homologues IKKα and IKKβ are known to have a key role. However it has been shown to take part in a number of alternative mechanisms for the regulation of NF-κB family members, all of which are known to be involved in controlling the expression of a number of regulatory proteins including pro-inflammatory cytokines. IKKε directly phosphorylates the C-terminal domain of the NF-κB family member cRel, leading to dissociation of the IkBα-cRel complex and nuclear accumulation of cRel (Harris et al., *J. Immunol.*, 2006, 177, 2527-2535). It has also been shown to phosphorylate p65/Rel A on Ser-536 a modification that is proposed to contribute to the transactivation potential of this transcription factor (Adli et al., *Journal of Biological Chemistry*, 2006, 281, 37, 26976-26984; Wietek et al., Journal of Biological Chemistry, 2006, 281, 46, 34973-34981).

Aberrant IKKε activity has been linked to a number of disease areas including cancer and obesity. Studies have shown that the gene encoding IKKε (IKBKE) is amplified and over expressed in certain breast cancer cell lines and patient derived tumours. Furthermore suppression of IKBKE gene expression in these cell lines induces cell death (Boehm et al., *Cell*, 2007, 129, 1065-1079). IKKε has also been shown to phosphorylate the estrogen receptor, and its activity has been linked to tamoxifen resistance in breast cancer tumours (Guo et al., *The Journal of Biological Chemistry*, 2010, 285, 3676-3684). IKKε is also frequently over expressed in human ovarian cancer lines and primary tumours. Moreover IKKε over expression renders cells resistant to cis-platin, whereas IKKε knockdown restores cis-platin sensitivity (Guo et al., *The American Journal of Pathology*, 2009, 175, 324-333). IKKε has been shown to play a role in determining chemosensitivity in NSCLC (non-small cell lung cancer) (Guo et al., Oncogene, 2013, 32, 151-159). Expression of IKBKE renders NSCLC cells resistant to chemotherapy whilst silencing of this gene increases sensitivity to the same agents. Furthermore, IKBKE is overexpressed in NSCLC biopsies from smokers and can also be induced in NSCLC cells by nicotine. This is believed to occur via STAT-3. IKKε has been shown to inhibit a number of tumour suppressors by phosphorylation of key serine residues, thereby promoting cell survival and growth. The tumour suppressors FOXO3a (Guo et al, *Plos One*, 2013, 8 (5), e63636) and CYLD (Hutti et al., *Mol. Cell.*, 2009, 34 (4), 461-472) are both inhibited by IKKε. These observations suggest that IKKε inhibitors may show efficacy in the treatment of certain cancers.

IKKε knockout mice are protected from high-fat diet induced obesity, chronic inflammation in liver and fat, hepatic steatosis, and whole body insulin resistance. Such mice also show increased energy expenditure via enhanced expression of the uncoupling protein UCP1 (Chiang et al., *Cell*, 2009, 138, 961-975). Amlexanox has been reported to be an inhibitor of TBK1 and IKKε and is able to reduce weight gain and lower blood glucose levels in mice models of obesity (Reilly et al., *Nature Medicine*, 2013, 19 (3), 313-321.). IKKε has also been linked to high fat diet induced arterial atherosclerosis (Cao et al., *PLOS*, 2013, 8 (5) e64930). These observations suggest that IKKε inhibitors and/or dual TBK1/IKKε inhibitors may have efficacy in the treatment of obesity and related disorders such as diabetes.

IKKε has been shown to play a role in IL-17 signalling and in maintaining the Th17 phenotype. IKKε mediates IL-17 signalling by phosphorylating the key adaptor protein Act-1. Furthermore, knockdown of IKKε in mouse cells reduces the production of a number cytokines in response to IL-17 signalling and mouse models deficient in IKKε show reduced neutrophil recruitment to the lungs after IL-17 challenge (Bulek et al., *Nature Immunology*, 2011, 12, 9, 844-853). IKKε deficient T-cells also show reduced production of IL-17 following stimulation with IL-1 (Gulen et al., *Immunity*, 2012, 37, 800-812). Together this data suggests that an IKKε inhibitor would be useful for the treatment of diseases in which IL-17 and/or neutrophils are believed to play an important role such as asthma, COPD, psoriasis, rheumatoid arthritis and Crohn's disease.

TBK-1 has shown to be activated in response to hypoxia and stimulates the production of pro-angiogenic factors such as vascular endothelial growth factor (VEGF) and IL-1. The expression of TBK-1 rises 2.5-3 fold after 24 h of hypoxia, similar to the increase in expression of VEGF. The hypoxia-induced VEGF expression can be abolished by siRNA knockdown of TBK1. The level of TBK1 mRNA and protein is elevated in malignant colon and breast cancer cells. TBK1 is also recruited and activated by the RalB/Sec5 effector complex; in cancer cells, constitutive engagement of this pathway via chronic RalB activation, restricts the initiation of apoptotic programmes. The proto-oncogene KRAS is mutated in a wide array of human tumours most of which are aggressive and respond poorly to standard therapies. The knockdown of TBK1 in KRAS dependant tumour cell lines has been shown to cause cell death (Barbie et al., *Nature*, 2009, 462, 5, 108-114). Phosphopreoteomic studies have also implicated PLK1 as downstream target of TBK1 in NSCLC cells (Kim et al, *PNAS*, 2013, 110 (30), 12414-12419). PLK1 is known to play an important role in cell division. TBK1 has also been implicated in drug resistance in prostate cancer (Kim et al., *Neoplasia*, 2013, 15 (9), 1064-1074.), TBK1 inhibitors have also been implicated in Her2+ breast cancers (Deng et al., *Cancer Research*, 2014, shRNA kinome screen identifies TBK1 as a therapeutic target for HER2+ breast cancer). These observations suggest that an inhibitor of TBK1 may have efficacy in the treatment of cancer.

Both IKKε and TBK-1 have been shown to phosphorylate and activate Akt in a number of cancer cell lines (Ou et al., *Molecular Cell*, 2011, 41, 458-70; Xie et al., *PNAS*, 2011, 108, 16, 6474-6479; Guo et al., *Journal of Biological Chemistry*, 2011, 286 (43), 37389-37398). Akt is a major signalling kinase which acts as a hub in a number of pathways playing a pivotal role in cell proliferation and survival. Furthermore, shRNA knockdown of TBK1 in a number of NSCLC cell lines has been shown to inhibit cell survival. These results were further validated by use of a small molecule dual inhibitor of TBK1 and IKKε kinase which was able to inhibit both the phosphorylation of Akt and the proliferation of a TBK1 knock-down sensitive NSCLC cancer cell line (Ou et al., *Molecular Cell*, 2011, 41, 458-70). A dual TBK1/IKKε inhibitor may also have application in cancers that are driven by mutations in the PI3 kinase pathway such as those cancers harbouring a PTEN or PIK3CA mutation (WO2013/024282). It has also been proposed that TBK1 and IKKε can contribute to autocrine signalling in cancers via cytokines such as IL-6 and CCL5 (Thu et al., *Cancer Discovery*, 2014, Inhibition of KRAS-driven tumorigenicity by interruption of autocrine cytokine circuit). Dual TBK1/IKKε inhibitors have also shown efficacy in mouse xenograft models, notably in oral cancer (Li et al, *International Journal of Cancer*, 2013, 134 (8), 172-1980). The combination of a TBK1/IKKε inhibitor in conjunction with compounds that can inhibit Jak kinases and/or MEK is also likely to find application in poorly treated KRAS driven tumours (Thu et al., *Cancer Discovery*, 2014, Inhibition of KRAS-driven tumorigenicity by interruption of autocrine cytokine circuit). These observations suggest that a dual TBK1/IKKε inhibitor may have efficacy in the treatment of cancer.

In summary, for these and related reasons, aberrant IKKε and/or TBK1 activity can lead to various disease states. Disease states mediated by IKKε and/or TBK1 mechanisms include inflammatory and tissue repair disorders, particularly rheumatoid arthritis, inflammatory bowel disease, asthma and chronic obstructive pulmonary disorder (COPD); osteoarthritis, osteoporosis and fibrotic diseases; dermatosis including psoriasis, atopic dermatitis and ultraviolet radiation (UV)-induced skin damage; autoimmune diseases including systemic lupus erythematosus, multiple sclerosis, psoriatic arthritis, and alkylosing spondylitis; tissue and organ rejection, Alzheimer's disease, stroke, atherosclerosis, restenosis, obesity, diabetes, glomerulonephritis, cancer, including Hodgkin's disease, cachexia, inflammation associated with infection including certain viral infections, including acquired immune deficiency syndrome (AIDS), adult respiratory distress syndrome, Ataxia Telangiestasia, primary open angle glaucoma and septic shock.

Certain pyrimidinyl-amines are known to act as protein kinase inhibitors. For example, WO 2005/012262 and WO 2009/032861 disclose certain such compounds. In the former document, the compounds are stated to be inhibitors of one or more of CDK1, CDK2, CDK4, CDK7, CDK9, GSK3, aurora kinase, and PLK1. In the latter document, the compounds are stated to be inhibitors of protein kinases, e.g. c-Jun N-terminal kinases (JNK). Certain amino-pyrimidine compounds have been disclosed in WO2011/046970 and WO2012/142329, certain pyrimidinyl-amines were disclosed as inhibitors of IKKε and/or TBK1. In WO2012/010826, certain pyrimidinyl-amines having a specific substitution pattern were disclosed as selective inhibitors of IKKε and/or TBK1. Surprisingly, we have now found that certain pyridine-substituted pyrimidinyl-amines having a specific substitution pattern are selective inhibitors of IKKε and/or TBK1. They are therefore expected to find utility in patient populations where aberrant IKKε and/or TBK1 activity leads to disease.

Accordingly, the present invention provides a compound of the general formula I:

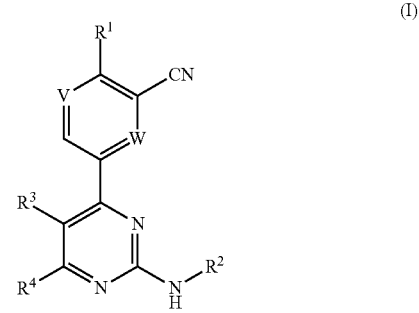

(I)

in which:
one of V and W is N, and the other of V and W is C—H;
$R^1$ represents an aliphatic heterocyclyl group having 4, 5, 6, 7, 8 or 9 ring atoms, bonded to the pyridyl group shown in formula I through a ring nitrogen atom, and optionally substituted by one or more substituents selected from halogen; OH; =O; $NO_2$; CN; $NR^aR^b$; $(CHR^a)_xCOR^c$; $O.CO.R^c$; $CO_2R^a$; $CONHR^d$; $(CHR^a)_xNR^a.COR^c$; $NR^aCO_2R^b$; $C(=NH)NH_2$; $SO_2R^c$; $NR^aSO_2R^c$; $CH(CF_3)NH_2$; and $C_{1-4}$alkyl, $C_{1-4}$alkoxy, $C_{1-4}$alkoxy$C_{1-4}$alkyl, $C_{2-4}$alkenyl and $C_{2-4}$alkynyl groups, each optionally substituted by one or more substituents independently selected from halogen atoms, OH, S-alkyl and and $NR^aR^b$ groups; or $R^1$ represents a $NR^a$—$(CHR^a)_x$—$C_{3-6}$cycloalkyl group or a $NR^a$—$(CHR^a)_x$—$C_{3-6}$heterocycloalkyl group, said heterocycloalkyl group containing one heteroatom, wherein the heteroatom is oxygen or nitrogen, and said cycloalkyl or heterocycloalkyl being optionally substituted by one or more substituents selected from halogen; OH; =O; $NO_2$; CN; $NR^aR^b$; $(CHR^a)_xCOR^c$; $O.CO.R^c$; $CO_2R^a$; $CONHR^d$; $(CHR^a)_xNR^a.COR^c$; $NR^aCO_2R^b$; $C(=NH)NH_2$; $SO_2R^c$; $NR^aSO_2R^c$; $CH(CF_3)NH_2$; and $C_{1-4}$alkyl, $C_{1-4}$alkoxy, $C_{1-4}$alkoxy$C_{1-4}$alkyl, $C_{2-4}$alkenyl and $C_{2-4}$alkynyl groups, each optionally substituted by one or more substituents independently selected from halogen atoms, OH, S-alkyl and and $NR^aR^b$ groups; or $R^1$ represents $NR^a$—$C_{1-6}$alkyl optionally substituted by one or more substituents independently selected from halogen; OH; =O; $NO_2$; CN; $NR^aR^b$; $(CHR^a)_xCOR^c$; $O.CO.R^c$; $CO_2R^a$; $CONHR^d$; $(CHR^a)_xNR^a.COR^c$; $NR^aCO_2R^b$; $C(=NH)NH_2$; $SO_2R^c$; $NR^aSO_2R^c$; $CH(CF_3)NH_2$; and $C_{1-4}$alkyl, $C_{1-4}$alkoxy, $C_{1-4}$alkoxy$C_{1-4}$alkyl, $C_{2-4}$alkenyl and $C_{2-4}$alkynyl groups, each optionally substituted by one or more substituents independently selected from halogen atoms, OH, S-alkyl and a $NR^aR^b$ group;

x is 0, 1 or 2;

$R^2$ represents

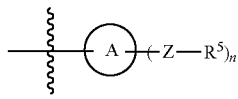

wherein A is a phenyl or 5 to 10 membered heteroaryl ring containing 1, 2 or 3 heteroatoms;

n is 0, 1, 2 or 3;

each Z is a group independently selected from $-(CHR^a)_p-$, $-(CHR^a)_p-O-(CHR^a)_r-$, $-(CHR^a)_p-NR^a-(CHR^a)_r-$, $-C(=O)-$, $C(=O)NR^a-$ and $-NR^aC(=O)(CHR^a)_p-$, in which p is 0, 1 or 2; and r is 0, 1, 2 or 3;

and each $R^5$ is a group independently selected from: 'H, halogen, $OR^b$, or $NR^aR^b$;

a 4 to 8 membered heterocyclyl ring containing 1, 2, or 3 heteroatoms, optionally substituted by one or more substituents independently selected from halogen atoms, OH, =O, $NR^aR^b$, $O-C_{1-4}$alkyl and $C_{1-4}$alkyl groups, optionally substituted with one or more halogen atoms, $O-C_{1-4}$alkyl, OH and $NR^aR^b$; $C_{1-4}$alkyl, $C_{3-7}$cycloalkyl, $C_{1-4}$alkoxy, $C_{1-4}$alkoxy$C_{1-4}$alkyl, $C_{2-4}$alkenyl or $C_{2-4}$alkynyl groups, each optionally substituted by one or more substituents independently selected from halogen, $O-C_{1-4}$alkyl, OH and $NR^aR^b$; '$NO_2$; CN; $O.CO.R^c$; $NR^a.COR^c$; $NR^aCO_2R^b$; $C(=NH)NH_2$; $SO_2R^c$; $NR^aSO_2R^c$; and $CH(CF_3)NH_2$;

or two $Z-R^5$ groups on adjacent ring atoms together with the two adjacent ring atoms form a 5-7 membered fused ring composed of the two adjacent ring atoms and $-(CHR^a)_r-(CHR^5)-(CHR^a)_r-$, wherein the $-CHR^5-$ moiety can be replaced with $-O-$ or $-NR^5-$ and each r is independently 0, 1, 2, 3 or 4; or a 5-7 membered fused ring composed of the two adjacent ring atoms and $-NR^a.CO.(CH_2)_q-$, wherein one $-CH_2-$ moiety can be replaced with $-O-$ or $-NR^a-$; and each $R^a$ independently represents a hydrogen atom or a $C_{1-4}$alkyl group;

each $R^b$ independently represents a hydrogen atom; a $C_{1-4}$alkyl group optionally substituted by one or more groups selected from OH, $O-C_{1-4}$alkyl, halogen, $SO_2R^c$, $CONHR^c$, $NR^a.COR^c$, $COR^c$, $N(R^a)_2$ and phenyl; or a $C_{3-8}$cycloalkyl group in which a $CH_2$ moiety may be replaced by an oxygen atom or an $NR^a$ group;

$R^c$ represents a hydrogen atom; a $-NR^aR^b$ group; a $C_{3-8}$cycloalkyl group, in which $CH_2$ moiety may optionally be replaced by an oxygen atom or an $NR^b$ group; or a $C_{1-4}$alkyl group optionally substituted by a OH, $O-C_{1-4}$alkyl or a $NR^aR^b$ group;

$R^d$ represents a 5- or 6-membered heteroaryl group containing 1 or 2 heteroatoms, optionally substituted with one or more $C_{1-4}$alkyl groups;

q represents 1, 2 or 3;

$R^3$ represents a hydrogen atom, a $C_{1-4}$alkyl group or a halogen atom; and $R^4$ represents a hydrogen atom, a $C_{1-4}$alkyl group or a halogen atom;

or a salt thereof.

In one embodiment of the invention, A represents a phenyl group. In another embodiment, A represents a heteroaryl group. Except where the context requires otherwise, it should be understood that any preferences or specific embodiments mentioned in this Specification may apply to compounds in which A is phenyl; similarly, any preferences mentioned in this Specification may apply to compounds in which A is heteroaryl. In each case, the A group is substituted by $(Z-R^5)_n$ groups as shown in the formula.

In one embodiment of the invention:

one of V and W is N, and the other of V and W is C—H;

$R^1$ represents an aliphatic heterocyclyl group having 4, 5, 6, 7 or 8 ring atoms, bonded to the pyridyl group shown in formula I through a ring nitrogen atom, and optionally substituted by one or more substituents selected from halogen; OH; =O; $NO_2$; CN; $NR^aR^b$; $COR^c$; $O.CO.R^c$; $CO_2R^a$; $CONHR^d$; $NR^a.COR^c$; $NR^aCO_2R^b$; $C(=NH)NH_2$; $SO_2R^c$; $NR^aSO_2R^c$; $CH(CF_3)NH_2$; and $C_{1-4}$alkyl, $C_{1-4}$alkoxy, $C_{1-4}$alkoxy$C_{1-4}$alkyl, $C_{2-4}$alkenyl and $C_{2-4}$alkynyl groups, each optionally substituted by one or more substituents independently selected from halogen atoms and $NR^aR^b$ groups;

$R^2$ represents

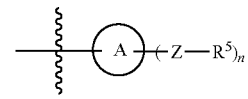

wherein A is a phenyl or 5 to 10 membered heteroaryl ring containing 1, 2 or 3 heteroatoms;

n is 0, 1, 2 or 3;

each Z is a group independently selected from $-(CH_2)_p-$, $-C(=O)-$ and $-NR^aC(=O)(CHR^a)_p-$, in which p is 0, 1 or 2;

and each $R^5$ is a group independently selected from:

H, halogen, $OR^b$, or $NR^aR^b$;

a 4 to 8 membered heterocycloalkyl ring containing 1, 2, or 3 heteroatoms, optionally substituted by one or more substituents independently selected from halogen atoms, OH, $NR^aR^b$, $O-C_{1-4}$alkyl and $C_{1-4}$alkyl groups, optionally substituted with halogen, $O-C_{1-4}$alkyl or OH;

$C_{1-4}$alkyl, $C_{3-7}$cycloalkyl, $C_{1-4}$alkoxy, $C_{1-4}$alkoxy$C_{1-4}$alkyl, $C_{2-4}$alkenyl or $C_{2-4}$alkynyl groups, each optionally substituted by one or more substituents independently selected from halogen, $O-C_{1-4}$alkyl, OH or $NR^aR^b$;

$NO_2$; CN; $O.CO.R^c$; $NR^a.COR^c$; $NR^aCO_2R^b$; $C(=NH)NH_2$; $SO_2R^c$; $NR^aSO_2R^c$; and $CH(CF_3)NH_2$; or and/or two $Z-R^5$ groups on adjacent ring atoms together with the two adjacent ring atoms form a 5-7 membered fused ring composed of the two adjacent ring atoms and $-NR^a.CO.(CH_2)_q-$, wherein one $-CH_2-$ moiety can be replaced with $-O-$ or $-NR^a-$;

each $R^a$ independently represents a hydrogen atom or a $C_{1-4}$alkyl group;

each $R^b$ independently represents a hydrogen atom; a $C_{1-4}$alkyl group optionally substituted by one or more groups selected from OH, $O-C_{1-4}$alkyl, halogen, and phenyl; or a $C_{3-8}$cycloalkyl group in which a $CH_2$ moiety may be replaced by an oxygen atom or an $NR^a$ group;

$R^c$ represents a hydrogen atom; a —$NR^aR^b$ group; a $C_{3-8}$cycloalkyl group, in which $CH_2$ moiety may optionally be replaced by an oxygen atom or an $NR^a$ group; or a $C_{1-4}$alkyl group optionally substituted by a $NR^aR^b$ group;

$R^d$ represents a 5- or 6-membered heteroaryl group containing 1 or 2 heteroatoms, optionally substituted with one or more $C_{1-4}$alkyl groups;

q represents 1, 2 or 3;

$R^3$ represents a hydrogen atom, a $C_{1-4}$alkyl group or a halogen atom; and $R^4$ represents a hydrogen atom, a $C_{1-4}$alkyl group or a halogen atom;

or a salt thereof.

The compounds of the invention are inhibitors of the IKKε and/or TBK-1 receptors, and are therefore useful in the treatment of diseases associated with or caused by aberrant IKKε and/or TBK-1 activity. In addition to being effective inhibitors of the IKKε and/or TBK-1 receptors, the compounds of the invention have advantageous properties, for example good metabolic stability. Many of the compounds of the invention have good in vivo pharmacokinetic properties.

An alkyl group may be either straight chain or branched. Examples of alkyl groups include methyl, ethyl, n-propyl, iso-propyl, n-butyl, t-butyl, i-butyl, and sec-butyl groups. Among unbranched alkyl groups, there are preferred methyl, ethyl, n-propyl, and n-butyl groups. Among branched alkyl groups, there may be mentioned iso-propyl, t-butyl, i-butyl, 1-ethylpropyl, 1-ethylbutyl, and 1-ethylpentyl groups.

An alkoxy group is the group O-alkyl, where "alkyl" is used as described above. Examples of alkoxy groups include methoxy and ethoxy groups. Other examples include propoxy and butoxy.

An alkenyl group may be straight chain or branched, and contains at least one carbon-carbon double bond. Examples of alkenyl groups include ethenyl, propenyl, and butenyl. Preferred alkenyl groups include ethenyl, 1-propenyl and 2-propenyl.

An alkynyl group may be straight chain or branched, and contains at least one carbon-carbon triple bond. Examples of alkynyl groups include ethynyl, propynyl, and butynyl. Preferred alkynyl groups include ethynyl, 1-propynyl and 2-propynyl.

A cycloalkyl group may be monocyclic or bicyclic. A bicyclic group may, for example, be fused or bridged. Examples of monocyclic cycloalkyl groups include cyclopropyl, cyclobutyl and cyclopentyl. Other examples of monocyclic cycloalkyl groups are cyclohexyl, cycloheptyl and cyclooctyl. Examples of bicyclic cycloalkyl groups include bicyclo[2.2.1]hept-2-yl. Preferably, a cycloalkyl group is monocyclic, and preferably it has up to 7 carbon atoms.

Halogen means fluorine, chlorine, bromine or iodine. Fluorine, chlorine and bromine are preferred. Fluorine and chlorine are particularly preferred.

A heterocyclyl group is a cyclic group of carbon atoms wherein from one to three of the carbon atoms is/are replaced by one or more heteroatoms independently selected from nitrogen, oxygen or sulfur. It may be aromatic or aliphatic. An aliphatic heterocyclyl group is referred to as a heterocycloalkyl group. An aromatic heterocyclyl group is referred to as a heteroaryl group. For a bicyclic heterocyclyl group, one or both rings may be aromatic, or one or both rings may be aliphatic. For a bicyclic heterocyclyl group, the rings may be, for example, fused, bridged or spirocyclic. A heteroaryl group may, for example, be monocyclic or bicyclic. In a bicyclic heterocyclyl group there may be one or more heteroatoms in each ring, or only in one of the rings. For a bicyclic heteroaryl group, one or both rings may be aromatic, and the one or more heteroatoms may be on one or both rings of the group. A heteroatom is preferably O or N. Heterocyclyl groups containing a suitable nitrogen atom include the corresponding N-oxides and for a suitable sulphur atom the corresponding S-mono- or di-oxides.

Embodiments of the present invention may have tautomeric forms. Where embodiments of the present invention can exist in tautomeric forms, all tautomers are compounds of the inventions, regardless of whether all tautomeric forms are within the structural definition of general formula (I).

In one embodiment of the invention V is N and W is C—H. In another embodiment of the invention, V is C—H and W is N. Except where the context requires otherwise, it should be understood that any preferences or specific embodiments mentioned in this Specification may apply to compounds in which V is N and W is C—H; similarly, any preferences mentioned in this Specification may apply to compounds in which V is C—H and W is N.

In embodiments where $R^1$ is a heterocyclyl group, $R^1$ preferably has 4, 5, 6 or 7, more preferably 4, 5 or 6, and especially 5 or 6, atoms in the ring. In certain embodiments, the ring may be a spirocyclic ring with 8 or 9 atoms in the ring.

In addition to the nitrogen atom through which the group is bonded to the pyridyl group shown in formula I, there may be one or more further heteroatoms, for example selected from nitrogen, oxygen and sulphur; for example there may be one further heteroatom, for example an oxygen atom. Any nitrogen atom in the ring in addition to the nitrogen atom through which the ring is bonded to the pyridyl group in formula I, may carry an $R^b$ group, while any sulfur atom in the ring may be in any desired degree of oxidation, i.e. it may be —S—, —SO—, or —SO$_2$—. Alternatively, there may be no additional heteroatom in the ring; that is to say that $R^1$ represents an aliphatic heterocyclyl group having 4, 5, 6, 7, 8 or 9 ring atoms (for example 4, 5 or 6), and having as heteroatom in the ring a single nitrogen atom, the nitrogen atom being the atom through which the $R^1$ group is bonded to the pyridyl group shown in formula I. For example, $R^1$ may represent a pyrrolidine, morpholine, piperazine, piperidine, azetidine, thiomorpholine, homopiperazine or homomorpholine ring. In certain embodiments, the $R^1$ group may be a bicyclic group, for example a bridged bicyclic group, for example an 8-aza-bicyclo[3.2.1]oct-8-yl group or an 3-oxa-8-aza-bicyclo[3.2.1]oct-8-yl group, or a spirocyclic bicyclic group, for example a spirocyclic group comprising a pyrrolidine group or piperidine group, for example a 2-oxa-6-azaspiro[3.4]octane, 2-oxa-6-aza-spiro[3.5]nonane, 2-oxa-7-aza-spiro[3.5]nonane, 2,6-diaza-spiro[3.4]octane, 2,7-diaza-spiro[3.5]nonane, 2,6-diaza-spiro[3.5]nonane group, especially a 2-oxa-6-azaspiro[3.4]octane group. In one embodiment $R^1$ may be a pyrrolidine, morpholine, piperazine, piperidine, azetidine, thiomorpholine, homopiperazine, homomorpholine, 8-aza-bicyclo[3.2.1]oct-8-yl group, 3-oxa-8-aza-bicyclo[3.2.1]oct-8-yl group or 2-oxa-6-azaspiro[3.4]octane group. In one embodiment $R^1$ may be a pyrrolidine, morpholine, piperazine, piperidine, azetidine, thiomorpholine, homopiperazine, homomorpholine, 8-aza-bicyclo[3.2.1]oct-8-yl group or 3-oxa-8-aza-bicyclo[3.2.1]oct-8-yl group. Preferably $R^1$ represents a pyrrolidine ring, an 8-aza-bicyclo[3.2.1]oct-8-yl group, an 3-oxa-8-aza-bicyclo[3.2.1]oct-8-yl group, a piperidine ring or an azetidine ring. Preferably $R^1$ represents a pyrrolidine ring, an 8-aza-bicyclo[3.2.1]oct-8-yl group, an 3-oxa-8-aza-bicyclo[3.2.1]oct-8-yl group, a piperidine ring, an azetidine ring or an 2-oxa-6-azaspiro[3.4]octane group. More preferably $R^1$ represents a pyrrolidine ring, an 8-aza-bicyclo[3.2.1]oct-8-yl group or an 2-oxa-6-azaspiro[3.4]octane group. More preferably $R^1$ represents a pyrrolidine ring or an 8-aza-bicyclo[3.2.1]oct-8-yl group. Most preferably, $R^1$ represents a pyrrolidine ring.

Alternatively, $R^1$ may be a $NR^a$—$(CHR^a)_x$—$C_{3-6}$cycloalkyl group, for example N—$C_{3-6}$cycloalkyl group, for example a N-cyclopropyl group, N-cyclobutyl group, N-cyclopentyl group, N-cyclohexyl group, N-methyl-cyclopropyl group, N-methyl-cyclobutyl group, N-methyl-cyclopentyl group or N-methyl-cyclohexyl group. Preferably $R^1$ is a N-cyclopropyl group or N-cyclopentyl. More preferably, $R^1$ is a N-cyclopentyl group.

Alternatively, $R^1$ may be a $NR^a$—$(CHR^a)_x$—$C_{3-6}$heterocycloalkyl group, said heterocycloalkyl group containing one heteroatom, wherein the heteroatom is oxygen or nitrogen. Preferably the heterocycloalkyl group comprises a 5 to 7 membered ring. Preferable the heteroatom is oxygen. Preferable $R^a$ is H or methyl. For example, $R^1$ may be selected from the group consisting of:

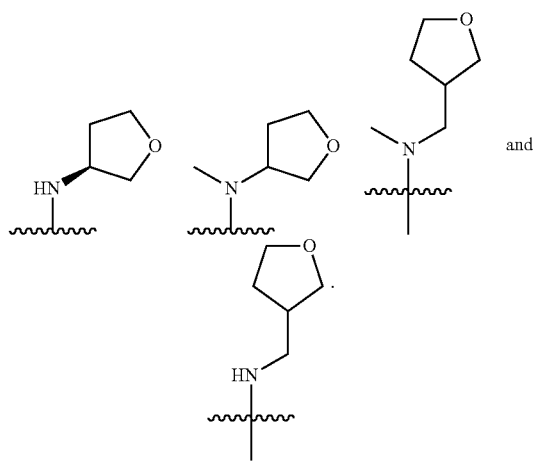

Alternatively, $R^1$ may be a $NR^a$—$C_{1-6}$alkyl group, preferably a $NR^a$—$C_{1-4}$alkyl group.

$R^1$ may carry one or more, for example up to 3, especially one, optional substituent(s). If a $C_{1-4}$alkyl, $C_{1-4}$alkoxy, $C_{1-4}$alkoxy$C_{1-4}$alkyl, $C_{2-4}$alkenyl or $C_{2-4}$alkynyl substituent is present, this may for example be substituted by one or more, for example 1 to 3, halogen atoms, for example chlorine and/or fluorine atoms, and/or $NR^aR^b$ groups and/or $CONHR^a$, for example $CONH_2$; and/or $NR^a.COR^a$; for example $NHCOC_{1-4}$alkyl. In one embodiment if a $C_{1-4}$alkyl, $C_{1-4}$alkoxy, $C_{1-4}$alkoxy$C_{1-4}$alkyl, $C_{2-4}$alkenyl or $C_{2-4}$alkynyl substituent is present, this may for example be substituted by one or more, for example 1 to 3, halogen atoms, for example chlorine and/or fluorine atoms, and/or OH and/or S-alkyl and/or $NR^aR^b$ groups. Such a substituent may for example be a methyl, methoxy, trifluoromethyl, trifluoromethoxy, difluoromethyl or difluoromethoxy group. Preferred substituents for $R^1$ include halogen atoms, for example one or two fluorine atoms; OH; =O; CN; $NR^aR^b$; $(CHR^a)_xCOR^c$; O.CO.$R^c$; $CO_2R^a$; $CONHR^d$; $(CHR^a)_xNR^a.COR^c$; $NR^aCO_2R^b$; methyl; methoxy; and $C_{1-4}$alkyl substituted with $CONHR^a$ or $NR^a.COR^a$; trifluoromethyl; and trifluoromethoxy; in each of which each of $R^a$, $R^b$ and $R^c$ preferably independently represents a $C_{1-4}$alkyl group, especially a methyl group, or a hydrogen atom, or $R^c$ may also represent an $NR^aR^b$ group, for example an $NH_2$ group. Preferred substituents for $R^1$ include halogen atoms, for example one or two fluorine atoms; OH; =O; CN; $NR^aR^b$; $COR^c$; O.CO.$R^c$; $CO_2R^a$; $CONHR^d$; $NR^a.COR^c$; $NR^aCO_2R^b$; methyl; methoxy; trifluoromethyl; and trifluoromethoxy; in each of which each of $R^a$, $R^b$ and $R^c$ preferably independently represents a $C_{1-4}$alkyl group, especially a methyl group, or a hydrogen atom, or $R^c$ may also represent an $NR^aR^b$ group, for example an $NH_2$ group. Particularly preferred substituents on the $R^1$ heterocyclic group include halogen atoms, for example one or two fluorine atoms; OH; CN; $COR^c$; $CO_2R^a$; $CONHR^d$; and methoxy; wherein $R^a$ represents a hydrogen atom or a $C_{1-4}$alkyl group, $R^c$ represents a $NH_2$ group, and $R^d$ represents a 5-membered heteroaryl group (for example a pyrazole group), optionally substituted with a $C_{1-4}$alkyl group, for example substituted with a methyl group. Particularly preferred substituents on the $R^1$ heterocyclic group include halogen atoms, for example one or two fluorine atoms; OH; CN; $(CHR^a)_xCOR^c$; $CO_2R^a$; $CONHR^d$; $(CHR^a)_xNR^a.COR^c$ or methoxy; wherein $R^a$ represents a hydrogen atom or a $C_{1-4}$alkyl group, $R^c$ represents a $NH_2$ group, and $R^d$ represents a 5-membered heteroaryl group (for example a pyrazole group), optionally substituted with a $C_{1-4}$alkyl group, for example substituted with a methyl group. A hydroxyl group or a methoxy group are preferred substituents, particularly hydroxy. One or two fluorine atoms are also preferred substituents. One $(CHR^a)_xCOR^c$ group or one $(CHR^a)_xNR^a.COR^a$ group are also a preferred substituents.

In embodiments where $R^1$ is $NR^a$—$C_{1-6}$alkyl, that group is preferably optionally substituted by one or more substituent independently selected from $COR^c$; $NR^a.COR^c$ and OH, $SO_2R^c$, $NR^aSO_2R^c$, halogen, OH, $NR^aR^B$ and $C_{1-4}$alkoxy. More preferably it is substituted by one or two substituent independently selected from $COR^c$; $NR^a.COR^c$, $C_{1-4}$alkoxy and OH. For example, $R^1$ may be selected from the group consisting of:

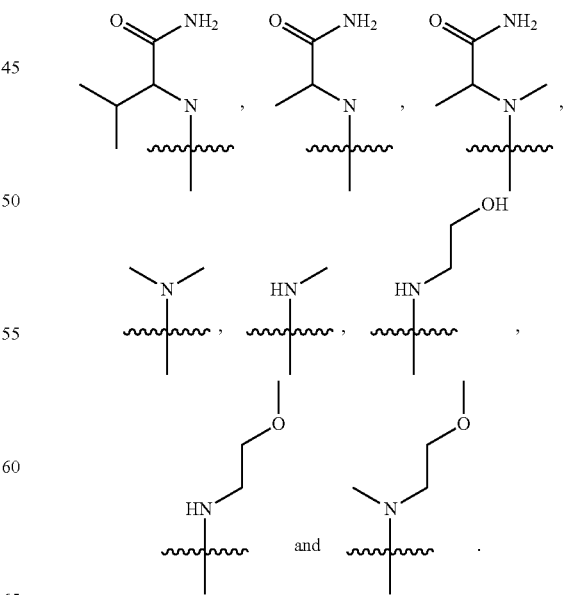

x may be 0, 1, 2, or 3. Preferably x is 0, 1 or 2.

For example, $R^1$ may be a pyrrolidine ring or an 8-azabicyclo[3.2.1]oct-8-yl group, unsubstituted or substituted by one fluorine atom (for example a fluorine at the 3 position of the pyrrolidine ring) or one hydroxy group (for example a 3-hydroxy group).
Preferred examples of $R^1$ groups are as follows:
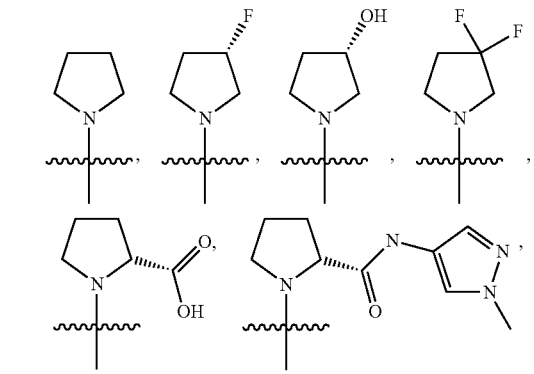
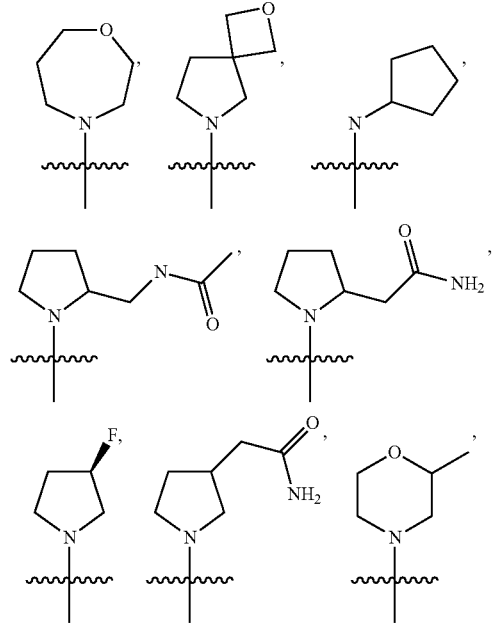
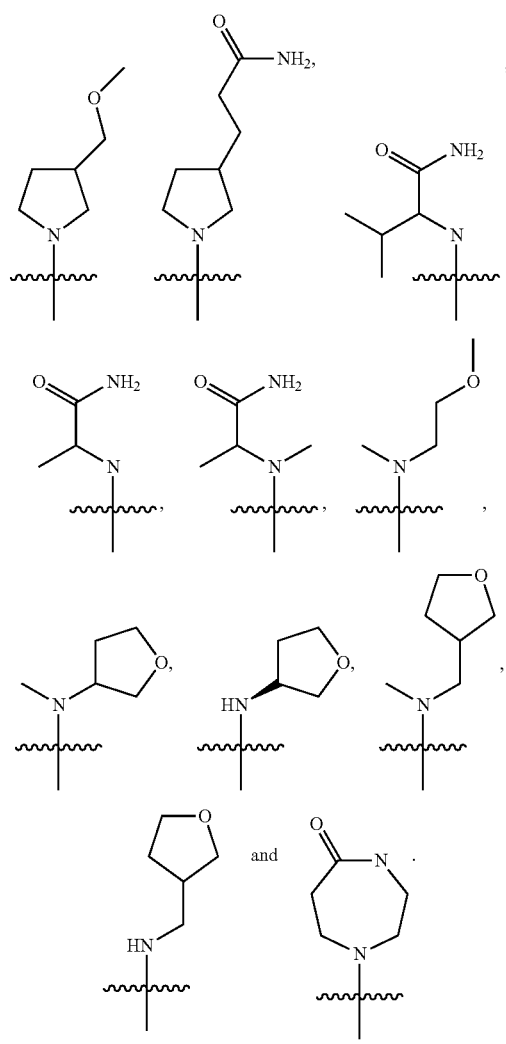
More preferred examples of $R^1$ groups are as follows:

-continued

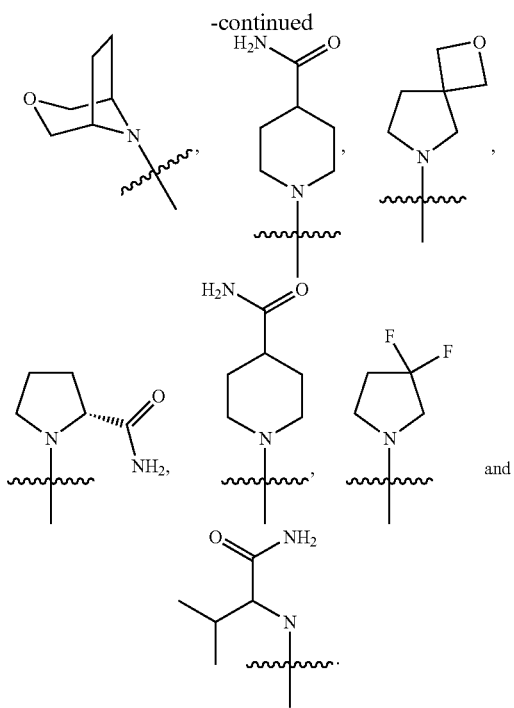

More preferred examples of R¹ groups are:

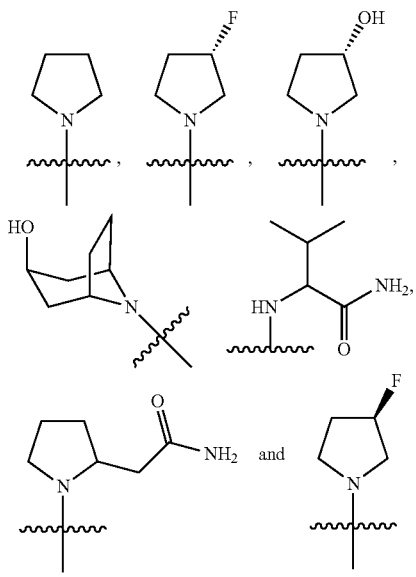

R² is represented by the following formula:

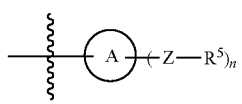

A is a phenyl group or a 5 to 10 membered heteroaryl ring containing 1, 2 or 3 heteroatoms. In one embodiment, A is a phenyl. In another embodiment it is a heteroaryl ring; preferably it is a 5 to 6 membered heteroaryl ring containing 1 or 2 heteroatoms, and more preferably a 6 membered heteroaryl ring containing 1 or 2 heteroatoms or a 5 membered heteroaryl ring containing 2 heteroatoms, more preferably it is a 6 membered heteroaryl ring containing 1 heteroatom or a 5 membered heteroaryl ring containing 2 heteroatoms. In embodiments where A is a heteroaryl ring, A is for example a pyridine, pyrazole, isoxazole, isothiazole, oxazole, imidazole, thiazole, 1,2,3-triazole, pyrimidine, pyrrole, furan, or thiophene ring. More preferably, A may be a pyridine (especially a pyridin-3-yl or pyridin-4-yl group), pyrazole (especially a pyrazol-3-yl group, for example 2-methyl-2H-pyrazol-3-yl or 5-methyl-2H-pyrazol-3-yl) or a pyrazol-4-yl group for example 1-methyl-1H-pyrazol-4-yl), pyrimidine (especially a pyrimid-5-yl group), thiophene, pyridazine (especially a pyridazin-4-yl group), imidazole (especially an imidazol-4-yl group for example 2-methyl-3H-imidazol-4yl), thiazole (especially a thiazo-5-yl group) or isoxazole (especially an isoxazol-4yl group). When A is a 5 to 6 membered heteroaryl ring, preferably the ring contains 1 or 2 nitrogen atoms. Preferably A represents a pyridine (especially a pyrdin-3-yl or pyridine-4-yl group), a pyrazole (especially a pyrazol-4-yl group), or a pyrimidine ring.

For example, A may be phenyl, pyridine or pyrazole.

In certain embodiments of the invention A is selected from the group consisting of:

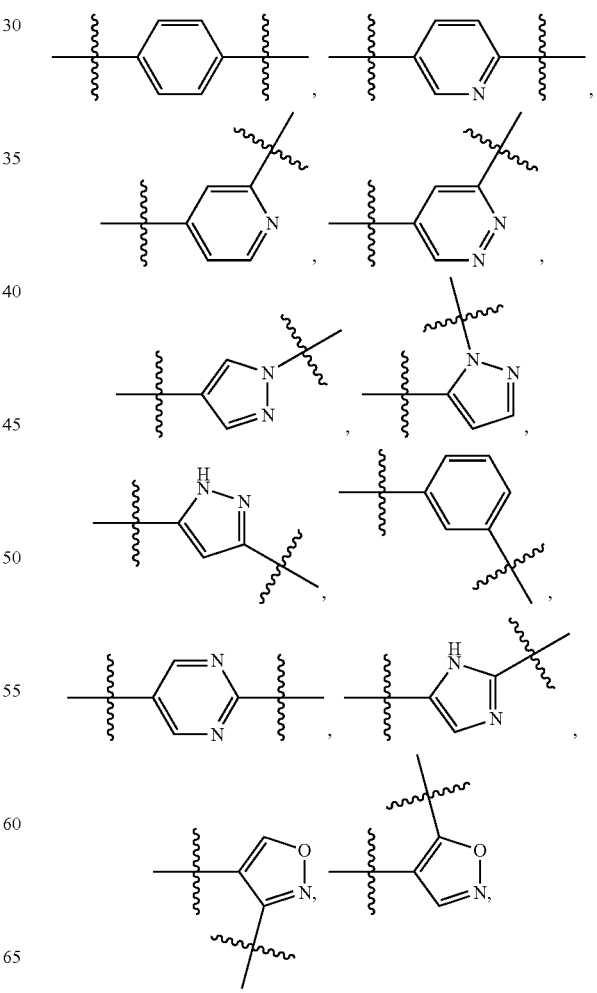

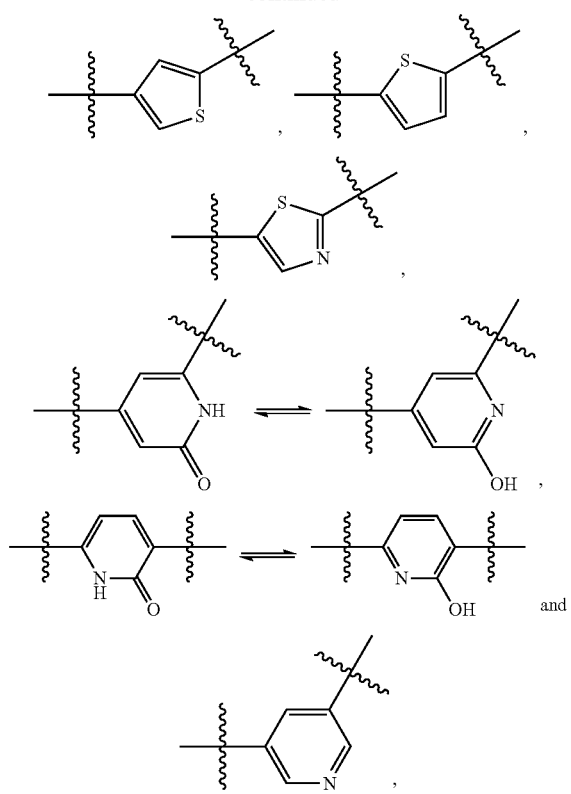
wherein the bond extending to the left is attached to the NH group of the pyrimidine in Formula I, and the bond extending to the right is attached to a —Z—R⁵ group.
Preferably A is selected from the group consisting of:
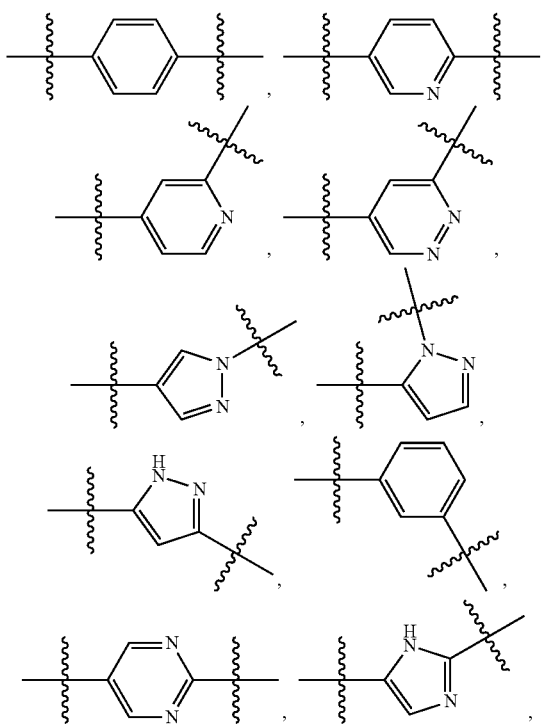
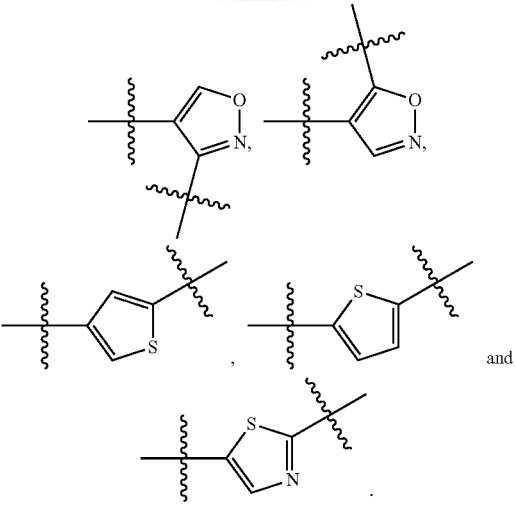
In more preferred embodiments A is selected from the group consisting of:
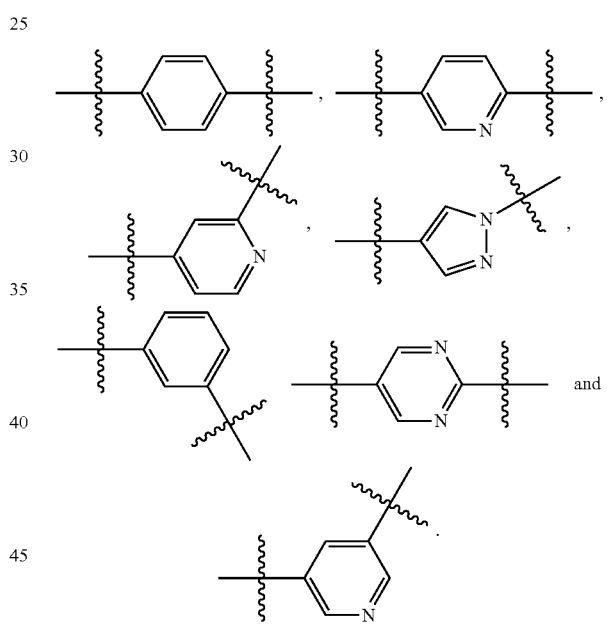
For example, A is selected from the group consisting of:
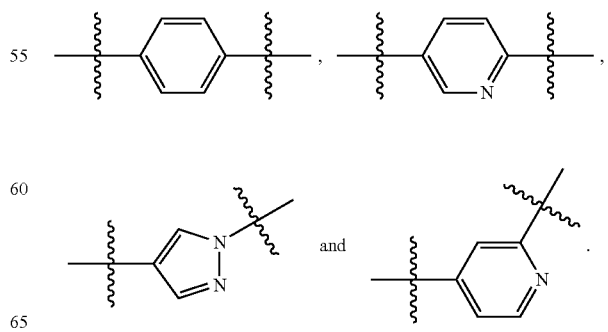

For example, from:

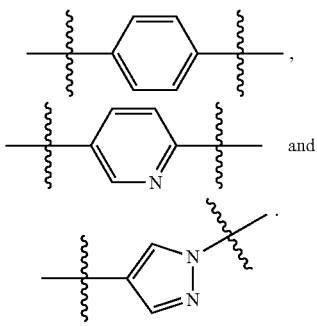

For example, from:

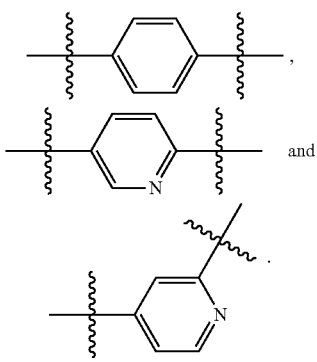

For example, from:

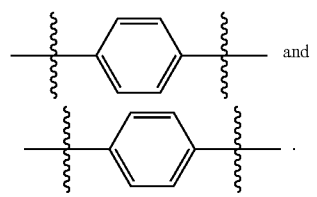

The group A may be substituted by n number of Z—R$^5$ groups. n is 0, 1, 2 or 3. In preferred embodiments n is 1 or 2; for example n is 1.

Each group Z may be a group independently selected from —(CHR$^a$)$_p$—, —(CHR$^a$)$_p$—O—(CHR$^a$)$_r$—, —(CHR$^a$)$_p$—NR$^a$—(CHR$^a$)$_r$—, —C(=O)—, C(=O)NR$^a$— and —NR$^a$C(=O)(CHR$^a$)$_p$—, in which p is 0, 1 or 2 and r is 0, 1, 2 or 3; in preferred embodiments, each Z is a group independently selected from —(CHR$^a$)$_p$—, —C(=O)— and —NR$^a$C(=O)(CHR$^a$)$_p$—, in which p is 0 or 1 (for example bond, —(CH$_2$)— and —C(=O)—), or O—(CHR$^a$)$_r$—, in which p is 0, 1, or 2. In certain embodiments of the invention, Z is —(CHR$^a$)$_p$— and p is 0, 1 or 2. In embodiments where Z is —NR$^a$C(=O)(CHR$^a$)$_p$—, p is preferably 0, 1 or 2, or preferably 1 or 2, more preferably p is 1, and each R$^a$ is preferably independently hydrogen or methyl. In certain embodiments of the invention, Z is —C(=O)—. In embodiments where Z is —(CHR$^a$)$_p$—O—(CHR$^a$)$_r$—, p is preferably 0 or 1 and r is 1, 2 or 3, more preferably Z is —O—(CHR$^a$)$_r$— wherein r is preferably 1 or 2. In embodiments where Z is —(CHR$^a$)$_p$—NR$^a$—(CHR$^a$)$_r$—, p is preferably 0 or 1 and r is 0, 1, 2 or 3, more preferably each R$^a$ is preferably independently selected from the group consisting of H or Me, and more preferably r is 1 or 2. For example, when Z is —(CHR$^a$)$_p$—NR$^a$—(CHR$^a$)$_r$—, p and r may both be 0, and R$^a$ may be selected from H and Me. In alternative preferred embodiments of the invention, Z is —C(=O)—; —NR$^a$C(=O)(CHR$^a$)— in which each R$^a$ is independently selected from the group consisting of H or Me; —NR$^a$C(=O)— in which each R$^a$ is independently selected from the group consisting of H or Me; or —(CHR$^a$)$_p$— wherein p is 0 or p is 1 and R$^a$ is independently selected from the group consisting of Me or H; or Z is —O—(CHR$^a$)$_r$— or —NR$^a$—(CHR$^a$)$_r$— wherein r is 2 and each R$^a$ is H.

Alternatively, each group Z may be a group independently selected from —(CH$_2$)$_p$—, —C(=O)— and —NR$^a$C(=O)(CHR$^a$)$_p$—, in which p is 0, 1 or 2; in preferred embodiments, each Z is a group independently selected from —(CH$_2$)$_p$—, —C(=O)— and —NR$^a$C(=O)(CHR$^a$)$_p$—, in which p is 0 or 1 (for example bond, —(CH$_2$)— and —C(=O)—). In certain embodiments of the invention, Z is —(CH$_2$)$_p$— and p is 0, 1 or 2. In embodiments where Z is —NR$^a$C(=O)(CHR$^a$)$_p$—, p is preferably 1 or 2, or more preferably p is 1, and each R$^a$ is preferably independently hydrogen or methyl. In certain embodiments of the invention, Z is —C(=O)—.

In alternative preferred embodiments of the invention, Z is —C(=O)—; —NR$^a$C(=O)(CHR$^a$)— in which each R$^a$ is independently selected from the group consisting of H or Me; or —(CH$_2$)$_p$— wherein p is 0.

Except where otherwise stated, p is preferably 0, 1 or 2. For example, p may be 1; or p may be 0; or p may be 2. For example, p may be 1; or p may be 0. In embodiments where more than one p is the general formula, each p is independently 0, 1 or 2.

Each R$^5$ is a group independently selected from the list set out above.

In certain embodiments, each R$^5$ is a group independently selected from:

H, halogen, OR$^b$ or NR$^a$R$^b$;

a 4- to 7-membered heterocyclyl ring containing 1 or 2 heteroatoms, optionally substituted by one or more substituents independently selected from halogen atoms, OH, =O, NR$^a$R$^b$, O—C$_{1-4}$alkyl and C$_{1-4}$alkyl groups, optionally substituted with halogen, O—C$_{1-4}$alkyl, OH or NR$^a$R$^b$; and C$_{1-4}$alkyl or C$_{3-7}$cycloalkyl groups, each optionally substituted by one or more substituents independently selected from halogen, OH, O—C$_{1-4}$alkyl and NR$^a$R$^b$; and CN, SO$_2$R$^c$ and NR$^a$SO$_2$R$^c$.

In such an embodiment, preferably each R$^a$ independently represents a hydrogen atom or a C$_{1-4}$alkyl group; each R$^b$ independently represents a hydrogen atom; a C$_{1-4}$alkyl group optionally substituted by one or more groups selected from OH, O—C$_{1-4}$alkyl, halogen, phenyl and SO$_2$R$^c$; or a C$_{3-8}$cycloalkyl group in which a CH$_2$ moiety may be replaced by an oxygen atom or an NR$^a$ group; and R$^c$ represents —NR$^a$R$^b$ or a C$_{1-4}$alkyl group optionally substituted by a group NR$^a$R$^b$.

In certain embodiments, R$^5$ is a group independently selected from:

H, halogen, OR$^b$ or NR$^a$R$^b$;

a 4- to 7-membered heterocycloalkyl ring containing 1 or 2 heteroatoms, optionally substituted by one or more substituents independently selected from halogen atoms, OH, NR$^a$R$^b$, O—C$_{1-4}$alkyl and C$_{1-4}$alkyl groups, optionally substituted with halogen, O—C$_{1-4}$alkyl or OH; and C$_{1-4}$alkyl or C$_{3-7}$cycloalkyl groups, each optionally substituted by one or more substituents independently selected from halogen, OH, O—C$_{1-4}$alkyl, or NR$^a$R$^b$; and CN, SO$_2$R$^c$ and NR$^a$SO$_2$R$^c$.

In such an embodiment, preferably each R$^a$ independently represents a hydrogen atom or a C$_{1-4}$alkyl group; each R$^b$ independently represents a hydrogen atom; a C$_{1-4}$alkyl group optionally substituted by one or more groups selected from OH, O—C$_{1-4}$alkyl, halogen, and phenyl; or a C$_{3-8}$cycloalkyl group in which a CH$_2$ moiety may be replaced by an oxygen atom or an NR$^a$ group; and R$^c$ represents —NR$^a$R$^b$ or a C$_{1-4}$alkyl group optionally substituted by a group NR$^a$R$^b$.

In preferred embodiments, R$^5$ is a group independently selected from:

H, halogen, OR$^b$ or NR$^a$R$^b$;

a 4- to 6-membered heterocyclyl ring containing 1 or 2 heteroatoms, optionally substituted by one or more substituents independently selected from halogen atoms, OH, =O, NR$^a$R$^b$, O—C$_{1-4}$alkyl and C$_{1-4}$alkyl groups, optionally substituted with one, two or three halogen atoms, OMe or OH;

C$_{1-4}$alkyl or C$_{3-7}$cycloalkyl groups, each optionally substituted by one or more substituents independently selected from halogen, OH, OMe and NR$^a$R$^b$; and CN, SO$_2$R$^c$ and NR$^a$SO$_2$R$^c$.

In such an embodiment, preferably each R$^a$ independently represents a hydrogen atom or a C$_{1-4}$alkyl group; and each R$^b$ independently represents a hydrogen atom; a C$_{1-4}$alkyl group optionally substituted by one or more groups selected from OH, O—C$_{1-4}$alkyl, halogen and SO$_2$R$^c$; or a C$_{3-8}$cycloalkyl group in which a CH$_2$ moiety may be replaced by an oxygen atom or an NR$^a$ group. For example each R$^b$ may represent a hydrogen atom or a C$_{1-4}$alkyl group; and each R$^c$ represents —NR$^a$R$^b$ or a methyl group.

In further preferred embodiments, R$^5$ is a group independently selected from:

H, halogen, OR$^b$ or NR$^a$R$^b$;

a 4- to 6-membered heterocyclyl ring containing 1 or 2 heteroatoms, optionally substituted by one or two substituents independently selected from halogen atoms, OH, =O, NR$^a$R$^b$, O—C$_{1-4}$alkyl and C$_{1-4}$alkyl groups, optionally substituted with one, two or three halogen atoms, OMe or OH;

C$_{1-4}$alkyl or C$_{3-7}$cycloalkyl groups, each optionally substituted by one or more substituents independently selected from halogen, OH, OMe and NR$^a$R$^b$; and CN, SO$_2$R$^c$ and NR$^a$SO$_2$R$^c$.

In such an embodiment, preferably each R$^a$ independently represents a hydrogen atom or a C$_{1-4}$alkyl group; and each R$^b$ independently represents a hydrogen atom; a C$_{1-4}$alkyl group optionally substituted by one or more groups selected from OH, O—C$_{1-4}$alkyl, halogen and SO$_2$R$^c$; or a C$_{3-8}$cycloalkyl group in which a CH$_2$ moiety may be replaced by an oxygen atom or an NR$^a$ group. For example each R$^b$ may represent a hydrogen atom or a C$_{1-4}$alkyl group; and each R$^c$ represents —NR$^a$R$^b$ or a methyl group.

In preferred embodiments, R$^5$ is a group independently selected from:

H, halogen, OR$^b$ or NR$^a$R$^b$;

a 5- to 6-membered heterocycloalkyl ring containing 1 or 2 heteroatoms, optionally substituted by one or more substituents independently selected from halogen atoms, OH, NR$^a$R$^b$, O—C$_{1-4}$alkyl and C$_{1-4}$alkyl groups, optionally substituted with halogen, OMe or OH;

C$_{1-4}$alkyl or C$_{3-7}$cycloalkyl groups, each optionally substituted by one or more substituents independently selected from halogen, OH, OMe or NR$^a$R$^b$; and CN, SO$_2$R$^c$ and NR$^a$SO$_2$R$^c$.

In such an embodiment, preferably each R$^a$ independently represents a hydrogen atom or a C$_{1-4}$alkyl group; and each R$^b$ independently represents a hydrogen atom; a C$_{1-4}$alkyl group optionally substituted by one or more groups selected from OH, O—C$_{1-4}$alkyl and halogen; or a C$_{3-8}$cycloalkyl group in which a CH$_2$ moiety may be replaced by an oxygen atom or an NR$^a$ group. For example each R$^b$ may represent a hydrogen atom or a C$_{1-4}$alkyl group; and each R$^c$ represents —NR$^a$R$^b$ or a methyl group.

In another preferred embodiment, R$^5$ is a group independently selected from:

H, OH, NR$^a$R$^b$ or cyclopropyl;

a 4- to 6-membered heterocyclyl ring containing 1 or 2 heteroatoms, optionally substituted by one substituent selected from F, OH, =O, O—C$_{1-4}$alkyl and C$_{1-4}$alkyl groups, optionally substituted with halogen, OMe or OH; and C$_{1-4}$alkyl optionally substituted by one or two OH groups.

In such an embodiment, preferably each R$^a$ independently represents a hydrogen atom or a C$_{1-4}$alkyl group; and each R$^b$ independently represents a hydrogen atom; a C$_{1-4}$alkyl group optionally substituted by one or more groups selected from OH, O—C$_{1-4}$alkyl and SO$_2$R$^c$; or a C$_{3-8}$cycloalkyl group in which a CH$_2$ moiety may be replaced by an oxygen atom or an NR$^a$ group;

In another preferred embodiment, R$^5$ is a group independently selected from:

H, OH, NR$^a$R$^b$ or cyclopropyl;

a 5- or 6-membered heterocycloalkyl ring containing 1 or 2 heteroatoms, optionally substituted by one substituent selected from OH, O—C$_{1-4}$alkyl and C$_{1-4}$alkyl groups, optionally substituted with halogen, OMe or OH; and C$_{1-4}$alkyl optionally substituted by one or two OH groups.

In such an embodiment, preferably each R$^a$ independently represents a hydrogen atom or a C$_{1-4}$alkyl group; and each R$^b$ independently represents a hydrogen atom; a C$_{1-4}$alkyl group optionally substituted by one or more groups selected from OH and O—C$_{1-4}$alkyl; or a C$_{3-8}$cycloalkyl group in which a CH$_2$ moiety may be replaced by an oxygen atom or an NR$^a$ group;

In a more preferred embodiment, R$^5$ is a group independently selected from:

H, OH, or NR$^a$R$^b$;

a 6-membered heterocyclyl ring containing 1 or 2 heteroatoms or a 5-membered heterocyclyl ring containing 1 or 2 heteroatoms, or a 4-membered heterocyclyl ring containing 1 nitrogen atom, optionally substituted by one or two substituent selected from F, =O, C$_{1-4}$alkyl, OMe, OH and C$_{1-4}$alkyl-OH groups; and C$_{1-4}$alkyl optionally substituted by one or two OH groups.

In such an embodiment, preferably each R$^a$ independently represents a hydrogen atom or a C$_{1-4}$alkyl group; and each R$^b$ independently represents a hydrogen atom; a C$_{1-4}$alkyl group optionally substituted by one or more groups selected from OH, O—C$_{1-4}$alkyl and SO$_2$R$^c$; or a C$_{3-8}$cycloalkyl group in which a CH$_2$ moiety may be replaced by an oxygen atom or an NR$^a$ group;

In a more preferred embodiment, $R^5$ is a group independently selected from:

H, OH, or $NR^aR^b$;

a 6-membered heterocycloalkyl ring containing 1 or 2 heteroatoms or a 5-membered heterocycloalkyl ring containing 1 heteroatom, optionally substituted by one substituent selected from $C_{1-4}$alkyl, OMe and OH groups; and $C_{1-4}$alkyl optionally substituted by one or two OH groups.

In such an embodiment, preferably each $R^a$ independently represents a hydrogen atom or a $C_{1-4}$alkyl group; and each $R^b$ independently represents a hydrogen atom; a $C_{1-4}$alkyl group optionally substituted by one or more groups selected from OH and O—$C_{1-4}$alkyl; or a $C_{3-8}$cycloalkyl group in which a $CH_2$ moiety may be replaced by an oxygen atom or an $NR^a$ group.

A particularly preferred embodiment of the invention, $R^5$ is a group independently selected from:

H or $NR^aR^b$; and a 6-membered heterocyclyl ring containing 1 or 2 heteroatoms (for example a 6-membered heterocycloalkyl ring containing 1 or 2 nitrogen atoms) or a 5-membered heterocyclyl ring containing 1 heteroatom or a 4-membered heterocycloalkyl ring containing 1 nitrogen atom, optionally substituted by one F, =O, $C_{1-4}$alkyl or OH group.

In such an embodiment, preferably each $R^a$ independently represents a hydrogen atom or a $C_{1-4}$alkyl group; and each $R^b$ independently represents a hydrogen atom; a $C_{1-4}$alkyl group optionally substituted by one or two OH groups; or a $C_{3-8}$cycloalkyl group in which a $CH_2$ moiety may be replaced by an oxygen atom or an $NR^a$ group;

A particularly preferred embodiment of the invention, $R^5$ is a group independently selected from:

H or $NR^aR^b$; and a 6-membered heterocycloalkyl ring containing 1 or 2 heteroatoms or a 5-membered heterocycloalkyl ring containing 1 heteroatom (for example a 6-membered heterocycloalkyl ring containing 1 or 2 nitrogen atoms), optionally substituted by one $C_{1-4}$alkyl or OH group.

In such an embodiment, preferably each $R^a$ independently represents a hydrogen atom or a $C_{1-4}$alkyl group; and each $R^b$ independently represents a hydrogen atom; a $C_{1-4}$alkyl group optionally substituted by one or two OH groups; or a $C_{3-8}$cycloalkyl group in which a $CH_2$ moiety may be replaced by an oxygen atom or an $NR^a$ group;

In embodiments of the invention two Z—$R^5$ groups on adjacent ring atoms together with the two adjacent ring atoms may form a 5-7 membered form a fused ring. For example, two Z—$R^5$ groups on adjacent ring atoms together with the two adjacent ring atoms may form a 5-7 membered fused ring composed of the two adjacent ring atoms and —$NR^a$.CO.(CH$_2$)$_q$— wherein one —CH$_2$— moiety can be replaced with —O— or —$NR^a$—; preferably A is, for example a pyridyl or, especially, a phenyl group, which is substituted on adjacent ring atoms forming a fused ring. For example, $R^2$ may represent:

 or

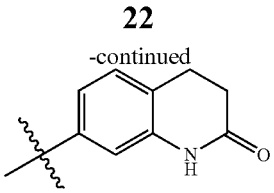

Or, for example, two Z—$R^5$ groups on adjacent ring atoms together with the two adjacent ring atoms may form a 5-7 membered fused ring composed of the two adjacent ring atoms and —(CHR$^a$)$_r$—(CHR$^5$)—(CHR$^a$)$_r$—, wherein the —CHR$^5$— moiety can be replaced with —O— or —NR$^5$— and each r is independently 0, 1, 2, 3 or 4; preferably A is, for example a pyridyl or, especially, a phenyl group, which is substituted on adjacent ring atoms forming a fused ring. Preferably each r is independently 1, 2, or 3, or more preferably each r is 1 or 2, for example each r=1, or one r=1 and one r=2. Preferably, the —CHR$^5$— moiety can be replaced with —NR$^5$—, and more preferably the —CHR$^5$— moiety is be replaced —NR$^5$—. For example, $R^2$ may represent:

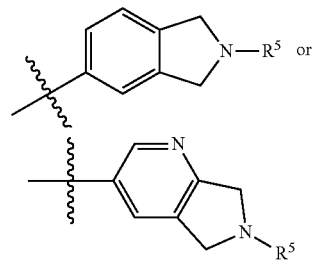

For example,

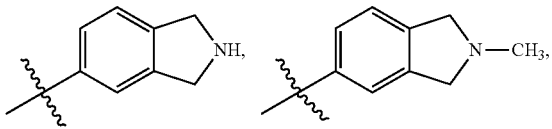

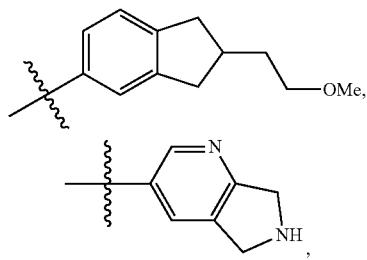

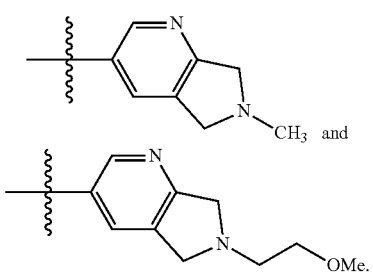

Preferably, for example,

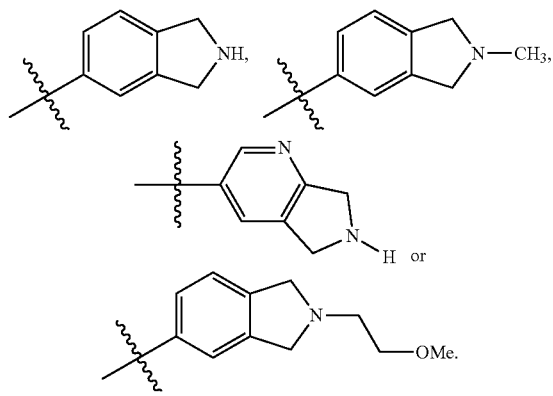

When R⁵ is a 5, 6 or 7 membered heterocycloalkyl ring, in certain embodiments the heterocycloalkyl ring contains one heteroatom and the heterocycloalkyl ring is substituted with one hydroxyl group.

When R⁵ is a 5, 6 or 7 membered heterocycloalkyl ring, in certain embodiments the heterocycloalkyl ring contains one heteroatom which is a nitrogen atom and the heterocycloalkyl ring is optionally substituted with one hydroxyl group.

When R⁵ is a 5, 6 or 7 membered heterocycloalkyl ring, in certain embodiments the heterocycloalkyl ring contains one heteroatom which is an oxygen atom.

When R⁵ is a 5, 6 or 7 membered heterocycloalkyl ring, in certain embodiments the heterocycloalkyl ring contains two heteroatoms, one of which is an nitrogen atom. Preferable the second heteroatom is an oxygen atom.

When R⁵ is a 6 membered heterocycloalkyl ring, in certain embodiments the heterocycloalkyl ring contains two heteroatoms and one of said heteroatoms is oxygen (for example R₅ is morpholine). In such embodiments the ring may be optionally substituted with a methyl group. In another embodiment when R⁵ is a 6 membered heterocycloalkyl ring, the heterocycloalkyl ring contains two heteroatoms both of which are nitrogen and is optionally substituted by an oxo group.

When R⁵ is a 5 membered heterocyclyl ring, in certain embodiments the heterocyclyl ring contains two heteroatoms and both of said heteroatoms are nitrogen. In such an embdoments the heterocyclyl may be aromatic or aliphatic, and may be optionally substituted with one methyl group.

When R⁵ is a 5 membered heterocycloalkyl ring, in certain embodiments the heterocycloalkyl ring contains one heteroatom which is a nitrogen atom and the heterocycloalkyl ring is optionally substituted with one fluorine, hydroxyl or methyl or OMe group.

When R⁵ is a 5 membered heterocycloalkyl ring, in certain embodiments the heterocycloalkyl ring contains two heteroatoms, one of which is a nitrogen atom and the other of which is a oxygen atom, and the heterocycloalkyl ring is optionally substituted with one or two groups independently selected from fluorine, hydroxyl, $C_{1-4}$alkyl, OMe, =O or $C_{1-4}$alkylOH groups. For example, groups independently selected from $C_{1-4}$alkyl or OMe group or =O or $C_{1-4}$alkylOH, for example two groups independently selected from =O or $C_{1-4}$alkylOH groups.

When R⁵ is a 4 membered heterocycloalkyl ring, in certain embodiments the heterocycloalkyl ring contains one heteroatom which is a nitrogen atom and the heterocycloalkyl ring is optionally substituted with one or two OH, Me or OMe groups, for example two Me groups or one OMe group or one Me and one OH.

When R⁵ is a $NR^aR^b$ group, in certain embodiments $R^a$ is H and $R^b$ is H or $C_{1-4}$alkyl optionally substituted with one OH group. When R⁵ is a $NR^aR^b$ group, in certain embodiments $R^a$ is H or methyl, and $R^b$ is H or $C_{1-4}$alkyl optionally substituted with one OH group or one OMe group or one $SO_2Me$ group, preferably optionally substituted with one OH group or one OMe group.

When R⁵ is a $C_{1-4}$alkyl group, in certain embodiments the $C_{1-4}$alkyl group is methyl or is a $C_{2-4}$alkyl group optionally substituted with one or two OH groups. When R⁵ is a $C_{1-4}$alkyl group, in certain embodiments the $C_{1-4}$alkyl group is methyl or is a $C_{2-4}$alkyl group optionally substituted with one or two OH groups or one $NH_2$ group.

The groups $R^a$ and $R^b$ may have one of the preferred meanings given below.

If the compound of the invention contains more than one moiety represented by $R^a$, these may be the same or different. Each $R^a$ independently represents a hydrogen atom or a $C_{1-4}$alkyl group. Except whether otherwise stated, preferably $R^a$ is a methyl group or, especially, a hydrogen atom.

If the compound of the invention contains more than one moiety represented by $R^b$, these may be the same or different. In an embodiment, each $R^b$ independently represents a hydrogen atom; a $C_{1-4}$alkyl group optionally substituted by one or more groups selected from OH, O—$C_{1-4}$alkyl, halogen, $SO_2R^c$ and phenyl; or a $C_{3-8}$cycloalkyl group in which a $CH_2$ moiety may be replaced by an oxygen atom or an $NR^a$ group. In an alternative embodiment, each $R^b$ independently represents a hydrogen atom; a $C_{1-4}$alkyl group optionally substituted by one or more groups selected from OH, O—$C_{1-4}$alkyl, halogen, and phenyl; or a $C_{3-8}$cycloalkyl group in which a $CH_2$ moiety may be replaced by an oxygen atom or an $NR^a$ group.

In preferred embodiments, each $R^b$ independently represents a hydrogen atom; a $C_{1-4}$alkyl group optionally substituted by one or more groups selected from OH and O—$C_{1-4}$alkyl and $SO_2R_c$, for example $SO_2Me$; or a $C_{3-8}$cycloalkyl group in which a $CH_2$ moiety may be replaced by an oxygen atom or an $NR^a$ group. In another preferred embodiments, each $R^b$ independently represents a hydrogen atom; a $C_{1-4}$alkyl group optionally substituted by one or more groups selected from OH and O—$C_{1-4}$alkyl; or a $C_{3-8}$cycloalkyl group in which a $CH_2$ moiety may be replaced by an oxygen atom or an $NR^a$ group. In the most preferred embodiments of the invention, $R^b$ independently represents a hydrogen atom; a $C_{1-4}$alkyl group optionally substituted by one or two OH groups or one OMe group or one $SO_2Me$; or a $C_{3-8}$cycloalkyl group in which a $CH_2$ moiety may be replaced by an oxygen atom or an $NR^a$ group. In one preferred embodiment, $R^b$ is $C_{1-4}$alkyl group optionally substituted by one $SO_2Me$. In another most preferred embodiment of the invention, $R^b$ independently represents a hydrogen atom; a $C_{1-4}$alkyl group optionally substituted by one or two OH groups; or a $C_{3-8}$cycloalkyl group in which a $CH_2$ moiety may be replaced by an oxygen atom or an $NR^a$ group.

$R^b$ may for example be a methyl group or, especially, a hydrogen atom.

$R^c$ represents a hydrogen atom; a —$NR^aR^b$ group; a $C_{3-8}$cycloalkyl group, in which $CH_2$ moiety may optionally be replaced by an oxygen atom or an $NR^a$ group; or a $C_{1-4}$alkyl group optionally substituted by a group $NR^aR^b$. In preferred embodiments $R^c$ is a —$NR^aR^b$ group; a $C_{3-8}$cycloalkyl group, in which $CH_2$ moiety may optionally be replaced by an oxygen atom or an $NR^a$ group; or a $C_{1-4}$alkyl group optionally substituted by a NR$^a$R$^b$ group. Except where otherwise stated, more preferably R$^c$ is a NR$^a$R$^b$ group. For example, R$^c$ may be a group NR$^a$R$^b$ in which each of R$^a$ and R$^b$ represents a hydrogen atom or a methyl group.

R$^d$ may be a 5- or 6-membered heteroaryl group containing 1 or 2 heteroatoms, optionally substituted with one or more C$_{1-4}$alkyl groups. Preferably, R$^d$ may be a heteroaryl group containing one or two nitrogen atoms. For example R$^d$ may be a pyrazole group or pyridine group. More preferably R$^d$ may a pyrazole group, for example a pyrazole group attached at its 4-position. For example R$^d$ may be selected from pyrazole and 1-methyl-pyrazole. Where R$^d$ is a pyrazole it is preferably attached at its 4 position. Where R$^d$ is a pyridine it is preferably attached at its 3- or 4-position. The heteroaryl group may be substituted with one or more C$_{1-4}$alkyl groups, for example methyl or ethyl groups. For example, it may be substituted with one methyl group (for example 1-methylpyrazole).

q is 1, 2 or 3. q is preferably 1 or 2. For example, q may be 1; or q may be 2.

Preferably R$^3$ represents a C$_{1-2}$alkyl group (for example methyl), a hydrogen atom or a halogen atom, for example fluorine or chlorine; more preferably, R$^3$ represents a methyl group, a hydrogen atom or a fluorine atom, for example a hydrogen atom or a fluorine atom. In preferred embodiments R$^3$ is a hydrogen or a fluorine atom, most preferably hydrogen.

Preferably R$^4$ represents a methyl group, a hydrogen atom or a halogen atom, for example fluorine; more preferably, R$^4$ represents a hydrogen atom. For example, R$^4$ represents a hydrogen atom, and R$^3$ represents a methyl group, a hydrogen atom or a fluorine atom, for example a hydrogen atom or a fluorine atom. In preferred embodiments R$^4$ is a hydrogen atom.

In a specific embodiment of the invention, R$^2$ represents

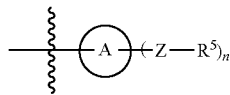

wherein A is a phenyl or 5 to 10 membered heteroaryl ring containing 1, 2 or 3 heteroatoms;

n is 1 or 2;

each Z is a group independently selected from —(CHR$^a$)$_p$—, —(CHR$^a$)$_p$—O—(CHR$^a$)$_r$—, —(CHR$^a$)$_p$—NR$^a$—(CHR$^a$)$_r$—, —C(=O)— and —NR$^a$C(=O)(CHR$^a$)$_p$—, in which p is 0, 1 or 2 and r is 1, 2, or 3;

and each R$^5$ is a group independently selected from:
H, halogen, OR$^b$, or NR$^a$R$^b$;
a 4- to 7-membered heterocyclyl ring containing 1 or 2 heteroatoms, optionally substituted by one or more substituents independently selected from halogen atoms, OH, =O, NR$^a$R$^b$, O—C$_{1-4}$alkyl and C$_{1-4}$alkyl groups, optionally substituted with halogen, O—C$_{1-4}$alkyl or OH; and
C$_{1-4}$alkyl or C$_{3-7}$cycloalkyl groups, each optionally substituted by one or more substituents independently selected from halogen, OH, O—C$_{1-4}$alkyl and NR$^a$R$^b$; and
CN, SO$_2$R$^c$ and NR$^a$SO$_2$R$^c$; or
n=2 and two Z—R$^5$ groups on adjacent ring atoms together with the two adjacent ring atoms form a 5-7 membered fused ring composed of the two adjacent ring atoms and —(CHR$^a$)$_r$—(CHR$^5$)—(CHR$^a$)$_r$—, wherein the —CHR$^5$— moiety can be replaced with —NR$^5$— and each r is independently 1 or 2; and each R$^a$ independently represents a hydrogen atom or a C$_{1-4}$alkyl group; and each R$^b$ independently represents a hydrogen atom; a C$_{1-4}$alkyl group optionally substituted by one or more groups selected from OH, O—C$_{1-4}$alkyl, halogen, SO$_2$R$^c$; and phenyl; or a C$_{3-8}$cycloalkyl group in which a CH$_2$ moiety may be replaced by an oxygen atom or an NR$^a$ group; and each R$^c$ represents —NR$^a$R$^b$ or a C$_{1-4}$alkyl group optionally substituted by a group NR$^a$R$^b$.

In another specific embodiment of the invention, R$^2$ represents

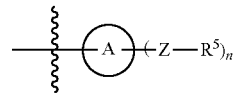

wherein A is a phenyl or 5 to 10 membered heteroaryl ring containing 1, 2 or 3 heteroatoms;

n is 1 or 2;

each Z is a group independently selected from —(CH$_2$)$_p$—, —C(=O)— and —NR$^a$C(=O)(CHR$^a$)$_p$—, in which p is 0, 1 or 2;

and each R$^5$ is a group independently selected from:
H, halogen, OR$^b$, or NR$^a$R$^b$;
a 4- to 7-membered heterocycloalkyl ring containing 1 or 2 heteroatoms, optionally substituted by one or more substituents independently selected from halogen atoms, OH, NR$^a$R$^b$, O—C$_{1-4}$alkyl and C$_{1-4}$alkyl groups, optionally substituted with halogen, O—C$_{1-4}$alkyl or OH; and
C$_{1-4}$alkyl or C$_{3-7}$cycloalkyl groups, each optionally substituted by one or more substituents independently selected from halogen, OH, O—C$_{1-4}$alkyl or NR$^a$R$^b$; and
CN, SO$_2$R$^c$ and NR$^a$SO$_2$R$^c$;

each R$^a$ independently represents a hydrogen atom or a C$_{1-4}$alkyl group; and each R$^b$ independently represents a hydrogen atom; a C$_{1-4}$alkyl group optionally substituted by one or more groups selected from OH, O—C$_{1-4}$alkyl, halogen, and phenyl; or a C$_{3-8}$cycloalkyl group in which a CH$_2$ moiety may be replaced by an oxygen atom or an NR$^a$ group; and each R$^c$ represents —NR$^a$R$^b$ or a C$_{1-4}$alkyl group optionally substituted by a group NR$^a$R$^b$.

In a preferred embodiment of the invention,

A is a phenyl or 5 to 6 membered heteroaryl ring containing 1 or 2 heteroatoms;

n is 1 or 2;

each Z is a group independently selected from —(CHR$^a$)$_p$—, —(CHR$^a$)$_p$—O—(CHR$^a$)$_r$—, —(CHR$^a$)$_p$—NR$^a$—(CHR$^a$)$_r$—, —C(=O)— and —NR$^a$C(=O)(CHR$^a$)$_p$—, in which p is 0, 1 or 2 and r is 1, 2, or 3;

and each R$^5$ is a group independently selected from:
H, halogen, OR$^b$ or NR$^a$R$^b$;
a 4- to 6-membered heterocyclyl ring containing 1 or 2 heteroatoms, optionally substituted by one or more substituents independently selected from halogen atoms, OH, =O, NR$^a$R$^b$, O—C$_{1-4}$alkyl and C$_{1-4}$alkyl groups, optionally substituted with halogen, OMe or OH;

$C_{1-4}$alkyl or $C_{3-7}$cycloalkyl groups, each optionally substituted by one or more substituents independently selected from halogen, OMe, OH and $NR^aR^b$; and CN, $SO_2R^c$ and $NR^aSO_2R^c$; or n=2 and two Z—$R^5$ groups on adjacent ring atoms together with the two adjacent ring atoms form a 5-7 membered fused ring composed of the two adjacent ring atoms and —$(CHR^a)_r$—$(CHR^5)$—$(CHR^a)_r$—, wherein the —$CHR^5$— moiety can be replaced with —$NR^5$— and each r is independently 1 or 2; and each $R^a$ independently represents a hydrogen atom or a $C_{1-4}$alkyl group; and each $R^b$ independently represents a hydrogen atom; a $C_{1-4}$alkyl group optionally substituted by one or more groups selected from OH, O—$C_{1-4}$alkyl, halogen and $SO_2R^c$; or a $C_{3-8}$cycloalkyl group in which a $CH_2$ moiety may be replaced by an oxygen atom or an $NR^a$ group; and each $R^c$ represents —$NR^aR^b$ or a methyl group.

In a preferred embodiment of the invention,

A is a phenyl or 5 to 6 membered heteroaryl ring containing 1 or 2 heteroatoms;

n is 1 or 2;

each Z is a group independently selected from —$(CH_2)_p$—, —C(=O)— and —$NR^aC(=O)(CHR^a)_p$—, in which p is 0, 1 or 2;

and each $R^5$ is a group independently selected from:

H, halogen, $OR^b$ or $NR^aR^b$;

a 5- to 6-membered heterocycloalkyl ring containing 1 or 2 heteroatoms, optionally substituted by one or more substituents independently selected from halogen atoms, OH, $NR^aR^b$, O—$C_{1-4}$alkyl and $C_{1-4}$alkyl groups, optionally substituted with halogen, OMe or OH;

$C_{1-4}$alkyl or $C_{3-7}$cycloalkyl groups, each optionally substituted by one or more substituents independently selected from halogen, OMe, OH and $NR^aR^b$; and CN, $SO_2R^c$ and $NR^aSO_2R^c$;

each $R^a$ independently represents a hydrogen atom or a $C_{1-4}$alkyl group; and each $R^b$ independently represents a hydrogen atom; a $C_{1-4}$alkyl group optionally substituted by one or more groups selected from OH, O—$C_{1-4}$alkyl and halogen; or a $C_{3-8}$cycloalkyl group in which a $CH_2$ moiety may be replaced by an oxygen atom or an $NR^a$ group; and each $R^c$ represents —$NR^aR^b$ or a methyl group.

In a further preferred embodiment of the invention,

A is a phenyl or 5 to 6 membered heteroaryl ring containing 1 or 2 heteroatoms;

n is 1;

each Z is a group independently selected from —$(CH_2)_p$—, —O—$(CHR^a)_r$—, —$NR^a$—$(CHR^a)_r$—, —C(=O)— and —$NR^aC(=O)(CHR^a)_p$—, in which p is 0, 1 or 2;

and each $R^5$ is a group independently selected from:

H, OH, $NR^aR^b$ or cyclopropyl; and a 5- or 6-membered heterocyclyl ring containing 1 or 2 heteroatoms, or a 4 memebered heterocyclyl ring containing 1 heteroatom, optionally substituted by one or two substituent selected from OH, F, =O, O—$C_{1-4}$alkyl and $C_{1-4}$alkyl groups, optionally substituted with halogen, OMe or OH; and $C_{1-4}$alkyl optionally substituted by one or two OH groups; or n=2 and two Z—$R^5$ groups on adjacent ring atoms together with the two adjacent ring atoms form a 5-7 membered fused ring composed of the two adjacent ring atoms and —$(CHR^a)_r$—$(NR^5)$—$(CHR^a)_r$—, and each r is independently 1 or 2; and each $R^a$ independently represents a hydrogen atom or a $C_{1-4}$alkyl group; and each $R^b$ independently represents a hydrogen atom; a $C_{1-4}$alkyl group optionally substituted by one or more groups selected from OH and O—$C_{1-4}$alkyl; or a $C_{3-8}$cycloalkyl group in which a $CH_2$ moiety may be replaced by an oxygen atom or an $NR^a$ group.

In a further preferred embodiment of the invention,

A is a phenyl or 5 to 6 membered heteroaryl ring containing 1 or 2 heteroatoms;

n is 1;

each Z is a group independently selected from —$(CH_2)_p$—, —C(=O)— and —$NR^aC(=O)(CHR^a)_p$—, in which p is 0, 1 or 2;

and each $R^5$ is a group independently selected from:

H, OH, $NR^aR^b$ or cyclopropyl; and a 5- or 6-membered heterocyclyl ring containing 1 or 2 heteroatoms, optionally substituted by one substituent selected from OH, O—$C_{1-4}$alkyl and $C_{1-4}$alkyl groups, optionally substituted with halogen, OMe or OH; and $C_{1-4}$alkyl optionally substituted by one or two OH groups;

each $R^a$ independently represents a hydrogen atom or a $C_{1-4}$alkyl group; and each $R^b$ independently represents a hydrogen atom; a $C_{1-4}$alkyl group optionally substituted by one or more groups selected from OH and O—$C_{1-4}$alkyl; or a $C_{3-8}$cycloalkyl group in which a $CH_2$ moiety may be replaced by an oxygen atom or an $NR^a$ group.

In a further preferred embodiment of the invention,

A is a phenyl or 5 to 6 membered heteroaryl ring containing 1 or 2 heteroatoms;

n is 1;

each Z is a group independently selected from —$(CH_2)_p$, $O(CHR^a)_r$—, —$NR^a$—$(CHR^a)_r$—, —C(=O)— and —$NR^aC(=O)(CHR^a)_p$—, in which p is 0, 1 or 2;

and each $R^5$ is a group independently selected from:

H, OH, or $NR^aR^b$; and a 6-membered heterocyclyl ring containing 1 or 2 heteroatoms or 5-membered heterocyclyl ring containing 1 or 2 heteroatoms, or a 4 membered heterocycloalkyl ring containing 1 heteroatom, optionally substituted by one or two substituent selected from, F, =O, $C_{1-4}$alkyl, OMe, OH and $C_{1-4}$alkylOH groups; and $C_{1-4}$alkyl optionally substituted by one or two OH; or n=2 and two Z—$R^5$ groups on adjacent ring atoms together with the two adjacent ring atoms form a 5-7 membered fused ring composed of the two adjacent ring atoms and —$(CHR^a)_r$—$(NR^5)$—$(CHR^a)_r$—, and each r is independently 1 or 2; and each $R^a$ independently represents a hydrogen atom or a $C_{1-4}$alkyl group; and each $R^b$ independently represents a hydrogen atom; a $C_{1-4}$alkyl group optionally substituted by one or more groups selected from $OH_2O$—$C_{1-4}$alkyl and $SO_2Me$; or a $C_{3-8}$cycloalkyl group in which a $CH_2$ moiety may be replaced by an oxygen atom or an $NR^a$ group;

In a further preferred embodiment of the invention,

A is a phenyl or 5 to 6 membered heteroaryl ring containing 1 or 2 heteroatoms;

n is 1;

each Z is a group independently selected from —$(CH_2)_p$, $O(CHR^a)_r$—, —$NR^a$—$(CHR^a)_r$—, —C(=O)— and —$NR^aC(=O)(CHR^a)_p$—, in which p is 0, 1 or 2;

and each $R^5$ is a group independently selected from:

H, OH, or $NR^aR^b$; and a 6-membered heterocyclyl ring containing 1 or 2 heteroatoms or 5-membered heterocyclyl ring containing 1 heteroatom, optionally substituted by one substituent selected from, F, =O, $C_{1-4}$alkyl, OMe, and OH groups; and $C_{1-4}$alkyl optionally substituted by one or two OH; or n=2 and two Z—$R^5$ groups on adjacent ring atoms together with the two adjacent ring atoms form a 5-7 membered fused ring composed of the two adjacent ring atoms and —$(CHR^a)_r$—$(NR^5)$—$(CHR^a)_r$—, and each r is independently 1 or 2; and each $R^a$ independently represents a hydrogen atom or a $C_{1-4}$alkyl group; and each $R^b$ independently represents a hydrogen atom; a $C_{1-4}$alkyl group optionally substituted by one or more groups selected from OH, O—$C_{1-4}$alkyl and $SO_2$Me; or a $C_{3-8}$cycloalkyl group in which a $CH_2$ moiety may be replaced by an oxygen atom or an $NR^a$ group;

In a further preferred embodiment of the invention,

A is a phenyl or 5 to 6 membered heteroaryl ring containing 1 or 2 heteroatoms;

n is 1;

each Z is a group independently selected from —$(CH_2)_p$—, —$C(=O)$— and —$NR^aC(=O)(CHR^a)_p$—, in which p is 0, 1 or 2;

and each $R^5$ is a group independently selected from:

H, OH, or $NR^aR^b$; and a 6-membered heterocyclyl ring containing 1 or 2 heteroatoms or 5-membered heterocyclyl ring containing 1 heteroatom, optionally substituted by one substituent selected from $C_{1-4}$alkyl, OMe and OH groups; and $C_{1-4}$alkyl optionally substituted by one or two OH groups;

each $R^a$ independently represents a hydrogen atom or a $C_{1-4}$alkyl group; and each $R^b$ independently represents a hydrogen atom; a $C_{1-4}$alkyl group optionally substituted by one or more groups selected from OH and O—$C_{1-4}$alkyl; or a $C_{3-8}$cycloalkyl group in which a $CH_2$ moiety may be replaced by an oxygen atom or an $NR^a$ group.

For example,

A is a phenyl, pyridine or pyrazole;

n is 1;

each Z is a group independently selected from —$(CH_2)_p$—, —$O$—$(CHR^a)_r$—, —$N$—$(CH_2)_p$—, —$C(=O)$—, and $NR^aC(=O)(CHR^a)_p$—, in which p is 0 or 1 and r is 2;

and each $R^5$ is a group independently selected from:

H or $NR^aR^b$; and a 6-membered heterocyclyl ring containing 1 or 2 heteroatoms or a 5-membered heterocyclyl ring containing 1 heteroatom (for example a 6-membered heterocyclyl ring containing 1 or 2 nitrogen atoms) or a 4-membered heterocyclyl ring containing 1 nitrogen atom, optionally substituted by one, F, =O, $C_{1-4}$alkyl or OH group; or n=2 and two Z—$R^5$ groups on adjacent ring atoms together with the two adjacent ring atoms form a 5-7 membered fused ring composed of the two adjacent ring atoms and —$(CHR^a)_r$—$(NR^5)$—$(CHR^a)_r$—, and each r is independently 1 or 2; and each $R^a$ independently represents a hydrogen atom or a $C_{1-4}$alkyl group; and each $R^b$ independently represents a hydrogen atom; a $C_{1-4}$alkyl group optionally substituted by one or two OH, OMe or $SO_2$Me groups; or a $C_{3-8}$cycloalkyl group in which a $CH_2$ moiety may be replaced by an oxygen atom or an $NR^a$ group.

For example,

A is a phenyl, pyridine or pyrazole;

n is 1;

each Z is a group independently selected from —$(CH_2)_p$— and —$C(=O)$—, and $NR^aC(=O)(CHR^a)_p$—, in which p is 0 or 1;

and each $R^5$ is a group independently selected from:

H or $NR^aR^b$; and a 6-membered heterocycloalkyl ring containing 1 or 2 heteroatoms or a 5-membered heterocycloalkyl ring containing 1 heteroatom (for example a 6-membered heterocycloalkyl ring containing 1 or 2 nitrogen atoms), optionally substituted by one $C_{1-4}$alkyl or OH group;

each $R^a$ independently represents a hydrogen atom or a $C_{1-4}$alkyl group; and each $R^b$ independently represents a hydrogen atom; a $C_{1-4}$alkyl group optionally substituted by one or two OH groups; or a $C_{3-8}$cycloalkyl group in which a $CH_2$ moiety may be replaced by an oxygen atom or an $NR^a$ group.

In alternative preferred embodiments of the invention:

A is pyridyl, phenyl or pyrazole;

Z is —$C(=O)$—, —$NR^aC(=O)(CHR^a)_p$— wherein $R^a$ is independently selected from the group consisting of H or Me and p is 0 or 1, or a bond;

and each $R^5$ is independently selected from:

a 5, 6 or 7 membered heterocylcoalkyl ring containing 1 or 2 heteroatoms, wherein if 1 heteroatom is present then the heterocylcoalkyl ring is substituted with one hydroxyl group, and wherein if the heterocylcoalkyl ring is a 6- or 7-membered ring containing 2 heteroatoms, one of said heteroatoms is oxygen (for example $R_5$ is morpholine);

$NR^aR^b$ wherein $R^a$ is H and $R^b$ is H or $C_{1-4}$alkyl optionally substituted with OH group; and $C_{1-4}$alkyl group optionally substituted with 1 or 2 OH groups (for example methyl).

In a further preferred embodiment:

A is pyridyl;

Z is —$NR^aC(=O)(CHR^a)_p$— wherein $R^a$ is independently selected from the group consisting of H or Me and p is 0 or 1; and $R^5$ is selected from:

a 5, 6 or 7 membered heterocylcoalkyl ring containing 1 or 2 heteroatoms wherein if 1 heteroatom is present then the heterocylcoalkyl ring is substituted with one hydroxyl group, or wherein if the heterocylcoalkyl ring is a 6- or 7-membered ring containing 2 heteroatoms, one of said heteroatoms is oxygen (for example $R_5$ is morpholine), and $C_{1-4}$alkyl group (for example methyl) optionally substituted with 1 or 2 OH groups.

In such an embodiment, preferably $R^5$ is selected from morpholine and methyl. Further, in such an embodiment, preferably $R^1$ is pyrrolidine, optionally substituted one F or OH group.

In a further preferred embodiment:

A is phenyl or pyridyl;

Z is —$C(=O)$—; and $R^5$ is $NR^aR^b$, wherein $R^a$ is H and $R^b$ is H or $C_{1-4}$alkyl optionally substituted with one OH group. In such an embodiment, preferably $R^1$ is pyrrolidine, optionally substituted with one F or OH group.

In a further preferred embodiment:

A is pyrazole;

Z is a bond; and $R^5$ selected from:

methyl, and $C_{2-4}$alkyl optionally substituted with one or two OH groups.

In such an embodiment, preferably $R^1$ is selected from the group consisting of pyrrolidine and 8-aza-bicyclo[3.2.1]oct-8-yl, optionally substituted with hydroxyl.

In a further preferred embodiment:
A is phenyl or pyridyl;
Z is a bond; and
$R^5$ is a 5 or 6 or 7 membered heterocylcoalkyl ring containing 1 oxygen atom.

In such an embodiment, preferably $R^1$ is an aliphatic heterocyclyl group having 4, 5, 6, 7 or 8 ring atoms, optionally substituted with one or two OH groups, and more preferably pyrrolidine optionally substituted with one OH group. In one embodiment, preferably $R^5$ is morpholine.

In a further preferred embodiment:
A is pyridyl;
Z is a bond; and
$R^5$ is $NR^aR^b$, wherein $R^a$ is H and $R^b$ is H or $C_{1-4}$alkyl optionally substituted with one OH or OMe or $SO_2R^c$ group, for example one OH or OMe.

In a further preferred embodiment:
A is phenyl or pyridyl;
n is 2,
and two Z—$R^5$ groups on adjacent ring atoms together with the two adjacent ring atoms form a 5-7 membered fused ring composed of the two adjacent ring atoms and —(CHR$^a$)$_r$—(NR$^5$)—(CHR$^a$)$_r$—, and each r is independently 1 or 2;

In such an embodiment, preferably $R^1$ is an aliphatic heterocyclyl group having 4, 5, 6, 7 or 8 ring atoms, optionally substituted with one or two F or OH groups, and more preferably pyrrolidine optionally substituted with one F or OH group. In one embodiment, preferably $R^5$ is morpholine.

In a further preferred embodiment:
A is pyridyl;
Z is a —(CH$_2$)— or —(CHMe)-; and
$R^5$ is a 4, 5 or 6 membered heterocylcoalkyl ring containing 1 nitrogen atom and optionally a second heteroatom, optionally substituted with one F, =O or OMe.

In such an embodiment, preferably $R^1$ is an aliphatic heterocyclyl group having 4, 5, 6, 7 or 8 ring atoms, optionally substituted with one or two F or OH groups, and more preferably pyrrolidine optionally substituted with one F or OH group. In one embodiment, preferably $R^5$ is morpholine.

In certain compounds of the invention, $R^2$ is selected from the group consisting of:

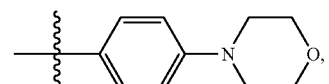

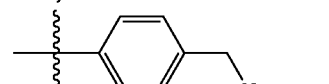

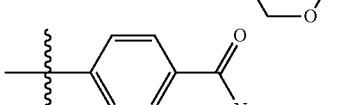

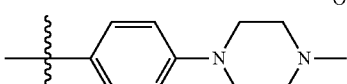

-continued

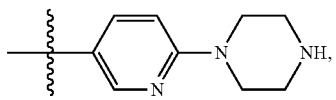

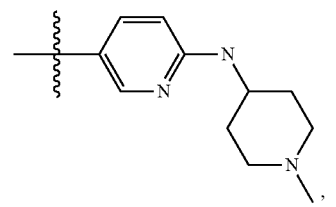

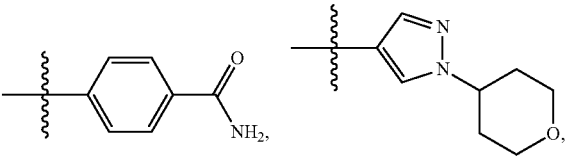

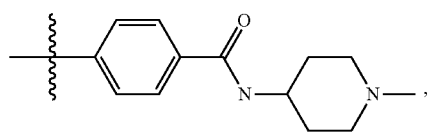

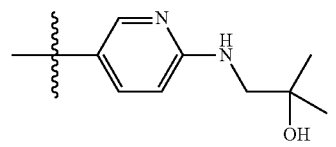

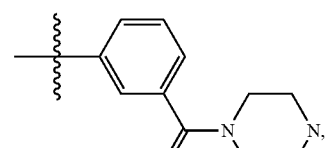

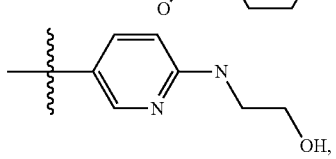

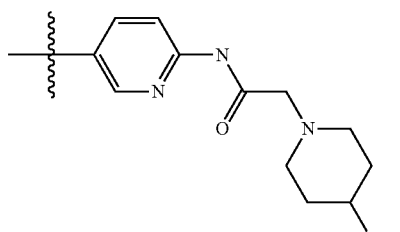

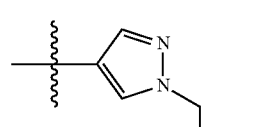

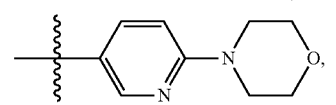

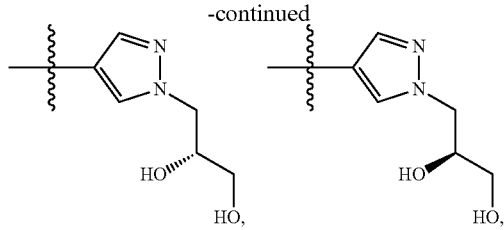
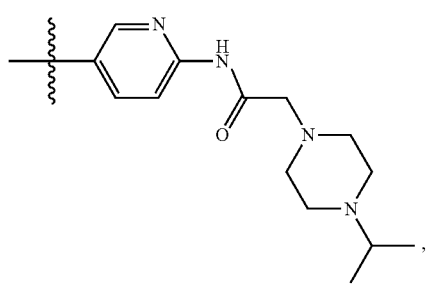
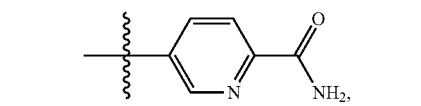
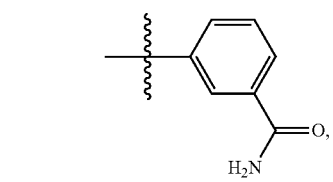
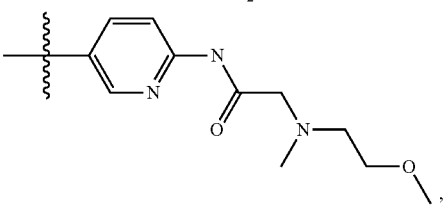
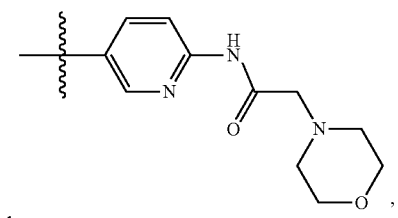
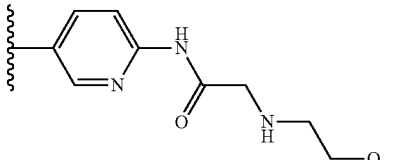
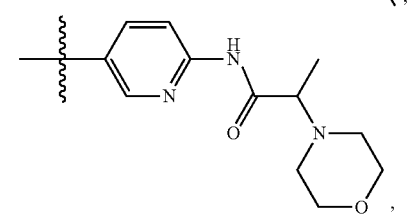
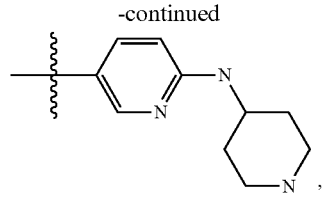
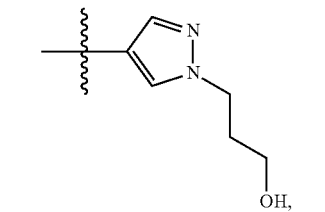
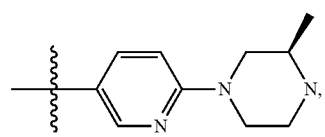
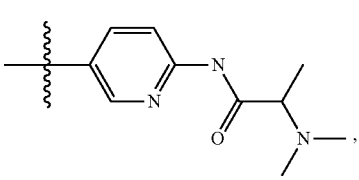
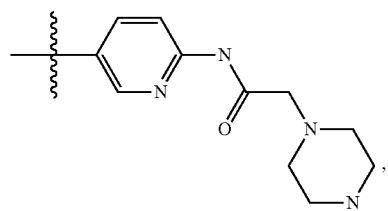
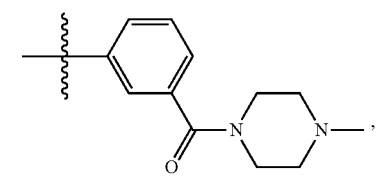
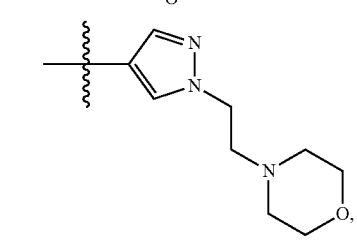
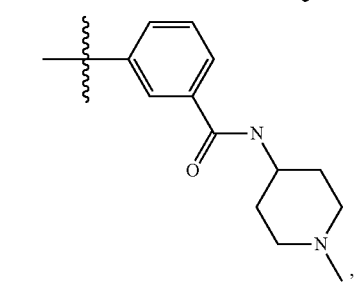

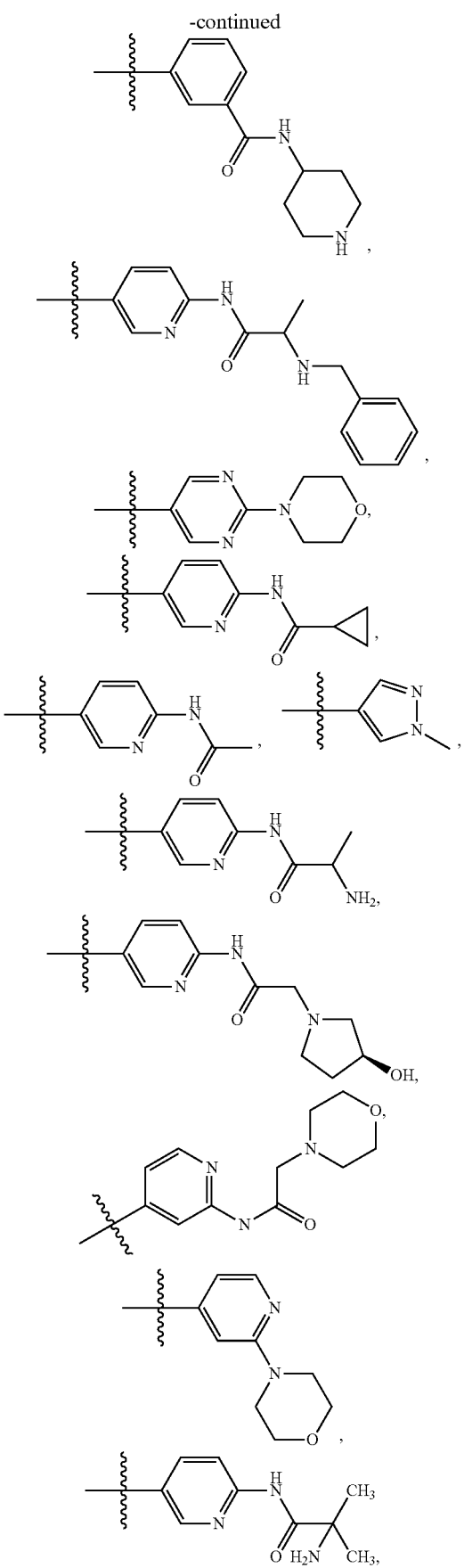
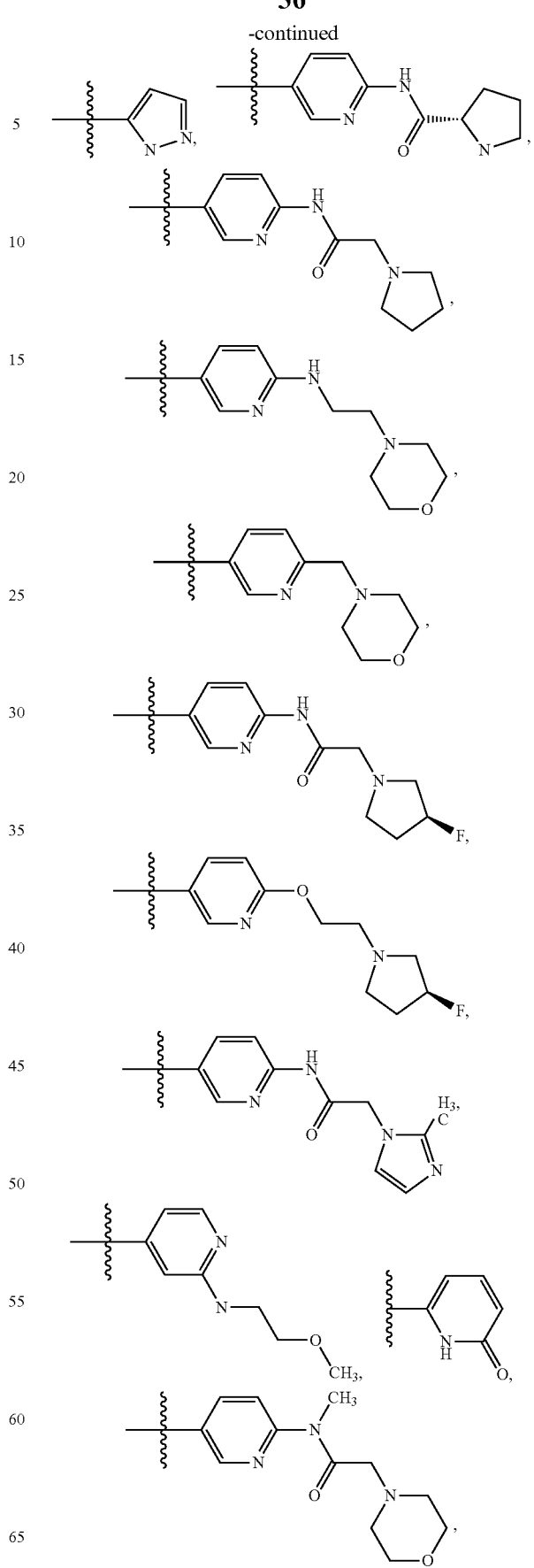

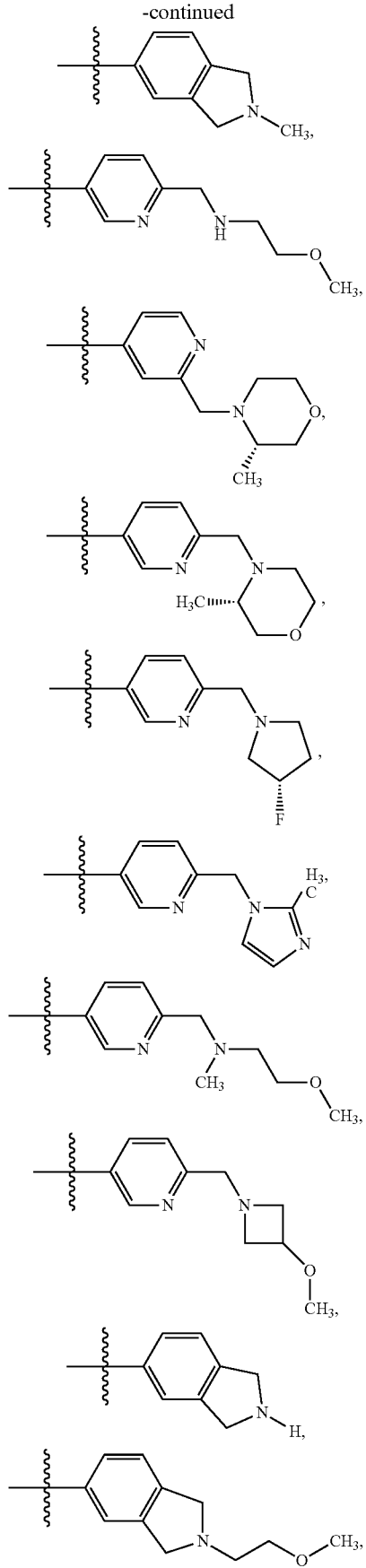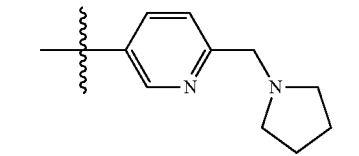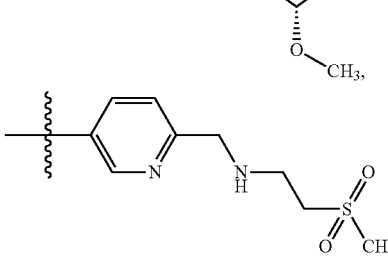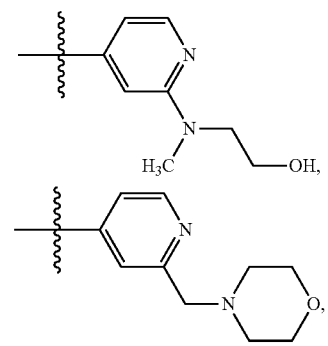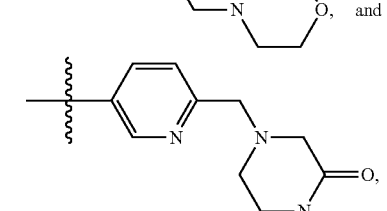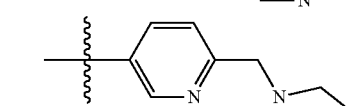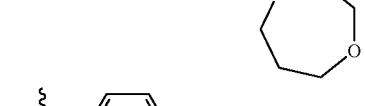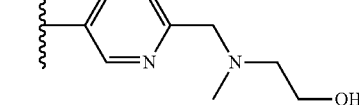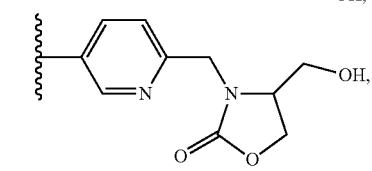

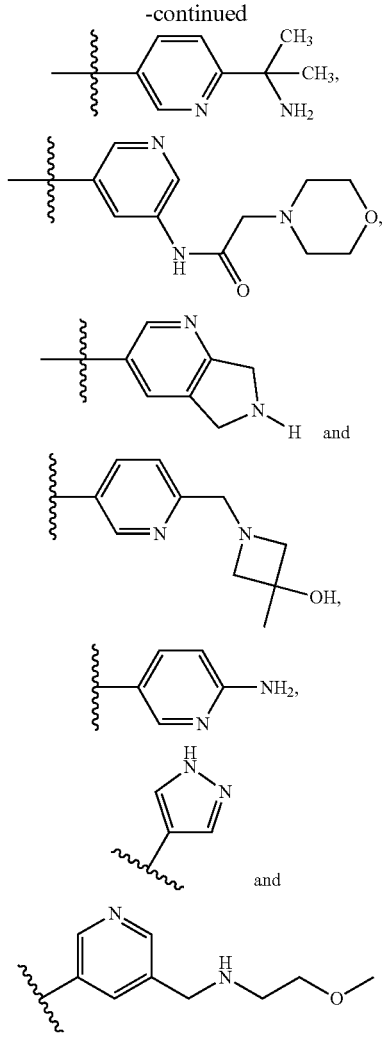
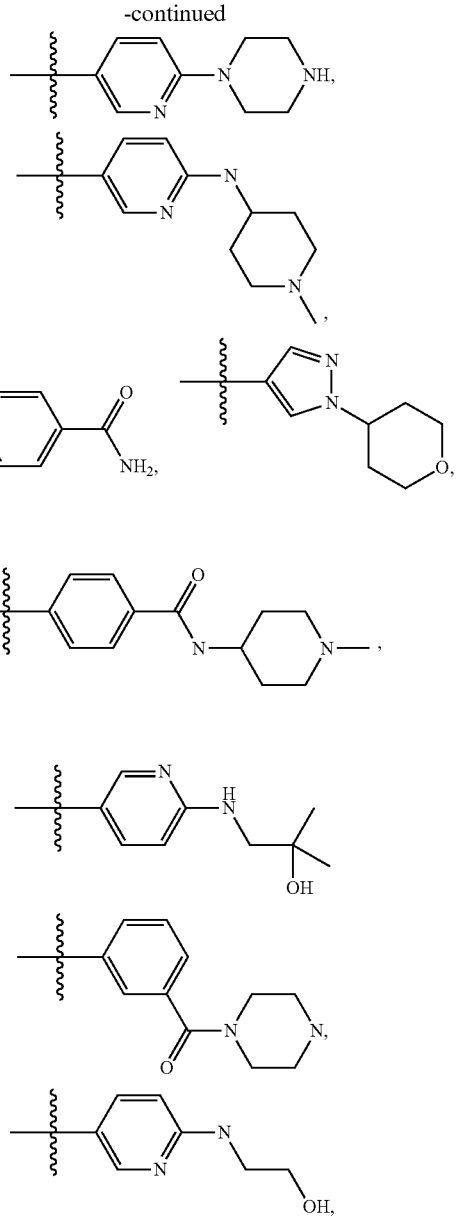
wherein the bond extending to the left is attached to the NH group of the pyrimidine in Formula I.
In certain compounds of the invention, $R^2$ is selected from the group consisting of:
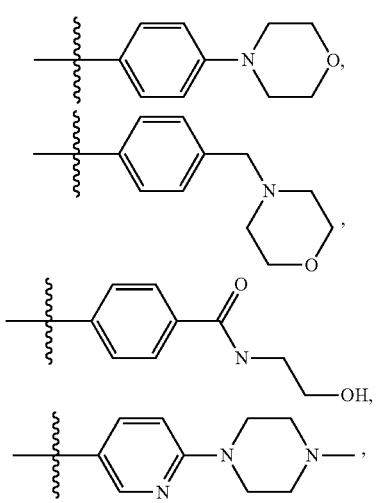

41
-continued
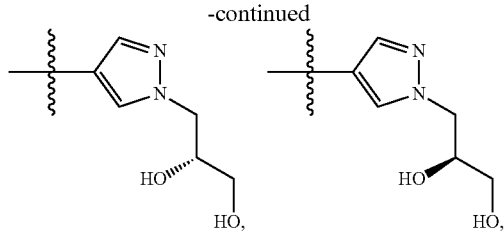
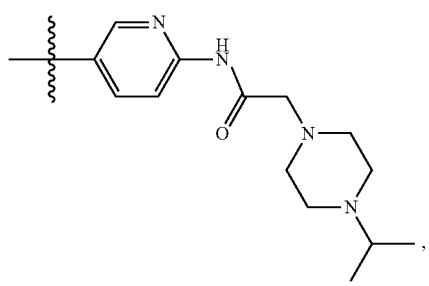
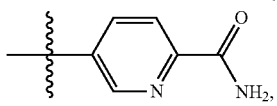
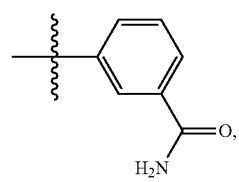
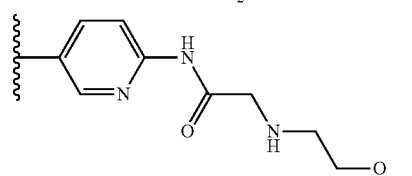
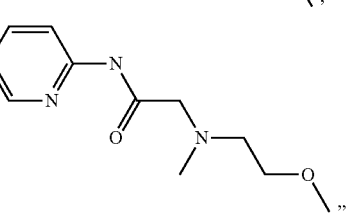
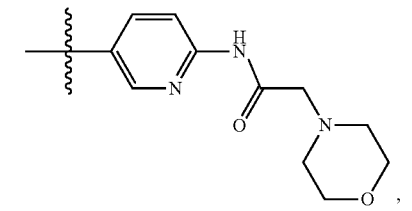
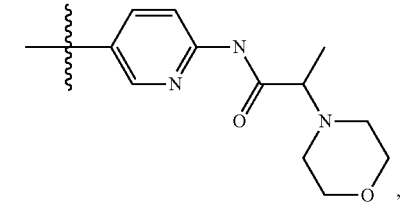
42
-continued
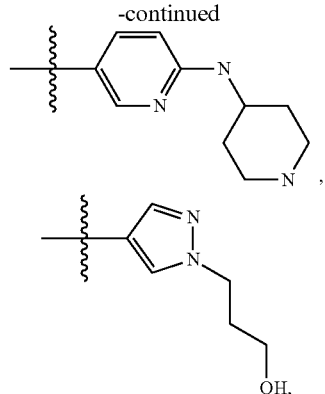
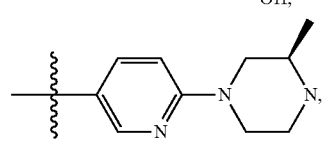
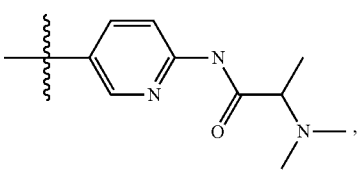
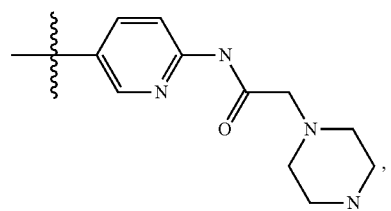
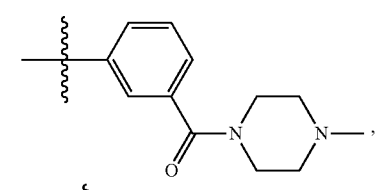
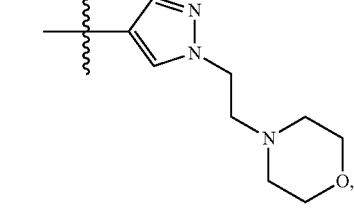
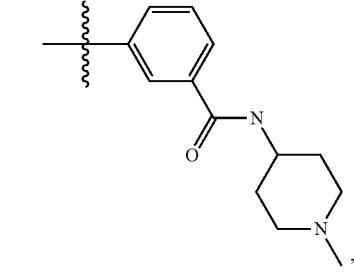

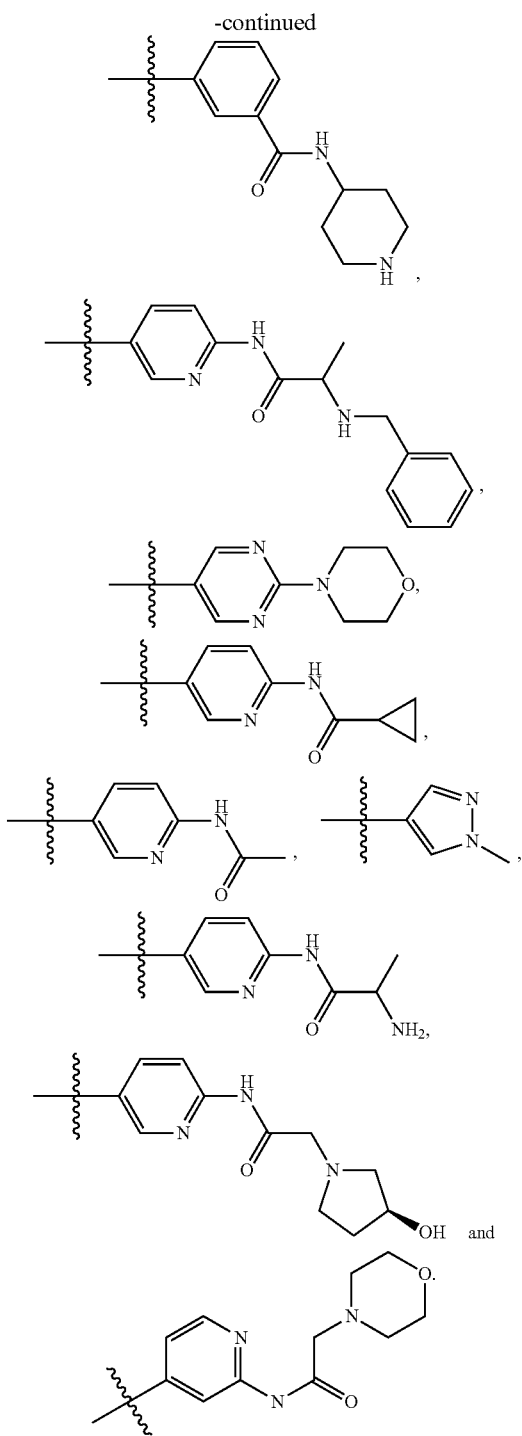
wherein the bond extending to the left is attached to the NH group of the pyrimidine in Formula I.
In one preferred embodiment of the invention, R² is selected from the group consisting of:
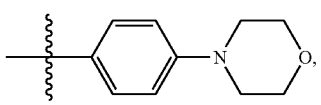
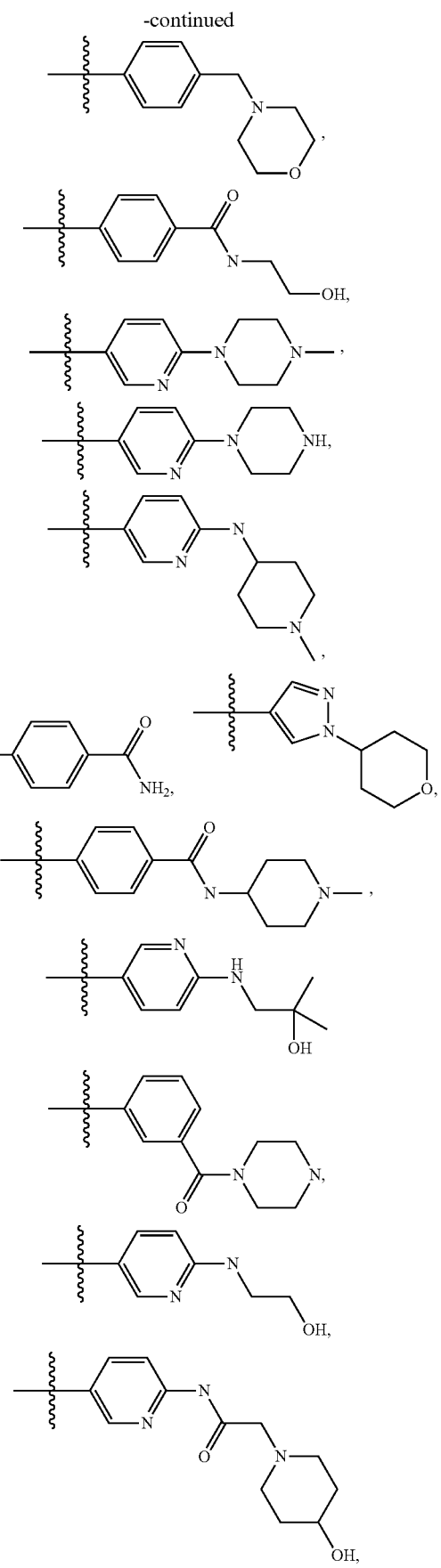

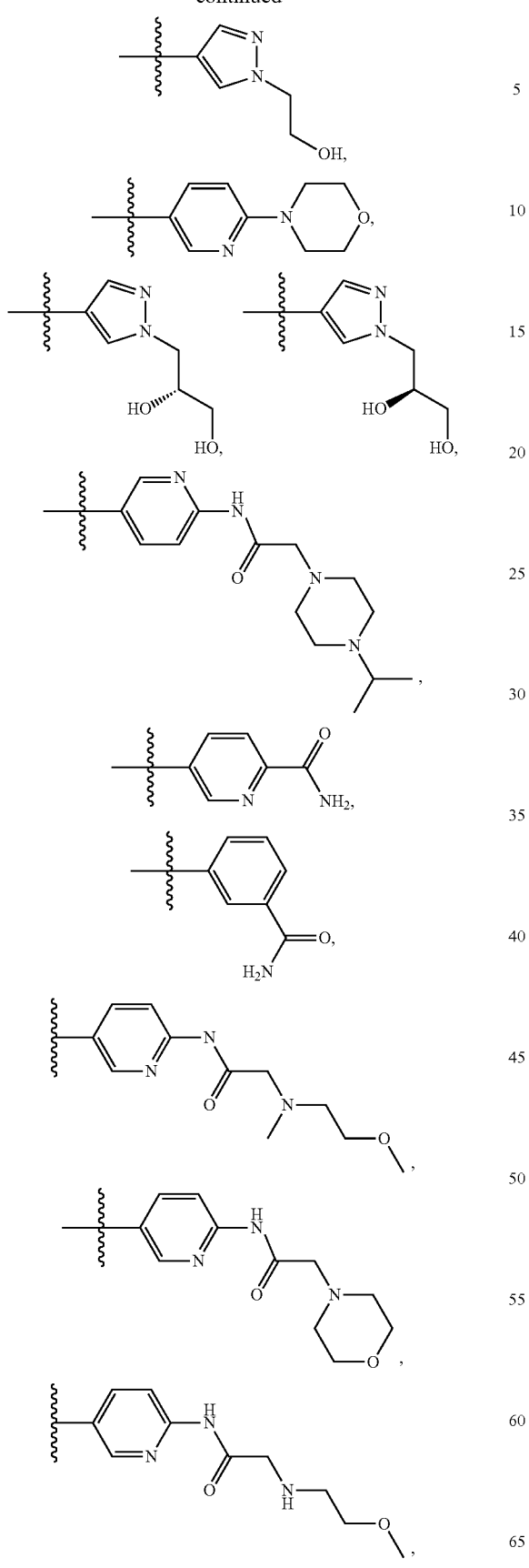
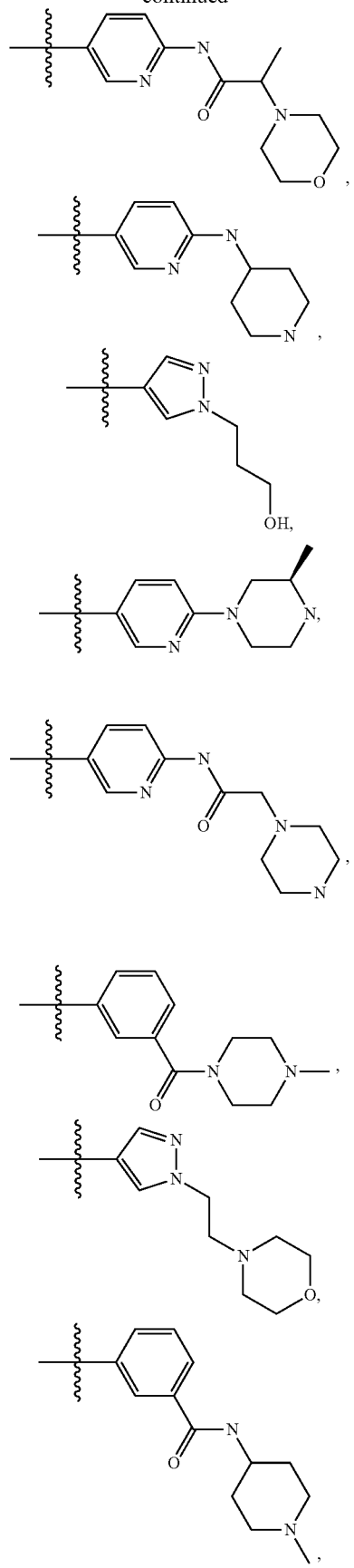

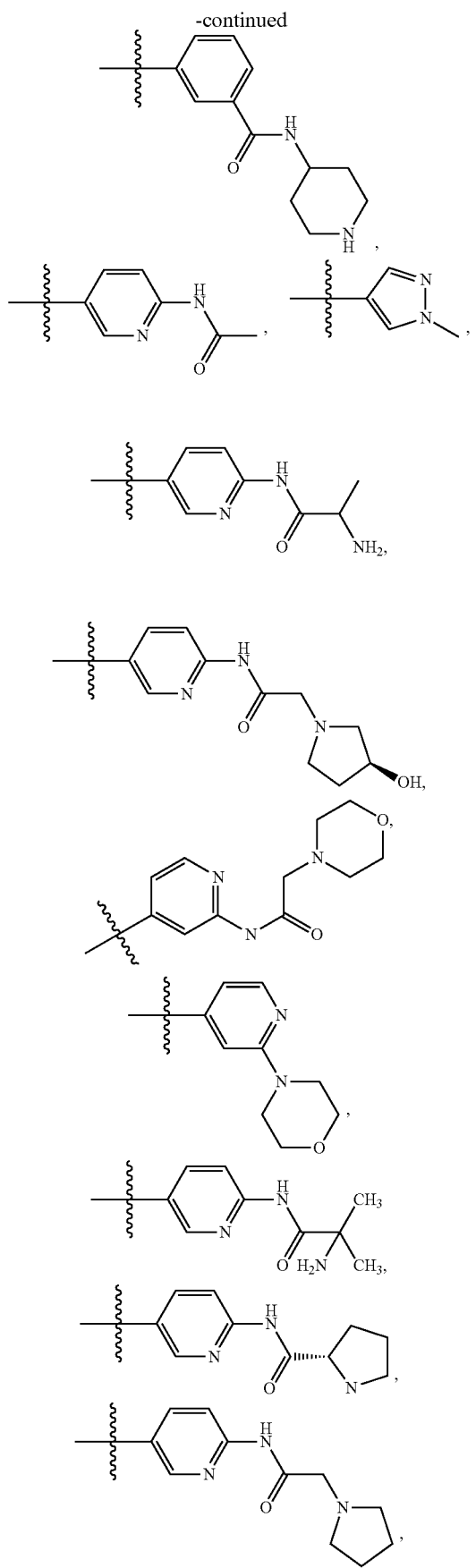
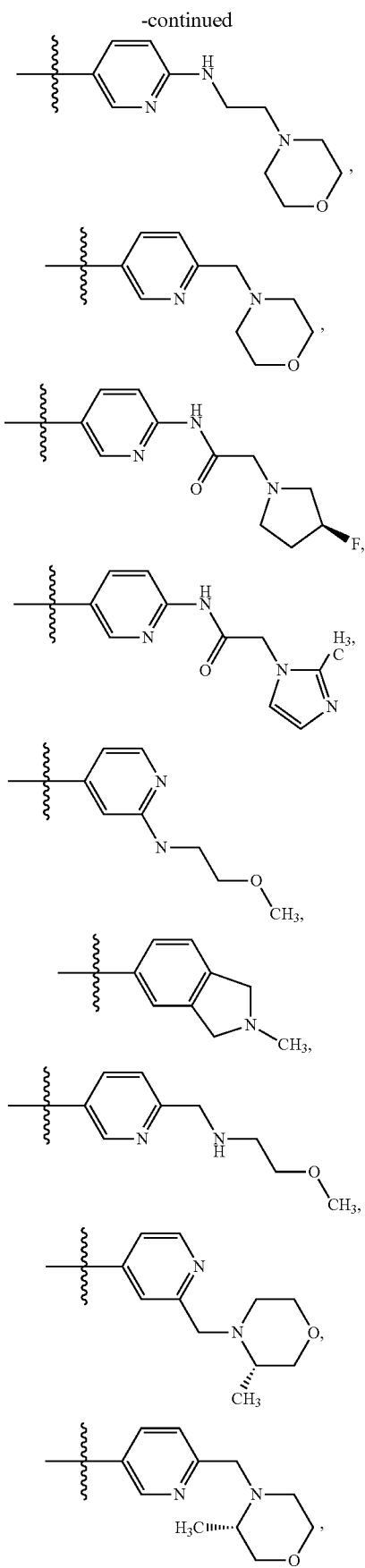

-continued
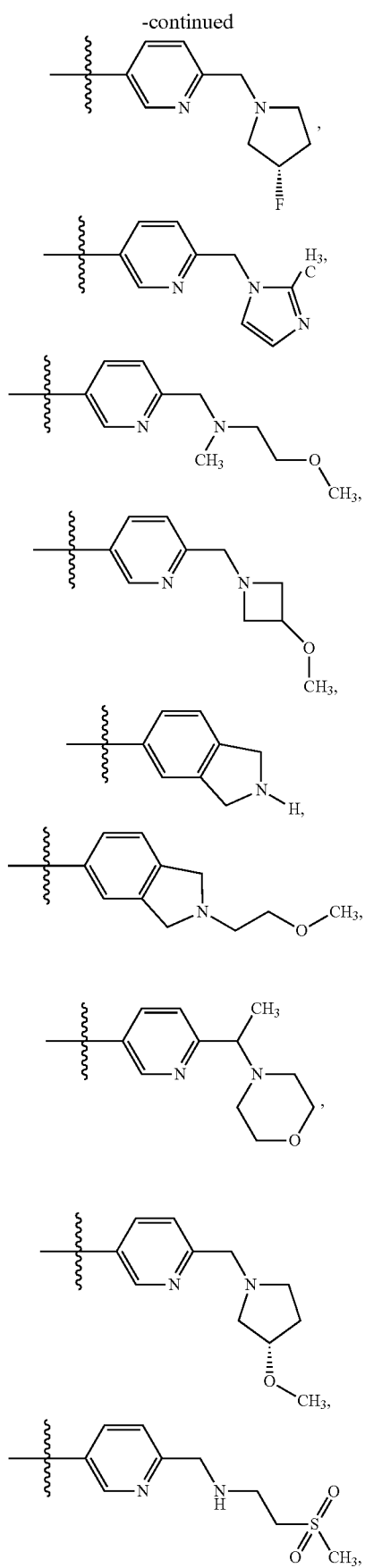
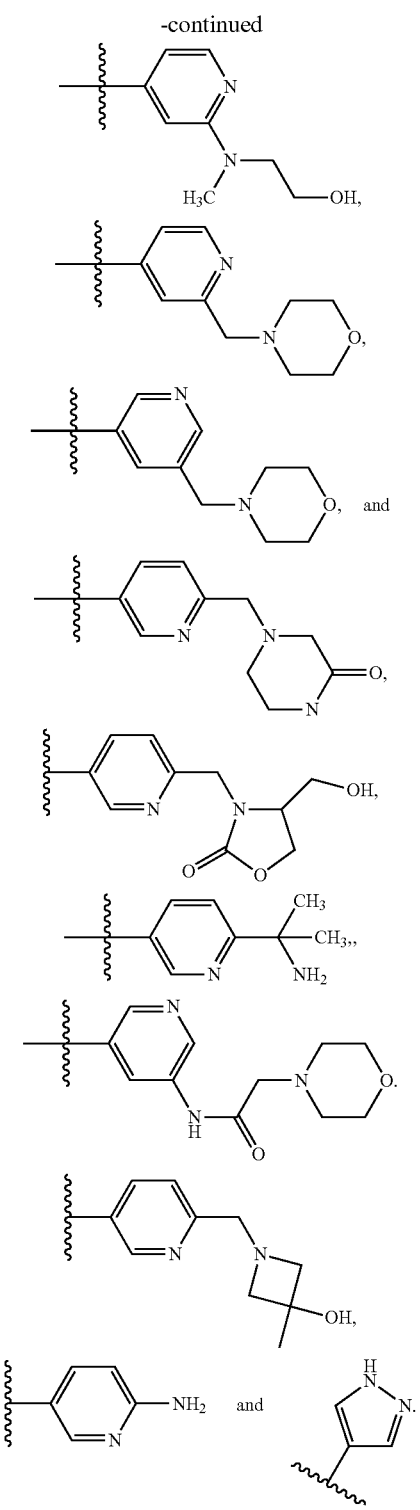
In another preferred embodiment of the invention, R² is selected from the group consisting of:
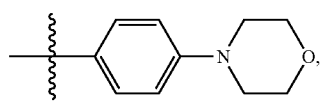

51
-continued
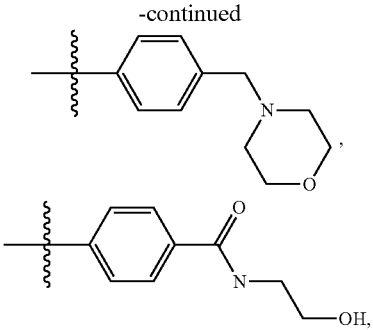
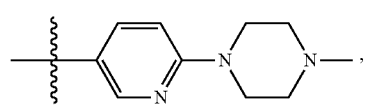
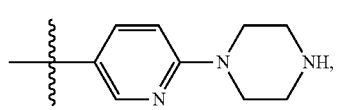
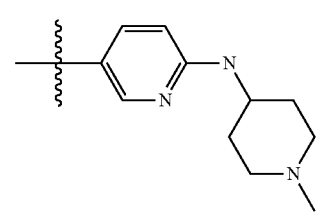
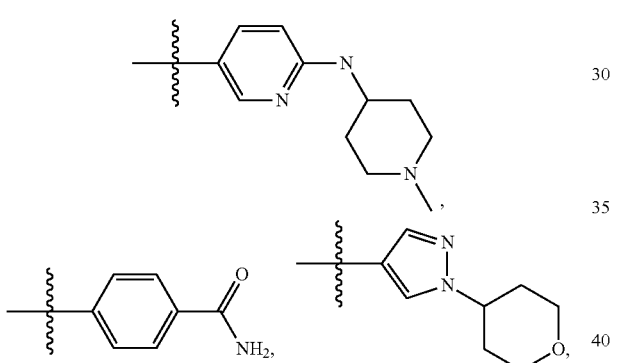
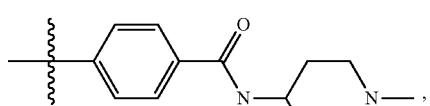
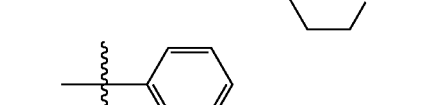
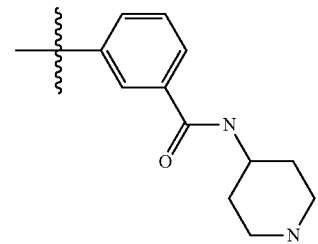
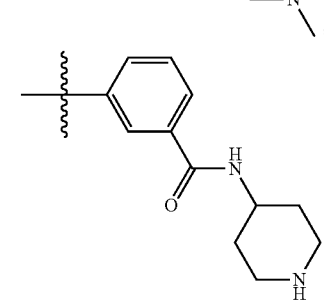
52
-continued
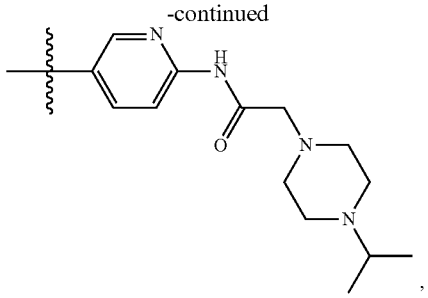
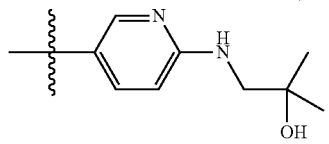
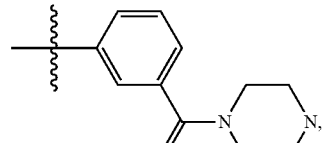
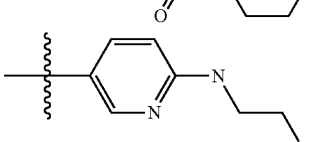
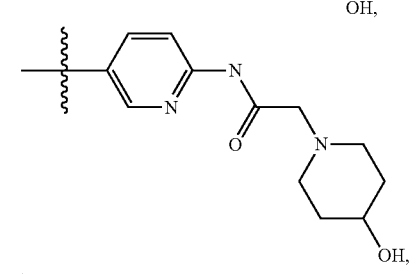
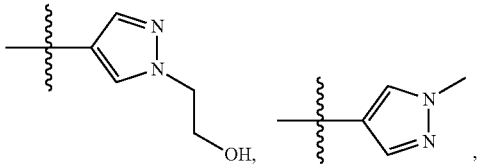
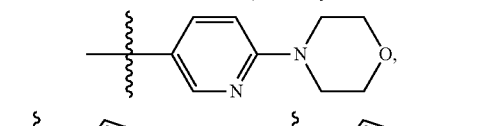
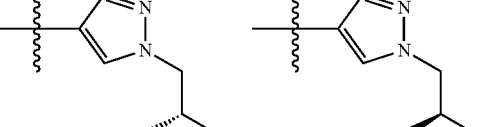
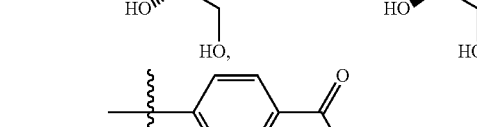
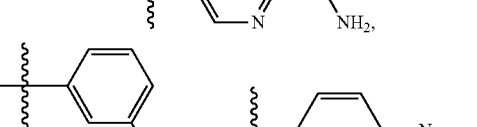
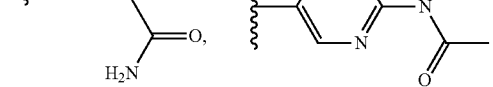

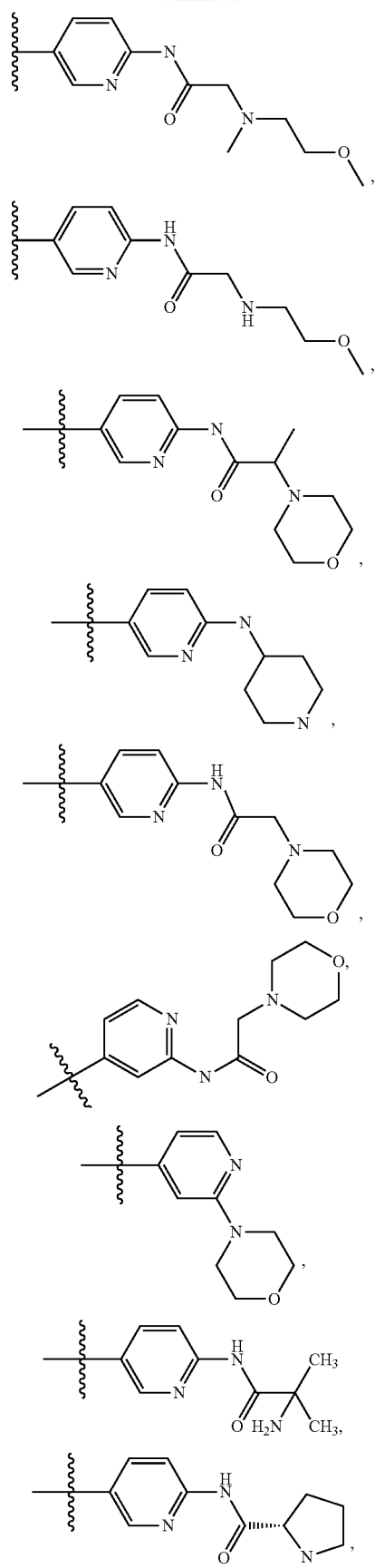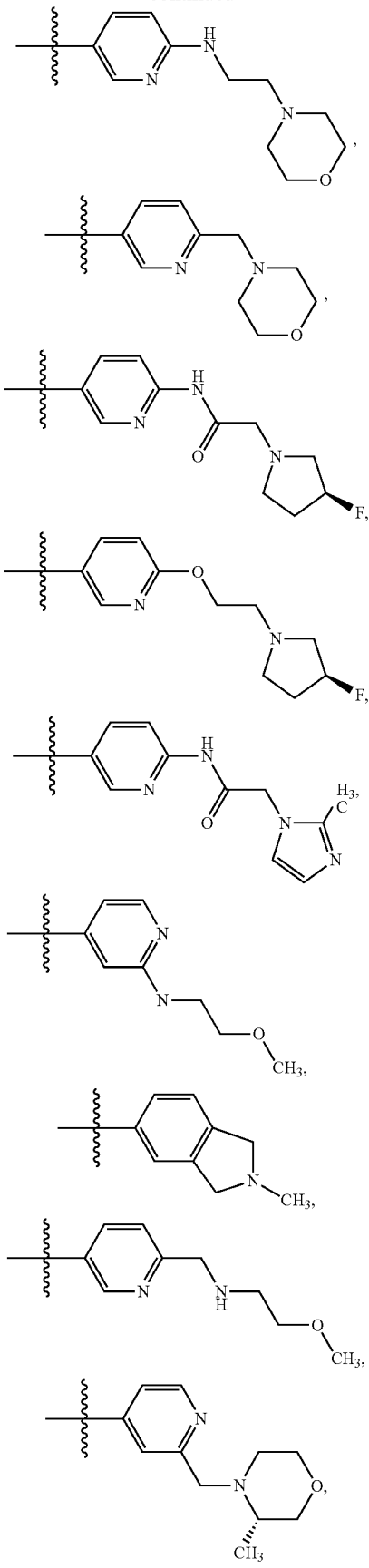

-continued
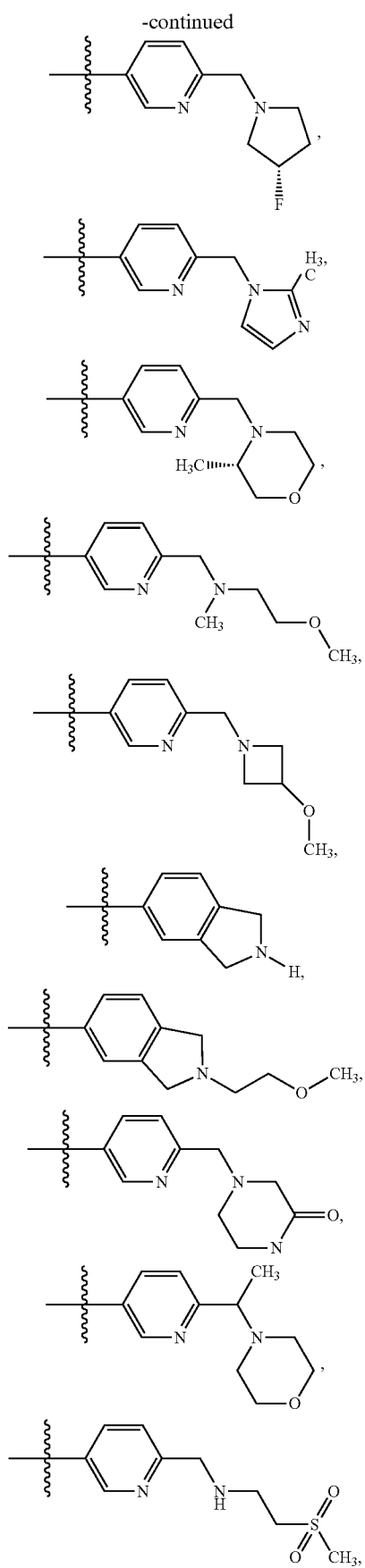
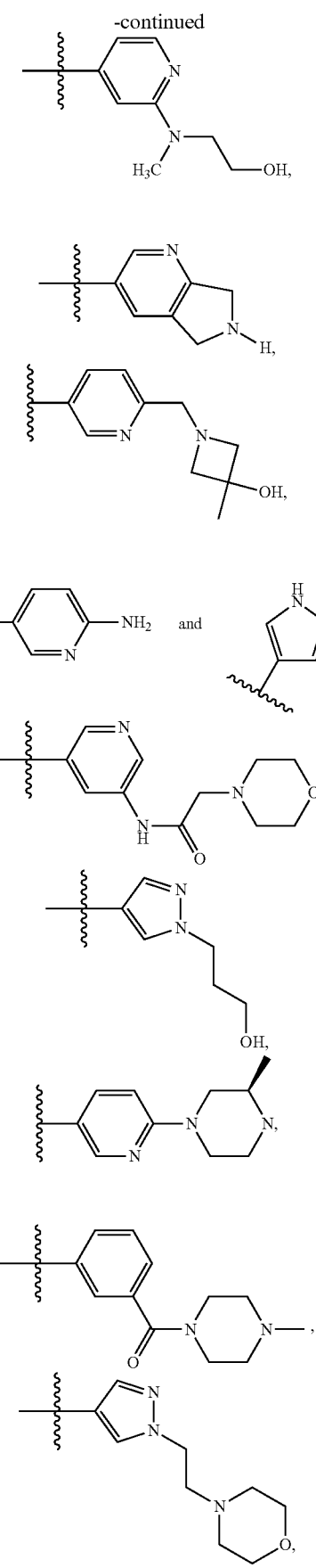

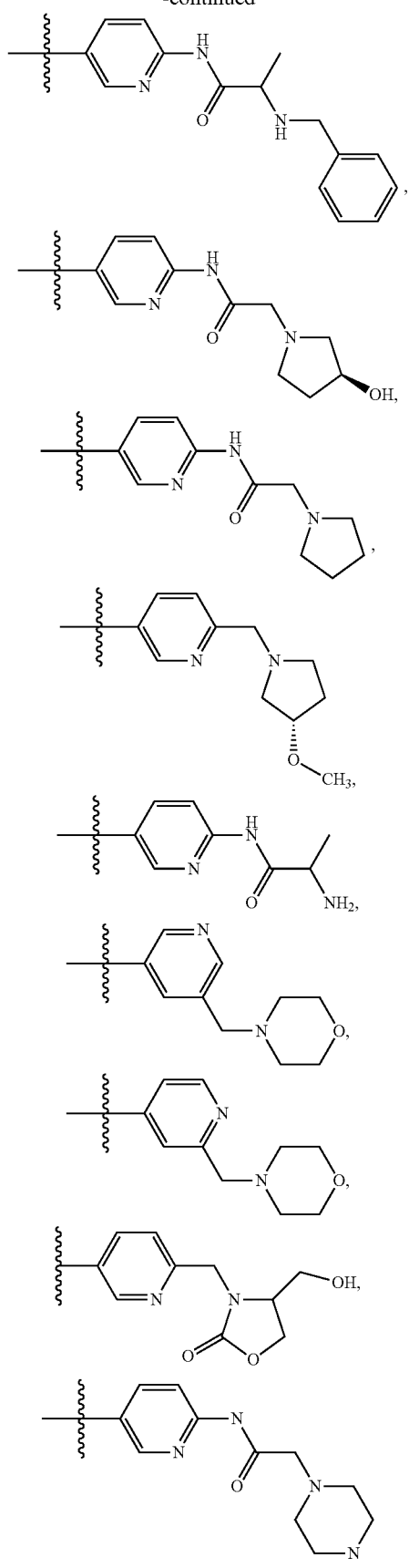
In a more preferred embodiment of the invention, $R^2$ is selected from the group consisting of:
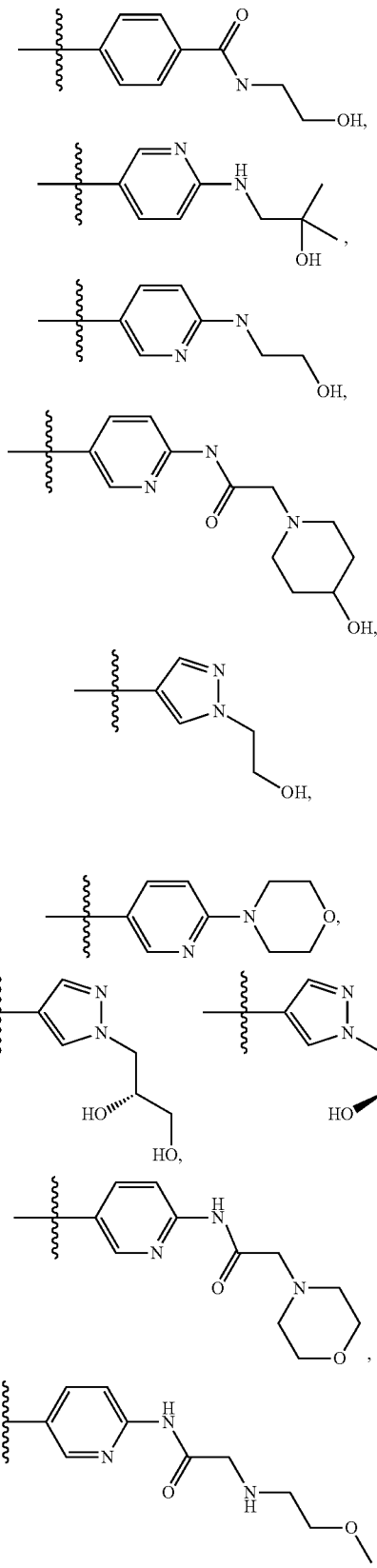

59
-continued
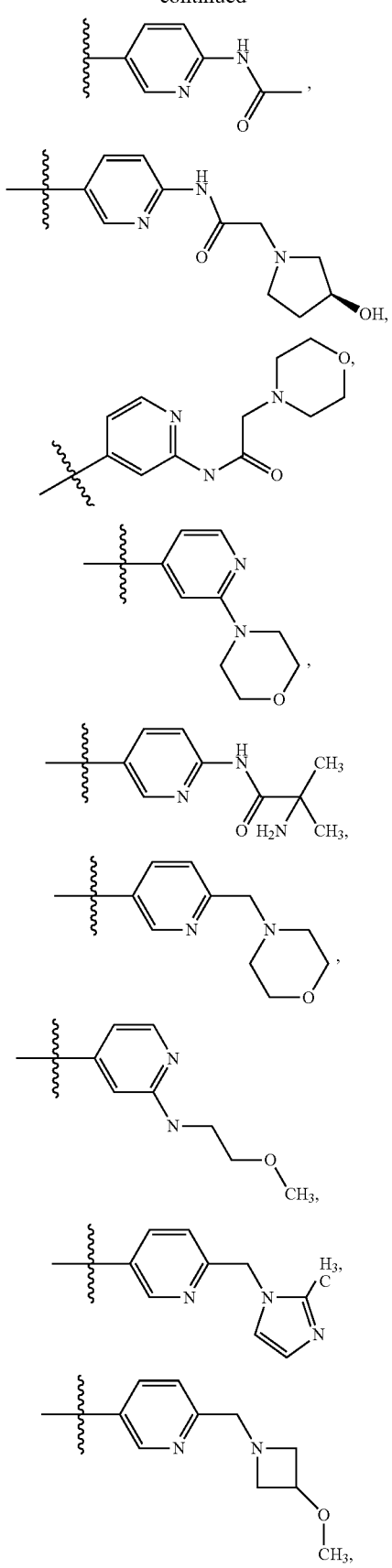
60
-continued
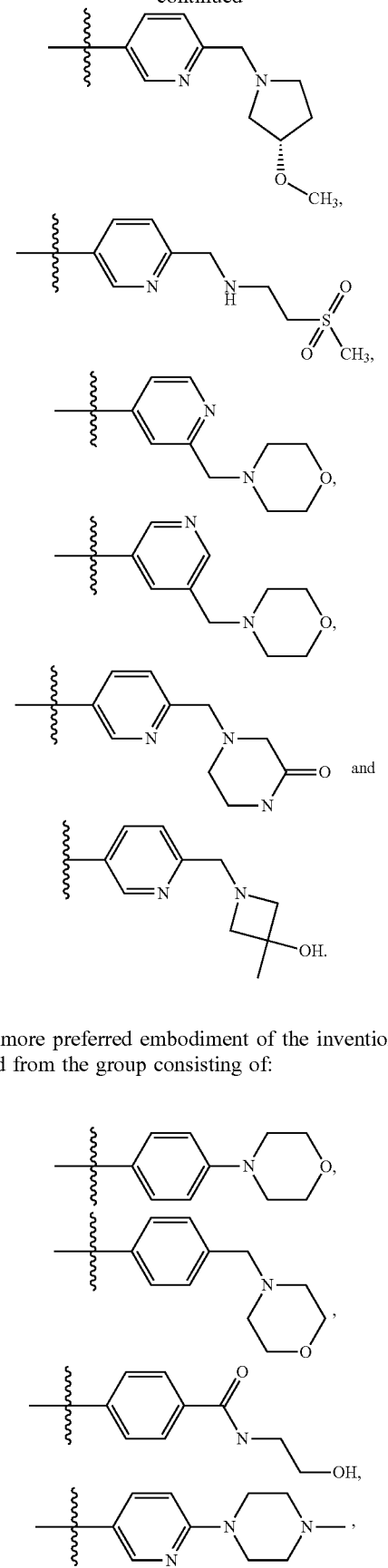
In a more preferred embodiment of the invention, $R^2$ is selected from the group consisting of:

61
-continued
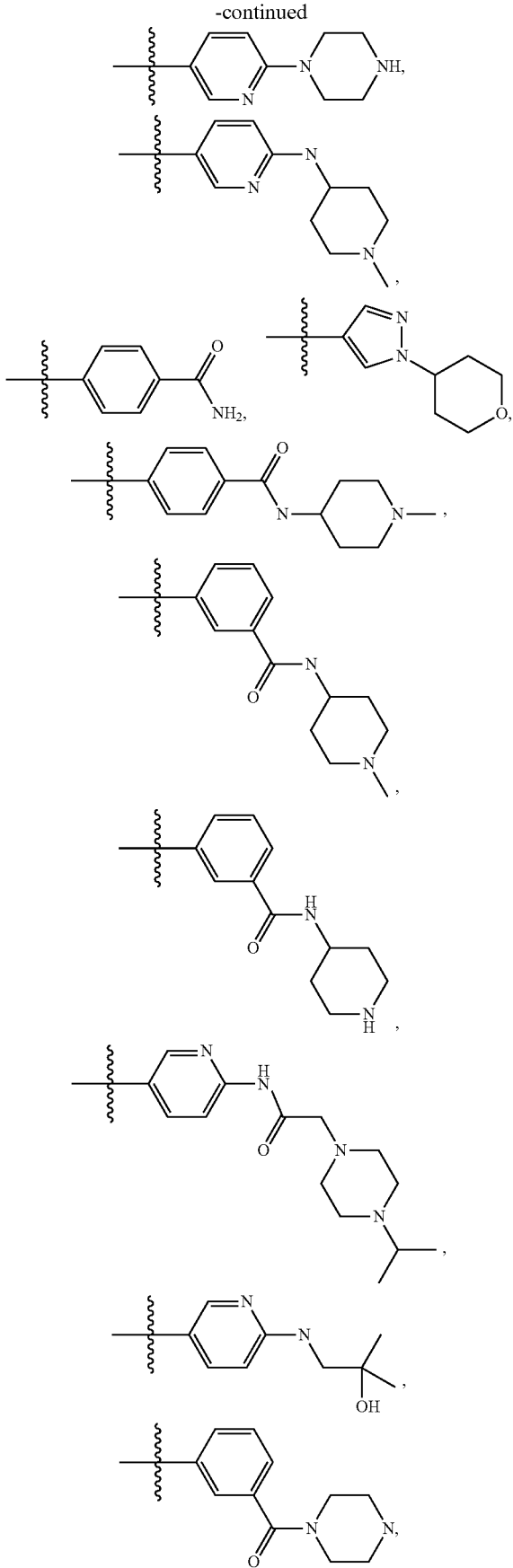
62
-continued
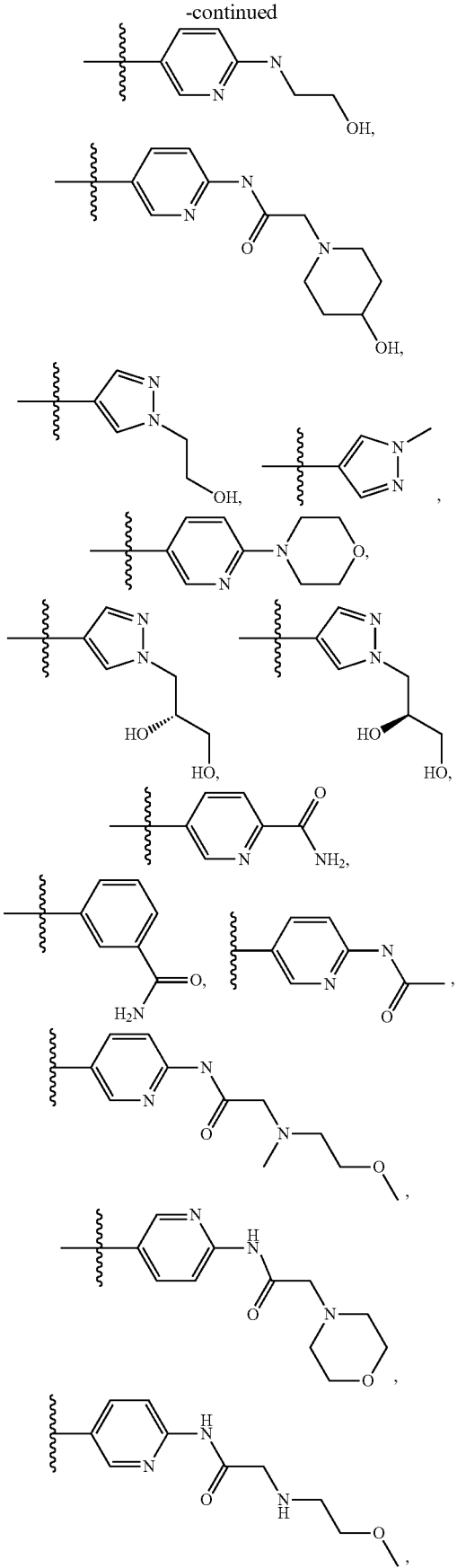

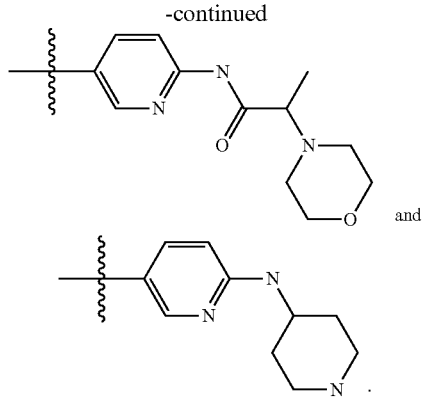
In specific embodiments of the invention, R² is selected from the group consisting of:
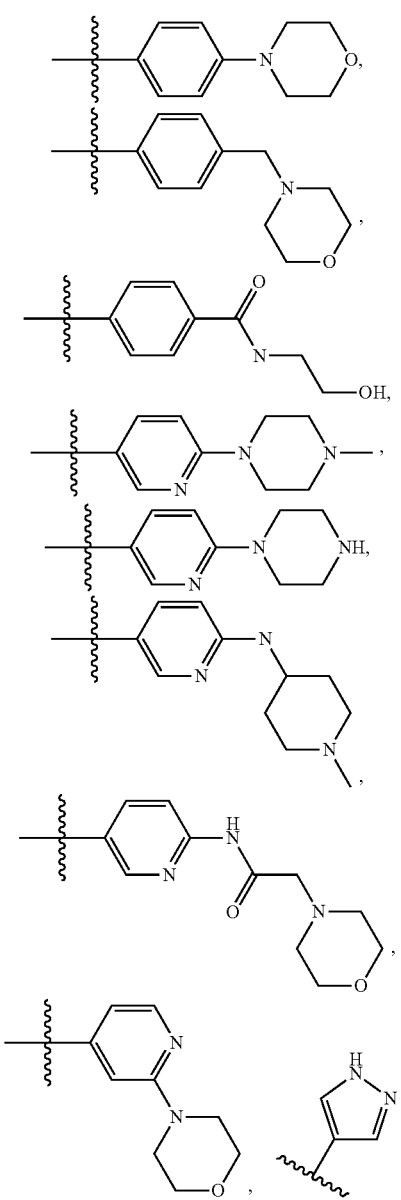
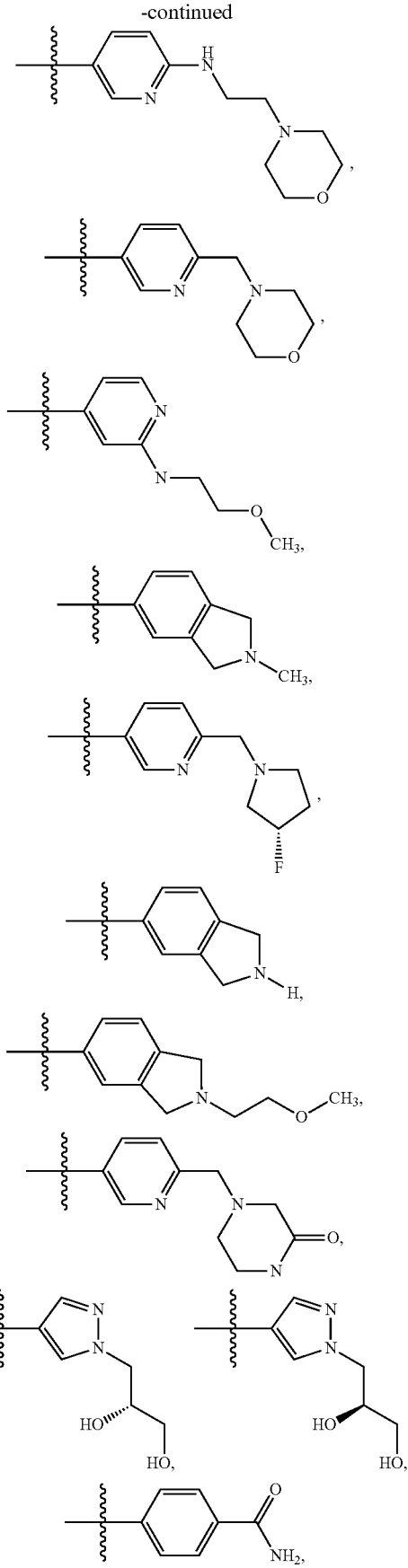

-continued
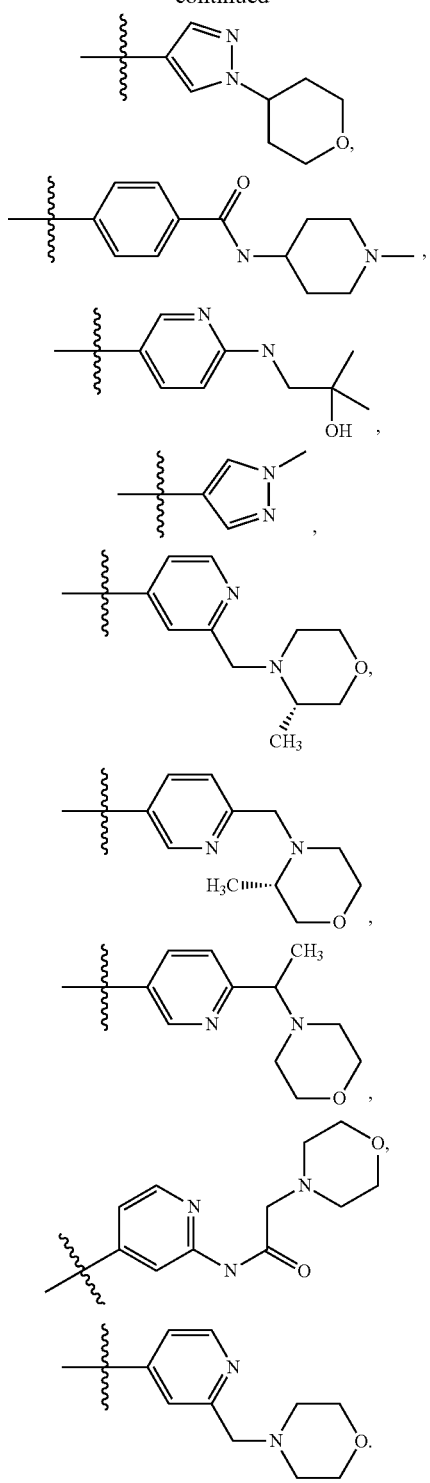
In specific compounds of the invention, R² is selected from the group consisting of:
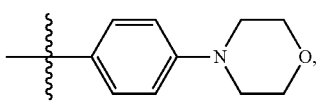
-continued
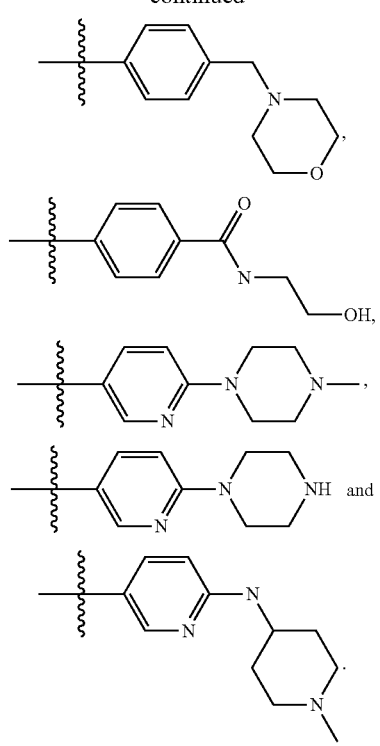
In further embodiments preferably R² is selected from the group consisting of:
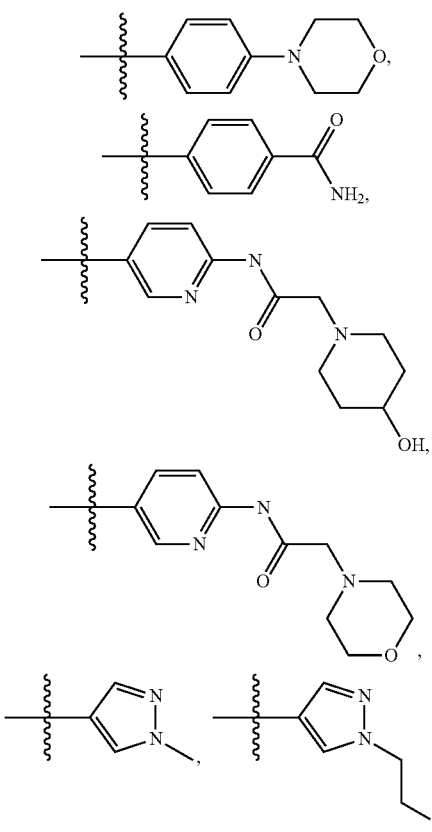

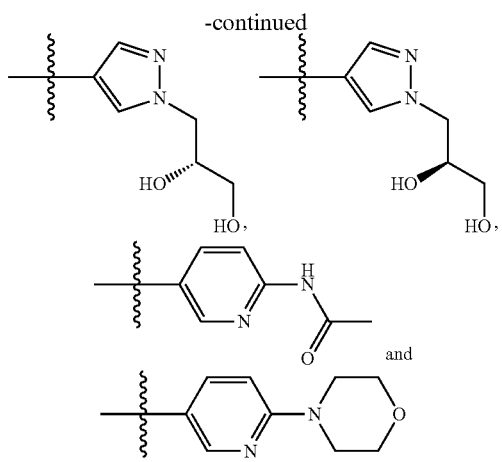

A preferred embodiment comprises compounds of the invention in which:
R¹ represents a pyrrolidine, morpholine, piperazine, piperidine, azetidine, 2-oxa-6-azaspiro[3.4]octane, thiomorpholine, homopiperazine, homomorpholine, 8-aza-bicyclo[3.2.1]oct-8-yl group or 3-oxa-8-aza-bicyclo[3.2.1]oct-8-yl group, which may be substituted, for example by halogen atoms, for example one or two fluorine atoms; OH; CN; $(CHR^a)_xCO_2R^c$; $(CHR^a)_x$-CONHR$^b$; methoxy; and $C_{1-4}$alkyl substituted with $CONH_2$ or NHCOMe; or a N-cyclopropyl group, N-cyclopentyl group or N-methyl-cyclopentyl group;

or R¹ represents NR$^a$—C$_{1-6}$alkyl, optionally substituted by one or more substituent independently selected from COR$^c$; NR$^a$.COR$^c$ and OH, SO$_2$R$^c$, NR$^a$SO$_2$R$^c$, halogen, OH, NR$^a$R$^B$ and C$_{1-4}$alkoxy.

or R¹ is NR$^a$—(CHR$^a$)$_x$—C$_{5-6}$heterocycloalkyl group, said heterocycloalkyl group containing one heteroatom, wherein the heteroatom is oxygen, and x is 0 or 1;

R² represents

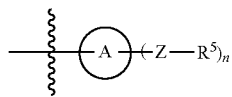

wherein A is a phenyl or 5 or 6 membered heteroaryl ring containing 1 or 2 heteroatoms;

n is 1 or 2;

each Z is a group independently selected from —(CHR$^a$)$_p$—, —(CHR$^a$)$_p$—O—(CHR$^a$)$_r$—, —(CHR$^a$)$_p$—NR$^a$—(CHR$^a$)$_r$—, —C(=O)— and —NR$^a$C(=O)(CHR$^a$)$_p$—, in which p is 0, 1 or 2;

and each R⁵ is a group independently selected from:
H, halogen, OR$^b$ or NR$^a$R$^b$; and a 4- to 7-membered heterocyclyl ring containing 1 or 2 heteroatoms, optionally substituted by one or more substituents independently selected from halogen atoms, OH, =O, NR$^a$R$^b$, O—C$_{1-4}$alkyl and C$_{1-4}$alkyl groups, optionally substituted with halogen, OMe or OH;

C$_{1-4}$alkyl or C$_{3-7}$cycloalkyl groups, each optionally substituted by one or more substituents independently selected from halogen, OMe, OH and NR$^a$R$^b$; and CN, SO$_2$R$^c$ and NR$^a$SO$_2$R$^c$; or n=2 and two Z—R⁵ groups on adjacent ring atoms together with the two adjacent ring atoms form a 5-7 membered fused ring composed of the two adjacent ring atoms and —(CHR$^a$)$_r$—(CHR⁵)—(CHR$^a$)$_r$—, wherein the —CHR⁵— moiety can be replaced with and each r is independently 1 or 2; and each R$^a$ independently represents a hydrogen atom or a C$_{1-4}$alkyl group;

each R$^b$ independently represents a hydrogen atom; a C$_{1-4}$alkyl group optionally substituted by one or more groups selected from OH, O—C$_{1-4}$alkyl, halogen and SO$_2$R$^c$; or a C$_{3-8}$cycloalkyl group in which a CH$_2$ moiety may be replaced by an oxygen atom or an NR$^a$ group; and each R$^c$ represents —NR$^a$R$^b$ or a methyl group.

A preferred embodiment comprises compounds of the invention in which:

R¹ represents a pyrrolidine, morpholine, piperazine, piperidine, azetidine, thiomorpholine, homopiperazine, homomorpholine, 8-aza-bicyclo[3.2.1]oct-8-yl group or 3-oxa-8-aza-bicyclo[3.2.1]oct-8-yl group, which may be substituted, for example by halogen atoms, for example one or two fluorine atoms; OH; CN; CO$_2$R$^a$; CONHR$^d$; and methoxy;

R² represents

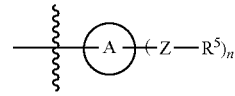

wherein A is a phenyl or 5 or 6 membered heteroaryl ring containing 1 or 2 heteroatoms;

n is 1 or 2;

each Z is a group independently selected from —(CH$_2$)$_p$—, —C(=O)— and —NR$^a$C(=O)(CHR$^a$)$_p$—, in which p is 0, 1 or 2;

and each R⁵ is a group independently selected from:
H, halogen, OR$^b$ or NR$^a$R$^b$; and a 5- to 6-membered heterocycloalkyl ring containing 1 or 2 heteroatoms, optionally substituted by one or more substituents independently selected from halogen atoms, OH, NR$^a$R$^b$, O—C$_{1-4}$alkyl and C$_{1-4}$alkyl groups, optionally substituted with halogen, OMe or OH;

C$_{1-4}$alkyl or C$_{3-7}$cycloalkyl groups, each optionally substituted by one or more substituents independently selected from halogen, OMe, OH and NR$^a$R$^b$; and CN, SO$_2$R$^c$ and NR$^a$SO$_2$R$^c$;

each R$^a$ independently represents a hydrogen atom or a C$_{1-4}$alkyl group;

each R$^b$ independently represents a hydrogen atom; a C$_{1-4}$alkyl group optionally substituted by one or more groups selected from OH, O—C$_{1-4}$alkyl and halogen; or a C$_{3-8}$cycloalkyl group in which a CH$_2$ moiety may be replaced by an oxygen atom or an NR$^a$ group; and each R$^c$ represents —NR$^a$R$^b$ or a methyl group.

A further preferred embodiment comprises compounds of the invention in which

R¹ represents a pyrrolidine ring, an 8-aza-bicyclo[3.2.1]oct-8-yl group, an 3-oxa-8-aza-bicyclo[3.2.1]oct-8-yl group, a piperidine ring, an azetidine ring or a 2-oxa-6-azaspiro[3.4]octane ring, which may be substituted, for example by halogen atoms, for example one or two fluorine atoms; OH; CN; CO$_2$R$^a$; methoxy and C$_{1-4}$alkyl substitured with CONH$_2$ or NHCOMe; or which is unsubstituted; or a N-cyclopentyl group;

or R¹ represents NR$^a$—C$_{1-6}$alkyl, optionally substituted by one or two substituents COR$^c$; NR$^a$.COR$^c$, C$_{1-4}$alkoxy and OH;

or R¹ is a 5 or 6 membered NH—(CHR$^a$)$_x$—O$_{5-6}$heterocycloalkyl group or NMe-(CHR$^a$)$_x$—C$_{5-6}$heterocycloalkyl group, wherein the heteroatom is oxygen, and x is 0 or 1;

R² represents

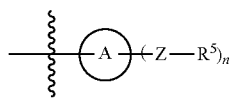

wherein A is a phenyl or 5 to 6 membered heteroaryl ring containing 1 or 2 heteroatoms;

n is 1;

each Z is a group independently selected from —(CH$_2$)$_p$—, —O—(CHR$^a$)$_r$—, —NR$^a$—(CHR$^a$)$_r$—, —C(=O)— and —NR$^a$C(=O)(CHR$^a$)$_p$—, in which p is 0, 1 or 2;

and each R⁵ is a group independently selected from:
H, OH, NR$^a$R$^b$ or cyclopropyl; and
a 4, 5- or 6-membered heterocyclyl ring containing 1 or 2 heteroatoms, optionally substituted by one substituent selected from OH, F, =O, O—C$_{1-4}$alkyl and C$_{1-4}$alkyl groups, optionally substituted with halogen, OMe or OH; and
C$_{1-4}$alkyl optionally substituted by one or two OH groups; or
n=2 and two Z—R⁵ groups on adjacent ring atoms together with the two adjacent ring atoms form a 5-7 membered fused ring composed of the two adjacent ring atoms and —(CHR$^a$)$_r$—(NR⁵)—(CHR$^a$)$_r$—, and each r is independently 1 or 2; and each R$^a$ independently represents a hydrogen atom or a C$_{1-4}$alkyl group; and each R$^b$ independently represents a hydrogen atom; a C$_{1-4}$alkyl group optionally substituted by one or more groups selected from OH$_2$O—C$_{1-4}$alkyl and SO$_2$Me; or a C$_{3-8}$cycloalkyl group in which a CH$_2$ moiety may be replaced by an oxygen atom or an NR$^a$ group;

A further preferred embodiment comprises compounds of the invention in which
R¹ represents a pyrrolidine ring, an 8-aza-bicyclo[3.2.1]oct-8-yl group, an 3-oxa-8-aza-bicyclo[3.2.1]oct-8-yl group, a piperidine ring or an azetidine ring, which may be substituted, for example by halogen atoms, for example one or two fluorine atoms; OH; CN; CO$_2$R$^a$; CONHR$^d$; and methoxy; or which is unsubstituted;
R² represents

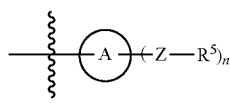

wherein A is a phenyl or 5 to 6 membered heteroaryl ring containing 1 or 2 heteroatoms;
n is 1;
each Z is a group independently selected from —(CH$_2$)$_p$—, —C(=O)— and —NR$^a$C(=O)(CHR$^a$)$_p$—, in which p is 0, 1 or 2;
and each R⁵ is a group independently selected from:
H, OH, NR$^a$R$^b$ or cyclopropyl;
a 5- to 6-membered heterocycloalkyl ring containing 1 or 2 heteroatoms, optionally substituted by one substituent selected from C$_{1-4}$alkyl, OMe and OH groups; and
C$_{1-4}$alkyl optionally substituted by one or two OH groups;
each R$^a$ independently represents a hydrogen atom or a C$_{1-4}$alkyl group; and
each R$^b$ independently represents a hydrogen atom; a C$_{1-4}$alkyl group optionally substituted by one or more groups selected from OH and O—C$_{1-4}$alkyl; or a C$_{3-8}$cycloalkyl group in which a CH$_2$ moiety may be replaced by an oxygen atom or an NR$^a$ group;

A further preferred embodiment of the invention comprises compounds in which
R¹ represents a pyrrolidine ring or an 8-aza-bicyclo[3.2.1]oct-8-yl group, which may be substituted, for example by a hydroxy group or a fluorine atom substituent, or which is unsubstituted;
R² represents

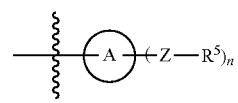

wherein A is a phenyl, pyridine or pyrazole;
n is 1;
each Z is a group independently selected from —(CH$_2$)$_p$—, —O—(CH$_2$)$_p$—, —N—(CH$_2$)$_p$—, —C(=O)—, and —NR$^a$C(=O)(CHR$^a$)$_p$—, in which p is 0 or 1;
and each R⁵ is a group independently selected from:
H or NR$^a$R$^b$; and
a 6-membered heterocyclyl ring containing 1 or 2 heteroatoms or a 5-membered heterocyclyl ring containing 1 heteroatom (for example a 6-membered heterocyclyl ring containing 1 or 2 nitrogen atoms) 4-membered heterocyclyl ring containing 1 nitrogen atom, optionally substituted by one F, =O, C$_{1-4}$alkyl or OH group.
C$_{1-4}$alkyl optionally substituted by one or two OH groups; or
n=2 and two Z—R⁵ groups on adjacent ring atoms together with the two adjacent ring atoms form a 5-7 membered fused ring composed of the two adjacent ring atoms and —(CHR$^a$)$_r$—(NR⁵)—(CHR$^a$)$_r$—, and each r is independently 1 or 2; and
each R$^a$ independently represents a hydrogen atom or a C$_{1-4}$alkyl group; and
each R$^b$ independently represents a hydrogen atom; a C$_{1-4}$alkyl group optionally substituted by one or two OH groups or one SO$_2$Me; or a C$_{3-8}$cycloalkyl group in which a CH$_2$ moiety may be replaced by an oxygen atom or an NR$^a$ group.

A further preferred embodiment of the invention comprises compounds in which
R¹ represents a pyrrolidine ring or an 8-aza-bicyclo[3.2.1]oct-8-yl group, which may be substituted, for example by a hydroxy group or a fluorine atom substituent, or which is unsubstituted;
R² represents

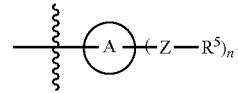

wherein A is a phenyl, pyridine or pyrazole;
n is 1;
each Z is a group independently selected from —(CH$_2$)$_p$—, —C(=O)—, and —NR$^a$C(=O)(CHR$^a$)$_p$—, in which p is 0 or 1;
and each R$^5$ is a group independently selected from:
H or NR$^a$R$^b$;
a 6-membered heterocyclyl ring containing 1 or 2 heteroatoms or a 5-membered heterocyclyl ring containing 1 heteroatom (for example a 6-membered heterocyclyl ring containing 2 heteroatoms), optionally substituted by one C$_{1-4}$alkyl or OH group; and
C$_{1-4}$alkyl optionally substituted by one or two OH groups;
each R$^a$ independently represents a hydrogen atom or a C$_{1-4}$alkyl group; and
each R$^b$ independently represents a hydrogen atom; a C$_{1-4}$alkyl group optionally substituted by one or two OH groups; or a C$_{3-8}$cycloalkyl group in which a CH$_2$ moiety may be replaced by an oxygen atom or an NR$^a$ group.

In certain embodiments, the compound of the invention is selected from the compounds of formula (I) described in the Examples section below, or a salt thereof, especially their pharmaceutically acceptable salts.

In certain embodiments, compounds of the invention include compounds DMX 1 to DMX-167 (using the numbering from the Examples section below), and their salts, especially their pharmaceutically acceptable salts.

In certain embodiments, compounds of the invention include compounds DMX-1 to DMX-60, and their salts, especially their pharmaceutically acceptable salts.

Preferred compounds of the invention include the following compounds, and their salts, especially their pharmaceutically acceptable salts:

DMX-1, DMX-2, DMX-3, DMX-4, DMX-5, DMX-6, DMX-7, DMX-8, DMX-9, DMX-10, DMX-15, DMX-17, DMX-21, DMX-22, DMX-23, DMX-24, DMX-25, DMX-26, DMX-27, DMX-28, DMX-29, DMX-30, DMX-31, DMX-32, DMX-33, DMX-34, DMX-35, DMX-61, DMX-62, DMX-63, DMX-65, DMX-66, DMX-67, DMX-68, DMX-69, DMX-70, DMX-71, DMX-72, DMX-76, DMX-78, DMX-79, DMX-80, DMX-81, DMX-83, DMX-85, DMX-89, DMX-91, DMX-92, DMX-96, DMX-97, DMX-98, DMX-99, DMX-100, DMX-101, DMX-102, DMX-103, DMX-105, DMX-107, DMX-108, DMX-109, DMX-110, DMX-111, DMX-112, DMX-126, DMX-127, DMX-36, DMX-37, DMX-38, DMX-39, DMX-44, DMX-47, DMX-48, DMX-49, DMX-50, DMX-51, DMX-52, DMX-53, DMX-54, DMX-55, DMX-56, DMX-128, DMX-129, DMX-131, DMX-136, DMX-139, DMX-57, DMX-58, DMX-59, DMX-141, DMX-142, DMX-143, DMX-144, DMX-145, DMX-146, DMX-147, DMX-149, DMX-150, DMX-151, DMX-152, DMX-153, DMX-154, DMX-156, DMX-157, DMX-161, DMX-162, DMX-163, DMX-164, DMX-165, DMX-166 and DMX-167.

In certain preferred compounds of the invention include the following compounds, and their salts, especially their pharmaceutically acceptable salts:

DMX-1, DMX-2, DMX-3, DMX-4, DMX-5, DMX-6, DMX-7, DMX-8, DMX-9, DMX-10, DMX-11, DMX-15, DMX-17, DMX-21, DMX-22, DMX-23, DMX-24, DMX-25, DMX-26, DMX-27, DMX-28, DMX-29, DMX-30, DMX-31, DMX-32, DMX-33, DMX-34, DMX-35, DMX-61, DMX-62, DMX-63, DMX-65, DMX-66, DMX-67, DMX-68, DMX-69, DMX-70, DMX-71, DMX-72, DMX-76, DMX-78, DMX-79, DMX-80, DMX-81, DMX-83, DMX-89, DMX-91, DMX-92, DMX-96, DMX-97, DMX-98, DMX-99, DMX-100, DMX-101, DMX-102, DMX-105, DMX-108, DMX-109, DMX-110, DMX-111, DMX-112, DMX-126, DMX-127, DMX-36, DMX-37, DMX-38, DMX-39, DMX-44, DMX-47, DMX-48, DMX-49, DMX-50, DMX-51, DMX-52, DMX-53, DMX-54, DMX-55, DMX-56, DMX-128, DMX-129, DMX-131, DMX-161, DMX-162, DMX-136, DMX-57, DMX-58, DMX-142, DMX-143, DMX-144, DMX-145, DMX-146, DMX-147, DMX-149, DMX-150, DMX-151, DMX-152, DMX-153, DMX-164, DMX-165, DMX-167 and DMX-154, DMX-156, DMX-157.

In certain preferred compounds of the invention include the following compounds, and their salts, especially their pharmaceutically acceptable salts:

3-[4-(5-Cyano-6-pyrrolidin-1-yl-pyridin-3-yl)-pyrimidin-2-ylamino]-benzamide

3-{4-[5-Cyano-6-((S)-3-fluoro-pyrrolidin-1-yl)-pyridin-3-yl]-pyrimidin-2-ylamino}-N-(1-methyl-piperidin-4-yl)-benzamide 2-((S)-3-Fluoro-pyrrolidin-1-yl)-5-{2-[3-(piperazine-1-carbonyl)-phenylamino]-pyrimidin-4-yl}-nicotinonitrile 2-((S)-3-Fluoro-pyrrolidin-1-yl)-5-{2-[3-(4-methyl-piperazine-1-carbonyl)-phenylamino]-pyrimidin-4-yl}-nicotinonitrile 2-((S)-3-Fluoro-pyrrolidin-1-yl)-5-[2-(1-methyl-1H-pyrazol-4-ylamino)-pyrimidin-4-yl]-nicotinonitrile 2-((S)-3-Fluoro-pyrrolidin-1-yl)-5-{2-[6-(piperidin-4-ylamino)-pyridin-3-ylamino]-pyrimidin-4-yl}-nicotinonitrile 3-{4-[5-Cyano-6-((S)-3-fluoro-pyrrolidin-1-yl)-pyridin-3-yl]-pyrimidin-2-ylamino}-N-piperidin-4-yl-benzamide 2-(3,3-Difluoro-pyrrolidin-1-yl)-5-{2-[6-(1-methyl-piperidin-4-ylamino)-pyridin-3-ylamino]-pyrimidin-4-yl}-nicotinonitrile N-(5-{4-[5-Cyano-6-((S)-3-fluoro-pyrrolidin-1-yl)-pyridin-3-yl]-pyrimidin-2-ylamino}-pyridin-2-yl)-2-dimethylamino-propionamide N-(5-{4-[5-Cyano-6-((S)-3-fluoro-pyrrolidin-1-yl)-pyridin-3-yl]-pyrimidin-2-ylamino}-pyridin-2-yl)-2-[(2-methoxy-ethyl)-methyl-amino]-acetamide N-(5-{4-[5-Cyano-6-((S)-3-fluoro-pyrrolidin-1-yl)-pyridin-3-yl]-pyrimidin-2-ylamino}-pyridin-2-yl)-2-(4-isopropyl-piperazin-1-yl)-acetamide 2-((S)-3-Hydroxy-pyrrolidin-1-yl)-5-{2-[6-((R)-3-methyl-piperazin-1-yl)-pyridin-3-ylamino]-pyrimidin-4-yl}-nicotinonitrile N-(5-{4-[5-Cyano-6-((S)-3-fluoro-pyrrolidin-1-yl)-pyridin-3-yl]-pyrimidin-2-ylamino}-pyridin-2-yl)-2-(2-methoxy-ethylamino)-acetamide 5-{4-[5-Cyano-6-((S)-3-fluoro-pyrrolidin-1-yl)-pyridin-3-yl]-pyrimidin-2-ylamino}-pyridine-2-carboxylic acid amide 2-((S)-3-Hydroxy-pyrrolidin-1-yl)-5-[2-(6-morpholin-4-yl-pyridin-3-ylamino)-pyrimidin-4-yl]-nicotinonitrile 2-((S)-3-Fluoro-pyrrolidin-1-yl)-5-{2-[1-(2-hydroxy-ethyl)-1H-pyrazol-4-ylamino]-pyrimidin-4-yl}-nicotinonitrile 2-((S)-3-Fluoro-pyrrolidin-1-yl)-5-{2-[1-(3-hydroxy-propyl)-1H-pyrazol-4-ylamino]-pyrimidin-4-yl}-nicotinonitrile N-(5-{4-[5-Cyano-6-((S)-3-fluoro-pyrrolidin-1-yl)-pyridin-3-yl]-pyrimidin-2-ylamino}-pyridin-2-yl)-2-piperazin-1-yl-acetamide N-(5-{4-[5-Cyano-6-((S)-3-fluoro-pyrrolidin-1-yl)-pyridin-3-yl]-pyrimidin-2-ylamino}-pyridin-2-yl)-2-morpholin-4-yl-propionamide 2-Benzylamino-N-(5-{4-[5-cyano-6-((S)-3-fluoro-pyrrolidin-1-yl)-pyridin-3-yl]-pyrimidin-2-ylamino}-pyridin-2-yl)-propionamide 2-((S)-3-Fluoro-pyrrolidin-1-yl)-5-{2-[1-(2-morpholin-4-yl-ethyl)-1H-pyrazol-4-ylamino]-pyrimidin-4-yl}-nicotinonirile 3-((S)-3-Hydroxy-pyrrolidin-1-yl)-6-[2-(1-methyl-1H-pyrazol-4-ylamino)-pyrimidin-4-yl]-pyridine-2-carbonitrile 4-[4-(5-Cyano-6-pyrrolidin-1-yl-pyridin-3-yl)-pyrimidin-2-ylamino]-benzamide 5-{2-[6-(4-Methyl-piperazin-1-yl)-pyridin-3-ylamino]-pyrimidin-4-yl}-2-pyrrolidin-1-yl-nicotinonitrile 5-{2-(4-Morpholin-4-yl-phenylamino)-pyrimidin-4-yl}-2-pyrrolidin-1-yl-nicotinonitrile N-(5-{4-[5-Cyano-6-((S)-3-fluoro-pyrrolidin-1-yl)-pyridin-3-yl]-pyrimidin-2-ylamino}-pyridin-2-yl)-acetamide 2-((S)-3-Fluoro-pyrrolidin-1-yl)-5-{2-[6-(1-methyl-piperidin-4-ylamino)-pyridin-3-ylamino]-pyrimidin-4-yl}-nicotinonitrile 5-{2-[1-(2-Hydroxy-ethyl)-1H-pyrazol-4-ylamino]-pyrimidin-4-yl}-2-pyrrolidin-1-yl-nicotinonitrile 5-{2-[1-((S)-2,3-Dihydroxy-propyl)-1H-pyrazol-4-ylamino]-pyrimdin-4-yl}-2-pyrrolidin-1-yl-nicotinonitrile 5-{2-[1-((R)-2,3-Dihydroxy-propyl)-1H-pyrazol-4-ylamino]-pyrimidin-4-yl}-2-pyrrolidin-1-yl-nicotinonitrile N-(5-{4-[5-Cyano-6-((S)-3-fluoro-pyrrolidin-1-yl)-pyridin-3-yl]-pyrimidin-2-ylamino}-pyridin-2-yl)-2-morpholin-4-yl-acetamide 2-((S)-3-Fluoro-pyrrolidin-1-yl)-5-{2-[6-(2-hydroxy-2-methyl-propylamino)-pyridin-3-ylamino]-pyrimidin-4-yl}nicotinonitrile 2-(3-Hydroxy-8-aza-bicyclo[3.2.1]oct-8-yl)-5-[2-(1-methyl-1H-pyrazol-4-ylamino)-pyrimidin-4-yl]-nicotinonitrile 2-((S)-3-Fluoro-pyrrolidin-1-yl)-5-{2-[6-(4-methyl-piperazin-1-yl)-pyridin-3-ylamino]-pyrimidin-4-yl}-nicotinonitrile 2-((S)-3-Fluoro-pyrrolidin-1-yl)-5-[2-(6-piperazin-1-yl-pyridin-3-ylamino)-pyrimidin-4-yl]-nicotinonitrile 2-((S)-3-Fluoro-pyrrolidin-1-yl)-5-{2-[6-(2-hydroxy-ethyl-amino)-pyridin-3-ylamino]-pyrimidin-4-yl}-nicotinonitrile 4-{4-[5-Cyano-6-((S)-3-fluoro-pyrrolidin-1-yl)-pyridin-3-yl]-5-fluoro-pyrimidin-2-ylamino}-N-(1-methyl-piperidin-4-yl)-benzamide 4-{4-[5-Cyano-6-((S)-3-fluoro-pyrrolidin-1-yl)-pyridin-3-yl]-pyrimidin-2-ylamino}-N-(2-hydroxy-ethyl)-benzamide N-(5-{4-[5-Cyano-6-((S)-3-fluoro-pyrrolidin-1-yl)-pyridin-3-yl]-pyrimidin-2-ylamino}-pyridin-2-yl)-2-(4-hydroxy-piperidin-1-yl)-acetamide 2-((S)-3-Hydroxy-pyrrolidin-1-yl)-5-[2-(4-morpholin-4-yl-phenylamino)-pyrimidin-4-yl]-nicotinonitrile 2-((S)-3-Fluoro-pyrrolidin-1-yl)-5-[2-(4-morpholin-4-ylmethyl-phenylamino)-pyrimidin-4-yl]-nicotinonitrile 2-((S)-3-Fluoro-pyrrolidin-1-yl)-5-{2-[1-(tetrahydro-pyran-4-yl)-1H-pyrazol-4-ylamino]-pyrimidin-4-yl}-nicotinonitrile 6-[2-(4-Morpholin-4-yl-phenylamino)-pyrimidin-4-yl]-3-pyrrolidin-1-yl-pyridine-2-carbonitrile 3-((S)-3-Hydroxy-pyrrolidin-1-yl)-6-[2-(4-morpholin-4-yl-phenylamino)-pyrimidin-4-yl]-pyridine-2-carbonitrile In certain especially preferred embodiments, compounds of the invention include the following compounds, and their salts, especially their pharmaceutically acceptable salts:

DMX-2, DMX-3, DMX-5, DMX-8, DMX-9, DMX-17, DMX-22, DMX-24, DMX-25, DMX-27, DMX-28, DMX-29, DMX-30, DMX-33, DMX-34, DMX-35, DMX-61, DMX-62, DMX-63, DMX-67, DMX-68, DMX-71, DMX-72, DMX-76, DMX-78, DMX-80, DMX-81, DMX-83, DMX-89, DMX-92, DMX-96, DMX-97, DMX-98, DMX-99, DMX-100, DMX-102, DMX-110, DMX-111, DMX-112, DMX-126, DMX-127, DMX-36, DMX-37, DMX-38, DMX-39, DMX-44, DMX-48, DMX-49, DMX-50, DMX-128, DMX-131, DMX-136, DMX-161, DMX-162, DMX-

57, DMX-58, DMX-142, DMX-143, DMX-149, DMX-150, DMX-151, DMX-153, DMX- DMX-156, DMX-164 and DMX-165

In certain especially preferred embodiments, compounds of the invention include the following compounds, and their salts, especially their pharmaceutically acceptable salts:

DMX-3, DMX-5, DMX-9, DMX-22, DMX-24, DMX-25, DMX-28, DMX-30, DMX-33, DMX-61, DMX-63, DMX-67, DMX-68, DMX-72, DMX-76, DMX-78, DMX-80, DMX-89, DMX-96, DMX-99, DMX-102, DMX-111, DMX-112, DMX-126, DMX-127, DMX-37, DMX-38, DMX-39, DMX-44, DMX-48, DMX-49, DMX-136, DMX-57, DMX-58, DMX-142, DMX-143, DMX-149, DMX-150, DMX-153, DMX-165 and DMX-154, DMX-156.

Especially preferred compounds of the invention have particularly good activity and/or a combination of good activity and good metabolic stability.

The compounds of the invention may contain chiral (asymmetric) centres or the molecule as a whole may be chiral. The individual stereoisomers (enantiomers and diastereoisomers) and mixtures of these are within the scope of the present invention. Where the stereochemistry is not specifically indicated, both enantiomers (or, for a compound with two or more stereocentres, all stereoisomers) are within the scope of the present invention.

The invention includes salts of compounds of the general formula I. Generally, the compounds form addition salts with acids such as, for example, mineral acids, strong organic carboxylic acids, such as alkanecarboxylic acids, for example of 1 to 4 carbon atoms, which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$)-alkyl- or aryl-sulfonic acids which are unsubstituted or substituted, for example by halogen. Pharmaceutically acceptable acid addition salts generally include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. Salts which are not themselves pharmaceutically acceptable, for example those derived from acids such as oxalic, may be useful as intermediates in obtaining the compounds of the invention and their pharmaceutical acceptable acid addition salts.

Depending upon the substituents present, the compounds of formula I may also form salts with bases. Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may furthermore be formed.

The compounds of the invention may also form solvates, for example hydrates, and these are also included within the scope of the present invention.

Depending upon the substituents present in the compounds of the general formula I, the compounds may exist as stereoisomers and/or geometric isomers. All individual stereoisomers and geometric isomers, as well as mixtures thereof, are included within the scope of the invention. Further, isotopic forms, for example where a hydrogen atom is replaced with deuterium, are included within the invention. Certain isotopic forms may have beneficial biological properties, for example improved metabolic stability or enhanced therapeutic activity over other isotopic forms; or a specific isotopic form may be useful for biological imaging purposes, for example carbon-11, nitrogen-13, oxygen-15 or fluorine 18 isotopic variants may be used for positron emission tomography.

The invention also provides a process for the preparation of a compound of formula I, which comprises: in the case where W is C—H and V is N (i.e. the compound has the formula Ia)

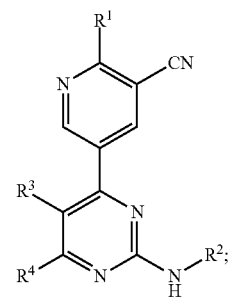

Ia (a) reacting a compound of the general formula II:

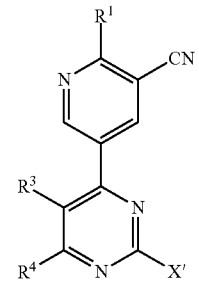

II with amines of the general formula $R^2NH_2$;

in which X' represents a leaving group, and $R^1$, $R^3$, $R^4$ and $R^2$ have the meanings given for the compound of general formula I.

The leaving group X' in compounds of the general formula II, may for example be a halogen atom or an alkyl (preferably methyl) sulfone or sulfoxide group. Nucleophilic SnAr displacement chemistry can be used to insert the $NR^2$ groups in which case X' is preferably fluorine, chlorine, or an alkyl (preferably methyl) sulfone or sulfoxide group. Alternatively palladium catalysed Buchwald-Hartwig type chemistry can be used in which case X' is preferably chlorine, bromine or iodine.

SnAr reactions are generally carried out in the presence of the amine, with heating if required, for example between 100-170° C. The reaction may for example be carried out using conventional heating at ambient pressure under reflux conditions, or in a sealed tube, alternatively a microwave reactor can be employed. A suitable solvent, for example, acetonitrile or 1,4-dioxane, may be used if desired.

The addition of a suitable base for example DIPEA or $K_2CO_3$ may help catalyse the reaction. Alternatively the addition of for example 0.5-2 equivalents of HCl can also be used to catalyse the reaction when an aryl or heteroaryl amine is used as the reaction partner.

Buchwald-Hartwig type reactions generally involve reacting the 2-chloro, 2-bromo or 2-iodo-compound with the requisite amine in the presence of a palladium catalyst. Examples of conditions that can be used to carry out such transformations are described in WO 2008/62044.

In another aspect, the invention also provides a compound of formula II per se.

Compounds of the general formula II may be made by methods analogous to known methods. One such method is via a Suzuki-Miyaura cross coupling of a boronic acid or boronic ester of the general formula III:

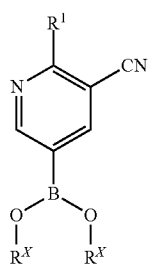

III in which each $R^x$ may be H or alkyl, or the two $R^x$ groups may be linked so as to form a cyclic boronic ester; with a pyrimidine of the general formula IV:

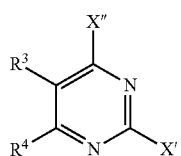

IV in which X' has the meaning given in formula II and X" is chlorine, bromine or iodine. Preferably X' and X" are the same or if different X' is fluorine, chlorine or an alkyl (preferably methyl) sulfone or sulfoxide group. Typical boronic esters used include for example the dimethylboronic ester and the pinacol ester. The compound of formula IV may for example be 2,4-diiodopyrimidine or 2,4-dichloropyrimidine. 2,4-Diiodo-pyrimidine may be prepared from 2,4-dichloropyrimidine by reaction with aqueous hydroiodic acid.

Compounds of the general formula III may be prepared for example by conversion of the corresponding bromide in compounds of the general formula V (see below) to the boronic ester or acid using methods known to those skilled in the art. One such method is to use a palladium cross coupling reaction with bis(pinacolato)diboron. Another such approach is to carry out a halogen lithium exchange followed by quenching with a suitable boronic ester such as trimethoxyborane:

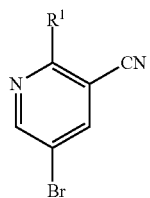

V

Compounds of general formula V can be prepared by nucleophilic displacement of a suitable leaving group in a compound of general formula VI,

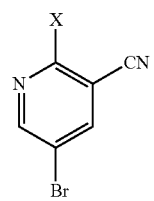

VI wherein X is preferably fluorine or chlorine.

Alternatively compounds of formula Ia may be prepared by reacting a compound of formula XI with an amine. Typical reaction conditions include heating the two components to reflux in a suitable solvent such as ethanol, in the presence of a suitable base such as triethylamine or diisopropylethylamine.

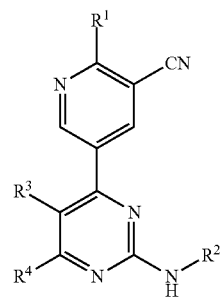

XI

Wherein X is preferably chlorine or fluorine.

The invention also provides a process for the preparation of a compound of formula I, which comprises: in the case where W is N and V is C—H (i.e. the compound has the formula Ib)

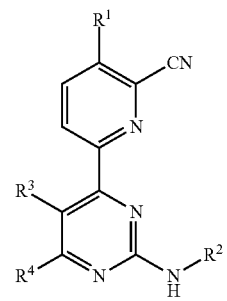

Ib either:
(a) reacting a compound of the general formula VII:

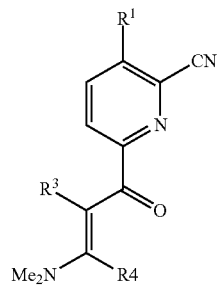

VII with a guanidine of formula VIII

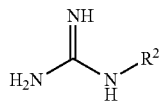

or
(b) reacting a compound of the general formula IX:

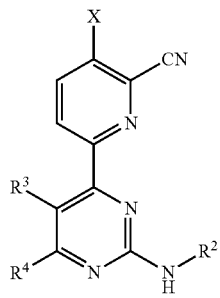

with an amine of formula R₁H, wherein X is a leaving group, preferably fluorine or chlorine.

Guanidines (e.g. guanidines of formula VIII) can be synthesised from the corresponding amines using methods known to those skilled in the art.

Compounds of formula IX can be made by reacting compounds of formula VIII with compounds of formula X

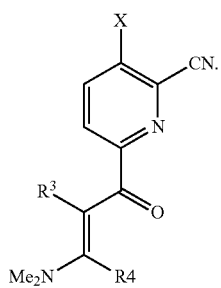

Aberrant kinase activity has been implicated in many diseases. For example, JNK has been implicated in diseases which involve excitotoxicity of hippocampal neurons, for example stroke, spinal cord injury, multiple sclerosis and head trauma; ischemia/reperfusion injury and conditions which may lead to or otherwise be associated with this, for example stroke, myocardial infarction, congestive heart failure, cardiac hypertrophy and atherosclerosis. JNK has also been associated with neurodegenerative diseases such as Parkinsons and Alzheimers diseases; neural tube birth defect; chronic inflammatory diseases such as rheumatoid arthritis and atherosclerosis; obesity and insulin resistant diabetes; and cancer. It is known that for many diseases wherein individual patients display the same gross symptomology, for example breast cancer, the disease may be caused and sustained by a number of different biochemical mechanisms which will vary from patient to patient. For many such diseases, the effectiveness of any treatment will therefore be highly dependent upon the biochemical mechanisms that precipitate and maintain the diseased state.

The compounds of the invention are inhibitors of IKKε and/or TBK-1, and are therefore useful in the treatment of diseases associated with, or caused by, aberrant IKKε and/or TBK-1 activity. Such diseases include inflammatory and tissue repair disorders, particularly rheumatoid arthritis, inflammatory bowel disease, asthma and chronic obstructive pulmonary disorder (COPD); osteoarthritis, osteoporosis and fibrotic diseases; dermatosis including psoriasis, atopic dermatitis and ultraviolet radiation (UV)-induced skin damage; autoimmune diseases including systemic lupus erythematosus, multiple sclerosis, psoriatic arthritis, and alkylosing spondylitis; tissue and organ rejection, Alzheimer's disease, stroke, atherosclerosis, restenosis, obesity, diabetes, glomerulonephritis, cancer, including Hodgkin's disease, cachexia, inflammation associated with infection including certain viral infections, including acquired immune deficiency syndrome (AIDS), adult respiratory distress syndrome, Ataxia Telangiestasia, primary open angle glaucoma and septic shock.

Because of the selectivity of the compounds of the invention to IKKε and TBK-1, it is expected that they may be used for treatment of disease with fewer side-effects than less selective compounds. It is also expected that they will find particular utility in targeting diseases in particular patient populations, i.e. where the disease is specifically caused by aberrant IKKε and/or TBK-1 activity.

In particular, the compounds of the invention are expected to be useful in the treatment of cancer, specifically, in the treatment of patient populations in which the disease is associated with aberrant IKKε and/or TBK-1 activity. IKKε has been implicated in breast cancer, including tamoxifen resistant breast cancer, ovarian cancer, including cis-platin resistant ovarian cancer, cancer in which tumour growth and/or survival is dependent upon IKKε kinase activity, cancers harbouring Ras mutations and Ras-dependant tumours, and cancers involving amplification of the 1q32 gene locus. TBK-1 has been implicated in cancers which harbour K-ras mutation and K-ras dependent tumours, cancers which harbour Ras mutations and cancers which are Ras-dependent, breast cancer, lung cancer, particularly non small cell lung cancer (NSCLC), ovarian cancer, prostate cancer, myeloma and leukemia.

In addition to cancer, specifically IKKε and/or TBK-1 associated cancers, the compounds of the invention are expected to be particularly useful in the treatment and prevention of obesity (in which IKKε is implicated); and diseases in which hypoxia-induced angiogenesis is important (which includes some cancers), the treatment and prevention of septic shock, and primary open angle glaucoma (in all of which TBK-1 is implicated).

The invention therefore provides a pharmaceutical composition which comprises a compound according to the invention, together with a pharmaceutically suitable carrier. Such compositions may contain the compound of the invention as the sole active ingredient, or they may contain an additional active ingredient.

The invention further provides a method of treating or preventing a disease mediated by IKKε and/or TBK-1 mechanisms in a subject, which comprises administration of a compound or a composition according to the invention, to the subject; a compound or a composition according to the invention for use in therapy, particularly for use in the treatment or prevention of any of the diseases mentioned above; and a compound according to the invention for use in the manufacture of a medicament for use in the treatment of any of the diseases mentioned above. Preferably the compound or composition is administered to a mammal, especially a human.

Whilst a compound of the invention may be used as the sole active agent, it is also possible for the compound to be used in combination with one or more further active agents.

Such further active agents may be further compounds according to the invention, or they may be different therapeutic agents, for example agents targeting one of the diseases mentioned above, particularly the same disease as that targeted by the compound of the invention. The compound of the invention may be co-formulated with the additional agent, or it may be formulated separately and administered consecutively, simultaneously or sequentially with the additional agent.

The amount of active ingredient which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician or veterinarian can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day, for adult humans. For oral administration, the compositions are preferably provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient, preferably from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The pharmaceutical formulations according to the invention include those suitable for oral, parenteral (including subcutaneous, intradermal, intramuscular, intravenous (bolus or infusion), and intraarticular), inhalation (including fine particle dusts or mists which may be generated by means of various types of metered doses pressurized aerosols), nebulizers or insufflators, rectal, intraperitoneal and topical (including dermal, buccal, sublingual, and intraocular) administration, although the most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets, pills or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

The present compounds can, for example, be administered in a form suitable for immediate release or extended release Immediate release or extended release can be achieved by the use of suitable pharmaceutical compositions comprising the present compounds, or, particularly in the case of extended release, by the use of devices such as subcutaneous implants or osmotic pumps.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose and/or lactose and/or other excipients, binders, extenders, disintegrants, diluents and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Disintegrators include without limitation starch, methylcellulose, agar, bentonite, xanthan gum and the like. The compounds of the invention can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. Lubricants used in these dosage forms include sodium oleate, sodium stearate, magnesium stearate, sodium benzoate, sodium acetate, sodium chloride and the like. For oral administration in liquid form, the oral drug components can be combined with any oral, non-toxic, pharmaceutically acceptable inert carrier such as ethanol, glycerol, water, and the like.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and *acacia* or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

It should be understood that in addition to the ingredients particularly mentioned above, the formulations of this invention may include other agents conventional in the art having regard to the type of formulation in question, for example those suitable for oral administration may include flavouring agents.

The following Examples illustrate the invention.

Abbreviations Used
Boc tert-Butoxycarbonyl
n-BuLi n-Butyl lithium
Dave-phos 2-Dicyclohexylphosphino-2'-(N,N-dimethylamino)biphenyl
DCM Dichloromethane
DIBALH Diisobutylaluminium hydride
DIPEA N,N-Diisopropylethylamine
DMF N,N-Dimethylformamide
DMSO Dimethyl sulfoxide
EDC.HCl 1-Ethyl-3-(3-dimethylaminopropyl)carbodiimide hydrochloride
$Et_2O$ Diethyl ether
EtOAc Ethyl acetate
EtOH Ethanol
EDTA Ethylenediaminetetraacetic acid
FA Formic acid
h hours
HEPES 4-(2-Hydroxyethyl)-1-piperazineethanesulfonic acid
HOB t Hydroxybenzotriazole
KOAc Potassium acetate
LC-MS Liquid chromatography-mass spectrometry
MeCN Acetonitrile
MeOH Methanol
min minutes
NaO$^t$Bu Sodium tert-butoxide
ND Not determined
$Pd_2(dba)_3$ Tris(dibenzylideneacetone)dipalladium(0)
$Pd(dppf)Cl_2$ 1,1'-Bis(diphenylphosphino)ferrocene]dichloropalladium
Pet ether Petroleum ether
Red_Al Sodium bis(2-methoxyethoxy)aluminumhydride
Rf Retention factor
rt room temperature
Rt Retention time
TBDMS tert-Butyldimethylsilyl
TBTU O-(benzotriazol-1-yl)-N,N,N',N'-tetramethyluronium tetrafluoroborate
TEA Triethylamine
THF Tetrahydrofuran
THP Tetrahydropyran
TFA Trifluoroacetic acid
TR-FRET Time-resolved fluorescence resonance energy transfer Analytical Methods Used MeOH-FA Method: Phenomenex Luna C18(2) 3 µm, 4.6×50 mm; $H_2O$+0.1% formic acid; B=MeOH; 45° C.; 0 min 5%, 1 min 37.5%, 3 min 95%, 3.5 min 95%, 3.51 min 5%, 4.5 min 5%; 2.2-2.3 mL/min Method A: Waters Sunfire C18 5 µm, 4.6×100 mm; A=$H_2O$+0.1% formic acid; B=MeOH+0.1% formic acid; 40° C.; 0 min 5%, 0.5 min 5%, 7.5 min 95%, 10 min 95%, 10.1 min 5%, 13 min 5%; 1.5 mL/min.

Method B: Waters Sunfire C18 5 µm, 4.6×100 mm; A=$H_2O$+0.01M ammonium bicarbonate; B=MeCN; 45° C.; 0 min 5%, 0.5 min 5%, 7.5 min 95%, 10 min 95%, 10.1 min 5%, 13 min 5%; 1.5 mL/min.

Method C: Phenomenex Luna C18 5 µm, 4.6×150 mm; $H_2O$+0.1% formic acid; B=MeOH+0.1% formic acid; 40° C.; 0 min 5%, 0.5 min 5%, 7.5 min 95%, 10 min 95%, 10.1 min 5%, 13 min 5%; 1.5 mL/min.

Method D: Phenomenex Gemini C18 5 µm, 4.6×150 mm; $H_2O$+0.1% formic acid; B=MeOH+0.1% formic acid; 40° C.; 0 min 5%, 0.5 min 5%, 7.5 min 95%, 10 min 95%, 10.1 min 5%, 13 min 5%; 1.5 mL/min.

Method E: Phenomenex Gemini C18 5 µm, 4.6×150 mm; $H_2O$+0.01M ammonium bicarbonate; B=MeOH; 45° C.; 0 min 5%, 0.5 min 5%, 7.5 min 95%, 10 min 95%, 10.1 min 5%, 13 min 5%; 1.5 mL/min.

Method X: Zodiacsil C18 5 µm, 4.6×50 mm; A=$H_2O$+0.01M ammonium formate; B=MeOH; 25° C.; % B 0 min 5%, 4 min 90%, 10 min 90%, 10.1 min 5%; 1.0 mL/min.

Method Y: Acquity UPLC BEH C18 1.7 µm, 2.1×50 mm; A=$H_2O$+0.025% TFA; B=MeCN+0.025% TFA; 25° C.; % B 0 min 15%, 3 min 95%, 4 min 95%, 4.1 min 15%; 0.4 mL/min.

Biological Testing

Compounds of the invention (synthesised as described below) were tested for activity against the IKKϵ and TBK-1 enzyme as follows:

Inhibitions studies were performed using a time-resolved fluorescence-based Lanthascreen™ assay. Phosphorylation of a fluorescein-labelled substrate peptide is measured using terbium-labeled phosphospecific antibodies. Terbium is excited at 340 nm and the FRET energy transfer to fluorescein is measured at 495 and 520 nm. The emission ratio between 520 and 495 is a measure of the level of phosphorylation of the substrate by the kinase.

Kinase inhibition assays (10 µL) were performed at 20° C. in 384-well plate format. Compound $IC_{50}$ values were determined at the apparent Km for ATP (20 µM) based on a radiometric assay (Invitrogen) using 8 or 10 point curves in duplicate. The final reaction conditions contained 400 nM fluorescein-IkBα substrate (DRHDSGLDSMKDE), 20 µM ATP, 2 nM or 8 nM IKKϵ or TBK1 kinase respectively, and 3% DMSO in kinase assay buffer consisting of 50 mM HEPES (pH 7.5), 10 mM MgCl, 1 mM EGTA, 0.01% Brij-35.

Compound dilutions were prepared from 10 mM DMSO stocks by dilution into DMSO. Compound dilution series were further diluted in kinase assay buffer to give a 12% DMSO stock, the final concentration in the assay being 3% DMSO.

The kinase phosphorylation assay was initiated by the addition of the kinase and the reaction was allowed to proceed for 1 h or 2.5 h for IKKε and TBK-1 kinase respectively. Both conditions were within the linearity of the phosphorylation. The reaction was stopped by the addition of 10 mM EDTA, and phosphorylation was detected after a 1 hr incubation with 1.5 nM terbium-labelled antibody against phosphorylation at Serine 32 on the IkBα peptide, both in TR-FRET dilution buffer (Invitrogen).

All compounds of the examples have an $IC_{50}$ of <1 µM against either IKKε or TBK1 and preferably an $IC_{50}$ of <1 µM against both IKKε and TBK1.

The results of the testing are show under Chemical Synthesis below. In the data presented for IKKε and TBK1, <1 µM means having an activity in the range from 100 nM≤1 µM; and <100 nM means having an activity in the range 30 nM≤100 nM and <30 nM means having activity in the range of 15 nM≤30 nM.

Many of the example compounds of the invention contain a centre that is sufficiently basic, and were purified in such a way, that it is likely that they were obtained formic acid (FA) salt or trifluoroacetic acid (TFA) salt. In the biological studies described herein, it is believed that the compounds described in the tables I to VII as being in their formic acid (FA) salt or trifluoroacetic acid (TFA) salt, were studied in that form.

CHEMICAL SYNTHESIS EXAMPLES

A number of compounds of formula Ia were synthesised from intermediate II by a $S_NAr$ reaction or palladium Buchwald-Hartwig catalysed chemistry

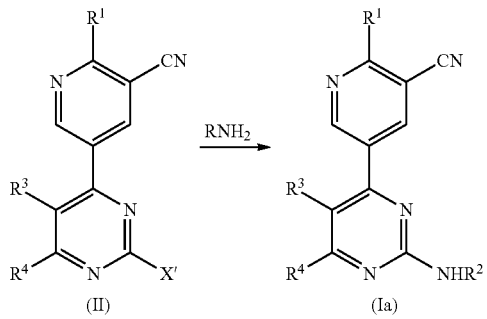

Example DMX-1

Synthesis of 3-{4-[5-Cyano-6-((S)-3-fluoro-pyrrolidin-1-yl)-pyridin-3-yl]-pyrimidin-2-ylamino}-N-(1-methyl-piperidin-4-yl)-benzamide 5-Bromo-2-fluoro-pyridine-3-carbaldehyde (2)

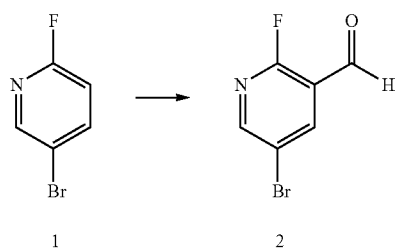 [SMILES: Fc1ccc(Br)cn1 ; O=Cc1cc(Br)cnc1F]

To a stirred solution of DIPEA (44.1 mL, 312 mmol) in dry THF (500 mL) at −78° C. was added dropwise n-BuLi (2.5M in hexanes, 125 mL, 313 mmol). The temperature was warmed to rt and stirred for 10 minutes. The solution was cooled to −78° C. and a solution of 5-bromo-2-fluoro-pyridine (1) (50.0 g, 284 mmol) in THF (500 mL) added dropwise. The reaction mixture was stirred at −78° C. for 45 minutes then quenched with 10% citric acid in THF (250 mL) at −78° C. The solution was warmed to rt then diluted with $H_2O$ (250 mL). The solution was extracted with EtOAc (3×250 mL) and the combined organics washed with saturated brine solution (250 mL), dried ($Na_2SO_4$), filtered and the solvent evaporated in vacuo. The crude product was purified by column chromatography (100-200 mesh silica gel, 20% EtOAc-pet ether) to provide the title compound as a white solid (36.0 g, 62%); Rf: 0.7 (10% EtOAc-pet ether).

5-Bromo-2-fluoro-pyridine-3-carbaldehyde oxime (3)

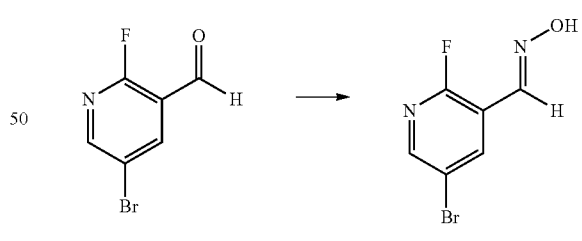

To a solution of 5-bromo-2-fluoro-pyridine-3-carbaldehyde (2) (20.0 g, 98.0 mmol) in 1:1 MeOH—$H_2O$ (250 mL) was added hydroxylamine hydrochloride (7.52 g, 108 mmol) and sodium carbonate (11.4 g, 108 mmol). The reaction mixture was stirred at rt for 1 hour. The solvent was evaporated in vacuo and the residue diluted with $H_2O$ (200 mL) and EtOAc (200 mL). The organic phase was separated, dried ($Na_2SO_4$), filtered and the solvent evaporated in vacuo. The product was obtained as a light pink solid (21.0 g, 93%); Rf: 0.4 (10% EtOAc-pet ether).

5-Bromo-2-fluoro-nicotinonitrile (4)

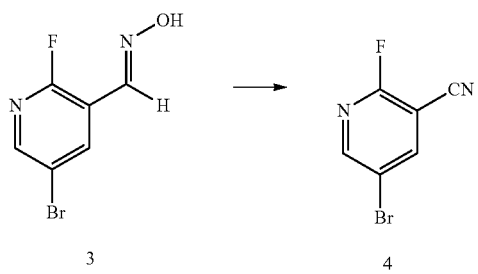 [SMILES: O/N=C/c1cc(Br)cnc1F ; N#Cc1cc(Br)cnc1F]

To a solution of 5-Bromo-2-fluoro-pyridine-3-carbaldehyde oxime (3) (19.0 g, 86.8 mmol) in MeCN (400 mL) was added dimethylacetylene dicarboxylate (25.0 g, 176 mmol) and TEA (24.1 mL, 173 mmol) dropwise. The reaction mixture was stirred at rt for 4 hours. The solvent was evaporated in vacuo and the residue diluted with CHCl$_3$ (300 mL) and H$_2$O (300 mL). The layers were separated and the organic phase washed with saturated brine solution (200 mL), then dried (Na$_2$SO$_4$), filtered and the solvent evaporated in vacuo. The crude product was purified by column chromatography (100-200 mesh silica gel, 10% EtOAc-pet ether) to provide the title compound as a white solid (12.0 g, 69%); Rf: 0.7 (20% EtOAc-pet ether).

5-Bromo-2-((S)-3-fluoro-pyrrolidin-1-yl)-nicotinonitrile (5)

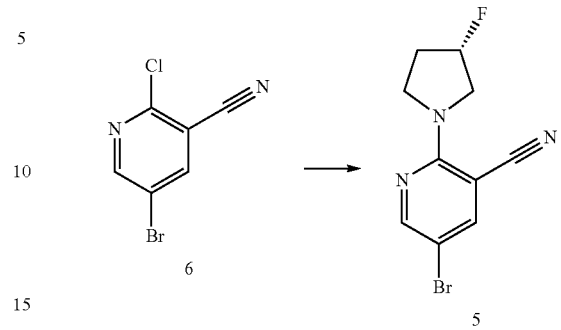

5-Bromo-2-chloro-nicotinonitrile (6) (5.0 g, 23.0 mmol) was dissolved in MeCN (100 mL). (S)-3-Fluoropyrrolidine hydrochloride (5.7 g, 53.0 mmol) and DIPEA (12.0 mL, 68.9 mmol) were added and the mixture was stirred at reflux for 1 hour. The solvent was evaporated in vacuo and the residue partitioned between EtOAc (100 mL) and H$_2$O (50 mL). The layers were separated and the organic phase washed with saturated brine solution (50 mL), then dried (MgSO$_4$), filtered and the solvent evaporated in vacuo. The title compound was obtained as an off-white solid (6.2 g, 100%); LCMS, Rt=2.91 min (MeOH-FA method), m/z 270, 272 (MH$^+$).

5-Bromo-2-((S)-3-fluoro-pyrrolidin-1-yl)-nicotinonitrile (5)

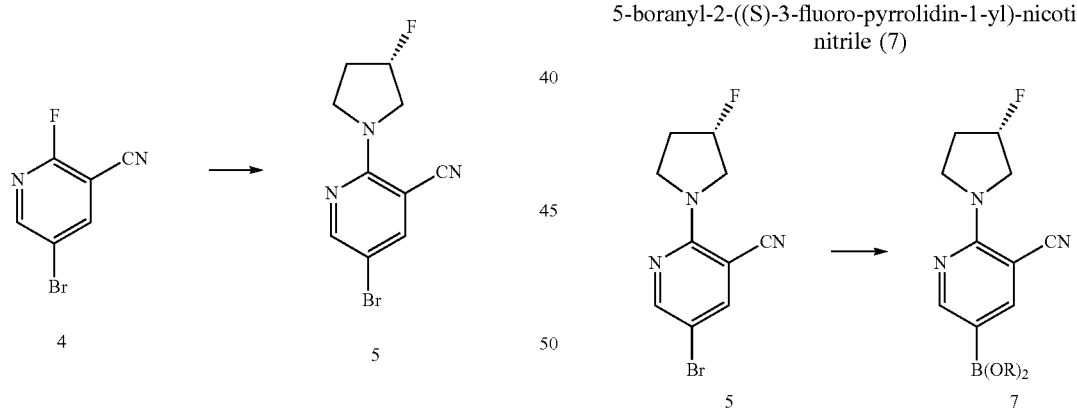

5-Bromo-2-fluoro-nicotinonitrile (4) (5.0 g, 24.9 mmol) and (S)-(+)-3-fluoropyrrolidine (3.3 g, 25.9 mmol) were dissolved in dry MeCN (100 mL). TEA (8.0 mL, 57.4 mol) was added and the mixture stirred at rt for 2 hours. The solvent was evaporated in vacuo and the residue partitioned between H$_2$O (100 mL) and EtOAc (100 mL). The organic phase was washed with saturated brine solution (100 mL), then dried (MgSO$_4$), filtered and the solvent evaporated in vacuo. The residue was dissolved in DCM (100 mL) and the solvent evaporated in vacuo. The title compound was obtained as an off-white solid (6.3 g, 94%); LCMS, Rt=2.86 min (MeOH-FA method), m/z 270, 272 (MH$^+$).

Alternatively 5-Bromo-2-((S)-3-fluoro-pyrrolidin-1-yl)-nicotinonitrile (5) could be made starting from the commercially available 5-bromo-2-chloro-nicotinonitrile (6).

2-((S)-3-Fluoro-pyrrolidin-1-yl)-5-(4,4,5,5-tetramethyl-[1,3,2]dioxaborolan-2-yl)-nicotinonitrile & 5-boranyl-2-((S)-3-fluoro-pyrrolidin-1-yl)-nicotinonitrile (7)

5-Bromo-2-((S)-3-fluoro-pyrrolidin-1-yl)-nicotinonitrile (5) (6.29 g, 23.0 mmol), bispinacolato diboron (8.87 g, 34.9 mmol), Pd(dppf)Cl$_2$ (1.70 g, 2.32 mmol) and KOAc (6.86 g, 69.9 mmol) were dissolved in 1,4-dioxane (100 mL) and the stirred solution degassed under nitrogen for 15 minutes. The reaction mixture was then stirred at 100° C. for 3 hours 45 minutes. The solvent was evaporated in vacuo and the residue partitioned between EtOAc (200 mL) and H$_2$O (100 mL). The organic phase was washed with saturated brine solution (100 mL), then dried (MgSO$_4$), filtered and the solvent evaporated in vacuo. The crude product was purified by column chromatography (40-63 mesh silica gel, DCM→99:1 DCM-MeOH) to provide a mixture of boronic acid and boronic ester as an orange solid (5.6 g, ~88%); LCMS, Rt=1.85, 3.07 min (MeOH-FA method), m/z 234, 316 (MH+) respectively.

5-(2-Chloro-primidin-4-yl)-2-((S)-3-fluoro-pyrrolidin-1-yl)-nicotinonitrile (8)

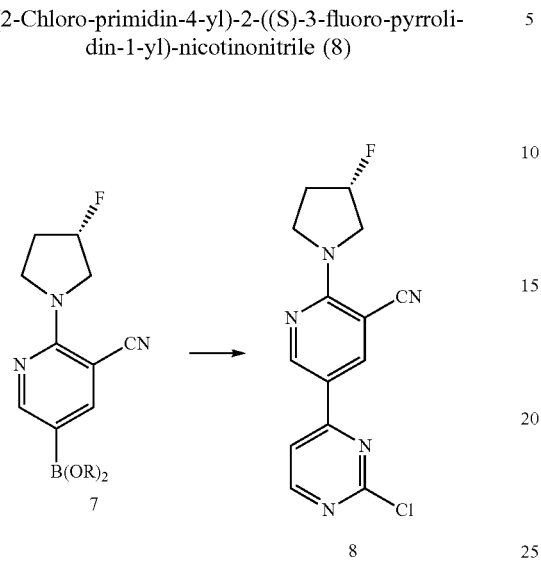

A mixture of 2-((S)-3-Fluoro-pyrrolidin-1-yl)-5-(4,4,5,5-tetramethyl-[1,3,2]dioxaborolan-2-yl)-nicotinonitrile and 5-boranyl-2-((S)-3-fluoro-pyrrolidin-1-yl)-nicotinonitrile (7) (2.64 g, ~9.6 mmol), 2,4-dichloropyrimidine (1.2 g, 9.6 mmol), tetrakis(triphenylphosphine)palladium(0) (1.1 g, 1.0 mmol) and Na$_2$CO$_3$ (3.1 g, 28.8 mmol) were dissolved in 1:1 1,4-dioxane-H$_2$O (40 mL) and the mixture was stirred at 120° C. in the microwave (250 W, stirring) for 30 minutes. The mixture was diluted with EtOAc (130 mL) and H$_2$O (40 mL) and the layers separated. The organic phase was washed with saturated brine solution (50 mL), then dried (MgSO$_4$), filtered and the solvent evaporated in vacuo. The crude product was purified by column chromatography (40-63 mesh silica gel, 1:1 isohexane-EtOAc) to provide the title compound as a pale yellow solid (1.6 g, 55%); LCMS, Rt=2.80 min (MeOH-FA method), m/z 304 (MH+).

3-{4-[5-Cyano-6-((S)-3-fluoro-pyrrolidin-1-yl)-pyridin-3-yl]-pyrimidin-2-ylamino}-N-(1-methyl-piperidin-4-yl)-benzamide (DMX-1)

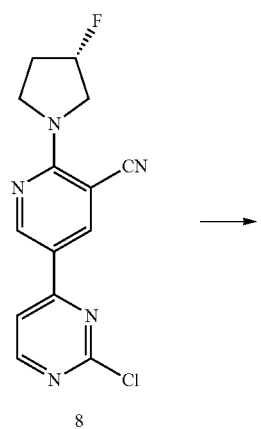

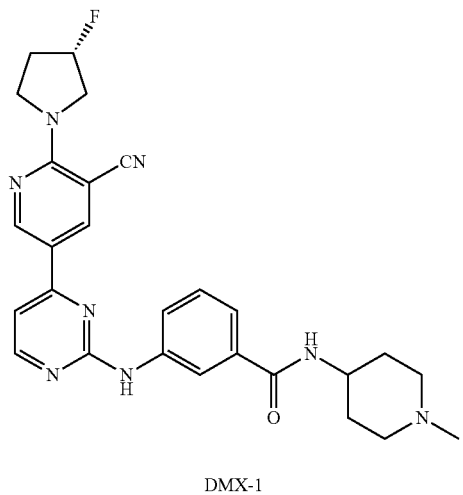

DMX-1

5-(2-Chloro-primidin-4-yl)-2-((S)-3-fluoro-pyrrolidin-1-yl)-nicotinonitrile (8) (100 mg, 0.329 mmol), 3-amino-N-(1-methyl-piperidin-4-yl)-benzamide (115 mg, 0.493 mmol), Pd$_2$(dba)$_3$ (30 mg, 0.0327 mmol), NaOtBu (48 mg, 0.499 mmol) and Dave-Phos (130 mg, 0.330 mmol) were dissolved in 1,4-dioxane (3 mL). Nitrogen was bubbled through the stirred mixture for 5 minutes. The reaction mixture was then stirred at 120° C. in the microwave (250 W, stirring) for 2 hours. The solvent was evaporated in vacuo and the residue dissolved in DMSO (3 mL). The crude product was purified by reversed phase preparative LC-MS. Fractions containing desired product were combined and the MeOH evaporated in vacuo. The aqueous solution was frozen (−78° C.) and the solvent evaporated in vacuo (freeze dried). The title compound was obtained as an off-white solid (68 mg, 38%); LCMS, Rt=4.94 min (Method A), m/z 501 (MH+).

For alternative compounds of the invention this step was carried out using similar conditions. This included for example stirring at 100-120° C. in the microwave for a time period varying between 10 minutes and 2 hours. Alternatively this reaction could be accomplished thermally by stirring for up to 3 hours at 100° C.

For many examples an additional work-up procedure was included. The crude reaction mixture was loaded onto an SCX-2 cartridge (Biotage), washed with up to 6 column volumes MeOH then eluted with either 0.5M NH$_3$-MeOH or 2M NH$_3$-MeOH. The solvent was evaporated in vacuo before purification by reversed phase preparative LC-MS.

The following compounds were made via this route:

TABLE I

| Structure | Ex. No. | Name | Analytical Data | Inhibition of IKKε | Inhibition of TBK1 | Salt Form |
|---|---|---|---|---|---|---|
| 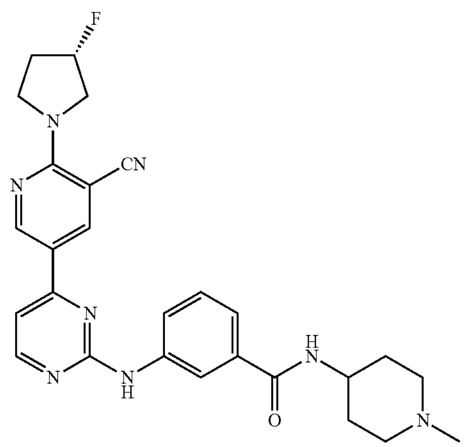 [SMILES: CN1CCC(NC(=O)c2cccc(Nc3nccc(-c4cnc(N5CC[C@H](F)C5)c(C#N)c4)n3)c2)CC1] | DMX-1 | 3-{4-[5-Cyano-6-((S)-3-fluoro-pyrrolidin-1-yl)-pyridin-3-yl]-pyrimidin-2-ylamino}-N-(1-methyl-piperidin-4-yl)-benzamide | Method A; Rt = 4.94 min; m/z 501 (MH+); white solid | <100 nM | <30 nM | FA |
| 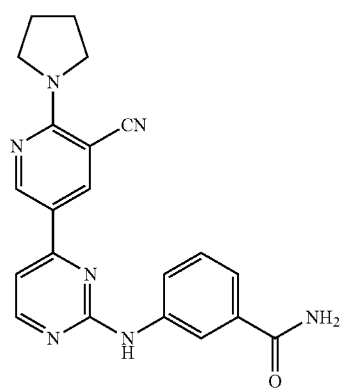 [SMILES: N#Cc1cc(-c2ccnc(Nc3cccc(C(N)=O)c3)n2)cnc1N1CCCC1] | DMX-2 | 3-[4-(5-Cyano-6-pyrrolidin-1-yl-pyridin-3-yl)-pyrimidin-2-ylamino]-benzamide | Method Y; Rt = 1.83 min; m/z 386 (MH+); white solid | <30 nM | <30 nM | None |
| 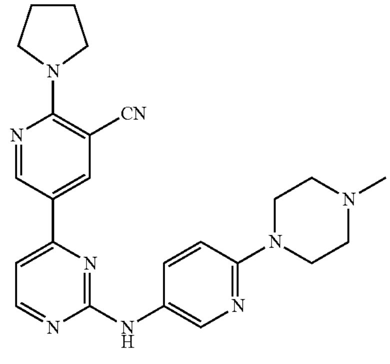 [SMILES: CN1CCN(c2ccc(Nc3nccc(-c4cnc(N5CCCC5)c(C#N)c4)n3)cn2)CC1] | DMX-3 | 5-{2-[6-(4-Methyl-piperazin-1-yl)-pyridin-3-ylamino]-pyrimidin-4-yl}-2-pyrrolidin-1-yl-nicotinonitrile | Method Y; Rt = 1.46 min; m/z 442 (MH+); off-white solid | <15 nM | <15 nM | None |

TABLE I-continued

| Structure | Ex. No. | Name | Analytical Data | Inhibition of IKKε | Inhibition of TBK1 | Salt Form |
|---|---|---|---|---|---|---|
| 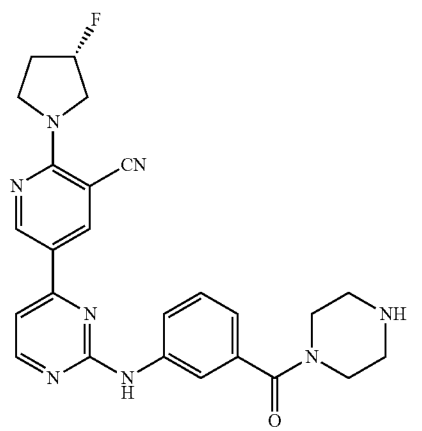 [SMILES: N#Cc1cc(-c2ccnc(Nc3cccc(C(=O)N4CCNCC4)c3)n2)cnc1N1CC[C@H](F)C1] | DMX-4* | 2-((S)-3-Fluoro-pyrrolidin-1-yl)-5-{2-[3-(piperazine-1-carbonyl)-phenylamino]-pyrimidin-4-yl}-nicotinonitrile | Method A; Rt = 4.71 min; m/z 442 (MH+); off-white solid | <30 nM | <30 nM | FA |
| 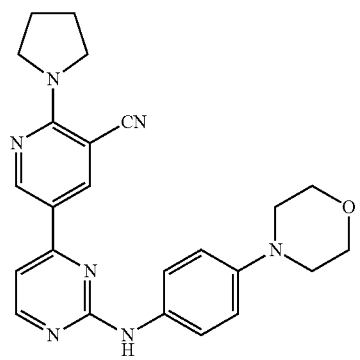 [SMILES: N#Cc1cc(-c2ccnc(Nc3ccc(N4CCOCC4)cc3)n2)cnc1N1CCCC1] | DMX-5 | 5-[2-(4-Morpholin-4-yl-phenylamino)-pyrimidin-4-yl]-2-pyrrolidin-1-yl-nicotinonitrile | Method B; Rt = 6.71 min; m/z 428 (MH$^+$); off-white solid | <30 nM | <15 nM | None |
| 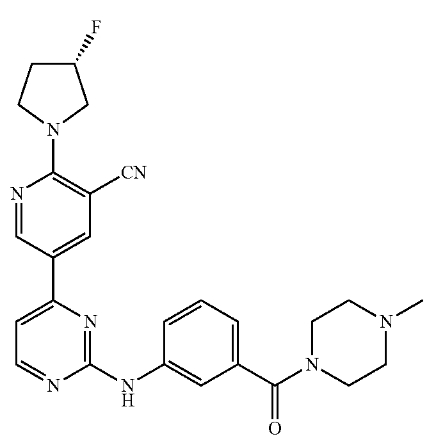 [SMILES: CN1CCN(C(=O)c2cccc(Nc3nccc(-c4cnc(N5CC[C@H](F)C5)c(C#N)c4)n3)c2)CC1] | DMX-6 | 2-((S)-3-Fluoro-pyrrolidin-1-yl)-5-{2-[3-(4-methyl-piperazine-1-carbonyl)-phenylamino]-pyrimidin-4-yl}-nicotinonitrile | Method A; Rt = 4.80 min; m/z 487 (MH$^+$); yellow solid | <100 nM | <30 nM | FA |

TABLE I-continued

| Structure | Ex. No. | Name | Analytical Data | Inhibition of IKKε | Inhibition of TBK1 | Salt Form |
|---|---|---|---|---|---|---|
| 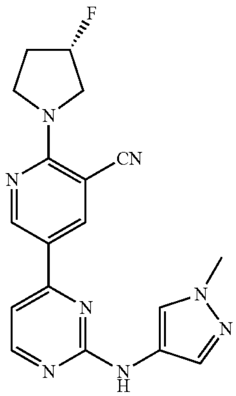 [SMILES: Cn1cc(Nc2nccc(-c3cnc(N4CC[C@H](F)C4)c(C#N)c3)n2)cn1] | DMX-7 | 2-((S)-3-Fluoro-pyrrolidin-1-yl)-5-[2-(1-methyl-1H-pyrazol-4-ylamino)-pyrimidin-4-yl]-nicotinonitrile | Method A; Rt = 6.77 min; m/z 365 (MH+); yellow solid | <30 nM | <30 nM | \None |
| 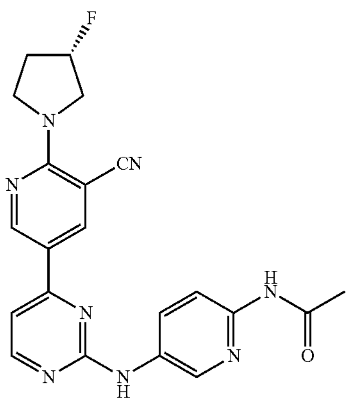 [SMILES: CC(=O)Nc1ccc(Nc2nccc(-c3cnc(N4CC[C@H](F)C4)c(C#N)c3)n2)cn1] | DMX-8 | N-(5-{4-[5-Cyano-6-((S)-3-fluoro-pyrrolidin-1-yl)-pyridin-3-yl]-pyrimidin-2-ylamino}-pyridin-2-yl)-acetamide | Method A; Rt = 6.81 min; m/z 419 (MH+); off-white solid | <30 nM | <30 nM | None |
| 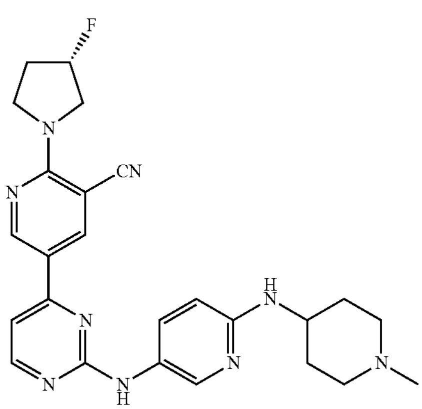 [SMILES: CN1CCC(Nc2ccc(Nc3nccc(-c4cnc(N5CC[C@H](F)C5)c(C#N)c4)n3)cn2)CC1] | DMX-9 | 2-((S)-3-Fluoro-pyrrolidin-1-yl)-5-{2-[6-(1-methyl-piperidin-4-ylamino)-pyridin-3-ylamino]-pyrimidin-4-yl}-nicotinonitrile | Method A; Rt = 3.70 min; m/z 474 (MH+); brown solid | <15 nM | <30 nM | FA |

TABLE I-continued

| Structure | Ex. No. | Name | Analytical Data | Inhibition of IKKε | Inhibition of TBK1 | Salt Form |
|---|---|---|---|---|---|---|
| 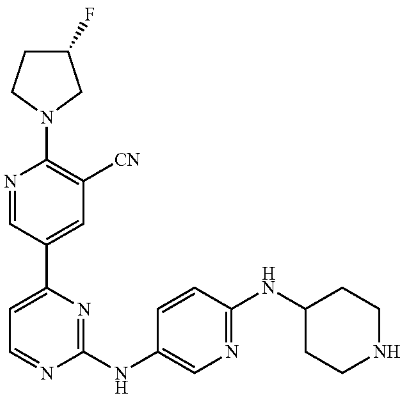 [SMILES: N#Cc1cc(-c2ccnc(Nc3ccc(NC4CCNCC4)nc3)n2)cnc1N1CC[C@H](F)C1] | DMX-10* | 2-((S)-3-Fluoro-pyrrolidin-1-yl)-5-{2-[6-(piperidin-4-ylamino)-pyridin-3-ylamino]-pyrimidin-4-yl}-nicotinonitrile | Method A; Rt = 3.70 min; m/z 460 (MH+); yellow/brown solid | <30 nM | <30 nM | FA |
| 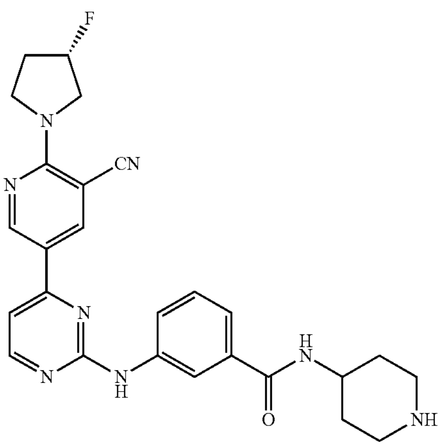 [SMILES: N#Cc1cc(-c2ccnc(Nc3cccc(C(=O)NC4CCNCC4)c3)n2)cnc1N1CC[C@H](F)C1] | DMX-11* | 3-{4-[5-Cyano-6-((S)-3-fluoro-pyrrolidin-1-yl)-pyridin-3-yl]-pyrimidin-2-ylamino}-N-piperidin-4-yl-benzamide | Method A; Rt = 5.03 min; m/z 487 (MH+); yellow/brown solid | <30 nM | <30 nM | FA |
| 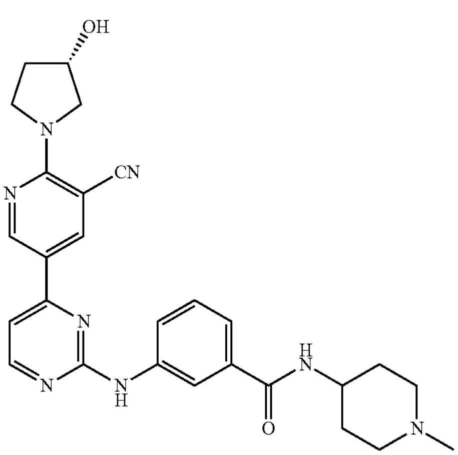 [SMILES: CN1CCC(NC(=O)c2cccc(Nc3nccc(-c4cnc(N5CC[C@H](O)C5)c(C#N)c4)n3)c2)CC1] | DMX-12 | 3-{4-[5-Cyano-6-((S)-3-hydroxy-pyrrolidin-1-yl)-pyridin-3-yl]-pyrimidin-2-ylamino}-N-(1-methyl-piperidin-4-yl)-benzamide | Method C; Rt = 5.25 min; m/z 499 (MH+); yellow solid | <1 μM | <100 nM | FA |

TABLE I-continued

| Structure | Ex. No. | Name | Analytical Data | Inhibition of IKKε | Inhibition of TBK1 | Salt Form |
|---|---|---|---|---|---|---|
| 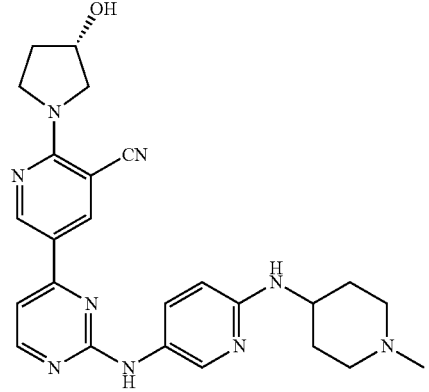 [SMILES: CN1CCC(Nc2ccc(Nc3nccc(-c4cnc(N5CC[C@H](O)C5)c(C#N)c4)n3)cn2)CC1] | DMX-13 | 2-((S)-3-Hydroxy-pyrrolidin-1-yl)-5-{2-[6-(1-methyl-piperidin-4-ylamino)-pyridin-3-ylamino]-pyrimidin-4-yl}-nicotinonitrile | Method C; Rt = 4.02 min; m/z 472 (MH$^+$); yellow solid | <100 nM | <100 nM | FA |
| 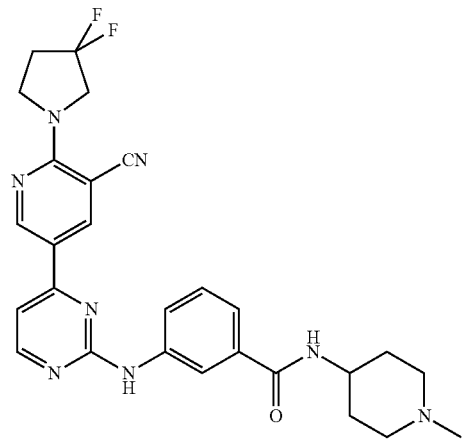 [SMILES: CN1CCC(NC(=O)c2cccc(Nc3nccc(-c4cnc(N5CCC(F)(F)C5)c(C#N)c4)n3)c2)CC1] | DMX-14 | 3-{4-[5-Cyano-6-(3,3-difluoro-pyrrolidin-1-yl)-pyridin-3-yl]-pyrimidin-2-ylamino}-N-(1-methyl-piperidin-4-yl)-benzamide | Method C; Rt = 6.04 min; m/z 519 (MH$^+$); off-white solid | <100 nM | <100 nM | FA |
| 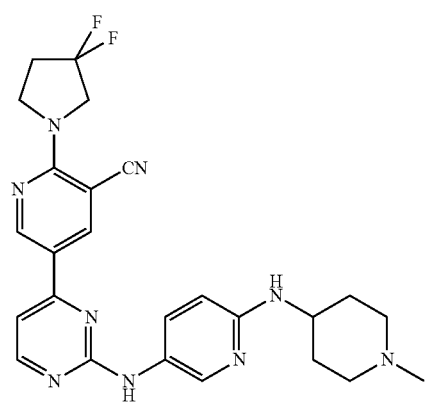 [SMILES: CN1CCC(Nc2ccc(Nc3nccc(-c4cnc(N5CCC(F)(F)C5)c(C#N)c4)n3)cn2)CC1] | DMX-15 | 2-(3,3-Difluoro-pyrrolidin-1-yl)-5-{2-[6-(1-methyl-piperidin-4-ylamino)-pyridin-3-ylamino]-pyrimidin-4-yl}-nicotinonitrile | Method C; Rt = 4.77 min; m/z 492 (MH$^+$); tan solid | <100 nM | <30 nM | FA |

TABLE I-continued

| Structure | Ex. No. | Name | Analytical Data | Inhibition of IKKε | Inhibition of TBK1 | Salt Form |
|---|---|---|---|---|---|---|
| 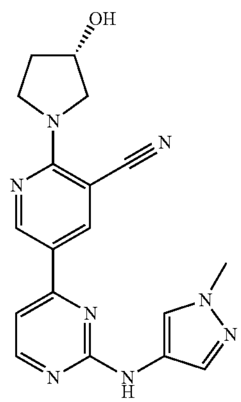 [SMILES: Cn1cc(Nc2nccc(-c3cnc(N4CC[C@H](O)C4)c(C#N)c3)n2)cn1] | DMX-16 | 2-((S)-3-Hydroxy-pyrrolidin-1-yl)-5-[2-(1-methyl-1H-pyrazol-4-ylamino)-pyrimidin-4-yl]-nicotinonitrile | Method C; Rt = 6.75 min; m/z 363 (MH+); yellow solid | <100 nM | <100 nM | None |
| 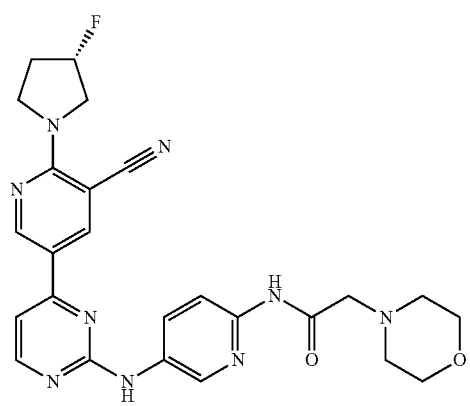 [SMILES: N#Cc1cc(-c2ccnc(Nc3ccc(NC(=O)CN4CCOCC4)nc3)n2)cnc1N1CC[C@H](F)C1] | DMX-17 | N-(5-{4-[5-Cyano-6-((S)-3-fluoro-pyrrolidin-1-yl)-pyridin-3-yl]-pyrimidin-2-ylamino}-pyridin-2-yl)-2-morpholin-4-yl-acetamide | Method C; Rt = 6.43 min; m/z 504 (MH+); yellow solid | <30 nM | <30 nM | None |
| 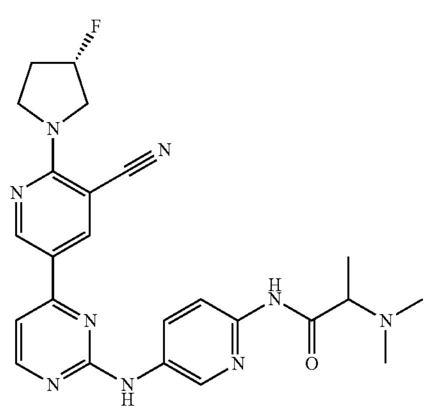 [SMILES: CC(C(=O)Nc1ccc(Nc2nccc(-c3cnc(N4CC[C@H](F)C4)c(C#N)c3)n2)cn1)N(C)C] | DMX-18 | N-(5-{4-[5-Cyano-6-((S)-3-fluoro-pyrrolidin-1-yl)-pyridin-3-yl]-pyrimidin-2-ylamino}-pyridin-2-yl)-2-dimethylamino-propionamide | Method C; Rt = 5.75 min; m/z 476 (MH+); yellow solid | <100 nM | <100 nM | None |

TABLE I-continued

| Structure | Ex. No. | Name | Analytical Data | Inhibition of IKKε | Inhibition of TBK1 | Salt Form |
|---|---|---|---|---|---|---|
| 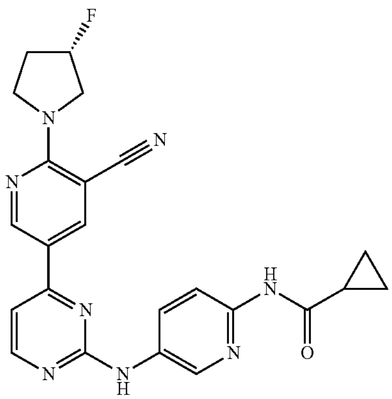 [SMILES: N#Cc1cc(-c2ccnc(Nc3ccc(NC(=O)C4CC4)nc3)n2)cnc1N1CC[C@H](F)C1] | DMX-19 | Cyclopropanecarboxylic acid (5-{4-[5-cyano-6-((S)-3-fluoro-pyrrolidin-1-yl)-pyridin-3-yl]-pyrimidin-2-ylamino}-pyridin-2-yl)-amide | Method C; Rt = 7.89 min; m/z 445 (MH+); brown solid | <100 nM | <100 nM | None |
| 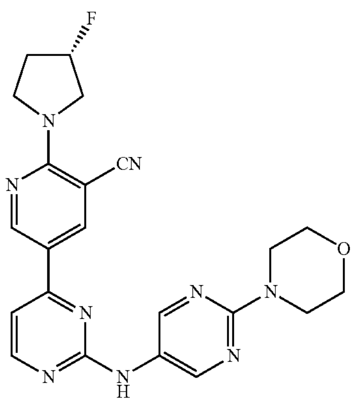 [SMILES: N#Cc1cc(-c2ccnc(Nc3cnc(N4CCOCC4)nc3)n2)cnc1N1CC[C@H](F)C1] | DMX-20 | 2-((S)-3-Fluoro-pyrrolidin-1-yl)-5-[2-(2-morpholin-4-yl-pyrimidin-5-ylamino)-pyrimidin-4-yl]-nicotinonitrile | Method C; Rt = 8.18 min; m/z 448 (MH+); yellow solid | <100 nM | <100 nM | None |
| 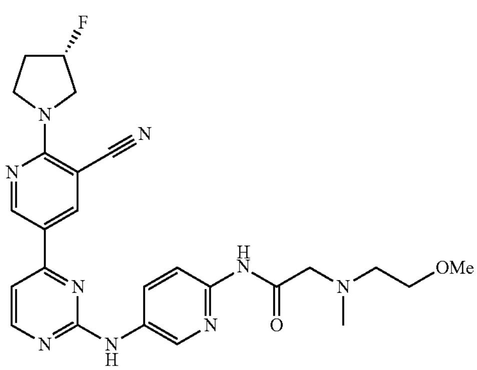 [SMILES: COCCN(C)CC(=O)Nc1ccc(Nc2nccc(-c3cnc(N4CC[C@H](F)C4)c(C#N)c3)n2)cn1] | DMX-21 | N-(5-{4-[5-Cyano-6-((S)-3-fluoro-pyrrolidin-1-yl)-pyridin-3-yl]-pyrimidin-2-ylamino}-pyridin-2-yl)-2-[(2-methoxy-ethyl)-methyl-amino]-acetamide | Method C; Rt = 5.89 min; m/z 506 (MH+); yellow solid | <30 nM | <30 nM | None |
| 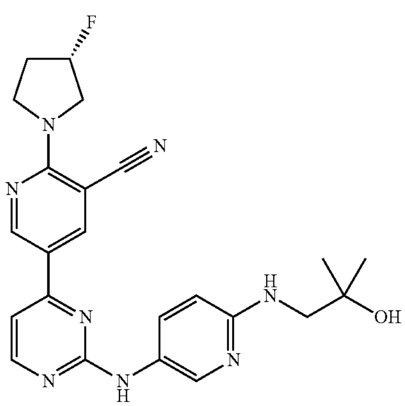 [SMILES: CC(C)(O)CNc1ccc(Nc2nccc(-c3cnc(N4CC[C@H](F)C4)c(C#N)c3)n2)cn1] | DMX-22 | 2-((S)-3-Fluoro-pyrrolidin-1-yl)-5-{2-[6-(2-hydroxy-2-methyl-propylamino)-pyridin-3-ylamino]-pyrimidin-4-yl}-nicotinonitrile | Method D; Rt = 5.29 min; m/z 449 (MH+); yellow solid | <15 nM | <30 nM | None |

TABLE I-continued

| Structure | Ex. No. | Name | Analytical Data | Inhibition of IKKε | Inhibition of TBK1 | Salt Form |
|---|---|---|---|---|---|---|
| 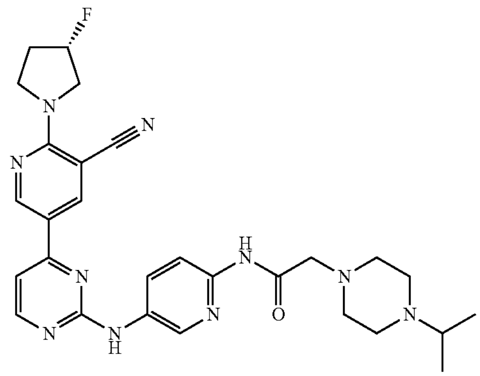 [SMILES: CC(C)N1CCN(CC(=O)Nc2ccc(Nc3nccc(-c4cnc(N5CC[C@H](F)C5)c(C#N)c4)n3)cn2)CC1] | DMX-23 | N-(5-{4-[5-Cyano-6-((S)-3-fluoro-pyrrolidin-1-yl)-pyridin-3-yl]-pyrimidin-2-ylamino}-pyridin-2-yl)-2-(4-isopropyl-piperazin-1-yl)-acetamide | Method D; Rt = 5.36 min; m/z 545 (MH⁺); yellow solid | <30 nM | <30 nM | FA |
| 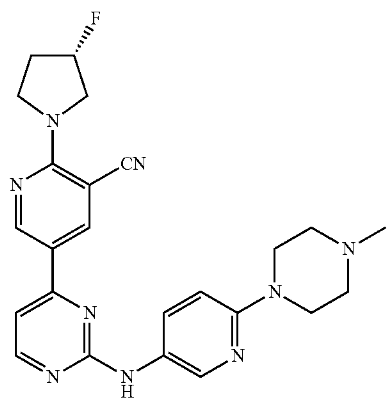 [SMILES: CN1CCN(c2ccc(Nc3nccc(-c4cnc(N5CC[C@H](F)C5)c(C#N)c4)n3)cn2)CC1] | DMX-24 | 2-((S)-3-Fluoro-pyrrolidin-1-yl)-5-{2-[6-(4-methyl-piperazin-1-yl)-pyridin-3-ylamino]-pyrimidin-4-yl}-nicotinonitrile | Method D; Rt = 4.97 min; m/z 460 (MH⁺); orange solid | <15 nM | <15 nM | FA |
| 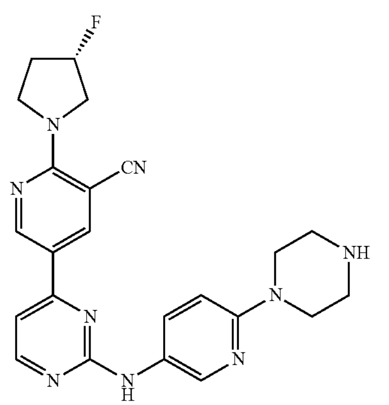 [SMILES: N#Cc1cc(-c2ccnc(Nc3ccc(N4CCNCC4)nc3)n2)cnc1N1CC[C@H](F)C1] | DMX-25* | 2-((S)-3-Fluoro-pyrrolidin-1-yl)-5-[2-(6-piperazin-1-yl-pyridin-3-ylamino)-pyrimidin-4-yl]-nicotinonitrile | Method D; Rt = 4.92 min; m/z 446 (MH⁺); yellow solid | <15 nM | <30 nM | FA |
| 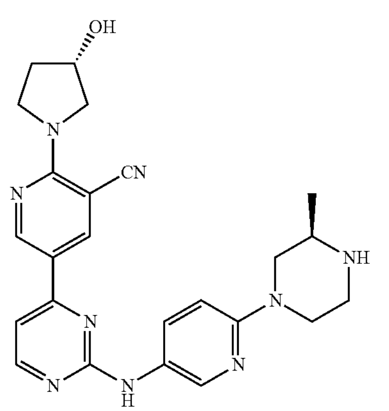 [SMILES: C[C@@H]1CN(c2ccc(Nc3nccc(-c4cnc(N5CC[C@H](O)C5)c(C#N)c4)n3)cn2)CCN1] | DMX-26* | 2-((S)-3-Hydroxy-pyrrolidin-1-yl)-5-{2-[6-((R)-3-methyl-piperazin-1-yl)-pyridin-3-ylamino]-pyrimidin-4-yl}-nicotinonitrile | Method D; Rt = 4.55 min; m/z 458 (MH⁺); yellow solid | <100 nM | <30 nM | FA |

TABLE I-continued

| Structure | Ex. No. | Name | Analytical Data | Inhibition of IKKε | Inhibition of TBK1 | Salt Form |
|---|---|---|---|---|---|---|
| 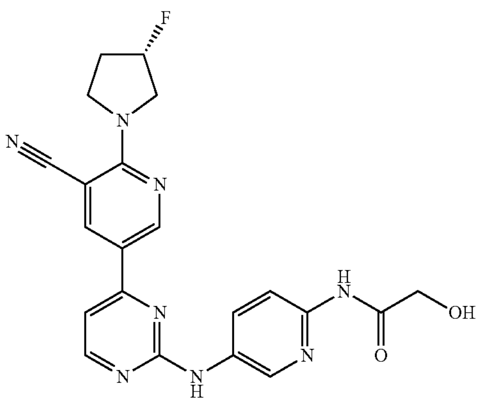 [SMILES: N#Cc1cc(-c2ccnc(Nc3ccc(NC(=O)CO)nc3)n2)cnc1N1CC[C@H](F)C1] | DMX-27 | 2-((S)-3-Fluoro-pyrrolidin-1-yl)-5-{2-[6-(2-hydroxy-ethylamino)-pyridin-3-ylamino]-pyrimidin-4-yl}-nicotinonitrile | Method D; Rt = 5.03 min; m/z 421 (MH+); yellow solid | <30 nM | <30 nM | None |
| 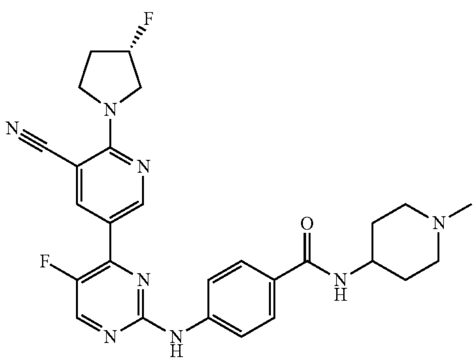 [SMILES: CN1CCC(NC(=O)c2ccc(Nc3ncc(F)c(-c4cnc(N5CC[C@H](F)C5)c(C#N)c4)n3)cc2)CC1] | DMX-28 | 4-{4-[5-Cyano-6-((S)-3-fluoro-pyrrolidin-1-yl)-pyridin-3-yl]-5-fluoro-pyrimidin-2-ylamino}-N-(1-methyl-piperidin-4-yl)-benzamide | Method D; Rt = 5.70 min; m/z 519 (MH+); yellow solid | <15 nM | <15 nM | FA |
| 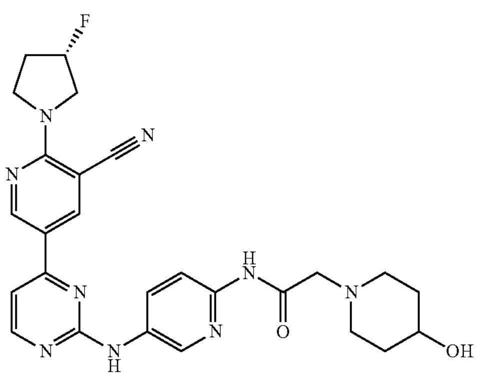 [SMILES: N#Cc1cc(-c2ccnc(Nc3ccc(NC(=O)CN4CCC(O)CC4)nc3)n2)cnc1N1CC[C@H](F)C1] | DMX-29** | N-(5-{4-[5-Cyano-6-((S)-3-fluoro-pyrrolidin-1-yl)-pyridin-3-yl]-pyrimidin-2-ylamino}-pyridin-2-yl)-2-(4-hydroxy-piperidin-1-yl)-acetamide | Method D; Rt = 5.16 min; m/z 518 (MH+); yellow solid | <30 nM | <30 nM | FA |
| 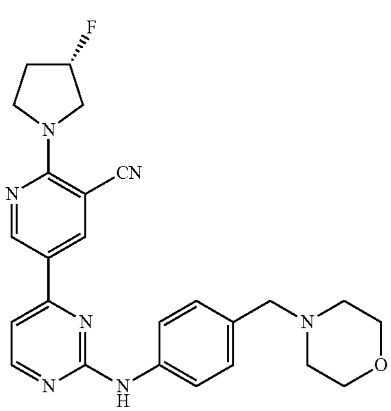 [SMILES: N#Cc1cc(-c2ccnc(Nc3ccc(CN4CCOCC4)cc3)n2)cnc1N1CC[C@H](F)C1] | DMX-30 | 2-((S)-3-Fluoro-pyrrolidin-1-yl)-5-[2-(4-morpholin-4-ylmethyl-phenylamino)-pyrimidin-4-yl]-nicotinonitrile | Method D; Rt = 5.17 min; m/z 460 (MH+); yellow solid | <15 nM | <15 nM | FA |

TABLE I-continued

| Structure | Ex. No. | Name | Analytical Data | Inhibition of IKKε | Inhibition of TBK1 | Salt Form |
|---|---|---|---|---|---|---|
| 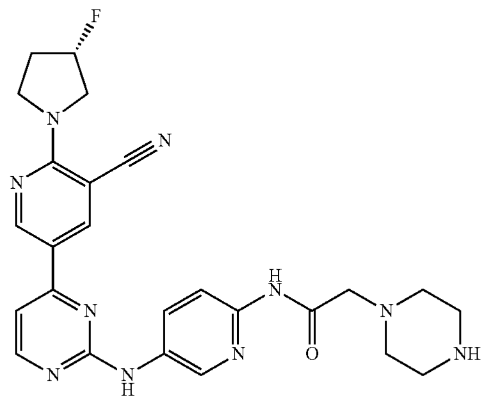 [SMILES: N#Cc1cc(-c2ccnc(Nc3ccc(NC(=O)CN4CCNCC4)nc3)n2)cnc1N1CC[C@H](F)C1] | DMX-31* | N-(5-{4-[5-Cyano-6-((S)-3-fluoro-pyrrolidin-1-yl)-pyridin-3-yl]-pyrimidin-2-ylamino}-pyridin-2-yl)-2-piperazin-1-yl-acetamide | Method D; Rt = 5.26 min; m/z 503 (MH$^+$); yellow solid | <100 nM | <30 nM | FA |
| 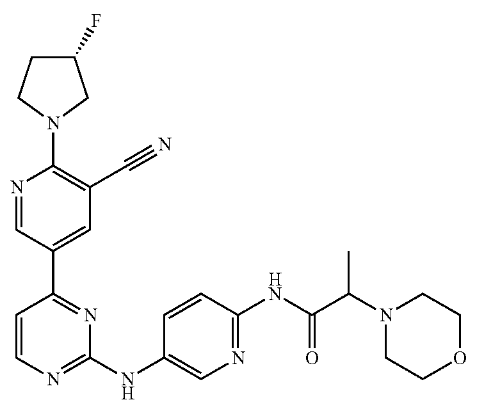 [SMILES: CC(C(=O)Nc1ccc(Nc2nccc(-c3cnc(N4CC[C@H](F)C4)c(C#N)c3)n2)cn1)N1CCOCC1] | DMX-32 | N-(5-{4-[5-Cyano-6-((S)-3-fluoro-pyrrolidin-1-yl)-pyridin-3-yl]-pyrimidin-2-ylamino}-pyridin-2-yl)-2-morpholin-4-yl-propionamide | Method D; Rt = 6.04 min; m/z 518 (MH$^+$); yellow solid | <30 nM | <30 nM | FA |
| 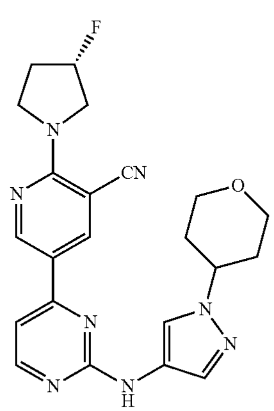 [SMILES: N#Cc1cc(-c2ccnc(Nc3cnn(C4CCOCC4)c3)n2)cnc1N1CC[C@H](F)C1] | DMX-33 | 2-((S)-3-Fluoro-pyrrolidin-1-yl)-5-{2-[1-(tetrahydro-pyran-4-yl)-1H-pyrazol-4-ylamino]-pyrimidin-4-yl}-nicotinonitrile | Method D; Rt = 7.36 min; m/z 435 (MH$^+$); yellow solid | <15 nM | <15 nM | None |

TABLE I-continued

| Structure | Ex. No. | Name | Analytical Data | Inhibition of IKKε | Inhibition of TBK1 | Salt Form |
|---|---|---|---|---|---|---|
| 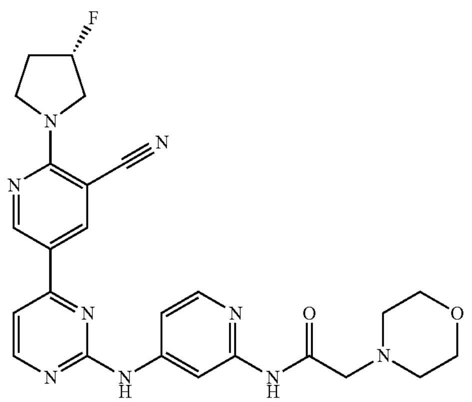 [SMILES: N#Cc1cc(-c2ccnc(Nc3ccnc(NC(=O)CN4CCOCC4)c3)n2)cnc1N1CC[C@H](F)C1] | DMX-34 | N-(4-{4-[5-Cyano-6-((S)-3-fluoro-pyrrolidin-1-yl)-pyridin-3-yl]-pyrimidin-2-ylamino}-pyridin-2-yl)-2-morpholin-4-yl-acetamide | Method D; Rt = 5.61 min; m/z 504 (MH+); yellow solid | <30 nM | <30 nM | FA |
| 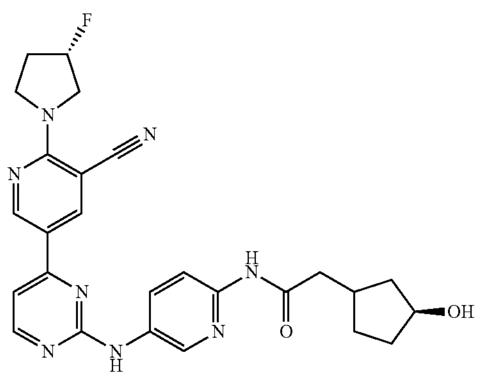 [SMILES: N#Cc1cc(-c2ccnc(Nc3ccc(NC(=O)CC4CC[C@H](O)C4)nc3)n2)cnc1N1CC[C@H](F)C1] | DMX-35 | N-(5-{4-[5-Cyano-6-((S)-3-fluoro-pyrrolidin-1-yl)-pyridin-3-yl]-pyrimidin-2-ylamino}-pyridin-2-yl)-2-((S)-3-hydroxy-pyrrolidin-1-yl)-acetamide | Method D; Rt = 5.14 min; m/z 504 (MH+); yellow solid | <30 nM | <100 nM | FA |
| 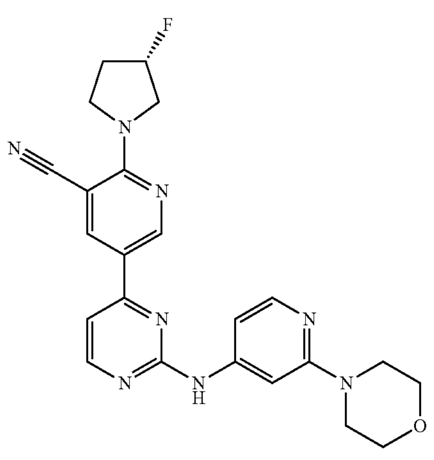 [SMILES: N#Cc1cc(-c2ccnc(Nc3ccnc(N4CCOCC4)c3)n2)cnc1N1CC[C@H](F)C1] | DMX-61 | 2-((S)-3-Fluoro-pyrrolidin-1-yl)-5-[2-(2-morpholin-4-yl-pyridin-4-ylamino)-pyrimidin-4-yl]-nicotinonitrile | Method D; Rt = 5.45 min; m/z 447 (MH+); white solid | <15 nM | <15 nM | None |

TABLE I-continued

| Structure | Ex. No. | Name | Analytical Data | Inhibition of IKKε | Inhibition of TBK1 | Salt Form |
|---|---|---|---|---|---|---|
| 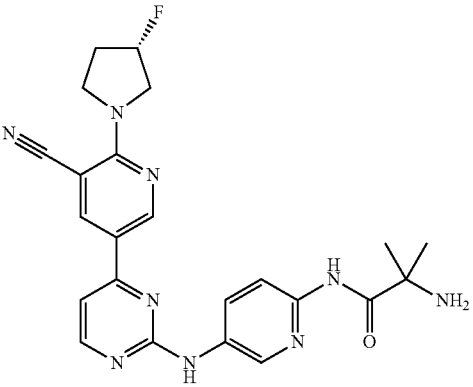 [SMILES: CC(C)(N)C(=O)Nc1ccc(Nc2nccc(-c3cnc(N4CC[C@H](F)C4)c(C#N)c3)n2)cn1] | DMX-62* | 2-Amino-N-(5-{4-[5-cyano-6-((S)-3-fluoro-pyrrolidin-1-yl)-pyridin-3-yl]-pyrimidin-2-ylamino}-pyridin-2-yl)-2-methyl-propionamide | Method D; Rt = 5.35 min; m/z 462 (MH+); white solid | <30 nM | <100 nM | FA |
| 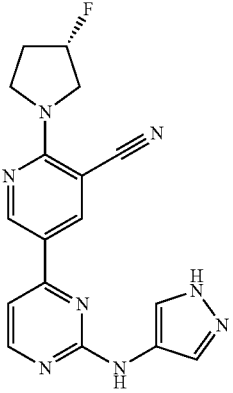 [SMILES: N#Cc1cc(-c2ccnc(Nc3cn[nH]c3)n2)cnc1N1CC[C@H](F)C1] | DMX-63† | 2-((S)-3-Fluoro-pyrrolidin-1-yl)-5-[2-(1H-pyrazol-4-ylamino)-pyrimidin-4-yl]-nicotinonitrile | Method D; Rt = 6.84 min; m/z 351 (MH+); white solid | <15 nM | <15 nM | None |
| 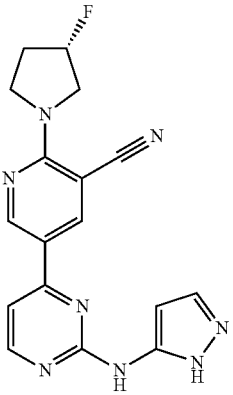 [SMILES: N#Cc1cc(-c2ccnc(Nc3ccn[nH]3)n2)cnc1N1CC[C@H](F)C1] | DMX-64* | 2-((S)-3-Fluoro-pyrrolidin-1-yl)-5-[2-(2H-pyrazol-3-ylamino)-pyrimidin-4-yl]-nicotinonitrile | Method D; Rt = 6.54 min; m/z 351 (MH+); white solid | <100 nM | <1 μM | None |

TABLE I-continued

| Structure | Ex. No. | Name | Analytical Data | Inhibition of IKKε | Inhibition of TBK1 | Salt Form |
|---|---|---|---|---|---|---|
| 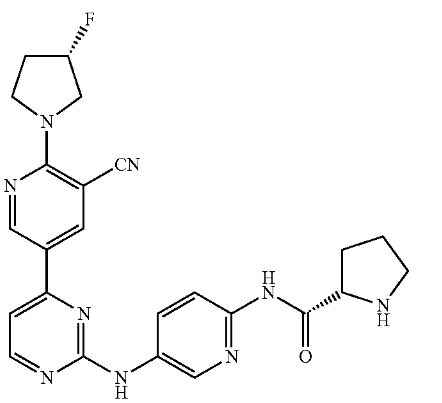 | DMX-65* | (S)-Pyrrolidine-2-carboxylic acid (5-{4-[5-cyano-6-((S)-3-fluoro-pyrrolidin-1-yl)-pyridin-3-yl]-pyrimidin-2-ylamino}-pyridin-2-yl)-amide | Method D; Rt = 5.28 min; m/z 474 (MH$^+$); white solid | <30 nM | <100 nM | None |
| 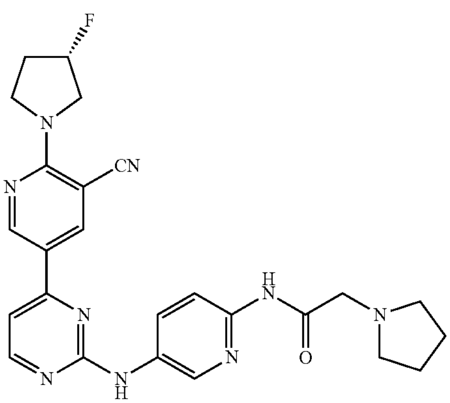 [SMILES: N#Cc1cc(-c2ccnc(Nc3ccc(NC(=O)CN4CCCC4)nc3)n2)cnc1N1CC[C@H](F)C1] | DMX-66 | N-(5-{4-[5-Cyano-6-((S)-3-fluoro-pyrrolidin-1-yl)-pyridin-3-yl]-pyrimidin-2-ylamino}-pyridin-2-yl)-2-pyrrolidin-1-yl-acetamide | Method D; Rt = 5.21 min; m/z 488 (MH$^+$); yellow solid | <100 nM | <30 nM | None |
| 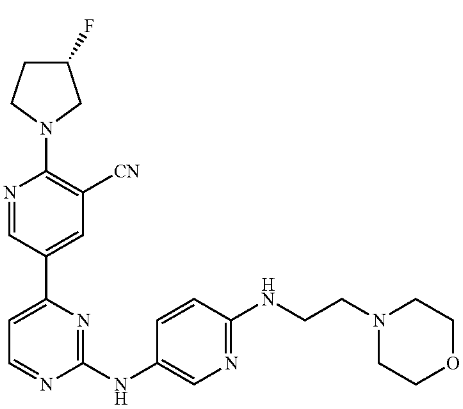 [SMILES: N#Cc1cc(-c2ccnc(Nc3ccc(NCCN4CCOCC4)nc3)n2)cnc1N1CC[C@H](F)C1] | DMX-67 | 2-((S)-3-Fluoro-pyrrolidin-1-yl)-5-{2-[6-(2-morpholin-4-yl-ethylamino)-pyridin-3-ylamino]-pyrimidin-4-yl}-nicotinonitrile | Method D; Rt = 4.56 min; m/z 490 (MH$^+$); brown solid | <15 nM | <30 nM | FA |

TABLE I-continued

| Structure | Ex. No. | Name | Analytical Data | Inhibition of IKKε | Inhibition of TBK1 | Salt Form |
|---|---|---|---|---|---|---|
| 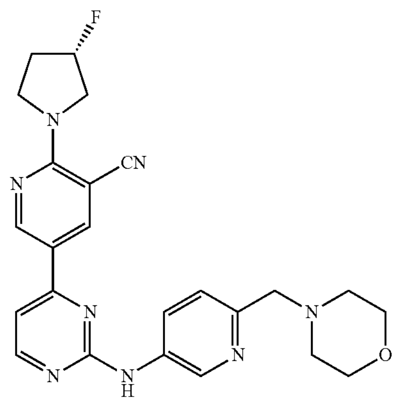 | DMX-68 | 2-((S)-3-Fluoro-pyrrolidin-1-yl)-5-[2-(6-morpholin-4-ylmethyl-pyridin-3-ylamino)-pyrimidin-4-yl]-nicotinonitrile | Method D; Rt = 5.30 min; m/z 461 (MH+); yellow solid | <15 nM | <15 nM | FA |
| 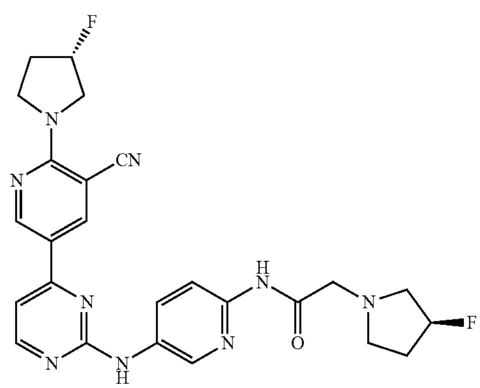 [SMILES: N#Cc1cc(-c2ccnc(Nc3ccc(NC(=O)CN4CC[C@H](F)C4)nc3)n2)cnc1N1CC[C@H](F)C1] | DMX-69 | N-(5-{4-[5-Cyano-6-((S)-3-fluoro-pyrrolidin-1-yl)-pyridin-3-yl]-pyrimidin-2-ylamino}-pyridin-2-yl)-2-((S)-3-fluoro-pyrrolidin-1-yl)-acetamide | Method D; Rt = 5.52 min; m/z 506 (MH+); white solid | <30 nM | <100 nM | None |
| 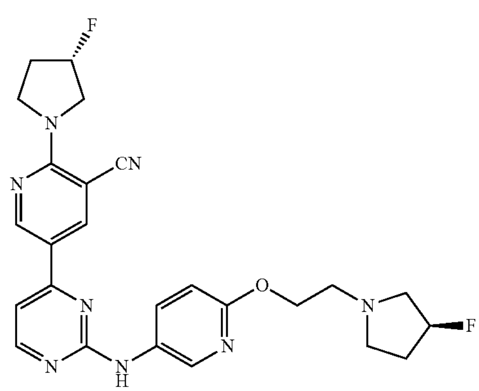 [SMILES: N#Cc1cc(-c2ccnc(Nc3ccc(OCCN4CC[C@H](F)C4)nc3)n2)cnc1N1CC[C@H](F)C1] | DMX-70 | 2-((S)-3-Fluoro-pyrrolidin-1-yl)-5-(2-{6-[2-((S)-3-fluoro-pyrrolidin-1-yl)-ethoxy]-pyridin-3-ylamino}-pyrimidin-4-yl)-nicotinonitrile | Method D; Rt = 5.45 min; m/z 493 (MH+); white solid | <100 nM | <100 nM | FA |

TABLE I-continued

| Structure | Ex. No. | Name | Analytical Data | Inhibition of IKKε | Inhibition of TBK1 | Salt Form |
|---|---|---|---|---|---|---|
| 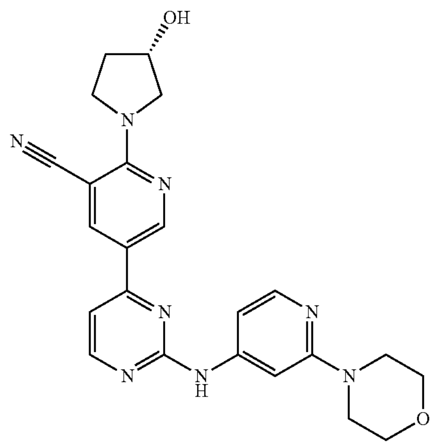 [SMILES: N#Cc1cc(-c2ccnc(Nc3ccnc(N4CCOCC4)c3)n2)cnc1N1CC[C@H](O)C1] | DMX-71 | 2-((S)-3-Hydroxy-pyrrolidin 1-yl)-5-[2-(2-morpholin-4-yl-pyridin-4-ylamino)-pyrimidin-4-yl]-nicotinonitrile | Method D; Rt = 5.22 min; m/z 445 (MH+); white solid | <30 nM | <30 nM | FA |
| 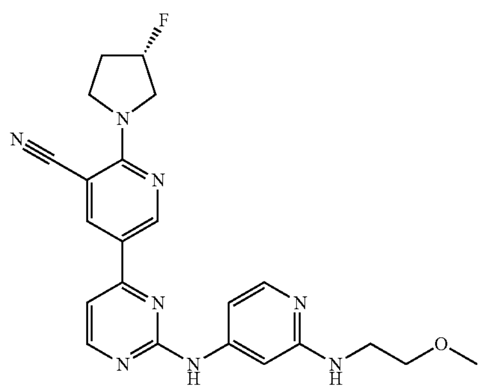 [SMILES: COCCNc1cc(Nc2nccc(-c3cnc(N4CC[C@H](F)C4)c(C#N)c3)n2)ccn1] | DMX-72 | 2-((S)-3-Fluoro-pyrrolidin-1-yl)-5-{2-[2-(2-methoxy-ethylamino)-pyridin-4-ylamino]-pyrimidin-4-yl}-nicotinonitrile | Method D; Rt = 5.70 min; m/z 435 (MH+); white solid | <30 nM | <15 nM | None |
| 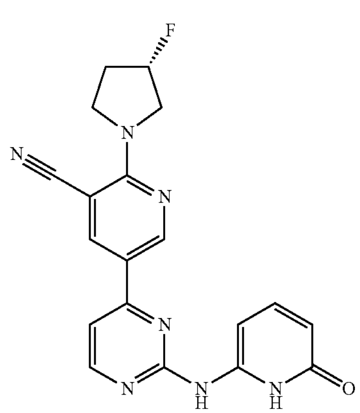 [SMILES: N#Cc1cc(-c2ccnc(Nc3cccc(=O)[nH]3)n2)cnc1N1CC[C@H](F)C1] | DMX-73 | 2-((S)-3-Fluoro-pyrrolidin-1-yl)-5-[2-(6-oxo-1,6-dihydro-pyridin-2-ylamino)-pyrimidin-4-yl]-nicotinonitrile | Method D; Rt = 7.36 min; m/z 378 (MH+); cream solid | <1 μM | <1 μM | None |

TABLE I-continued

| Structure | Ex. No. | Name | Analytical Data | Inhibition of IKKε | Inhibition of TBK1 | Salt Form |
|---|---|---|---|---|---|---|
| 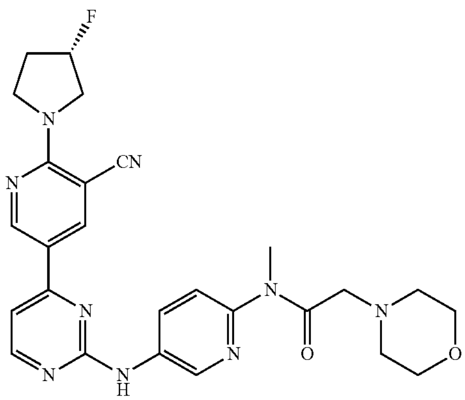 [SMILES: CN(C(=O)CN1CCOCC1)c1ccc(Nc2nccc(-c3cnc(N4CC[C@H](F)C4)c(C#N)c3)n2)cn1] | DMX-74 | N-(5-{4-[5-Cyano-6-((S)-3-fluoro-pyrrolidin-1-yl)-pyridin-3-yl]-pyrimidin-2-ylamino}-pyridin-2-yl)-N-methyl-2-morpholin-4-yl-acetamide | Method D; Rt = 5.56 min; m/z 518 (MH+); yellow solid | <100 nM | <100 nM | FA |
| 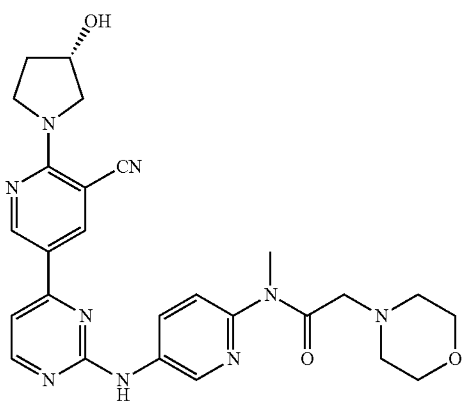 [SMILES: CN(C(=O)CN1CCOCC1)c1ccc(Nc2nccc(-c3cnc(N4CC[C@H](O)C4)c(C#N)c3)n2)cn1] | DMX-75 | N-(5-{4-[5-Cyano-6-((S)-3-hydroxy-pyrrolidin-1-yl)-pyridin-3-yl]-pyrimidin-2-ylamino}-pyridin-2-yl)-N-methyl-2-morpholin-4-yl-acetamide | Method D; Rt = 5.10 min; m/z 516 (MH+); yellow solid | <1 μM | <1 μM | FA |
| 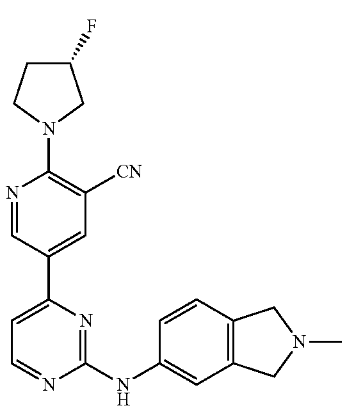 [SMILES: CN1Cc2ccc(Nc3nccc(-c4cnc(N5CC[C@H](F)C5)c(C#N)c4)n3)cc2C1] | DMX-76 | 2-((S)-3-Fluoro-pyrrolidin-1-yl)-5-[2-(2-methyl-2,3-dihydro-1H-isoindol-5-ylamino)-pyrimidin-4-yl]-nicotinonitrile | Method D; Rt = 5.24 min; m/z 416 (MH+); yellow solid | <15 nM | <15 nM | FA |

TABLE I-continued

| Structure | Ex. No. | Name | Analytical Data | Inhibition of IKKε | Inhibition of TBK1 | Salt Form |
|---|---|---|---|---|---|---|
| 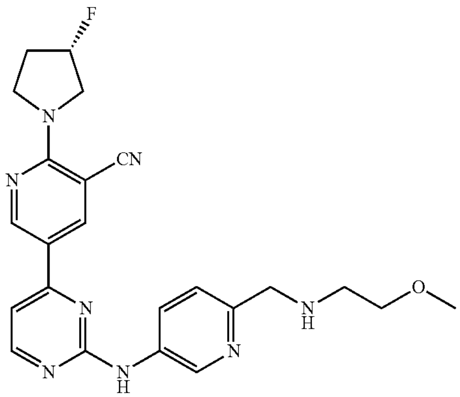 [SMILES: COCCNCc1ccc(Nc2nccc(-c3cnc(N4CC[C@H](F)C4)c(C#N)c3)n2)cn1] | DMX-77* | 2-((S)-3-Fluoro-pyrrolidin-1-yl)-5-(2-{6-[(2-methoxy-ethylamino)-methyl]-pyridin-3-ylamino}-pyrimidin-4-yl)-nicotinonitrile | Method D; Rt = 5.43 min; m/z 449 (MH$^+$); yellow solid | <100 nM | <100 nM | TFA |
| 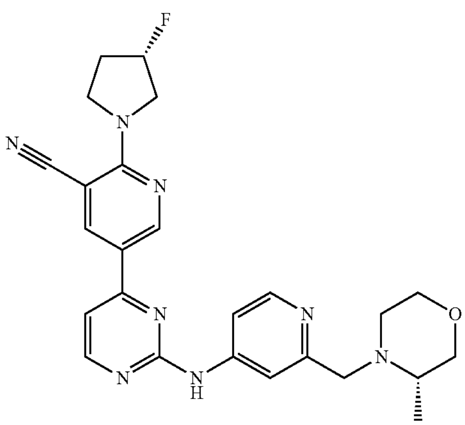 [SMILES: C[C@H]1COCCN1Cc1cc(Nc2nccc(-c3cnc(N4CC[C@H](F)C4)c(C#N)c3)n2)ccn1] | DMX-78 | 2-((S)-3-Fluoro-pyrrolidin-1-yl)-5-{2-[2-((S)-3-methyl-morpholin-4-ylmethyl)-pyridin-4-ylamino]-pyrimidin-4-yl}-nicotinonitrile | Method D; Rt = 5.65 min; m/z 475 (MH$^+$); white solid | <30 nM | <15 nM | None |
| 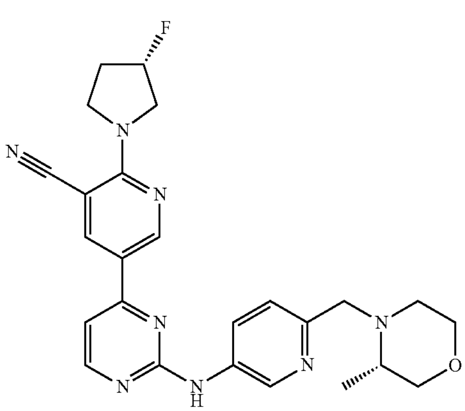 [SMILES: C[C@H]1COCCN1Cc1ccc(Nc2nccc(-c3cnc(N4CC[C@H](F)C4)c(C#N)c3)n2)cn1] | DMX-79 | 2-((S)-3-Fluoro-pyrrolidin-1-yl)-5-{2-[6-((S)-3-methyl-morpholin-4-ylmethyl)-pyridin-3-ylamino]-pyrimidin-4-yl}-nicotinonitrile | Method D; Rt = 5.46 min; m/z 475 (MH$^+$); yellow solid | <100 nM | <30 nM | None |

TABLE I-continued

| Structure | Ex. No. | Name | Analytical Data | Inhibition of IKKε | Inhibition of TBK1 | Salt Form |
|---|---|---|---|---|---|---|
| 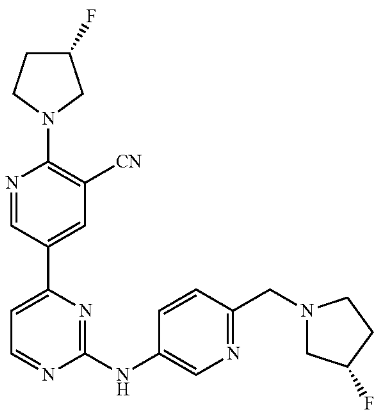 [SMILES: N#Cc1cc(-c2ccnc(Nc3ccc(CN4CC[C@H](F)C4)nc3)n2)cnc1N1CC[C@H](F)C1] | DMX-80 | 2-((S)-3-Fluoro-pyrrolidin-1-yl)-5-{2-[6-((S)-3-fluoro-pyrrolidin-1-ylmethyl)-pyridin-3-ylamino]-pyrimidin-4-yl}-nicotinonitrile | Method D; Rt = 5.39 min; m/z 463 (MH+); yellow solid | <15 nM | <30 nM | FA |
| 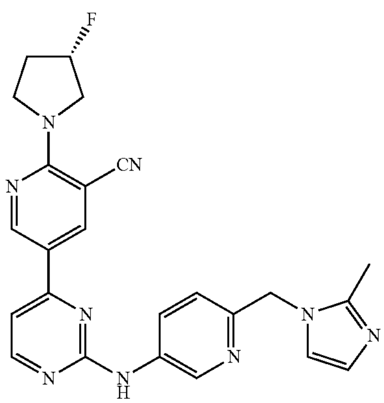 [SMILES: Cc1nccn1Cc1ccc(Nc2nccc(-c3cnc(N4CC[C@H](F)C4)c(C#N)c3)n2)cn1] | DMX-81 | 2-((S)-3-Fluoro-pyrrolidin-1-yl)-5-{2-[6-(2-methyl-imidazol-1-ylmethyl)-pyridin-3-ylamino]-pyrimidin-4-yl}-nicotinonitrile | Method D; Rt = 5.38 min; m/z 456 (MH+); white solid | <30 nM | <30 nM | FA |
| 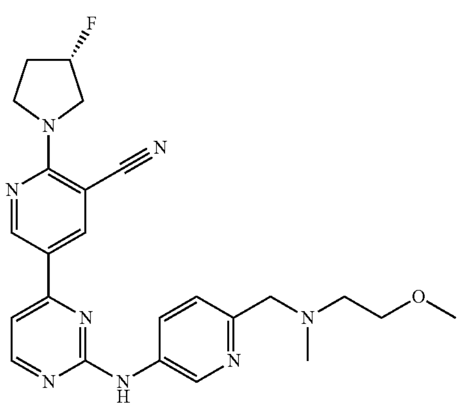 [SMILES: COCCN(C)Cc1ccc(Nc2nccc(-c3cnc(N4CC[C@H](F)C4)c(C#N)c3)n2)cn1] | DMX-82 | 2-((S)-3-Fluoro-pyrrolidin-1-yl)-5-[2-(6-{[(2-methoxy-ethyl)-methyl-amino]-methyl}-pyridin-3-ylamino)-pyrimidin-4-yl]-nicotinonitrile | Method D; Rt = 5.46 min; m/z 463 (MH+); yellow solid | <100 nM | <100 nM | FA |

TABLE I-continued

| Structure | Ex. No. | Name | Analytical Data | Inhibition of IKKε | Inhibition of TBK1 | Salt Form |
|---|---|---|---|---|---|---|
| 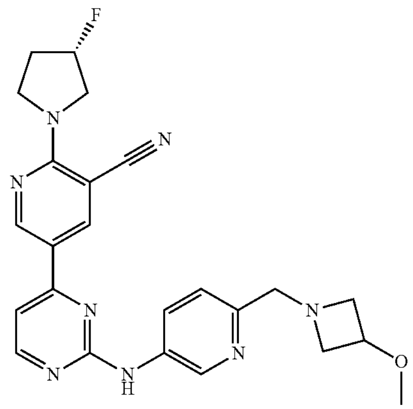 [SMILES: COC1CN(Cc2ccc(Nc3nccc(-c4cnc(N5CC[C@H](F)C5)c(C#N)c4)n3)cn2)C1] | DMX-83 | 2-((S)-3-Fluoro-pyrrolidin-1-yl)-5-{2-[6-(3-methoxy-azetidin-1-ylmethyl)-pyridin-3-ylamino]-pyrimidin-4-yl}-nicotinonitrile | Method D; Rt = 5.41 min; m/z 461 (MH+); yellow solid | <30 nM | <30 nM | None |
| 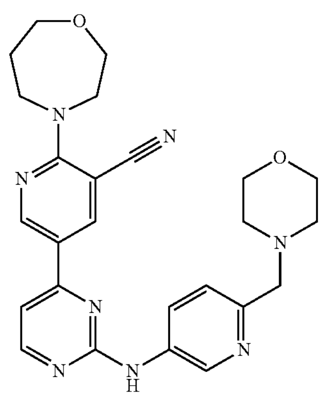 [SMILES: N#Cc1cc(-c2ccnc(Nc3ccc(CN4CCOCC4)nc3)n2)cnc1N1CCCOCC1] | DMX-84 | 5-[2-(6-Morpholin-4-ylmethyl-pyridin-3-ylamino)-pyrimidin-4-yl]-2-[1,4]oxazepan-4-yl-nicotinonitrile | Method D; Rt = 5.34 min; m/z 473 (MH+); brown solid | <100 nM | <100 nM | FA |
| 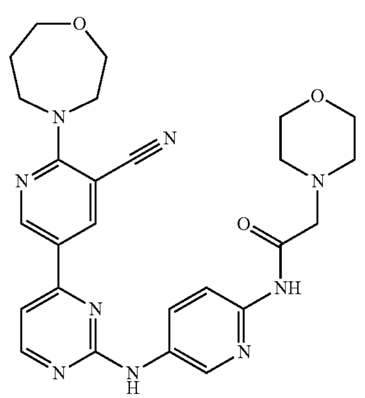 [SMILES: N#Cc1cc(-c2ccnc(Nc3ccc(NC(=O)CN4CCOCC4)nc3)n2)cnc1N1CCCOCC1] | DMX-85 | N-{5-[4-(5-Cyano-6-[1,4]oxazepan-4-yl-pyridin-3-yl)-pyrimidin-2-ylamino]-pyridin-2-yl}-2-morpholin-4-yl-acetamide | Method D; Rt = 6.05 min; m/z 516 (MH+); brown solid | <100 nM | <100 nM | FA |
| 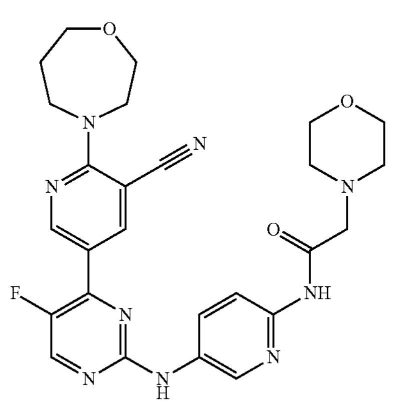 [SMILES: N#Cc1cc(-c2nc(Nc3ccc(NC(=O)CN4CCOCC4)nc3)ncc2F)cnc1N1CCCOCC1] | DMX-86 | N-{5-[4-(5-Cyano-6-[1,4]oxazepan-4-yl-pyridin-3-yl)-5-fluoro-pyrimidin-2-ylamino]-pyridin-2-yl}-2-morpholin-4-yl-acetamide | Method D; Rt = 6.54 min; m/z 534 (MH+); brown solid | <1 μM | <100 nM | FA |

TABLE I-continued

| Structure | Ex. No. | Name | Analytical Data | Inhibition of IKKε | Inhibition of TBK1 | Salt Form |
|---|---|---|---|---|---|---|
| 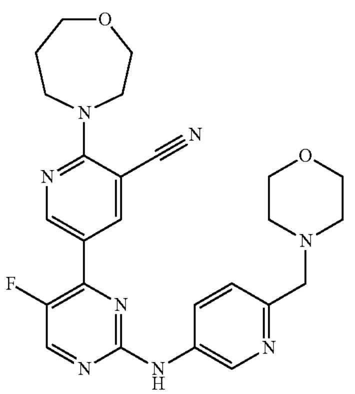 [SMILES: N#Cc1cc(-c2nc(Nc3ccc(CN4CCOCC4)nc3)ncc2F)cnc1N1CCCOCC1] | DMX-87 | 5-[5-Fluoro-2-(6-morpholin-4-ylmethyl-pyridin-3-ylamino)-pyrimidin-4-yl]-2-[1,4]oxazepan-4-yl-nicotinonitrile | Method D; Rt = 5.63 min; m/z 491 (MH+); yellow solid | <100 nM | <100 nM | FA |
| 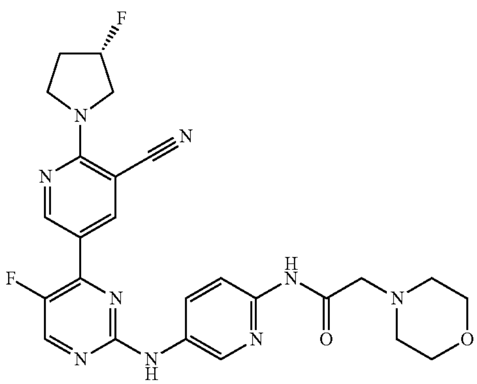 [SMILES: N#Cc1cc(-c2nc(Nc3ccc(NC(=O)CN4CCOCC4)nc3)ncc2F)cnc1N1CC[C@H](F)C1] | DMX-88 | N-(5-{4-[5-Cyano-6-((S)-3-fluoro-pyrrolidin-1-yl)-pyridin-3-yl]-5-fluoro-pyrimidin-2-ylamino}-pyridin-2-yl)-2-morpholin-4-yl-acetamide | Method D; Rt = 6.57 min; m/z 522 (MH+); yellow solid | <100 nM | <100 nM | FA |
| 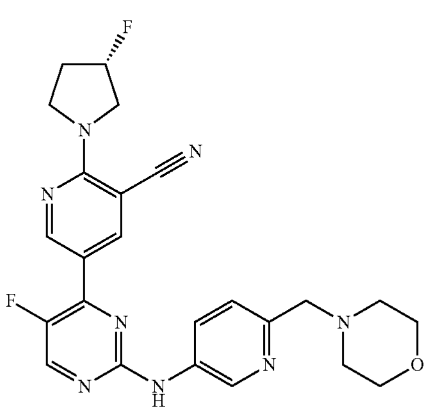 [SMILES: N#Cc1cc(-c2nc(Nc3ccc(CN4CCOCC4)nc3)ncc2F)cnc1N1CC[C@H](F)C1] | DMX-89 | 5-[5-Fluoro-2-(6-morpholin-4-ylmethyl-pyridin-3-ylamino)-pyrimidin-4-yl]-2-((S)-3-fluoro-pyrrolidin-1-yl)-nicotinonitrile | Method D; Rt = 5.66 min; m/z 479 (MH+); orange solid | <30 nM | <15 nM | FA |

TABLE I-continued

| Structure | Ex. No. | Name | Analytical Data | Inhibition of IKKε | Inhibition of TBK1 | Salt Form |
|---|---|---|---|---|---|---|
| 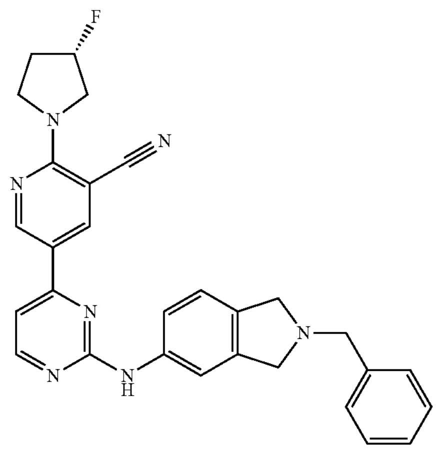 [SMILES: N#Cc1cc(-c2ccnc(Nc3ccc4c(c3)CN(Cc3ccccc3)C4)n2)cnc1N1CC[C@H](F)C1] | DMX-90 | 5-[2-(2-Benzyl-2,3-dihydro-1H-isoindol-5-ylamino)-pyrimidin-4-yl]-2-((S)-3-fluoro-pyrrolidin-1-yl)-nicotinonitrile | MeOH-FA; Rt = 2.36 min; m/z 492 (MH+); tan solid | ND | ND | None |
| 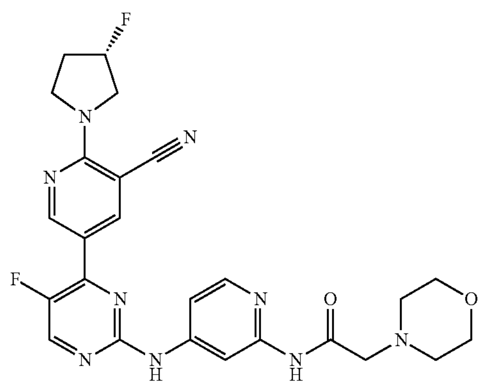 [SMILES: N#Cc1cc(-c2nc(Nc3ccnc(NC(=O)CN4CCOCC4)c3)ncc2F)cnc1N1CC[C@H](F)C1] | DMX-91 | N-(4-{4-[5-Cyano-6-((S)-3-fluoro-pyrrolidin-1-yl)-pyridin-3-yl]-5-fluoro-pyrimidin-2-ylamino}-pyridin-2-yl)-2-morpholin-4-yl-acetamide | Method D; Rt = 6.16 min; m/z 452 (MH+); yellow solid | <100 nM | <30 nM | FA |
| 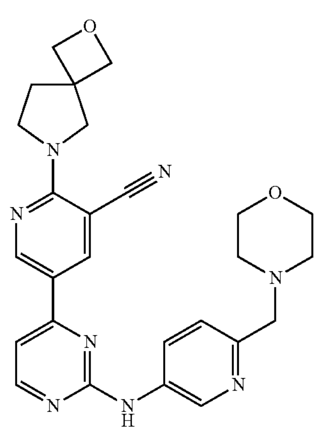 [SMILES: N#Cc1cc(-c2ccnc(Nc3ccc(CN4CCOCC4)nc3)n2)cnc1N1CCC2(COC2)C1] | DMX-92 | 5-[2-(6-Morpholin-4-ylmethyl-pyridin-3-ylamino)-pyrimidin-4-yl]-2-(2-oxa-6-aza-spiro[3.4]oct-6-yl)-nicotinonitrile | Method D; Rt = 5.15 min; m/z 485 (MH+); brown solid | <30 nM | <100 nM | FA |

TABLE I-continued

| Structure | Ex. No. | Name | Analytical Data | Inhibition of IKKε | Inhibition of TBK1 | Salt Form |
|---|---|---|---|---|---|---|
| 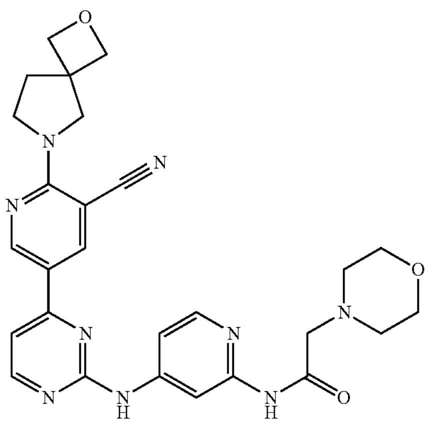 [SMILES: N#Cc1cc(-c2ccnc(Nc3ccnc(NC(=O)CN4CCOCC4)c3)n2)cnc1N1CCC2(COC2)C1] | DMX-93 | N-(4-{4-[5-Cyano-6-(2-oxa-6-aza-spiro[3.4]oct-6-yl)-pyridin-3-yl]-pyrimidin-2-ylamino}-pyridin-2-yl)-2-morpholin-4-yl-acetamide | Method D; Rt = 5.64 min; m/z 528 (MH+); beige solid | <100 nM | <100 nM | None |
| 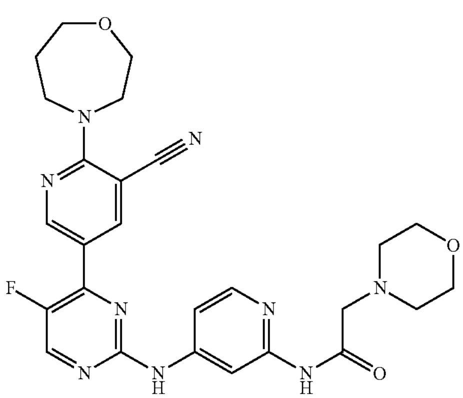 [SMILES: N#Cc1cc(-c2nc(Nc3ccnc(NC(=O)CN4CCOCC4)c3)ncc2F)cnc1N1CCCOCC1] | DMX-94 | N-{4-[4-(5-Cyano-6-[1,4]oxazepan-4-yl-pyridin-3-yl)-5-fluoro-pyrimidin-2-ylamino]-pyridin-2-yl}-2-morpholin-4-yl-acetamide | Method D; Rt = 6.30 min; m/z 534 (MH+); brown solid | <1 µM | <100 nM | FA |
| 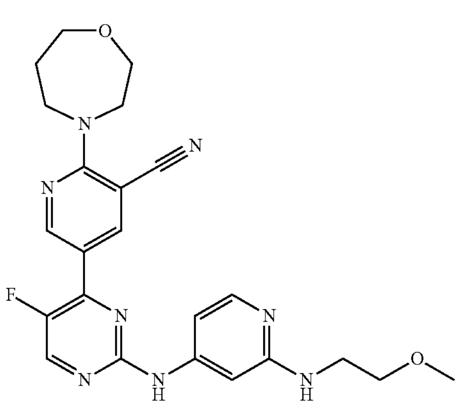 [SMILES: COCCNc1cc(Nc2ncc(F)c(-c3cnc(N4CCCOCC4)c(C#N)c3)n2)ccn1] | DMX-95 | 5-{5-Fluoro-2-[2-(2-methoxy-ethylamino)-pyridin-4-ylamino]-pyrimidin-4-yl}-2-[1,4]oxazepan-4-yl-nicotinonitrile | Method D; Rt = 6.06 min; m/z 465 (MH+); cream solid | <1 µM | <100 nM | None |

TABLE I-continued

| Structure | Ex. No. | Name | Analytical Data | Inhibition of IKKε | Inhibition of TBK1 | Salt Form |
|---|---|---|---|---|---|---|
| 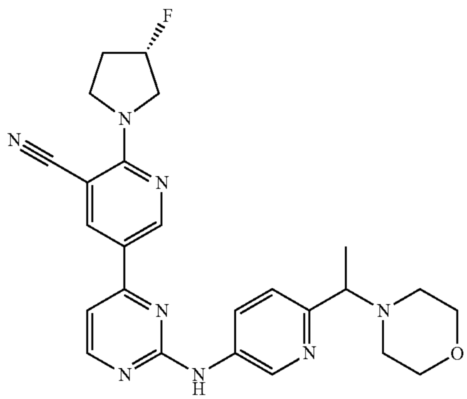 [SMILES: CC(c1ccc(Nc2nccc(-c3cnc(N4CC[C@H](F)C4)c(C#N)c3)n2)cn1)N1CCOCC1] | DMX-96 | 2-((S)-3-Fluoro-pyrrolidin-1-yl)-5-{2-[6-(1-morpholin-4-yl-ethyl)-pyridin-3-ylamino]-pyrimidin-4-yl}-nicotinonitrile | Method D; Rt = 5.49 min; m/z 475 (MH$^+$); white solid | <30 nM | <15 nM | None |
| 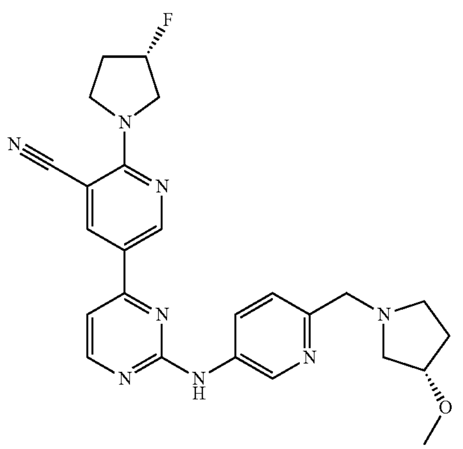 [SMILES: CO[C@H]1CCN(Cc2ccc(Nc3nccc(-c4cnc(N5CC[C@H](F)C5)c(C#N)c4)n3)cn2)C1] | DMX-97 | 2-((S)-3-Fluoro-pyrrolidin-1-yl)-5-{2-[6-((S)-3-methoxy-pyrrolidin-1-ylmethyl)-pyridin-3-ylamino]-pyrimidin-4-yl}-nicotinonitrile | Method D; Rt = 5.74 min; m/z 475 (MH$^+$); grey solid | <100 nM | <30 nM | None |
| 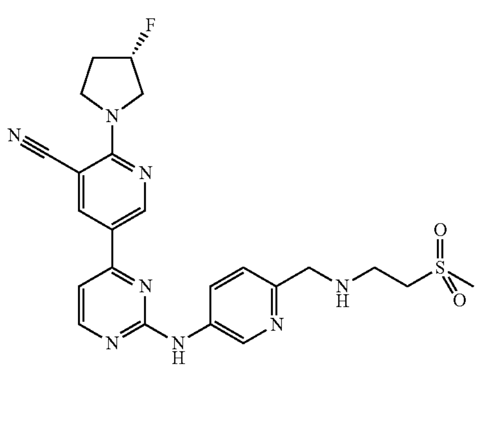 [SMILES: CS(=O)(=O)CCNCc1ccc(Nc2nccc(-c3cnc(N4CC[C@H](F)C4)c(C#N)c3)n2)cn1] | DMX-98* | 2-((S)-3-Fluoro-pyrrolidin-1-yl)-5-(2-{6-[(2-methanesulfonyl-ethylamino)-methyl]-pyridin-3-ylamino}-pyrimidin-4-yl)-nicotinonitrile | Method D; Rt = 5.51 min; m/z 497 (MH$^+$); brown solid | <30 nM | <30 nM | None |

TABLE I-continued

| Structure | Ex. No. | Name | Analytical Data | Inhibition of IKKε | Inhibition of TBK1 | Salt Form |
|---|---|---|---|---|---|---|
| 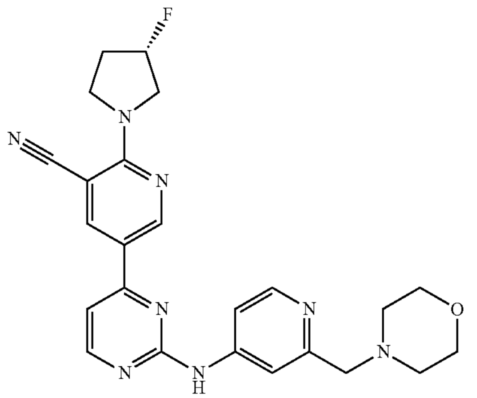 [SMILES: N#Cc1cc(-c2ccnc(Nc3ccnc(CN4CCOCC4)c3)n2)cnc1N1CC[C@H](F)C1] | DMX-99 | 2-((S)-3-Fluoro-pyrrolidin-1-yl)-5-[2-(2-morpholin-4-ylmethyl-pyridin-4-ylamino)-pyrimidin-4-yl]-nicotinonitrile | Method D; Rt = 5.75 min; m/z 461 (MH+); white solid | <30 nM | <15 nM | None |
| 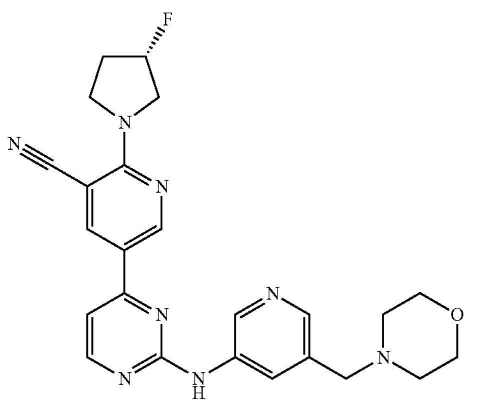 [SMILES: N#Cc1cc(-c2ccnc(Nc3cncc(CN4CCOCC4)c3)n2)cnc1N1CC[C@H](F)C1] | DMX-100 | 2-((S)-3-Fluoro-pyrrolidin-1-yl)-5-[2-(5-morpholin-4-ylmethyl-pyridin-3-ylamino)-pyrimidin-4-yl]-nicotinonitrile | Method D; Rt = 5.60 min; m/z 461 (MH+); white solid | <30 nM | <30 nM | None |
| 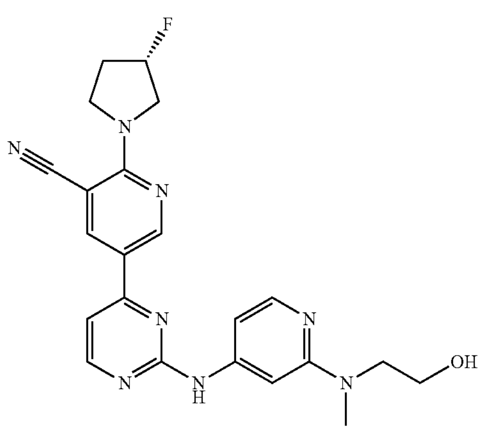 [SMILES: CN(CCO)c1cc(Nc2nccc(-c3cnc(N4CC[C@H](F)C4)c(C#N)c3)n2)ccn1] | DMX-101 | 2-((S)-3-Fluoro-pyrrolidin-1-yl)-5-(2-{2-[(2-hydroxy-ethyl)-methyl-amino]-pyridin-4-ylamino}-pyrimidin-4-yl)-nicotinonitrile | Method D; Rt = 5.71 min; m/z 435 (MH+); white solid | <30 nM | <30 nM | None |

TABLE I-continued

| Structure | Ex. No. | Name | Analytical Data | Inhibition of IKKε | Inhibition of TBK1 | Salt Form |
|---|---|---|---|---|---|---|
| 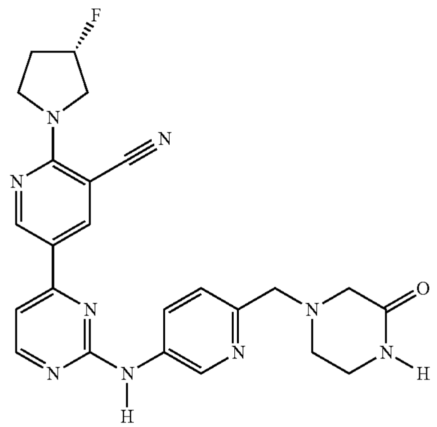 [SMILES: N#Cc1cc(-c2ccnc(Nc3ccc(CN4CCNC(=O)C4)nc3)n2)cnc1N1CC[C@H](F)C1] | DMX-102 | 2-((S)-3-Fluoro-pyrrolidin-1-yl)-5-{2-[6-(3-oxo-piperazin-1-ylmethyl)-pyridin-3-ylamino]-pyrimidin-4-yl}-nicotinonitrile | Method D; Rt = 6.19 min; m/z 474 (MH+); off-white solid | <15 nM | <15 nM | None |
| 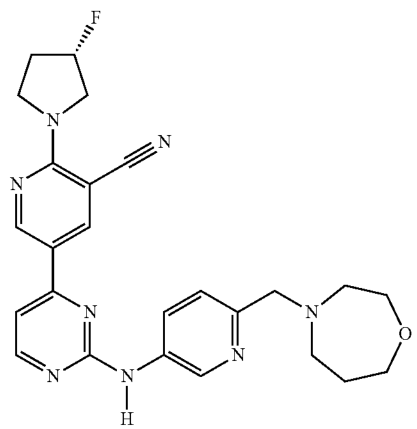 [SMILES: N#Cc1cc(-c2ccnc(Nc3ccc(CN4CCCOCC4)nc3)n2)cnc1N1CC[C@H](F)C1] | DMX-103 | 2-((S)-3-Fluoro-pyrrolidin-1-yl)-5-[2-(6-[1,4]oxazepan-4-ylmethyl-pyridin-3-ylamino)-pyrimidin-4-yl]-nicotinonitrile | Method D; Rt = 5.64 min; m/z 475 (MH+); off-white solid | <100 nM | <100 nM | None |
| 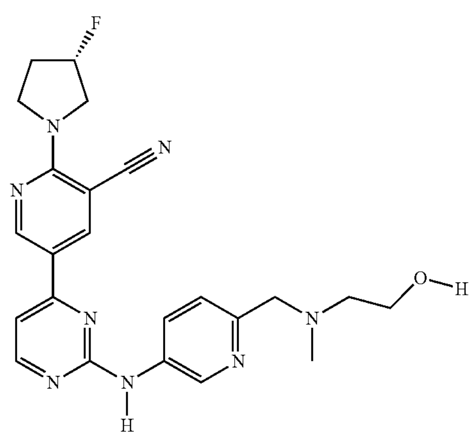 [SMILES: CN(CCO)Cc1ccc(Nc2nccc(-c3cnc(N4CC[C@H](F)C4)c(C#N)c3)n2)cn1] | DMX-104 | 2-((S)-3-Fluoro-pyrrolidin-1-yl)-5-[2-(6-{[(2-hydroxy-ethyl)-methyl-amino]-methyl}-pyridin-3-ylamino)-pyrimidin-4-yl]-nicotinonitrile | Method D; Rt = 5.52 min; m/z 449 (MH+); off-white solid | <100 nM | <100 nM | None |

TABLE I-continued

| Structure | Ex. No. | Name | Analytical Data | Inhibition of IKKε | Inhibition of TBK1 | Salt Form |
|---|---|---|---|---|---|---|
| 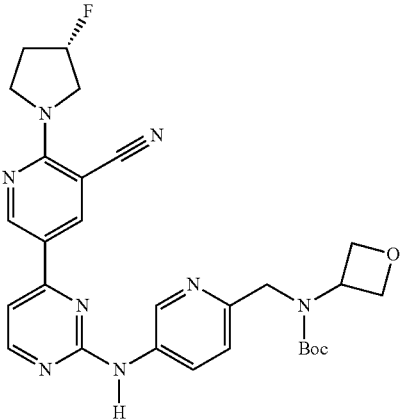 [SMILES: CC(C)(C)OC(=O)N(Cc1ccc(Nc2nccc(-c3cnc(N4CC[C@H](F)C4)c(C#N)c3)n2)cn1)C1COC1] | DMX-121 | (5-{4-[5-Cyano-6-((S)-3-fluoro-pyrrolidin-1-yl)-pyridin-3-yl]-pyrimidin-2-ylamino}-pyridin-2-ylmethyl)-oxetan-3-yl-carbamic acid tert-butyl ester | m/z 547 (MH+) | ND | ND | None |
| 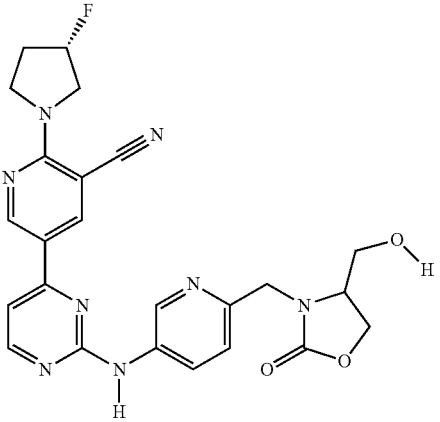 [SMILES: N#Cc1cc(-c2ccnc(Nc3ccc(CN4C(=O)OCC4CO)nc3)n2)cnc1N1CC[C@H](F)C1] | DMX-105†† | 2-((S)-3-Fluoro-pyrrolidin-1-yl)-5-{2-[6-(4-hydroxymethyl-2-oxo-oxazolidin-3-ylmethyl)-pyridin-3-ylamino]-pyrimidin-4-yl}-nicotinonitrile | Method D; Rt = 7.08 min; m/z 492 (MH+); $^1$H NMR (400 MHz, DMSO-$d_6$): δ 9.85 (1H, s), 9.14 (1H, d, J = 2.0 Hz), 8.88 (1H, d, J = 2.4 Hz), 8.70 (1H, d, J = 2.4 Hz), 8.53 (1H, d, J = 5.9 Hz), 8.22 (1H, dd, J = 7.8, 2.0 Hz), 7.49 (1H, d, J = 5.9 Hz), 7.35 (1H, d, J = 7.8 Hz), 5.48 (1H, d, J = 53.2 Hz), 5.22 (1H, br s), 4.58 (1H, d, J = 15.7 Hz), 4.35 (1H, t, J = 8.8 Hz), 4.31 (1H, d, J = 15.7 Hz) 4.15-3.92(4H, m), 3.90-3.78 (2H, m), 3.64-3.56 (1H, m), 3.46-3.38 (1H, m), 2.32-2.28 (2H, m); dark brown solid | <30 nM | <30 nM | None |
| 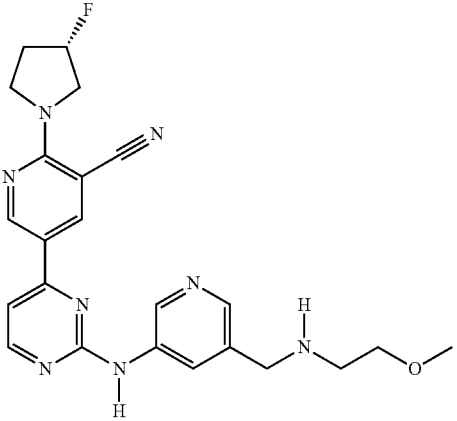 [SMILES: COCCNCc1cncc(Nc2nccc(-c3cnc(N4CC[C@H](F)C4)c(C#N)c3)n2)c1] | DMX-106 | 2-((S)-3-Fluoro-pyrrolidin-1-yl)-5-(2-{5-[(2-methoxy-ethylamino)-methyl]-pyridin-3-ylamino}-pyrimidin-4-yl)-nicotinonitrile | Method D; Rt = 5.45 min; m/z 449 (MH+); $^1$H NMR (400 MHz, DMSO-$d_6$): δ 9.82 (1H, s), 9.16 (1H, d, J = 2.0 Hz), 8.77 (1H, d, J = 2.0 Hz), 8.72 (1H, d, J = 2.9 Hz), 8.54 (1H, d, J = 5.6 Hz), 8.29 (1H, brs), 8.12 (1H, brs), 7.48 (1H, d, J = 5.6 Hz), 5.49 (1H, d, J = 52.2 Hz), 4.09-3.81 (4H, m), 3.76 (2H, s), 3.44-3.41 (3H, m), 3.22 (3H, s), 2.72-2.67 (2H, m), 2.17-2.15 (2H, m); light brown solid | <100 nM | <100 nM | None |

TABLE I-continued

| Structure | Ex. No. | Name | Analytical Data | Inhibition of IKKε | Inhibition of TBK1 | Salt Form |
|---|---|---|---|---|---|---|
| 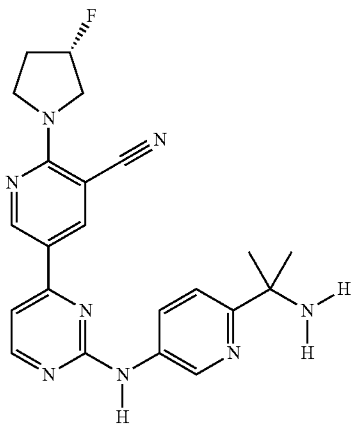 [SMILES: CC(C)(N)c1ccc(Nc2nccc(-c3cnc(N4CC[C@H](F)C4)c(C#N)c3)n2)cn1] | DMX-107* | 5-{2-[6-(1-Amino-1-ethyl-ethyl)-pyridin-3-ylamino]-pyrimidin-4-yl}-2-((S)-3-fluoro-pyrrolidin-1-yl)-nicotinonitrile | Method D; Rt = 5.86 min; m/z 419 (MH⁺); off-white solid | <100 nM | <100 nM | None |
| 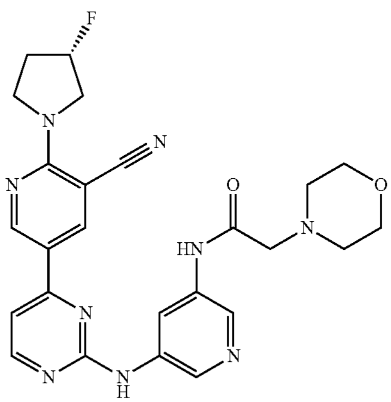 [SMILES: N#Cc1cc(-c2ccnc(Nc3cncc(NC(=O)CN4CCOCC4)c3)n2)cnc1N1CC[C@H](F)C1] | DMX-108 | N-(5-{4-[5-Cyano-6-((S)-3-fluoro-pyrrolidin-1-yl)-pyridin-3-yl]-pyrimidin-2-ylamino}-pyridin-3-yl)-2-morpholin-4-yl-acetamide | Method D; Rt = 5.88 min; m/z 504 (MH⁺); white solid | <100 nM | <30 nM | None |
| 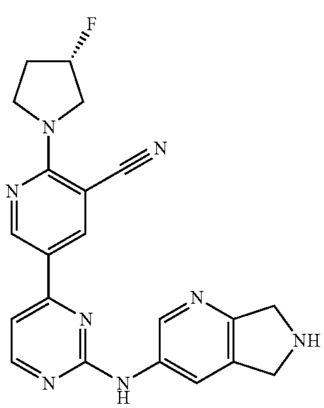 [SMILES: N#Cc1cc(-c2ccnc(Nc3cnc4c(c3)CNC4)n2)cnc1N1CC[C@H](F)C1] | DMX-109* | 5-[2-(6,7-Dihydro-5H-pyrrolo[3,4-b]pyridin-3-ylamino)-pyrimidin-4-yl]-2-((S)-3-fluoro-pyrrolidin-1-yl)-nicotinonitrile | Method E; Rt = 7.39 min; m/z 403(MH⁺); yellow solid | <30 nM | <100 nM | TFA |

TABLE I-continued

| Structure | Ex. No. | Name | Analytical Data | Inhibition of IKKε | Inhibition of TBK1 | Salt Form |
|---|---|---|---|---|---|---|
| 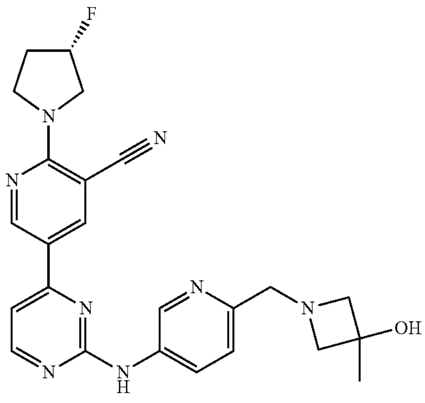 [SMILES: CC1(O)CN(Cc2ccc(Nc3nccc(-c4cnc(N5CC[C@H](F)C5)c(C#N)c4)n3)cn2)C1] | DMX-110 | 2-((S)-3-Fluoro-pyrrolidin-1-yl)-5-{2-[6-(3-hydroxy-3-methyl-azetidin-1-ylmethyl)-pyridin-3-ylamino]-pyrimidin-4-yl}-nicotinonitrile | Method D; Rt = 5.56 min; m/z 461 (MH+); cream solid | <30 nM | <100 nM | None |
| 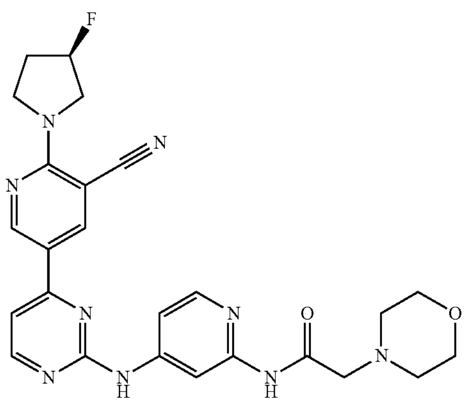 [SMILES: N#Cc1cc(-c2ccnc(Nc3ccnc(NC(=O)CN4CCOCC4)c3)n2)cnc1N1CC[C@@H](F)C1] | DMX-111 | N-(4-{4-[5-Cyano-6-((R)-3-fluoro-pyrrolidin-1-yl)-pyridin-3-yl]-pyrimidin-2-ylamino}-pyridin-2-yl)-2-morpholin-4-yl-acetamide | Method D; Rt = 6.07 min; m/z 504 (MH+); cream solid | <30 nM | <15 nM | FA |
| 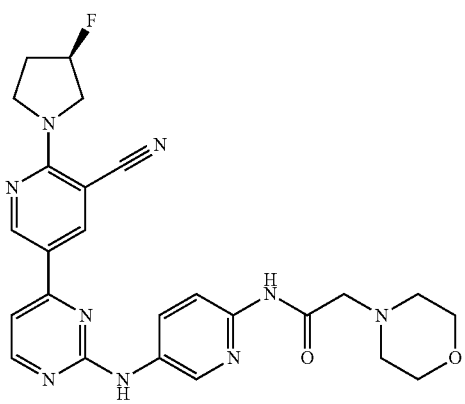 [SMILES: N#Cc1cc(-c2ccnc(Nc3ccc(NC(=O)CN4CCOCC4)nc3)n2)cnc1N1CC[C@@H](F)C1] | DMX-112 | N-(5-{4-[5-Cyano-6-((R)-3-fluoro-pyrrolidin-1-yl)-pyridin-3-yl]-pyrimidin-2-ylamino}-pyridin-2-yl)-2-morpholin-4-yl-acetamide | Method D; Rt = 6.37 min; m/z 504 (MH+); yellow solid | <15 nM | <30 nM | FA |
| 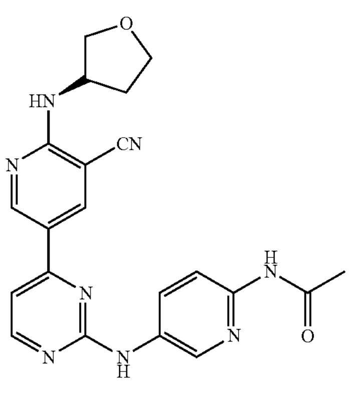 | DMX-113 | N-[5-(4-{5-Cyano-6-[(R)-(tetrahydro-furan-3-yl)amino]-pyridin-3-yl}-pyrimidin-2-ylamino)-pyridin-2-yl]-acetamide | Method A; Rt = 6.35 min; m/z 417 (MH+); yellow solid | <1 μM | <1 μM | None |

TABLE I-continued

| Structure | Ex. No. | Name | Analytical Data | Inhibition of IKKε | Inhibition of TBK1 | Salt Form |
|---|---|---|---|---|---|---|
| 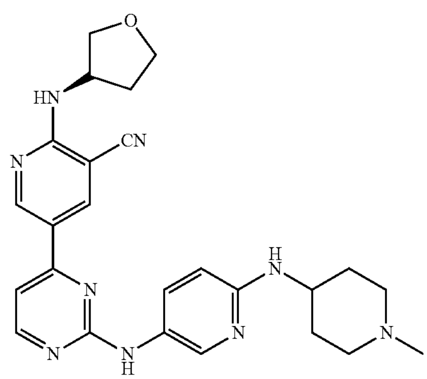 | DMX-114 | 5-{2-[6-(1-Methyl-piperidin-4-ylamino)-pyridin-3-ylamino]-pyrimidin-4-yl}-2-[(R)-(tetrahydro-furan-3-yl)amino]-nicotinonitrile | Method A; Rt = 3.41 min; m/z 472 (MH+); cream solid | <100 nM | <100 nM | FA |
| 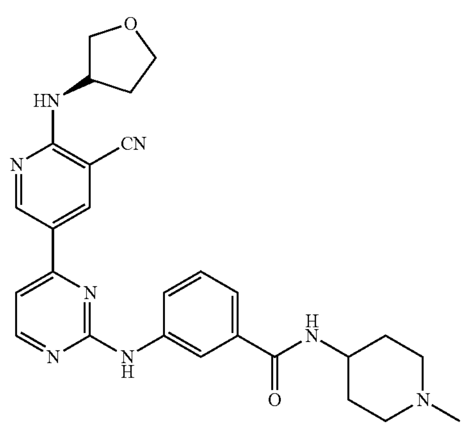 | DMX-115 | 3-(4-{5-Cyano-6-[(R)-(tetrahydro-furan-3-yl)amino]-pyridin-3-yl}-pyrimidin-2-ylamino)-N-(1-methyl-piperidin-4-yl)-benzamide | Method A; Rt = 4.73 min; m/z 499 (MH+); brown solid | <1 μM | <1 μM | FA |
| 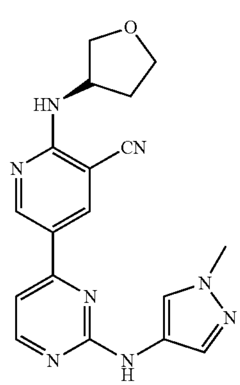 | DMX-116 | 5-[2-(1-Methyl-1H-pyrazol-4-ylamino)-pyrimidin-4-yl]-2-[(R)-(tetrahydro-furan-3-yl)amino]-nicotinonitrile | Method C; Rt = 7.07 min; m/z 363 (MH+); yellow solid | <1 μM | <1 μM | None |

TABLE I-continued

| Structure | Ex. No. | Name | Analytical Data | Inhibition of IKKε | Inhibition of TBK1 | Salt Form |
|---|---|---|---|---|---|---|
| 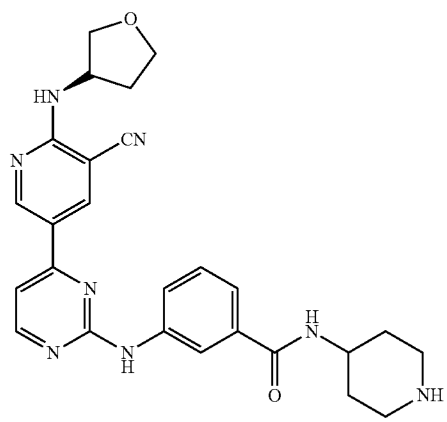 | DMX-117 | 3-(4-{5-Cyano-6-[(R)-(tetrahydro-furan-3-yl)amino]-pyridin-3-yl}-pyrimidin-2-ylamino)-N-piperidin-4-yl-benzamide | Method C; Rt = 5.36 min; m/z 485 (MH+); white solid | <1 μM | <1 μM | FA |
| 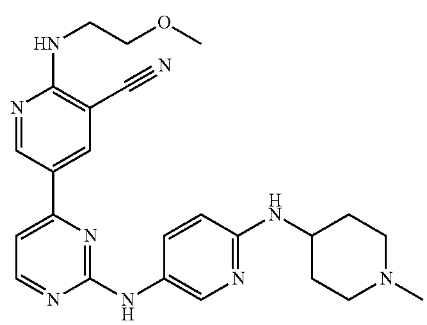 [SMILES: COCCNc1ncc(-c2ccnc(Nc3ccc(NC4CCN(C)CC4)nc3)n2)cc1C#N] | DMX-118 | 2-(2-Methoxy-ethylamino)-5-{2-[6-(1-methyl-piperidin-4-ylamino)-pyridin-3-ylamino]-pyrimidin-4-yl}-nicotinonitrile | Method C; Rt = 4.16 min; m/z 460 (MH+); tan solid | <1 μM | <1 μM | FA |
| 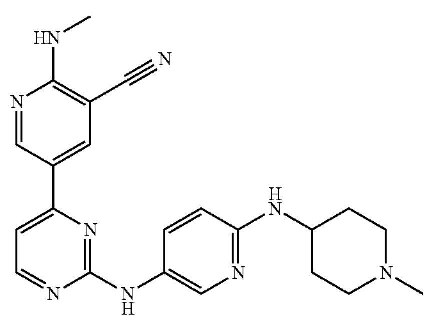 [SMILES: CNc1ncc(-c2ccnc(Nc3ccc(NC4CCN(C)CC4)nc3)n2)cc1C#N] | DMX-119 | 2-Methylamino-5-{2-[6-(1-methyl-piperidin-4-ylamino)-pyridin-3-ylamino]-pyrimidin-4-yl}-nicotinonitrile | Method C; Rt = 3.90 min; m/z 416 (MH+); brown solid | <1 μM | <100 nM | FA |
| 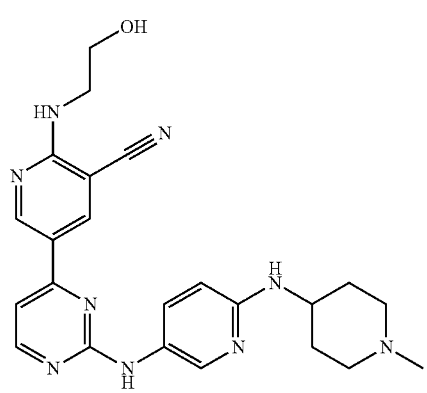 [SMILES: CN1CCC(Nc2ccc(Nc3nccc(-c4cnc(NCCO)c(C#N)c4)n3)cn2)CC1] | DMX-120 | 2-(2-Hydroxy-ethylamino)-5-{2-[6-(1-methyl-piperidin-4-ylamino)-pyridin-3-ylamino]-pyrimidin-4-yl}-nicotinonitrile | Method C; Rt = 3.74 min; m/z 446 (MH+); brown solid | <1 μM | <100 nM | FA |

TABLE I-continued

| Structure | Ex. No. | Name | Analytical Data | Inhibition of IKKε | Inhibition of TBK1 | Salt Form |
|---|---|---|---|---|---|---|
| (structure) | DMX-122 | 2-Cyclopropylamino-5-[2-(6-morpholin-4-ylmethyl-pyridin-3-ylamino)-pyrimidin-4-yl]-nicotinonitrile | Method D; Rt = 5.11 min; m/z 429 (MH+); brown solid | <1 μM | <100 nM | FA |
| (structure) | DMX-123 | 2-Cyclopropylamino-5-[5-fluoro-2-(6-morpholin-4-ylmethyl-pyridin-3-ylamino)-pyrimidin-4-yl]-nicotinonitrile | Method D; Rt = 5.40 min; m/z 447 (MH+); brown solid | <1 μM | <100 nM | FA |
| (structure) | DMX-124 | N-{4-[4-(5-Cyano-6-cyclopropylamino-pyridin-3-yl)-5-fluoro-pyrimidin-2-ylamino]-pyridin-2-yl}-2-morpholin-4-yl-acetamide | Method D; Rt = 5.85 min; m/z 490 (MH+); brown solid | <1 μM | <100 nM | FA |
| (structure) | DMX-125 | 2-Cyclopropylamino-5-{5-fluoro-2-[2-(2-methoxy-ethylamino)-pyridin-4-ylamino]-pyrimidin-4-yl}-nicotinonitrile | Method D; Rt = 5.91 min; m/z 421 (MH+); cream solid | <1 μM | <100 nM | None |

*The synthesis of these examples involved an additional deprotection step to furnish the target compound which typically involved removal of a Boc group from a protected amine as the final step using standard acidic conditions well known to those skilled in the art.
**The synthesis of this compound required the alcohol to be protected with a TBDMS group, which could then be removed as a final step using standard conditions well known to those skilled in the art. A review of alcohol protecting groups can be found for example in, *Protective Groups in Organic Synthesis*, 3rd Ed., (T. Greene and P. Wutts, Wiley-Interscience, 1999), pp. 17-245.
†The synthesis of this compound required the pyrazole to be protected with a THP group, which could be removed as a final step by stirring with TFA in a mixture of dichloromethane and methanol.
††DMX-105 was the major product from the attempted Boc deprotection of DMX-121. To DMX-121 (300 mg, crude, LCMS ~50%) in DCM (5 mL) was added TFA (0.1 mL) and stirred at room temperature for 1 h. The reaction mixture was concentrated, the residue was partitioned with saturated aq. NaHCO₃ and EtOAc, the organic layer was separated, dried (Na₂SO₄) and evaporated. The crude compound was purified by reverse phase preparative HPLC to obtain DMX-105 (15 mg). DMX-121 was made using amine A4-20

In addition a number of compounds were made from DMX-90:

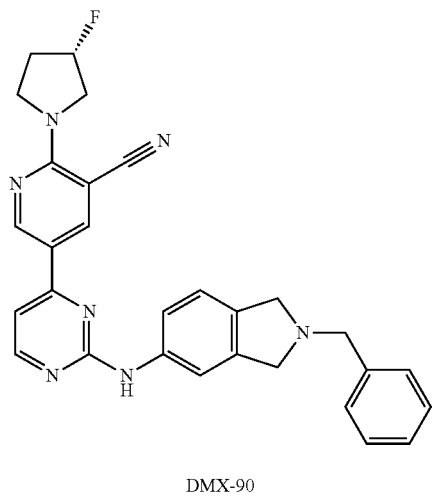

DMX-90

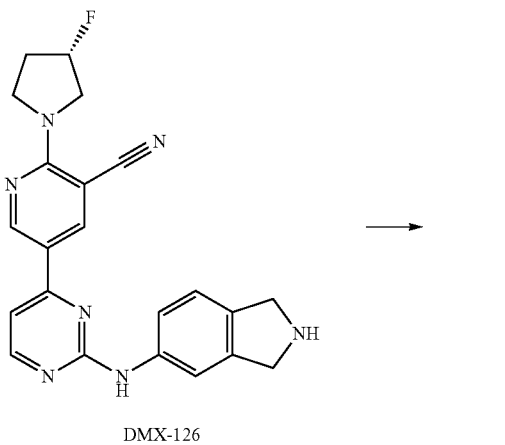

DMX-126

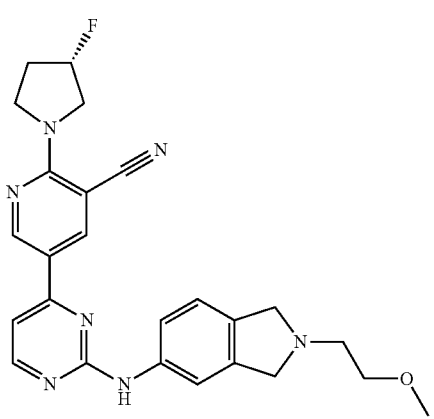

DMX-127

Example DMX-126

Synthesis of 5-[2-(2,3-Dihydro-1H-isoindol-5-ylamino)-pyrimidin-4-yl]-2-((S)-3-fluoro-pyrrolidin-1-yl)-nicotinonitrile DMX-90 (112 mg, 0.23 mmol), ammonium formate (100 mg, 1.6 mmol), and Pd/C (15 mg) in ethanol (5 mL) were heated to reflux for 1 h. The mixture was cooled and filtered through an ion exchange SCX-2 (Biotage) cartridge. The catridge was washed with 4 column volumes of methanol, then the desired product eluted with 3 column volumes of 0.5 M $NH_3$/MeOH. The solvent was evaporated and the crude product dissolved in DMSO and purified by mass directed reverse-phase preparative HPLC. The title compound was isolated as a tan solid (19 mg, 19%); LCMS, Rt=5.29 min (Method D), m/z 402 ($MH^+$).

Example DMX-127

2-((S)-3-Fluoro-pyrrolidin-1-yl)-5-{2-[2-(2-methoxy-ethyl)-2,3-dihydro-1H-isoindol-5-ylamino]-pyrimidin-4-yl}-nicotinonitrile DMX-90 (112 mg, 0.23 mmol), ammonium formate (100 mg, 1.6 mmol), and Pd/C (15 mg) in ethanol (5 mL) was heated to reflux for 1 h. The mixture was cooled and filtered through an ion exchange SCX-2 (Biotage) cartridge. The catridge was washed with 4 column volumes of methanol, then the desired product eluted with 3 column volumes of 0.5 M $NH_3$/MeOH. The solvent was evaporated to give crude DMX-126 (100 mg~50% pure by LCMS). This was dissolved in acetonitrile (10 mL) and 2-bromoethyl-methylether (24 µL, 0.26 mmol), $K_2CO_3$ (70 mg, 0.51 mmol) and KI (17 mg, 0.10 mmol) were added. The mixture was stirred at reflux for 2 h after which time a further amount of 2-bromoethyl-methylether (24 µL, 0.26 mmol) was added and the mixture stirred at reflux for a further 5 h. After which the mixture was filtered and the precipitate washed with acetonitrile. The filtrate was evaporated, the crude residue dissolved in DMSO and purified by mass directed reverse-phase preparative HPLC. The title compound was isolated as a yellow solid (8 mg, 13%); LCMS, Rt=5.40 min (Method D), m/z 460 ($MH^+$).

The following compounds were made from DMX-90:

TABLE II

| Structure | Ex. No. | Ex. No. | Analytical Data | Inhibition of IKKε | Inhibition of TBK1 | Salt |
|---|---|---|---|---|---|---|
| 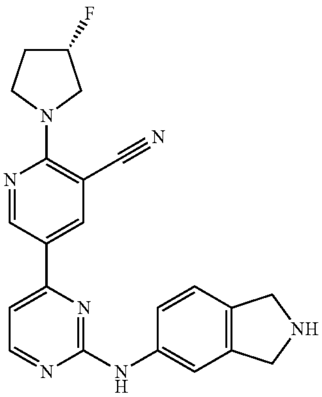 [SMILES: N#Cc1cc(-c2ccnc(Nc3ccc4c(c3)CNC4)n2)cnc1N1CC[C@H](F)C1] | DMX-126 | 5-[2-(2,3-Dihydro-1H-isoindol-5-ylamino)-pyrimidin-4-yl]-2-((S)-3-fluoro-pyrrolidin-1-yl)-nicotinonitrile | Method D; Rt = 5.29 min; m/z 402 (MH+); brown solid | <15 nM | <15 nM | FA |
| 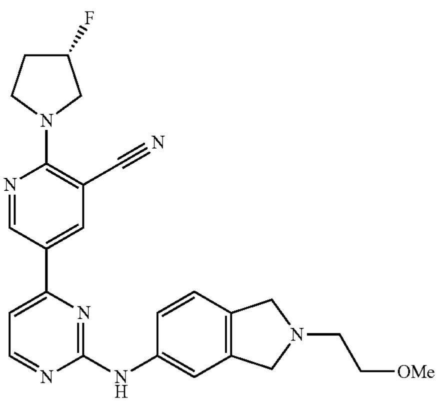 [SMILES: COCCN1Cc2ccc(Nc3nccc(-c4cnc(N5CC[C@H](F)C5)c(C#N)c4)n3)cc2C1] | DMX-127 | 2-((S)-3-Fluoro-pyrrolidin-1-yl)-5-{2-[2-(2-methoxy-ethyl)-2,3-dihydro-1H-isoindol-5-ylamino]-pyrimidin-4-yl}-nicotinonitrile | Method D; Rt = 5.40 min; m/z 460 (MH+); yellow solid | <15 nM | <15 nM | FA |

Other compounds of the invention were synthesised from compounds of formula (II) using a $S_NAr$ type reaction between for example the appropriate 2-chloropyridimidine building block and the requisite amine.

Example DMX-36

Synthesis of 5-{2-[1-(2-Hydroxy-ethyl)-1H-pyrazol-4-ylamino]-pyrimidin-4-yl}-2-pyrrolidin-1-yl-nicotinonitrile

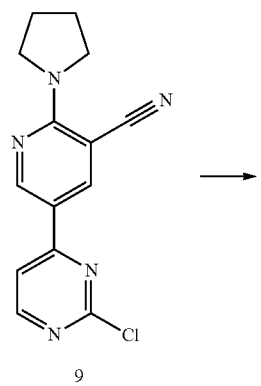

9

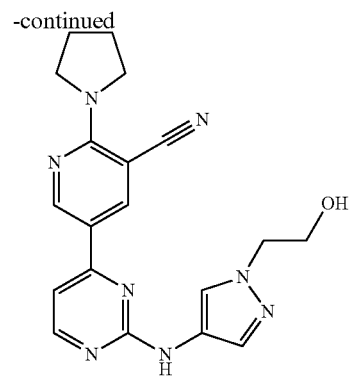

DMX-36

5-(2-Chloro-pyrimidin-4-yl)-2-pyrrolidin-1-yl-nicotinonitrile (9) (31 mg, 0.108 mmol) and 2-(4-amino-pyrazol-1-yl)-ethanol (32 mg, 0.252 mmol) were dissolved in 1,4-dioxane (1 mL). 4N HCl in 1,4-dioxane (30 μL, 0.120 mmol) was added and the mixture was heated at 140° C. in the microwave (250 W, stirring) for 90 minutes. The solvent was evaporated in vacuo and the residue dissolved in DMSO (1 mL). The crude product was purified twice by reversed phase preparative LC-MS. Fractions containing desired product were combined and the solvents evaporated in vacuo. The title compound was obtained as a yellow solid (3.7 mg, 9%); LCMS, Rt=7.43 min (Method C), m/z 377 (MH+).

Compound 9 was made using the same methodology described for compound 8.

Alternative examples of the invention were made using similar conditions. In some cases 4N HCl in dioxane may was omitted from the reaction. Reactions were generally carried out by heating in the microwave at 120-140° C. for up to 2 hours.

In addition to purification by reverse phase preparative LC-MS some compounds were further purified by loading onto an SCX-2 cartridge (Biotage), washed with up to 6 column volumes MeOH then eluted with either 0.5M NH$_3$-MeOH or 2M NH$_3$-MeOH, followed by evaporation of solvent.

Alternatively the final compound may have been purified via trituration with suitable solvent(s).

The following compounds were prepared using this route:

TABLE III

| Structure | Ex. No. | Analytical Data | Analytical Data | Inhibition of IKKε | Inhibition of TBK1 | Salt form |
|---|---|---|---|---|---|---|
| 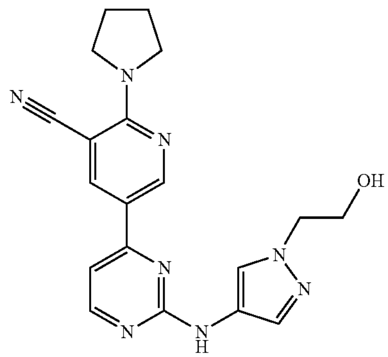 [SMILES: N#Cc1cc(-c2ccnc(Nc3cnn(CCO)c3)n2)cnc1N1CCCC1] | DMX-36 | 5-{2-[1-(2-Hydroxy-ethyl)-1H-pyrazol-4-ylamino]-pyrimidin-4-yl}-2-pyrrolidin-1-yl-nicotinonitrile | Method C, Rt = 7.43 min; m/z 377 (MH+); yellow solid | <30 nM | <30 nM | None |
| 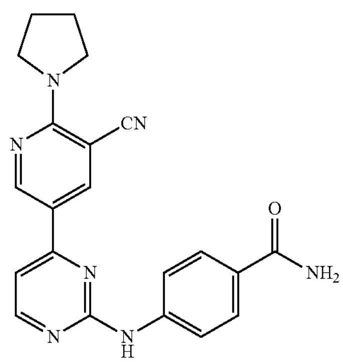 [SMILES: N#Cc1cc(-c2ccnc(Nc3ccc(C(N)=O)cc3)n2)cnc1N1CCCC1] | DMX-37 | 4-[4-(5-Cyano-6-pyrrolidin-1-yl-pyridin-3-yl)-pyrimidin-2-ylamino]-benzamide | Method X, Rt = 2.71 min; m/z 386 (MH+); off-white solid | <15 nM | <15 nM | None |
| 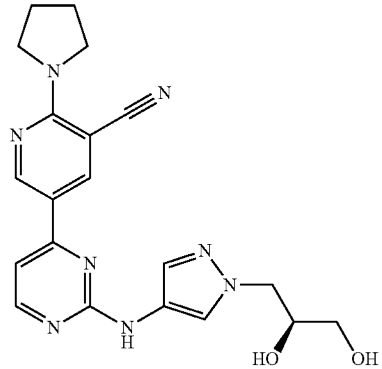 [SMILES: N#Cc1cc(-c2ccnc(Nc3cnn(C[C@H](O)CO)c3)n2)cnc1N1CCCC1] | DMX-38 | 5-{2-[1-((S)-2,3-Dihydroxy-propyl)-1H-pyrazol-4-ylamino]-pyrimidin-4-yl}-2-pyrrolidin-1-yl-nicotinonitrile | Method C; Rt = 7.29 min; m/z 407 (MH+); yellow solid | <100 nM | <15 nM | None |

TABLE III-continued

| Structure | Ex. No. | Analytical Data | Analytical Data | Inhibition of IKKε | Inhibition of TBK1 | Salt form |
|---|---|---|---|---|---|---|
| 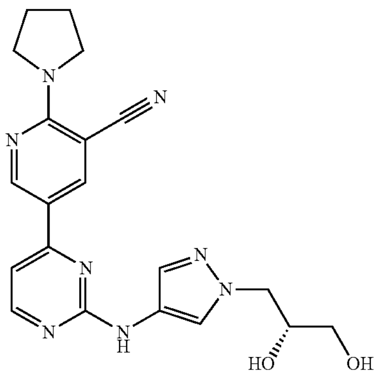 [SMILES: N#Cc1cc(-c2ccnc(Nc3cnn(C[C@@H](O)CO)c3)n2)cnc1N1CCCC1] | DMX-39 | 5-{2-[1-((R)-2,3-Dihydroxy-propyl)-1H-pyrazol-4-ylamino]-pyrimidin-4-yl}-2-pyrrolidin-1-yl-nicotinonitrile | Method C; Rt = 7.27 min; m/z 407 (MH$^+$); yellow solid | <30 nM | <15 nM | None |
| 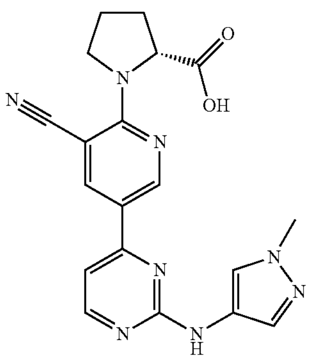 [SMILES: Cn1cc(Nc2nccc(-c3cnc(N4CCC[C@@H]4C(=O)O)c(C#N)c3)n2)cn1] | DMX-40† | (R)-1-{3-Cyano-5-[2-(1-methyl-1H-pyrazol-4-ylamino)-pyrimidin-4-yl]-pyridin-2-yl}-pyrrolidine-2-carboxylic acid | Method D; Rt = 6.77 min; m/z 391 (MH$^+$); yellow solid | <9 μM | <1 μM | None |
| 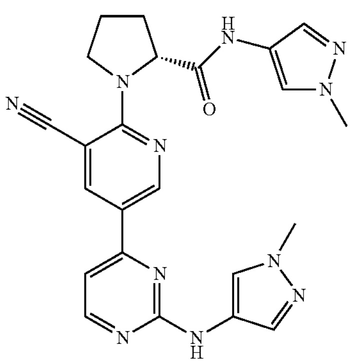 [SMILES: Cn1cc(NC(=O)[C@H]2CCCN2c2ncc(-c3ccnc(Nc4cnn(C)c4)n3)cc2C#N)cn1] | DMX-41† | (R)-1-{3-Cyano-5-[2-(1-methyl-1H-pyrazol-4-ylamino)-pyrimidin-4-yl]-pyridin-2-yl}-pyrrolidine-2-carboxylic acid (1-methyl-1H-pyrazol-4-yl)-amide | Method D; Rt = 6.33 min; m/z 470 (MH$^+$); yellow solid | <1 μM | <100 nM | None |
| 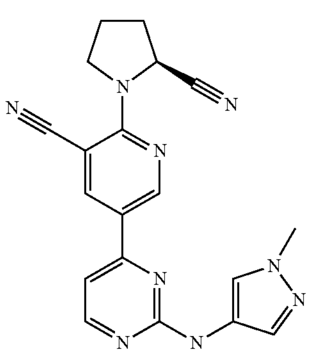 [SMILES: Cn1cc(Nc2nccc(-c3cnc(N4CCC[C@H]4C#N)c(C#N)c3)n2)cn1] | DMX-42 | 2-((S)-2-Cyano-pyrrolidin-1-yl)-5-[2-(1 methyl-1H-pyrazol-4-ylamino)-pyrimidin-4-yl]-nicotinonitrile | Method D; Rt = 6.75 min; m/z 372 (MH$^+$); pale brown solid | <1 μM | <100 nM | None |

TABLE III-continued

| Structure | Ex. No. | Analytical Data | Analytical Data | Inhibition of IKKε | Inhibition of TBK1 | Salt form |
|---|---|---|---|---|---|---|
| 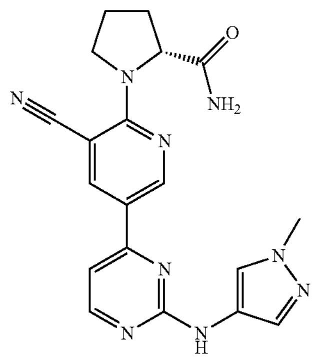 [SMILES: Cn1cc(Nc2nccc(-c3cnc(N4CCC[C@@H]4C(N)=O)c(C#N)c3)n2)cn1] | DMX-43† | (R)-1-{3-Cyano-5-[2-(1-methyl-1H-pyrazol-4-ylamino)-pyrimidin-4-yl]-pyridin-2-yl}-pyrrolidine-2-carboxylic acid amide | Method D; Rt = 6.03 min; m/z 390 (MH+); yellow solid | <100 nM | <100 nM | None |
| 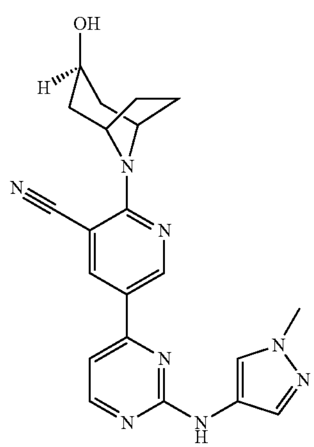 | DMX-44 | 2-(3-Hydroxy-8-aza-bicyclo[3.2.1]oct-8-yl)-5-[2-(1-methyl-1H-pyrazol-4-ylamino)-pyrimidin-4-yl]-nicotinonitrile | Method D; Rt = 7.22 min; m/z 403 (MH+); yellow solid | <30 nM | <15 nM | None |
| 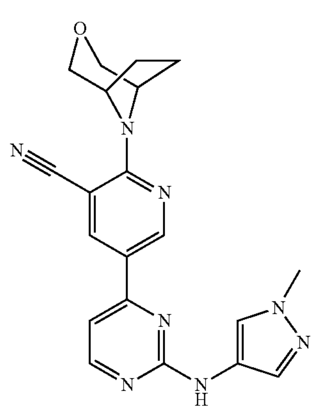 [SMILES: Cn1cc(Nc2nccc(-c3cnc(N4C5CCC4COC5)c(C#N)c3)n2)cn1] | DMX-45 | 5-[2-(1-Methyl-1H-pyrazol-4-ylamino)-pyrimidin-4-yl]-2-(3-oxa-8-aza-bicyclo[3.2.1]oct-8-yl)-nicotinonitrile | Method D; Rt = 7.40 min; m/z 389 (MH+); yellow solid | <100 nM | <100 nM | None |

TABLE III-continued

| Structure | Ex. No. | Analytical Data | Analytical Data | Inhibition of IKKε | Inhibition of TBK1 | Salt form |
|---|---|---|---|---|---|---|
| 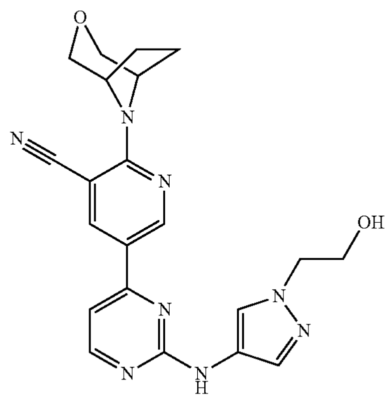 [SMILES: N#Cc1cc(-c2ccnc(Nc3cnn(CCO)c3)n2)cnc1N1C2CCC1COC2] | DMX-46 | 5-{2-[1-(2-Hydroxy-ethyl)-1H-pyrazol-4-ylamino]-pyrimidin-4-yl}-2-(3-oxa-8-aza-bicyclo[3.2.1]oct-8-yl)-nicotinonitrile | Method D; Rt = 6.95 min; m/z 419 (MH$^+$); yellow solid | <1 μM | <100 nM | None |
| 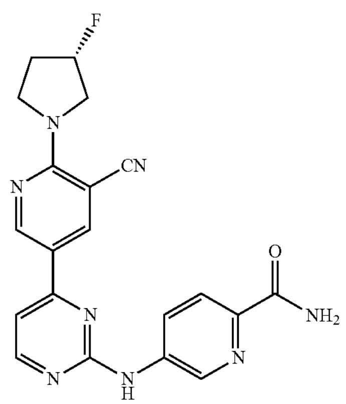 [SMILES: N#Cc1cc(-c2ccnc(Nc3ccc(C(N)=O)nc3)n2)cnc1N1CC[C@H](F)C1] | DMX-47 | 5-{4-[5-Cyano-6-((S)-3-fluoro-pyrrolidin-1-yl)-pyridin-3-yl]-pyrimidin-2-ylamino}-pyridine-2-carboxylic acid amide | Method D; Rt = 7.18 min; m/z 405 (MH$^+$); tan solid | <30 nM | <30 nM | None |
| 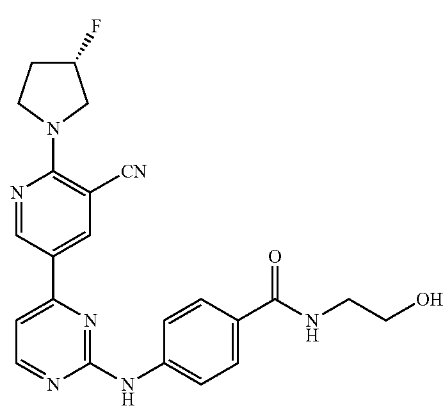 [SMILES: N#Cc1cc(-c2ccnc(Nc3ccc(C(=O)NCCO)cc3)n2)cnc1N1CC[C@H](F)C1] | DMX-48 | 4-{4-[5-Cyano-6-((S)-3-fluoro-pyrrolidin-1-yl)-pyridin-3-yl]-pyrimidin-2-ylamino}-N-(2-hydroxy-ethyl)-benzamide | Method D; Rt = 7.10 min; m/z 448 (MH$^+$); off-white solid | <15 nM | <15 nM | None |

TABLE III-continued

| Structure | Ex. No. | Analytical Data | Analytical Data | Inhibition of IKKε | Inhibition of TBK1 | Salt form |
|---|---|---|---|---|---|---|
| 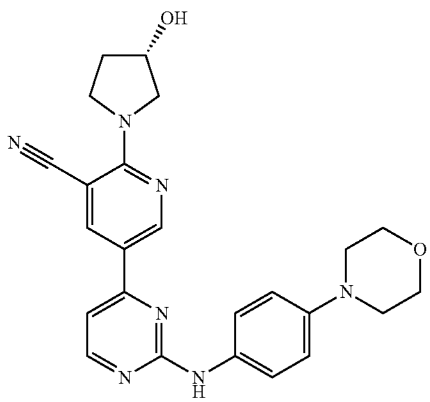 [SMILES: N#Cc1cc(-c2ccnc(Nc3ccc(N4CCOCC4)cc3)n2)cnc1N1CC[C@H](O)C1] | DMX-49 | 2-((S)-3-Hydroxy-pyrrolidin-1-yl)-5-[2-(4-morpholin-4-yl-phenylamino)-pyrimidin-4-yl]-nicotinonitrile | Method D; Rt = 6.89 min; m/z 444 (MH⁺); yellow solid | <15 nM | <15 nM | None |
| 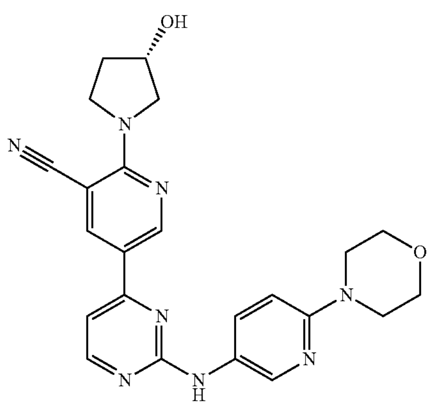 [SMILES: N#Cc1cc(-c2ccnc(Nc3ccc(N4CCOCC4)nc3)n2)cnc1N1CC[C@H](O)C1] | DMX-50 | 2-((S)-3-Hydroxy-pyrrolidin-1-yl)-5-[2-(6-morpholin-4-yl-pyridin-3-ylamino)-pyrimidin-4-yl]-nicotinonitrile | Method D; Rt = 5.61 min; m/z 445 (MH⁺); yellow solid | <100 nM | <30 nM | None |
| 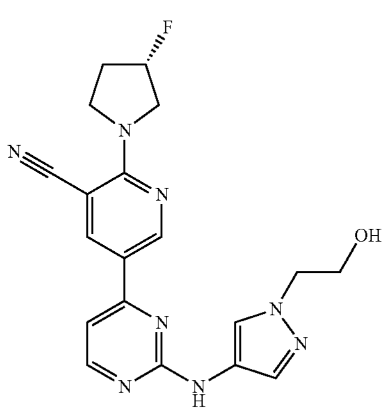 [SMILES: N#Cc1cc(-c2ccnc(Nc3cnn(CCO)c3)n2)cnc1N1CC[C@H](F)C1] | DMX-51 | 2-((S)-3-Fluoro-pyrrolidin-1-yl)-5-{2-[1-(2-hydroxy-ethyl)-1H-pyrazol-4-ylamino]-pyrimidin-4-yl}-nicotinonitrile | Method D; Rt = 6.67 min; m/z 395 (MH⁺); yellow solid | <30 nM | <30 nM | None |

TABLE III-continued

| Structure | Ex. No. | Analytical Data | Analytical Data | Inhibition of IKKε | Inhibition of TBK1 | Salt form |
|---|---|---|---|---|---|---|
| 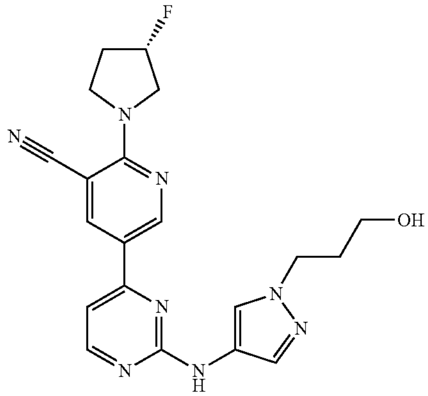 [SMILES: N#Cc1cc(-c2ccnc(Nc3cnn(CCCO)c3)n2)cnc1N1CC[C@H](F)C1] | DMX-52 | 2-((S)-3-Fluoro-pyrrolidin-1-yl)-5-{2-[1-(3-hydroxy-propyl)-1H-pyrazol-4-ylamino]-pyrimidin-4-yl}-nicotinonitrile | Method D; Rt = 6.89 min; m/z 409 (MH+); yellow solid | <100 nM | <30 nM | None |
| 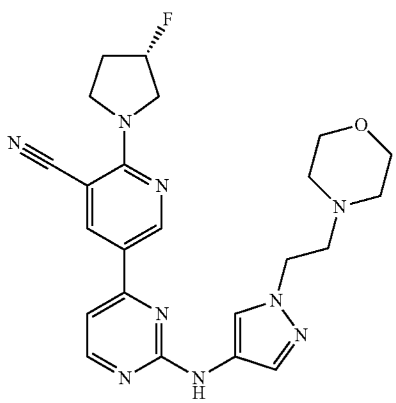 [SMILES: N#Cc1cc(-c2ccnc(Nc3cnn(CCN4CCOCC4)c3)n2)cnc1N1CC[C@H](F)C1] | DMX-53 | 2-((S)-3-Fluoro-pyrrolidin-1-yl)-5-{2-[1-(2-morpholin-4-yl-ethyl)-1H-pyrazol-4-ylamino]-pyrimidin-4-yl}-nicotinonitrile | Method D; Rt = 4.99 min; m/z 464 (MH+); yellow solid | <100 nM | <30 nM | FA |

†DMX-40 and DMX-41 where the major products from the reaction of compound 10 with 1-methyl-1H-pyrazol-4-ylamine in the presence of 1 equiv of HCl. In the absence of HCl the major product was DMX-43.

-continued

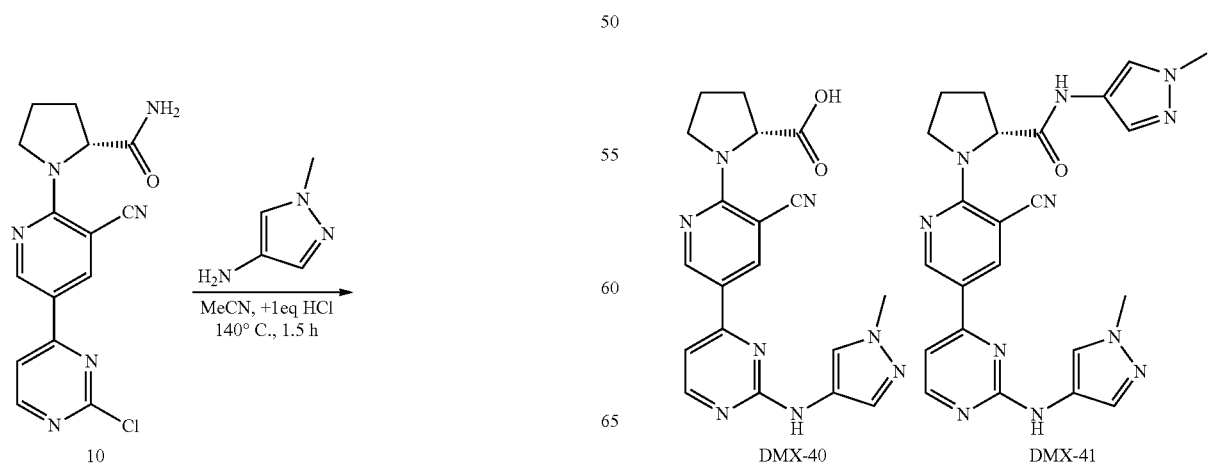

In some cases compounds of formula Ia necessitated variations in the sequence of the synthetic steps.

For example, some compounds of general structure 13 were prepared via intermediate 8 by reaction with 2,5-diaminopyridine using the Buchwald-Hartwig conditions followed by reaction with an appropriate chloroacetylchloride, followed by displacement with a suitable amine using standard literature conditions known to those skilled in the art.

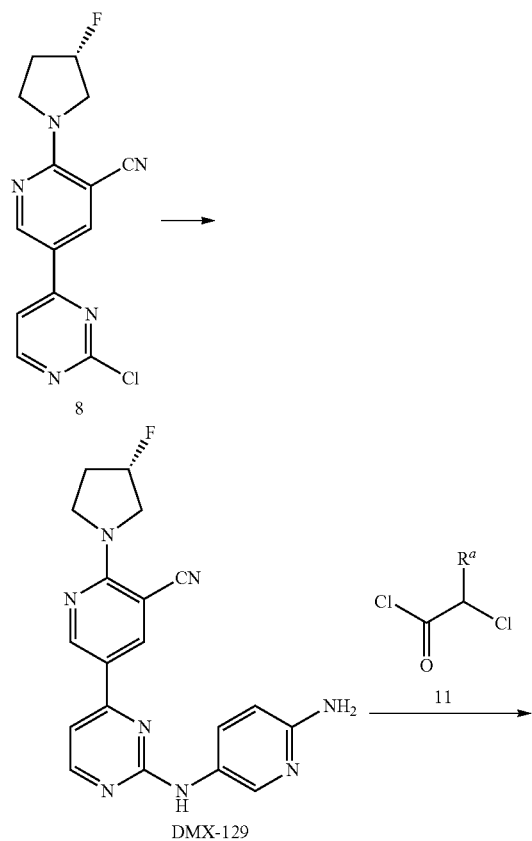

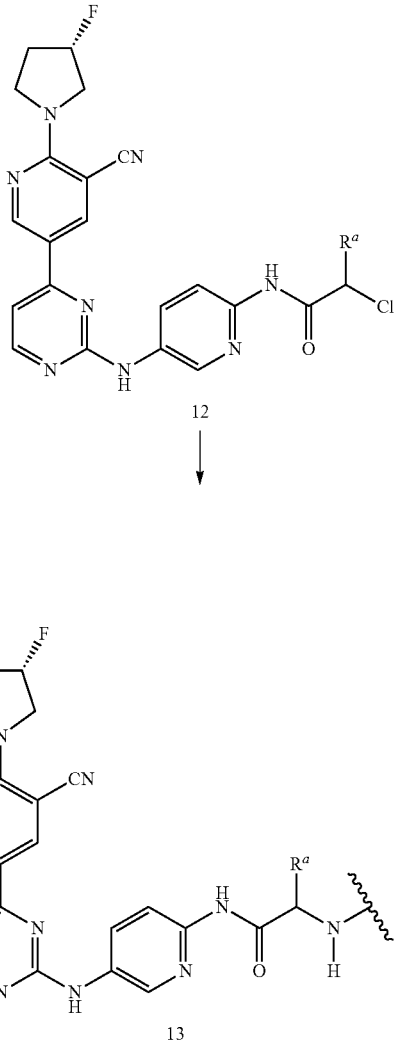

Compounds made via this route include:

TABLE IV

| Structure | Ex. No. | Name | Analytical Data | Inhibition of IKKε | Inhibition of TBK1 | Salt Form |
|---|---|---|---|---|---|---|
| 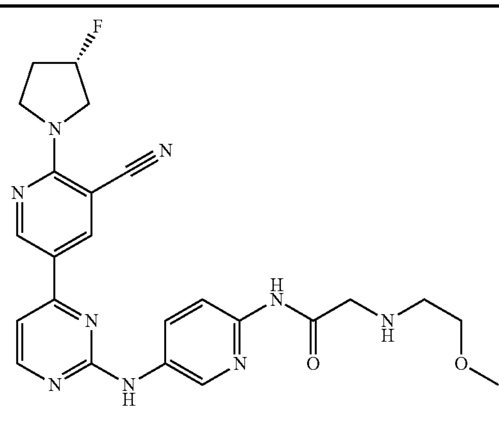 | DMX-54 | N-(5-{4-[5-Cyano-6-((S)-3-fluoro-pyrrolidin-1-yl)-pyridin-3-yl]-pyrimidin-2-ylamino}-pyridin-2-yl)-2-(2-methoxy-ethylamino)-acetamide | Method D; Rt = 5.20 min; m/z 492 (MH+); white solid | <30 nM | <100 nM | None |

TABLE IV-continued

| Structure | Ex. No. | Name | Analytical Data | Inhibition of IKKε | Inhibition of TBK1 | Salt Form |
|---|---|---|---|---|---|---|
| 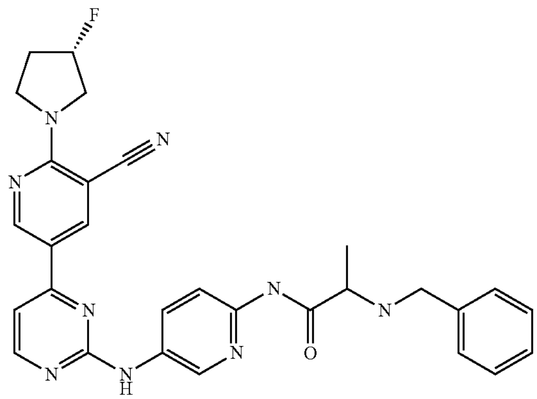 [SMILES: CC(NCc1ccccc1)C(=O)Nc1ccc(Nc2nccc(-c3cnc(N4CC[C@H](F)C4)c(C#N)c3)n2)cn1] | DMX-55 | 2-Benzylamino-N-(5-{4-[5-cyano-6-((S)-3-fluoro-pyrrolidin-1-yl)-pyridin-3-yl]-pyrimidin-2-ylamino}-pyridin-2-yl)-propionamide | Method D; Rt = 5.89 min; m/z 538 (MH$^+$); yellow solid | <100 nM | <30 nM | FA |
| 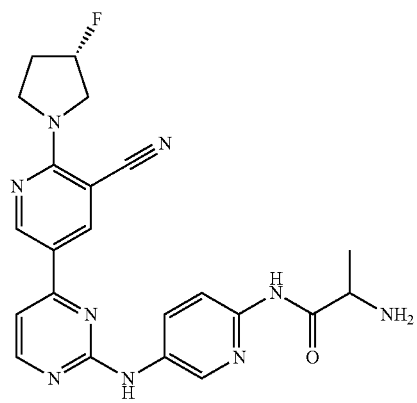 [SMILES: CC(N)C(=O)Nc1ccc(Nc2nccc(-c3cnc(N4CC[C@H](F)C4)c(C#N)c3)n2)cn1] | DMX-56* | 2-Amino-N-(5-{4-[5-cyano-6-((S)-3-fluoro-pyrrolidin-1-yl)-pyridin-3-yl]-pyrimidin-2-ylamino)-pyridin-2-yl)-propionamide | Method D; Rt = 5.19 min; m/z 448 (MH$^+$); yellow solid | <30 nM | <100 nM | FA |
| 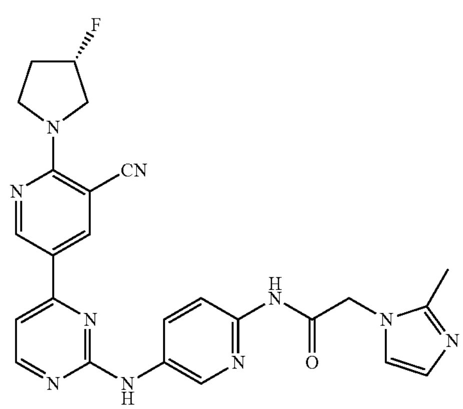 [SMILES: Cc1nccn1CC(=O)Nc1ccc(Nc2nccc(-c3cnc(N4CC[C@H](F)C4)c(C#N)c3)n2)cn1] | DMX-128 | N-(5-{4-[5-Cyano-6-((S)-3-fluoro-pyrrolidin-1-yl)-pyridin-3-yl]-pyrimidin-2-ylamino)-pyridin-2-yl)-2-(2-methyl-imidazol-1-yl)-acetamide | Method D; Rt = 5.43 min; m/z 499 (MH$^+$); pink solid | <30 nM | <30 nM | FA |

TABLE IV-continued

| Structure | Ex. No. | Name | Analytical Data | Inhibition of IKKε | Inhibition of TBK1 | Salt Form |
|---|---|---|---|---|---|---|
| 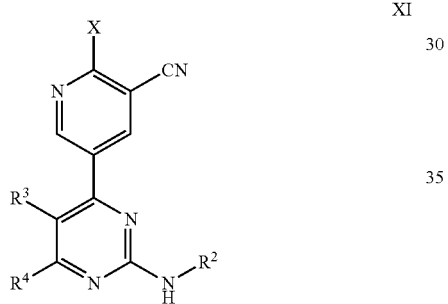 | DMX-129 | 5-[2-(6-Amino-pyridin-3-ylamino)-pyrimidin-4-yl]-2-((S)-3-fluoro-pyrrolidin-1-yl)-nicotinonitrile | Method D; Rt = 4.98 min; m/z 499 (MH+); yellow solid | <30 nM | <30 nM | None |

*DMX-56 was prepared from DMX-55 via hydrogenation of the benzyl group using conditions known to those skilled in the art. A review of amine protecting groups can be found for example in, *Protective Groups in Organic Synthesis*, 3rd Ed., (T. Greene and P. Wutts, Wiley-Interscience, 1999), pp. 494-653.

Other compounds of the invention were synthesised from compounds of formula (XI), wherein X=chlorine, using a SNAr type reaction.

XI

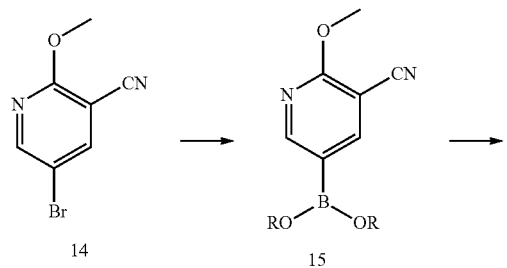

Example DMX-130

Synthesis of 2-(1-{3-Cyano-5-[2-(6-morpholin-4-ylmethyl-pyridin-3-ylamino)-pyrimidin-4-yl]-pyridin-2-yl}-pyrrolidin-2-yl)-acetamide 5-(2-Chloro-pyrimidin-4-yl)-2-methoxy-nicotinonitrile (16)

-continued

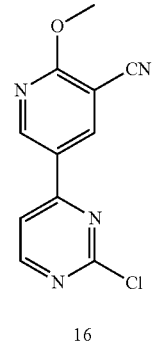

16

To a stirred solution of 5-bromo-2-methoxy-nicotinonitrile (10 g, 46.9 mmol) and bis(pinacolato)diboron (17.9 g, 70.4 mmol) in 1,4-dioxane (300 mL) was added potassium acetate (13.8 g, 140.8 mmol). The reaction mixture was deoxygenated with argon, Pd(dppf)Cl₂ was added and the mixture deoxygentated for a further 20 min. The resulting mixture was heated at 100° C. for 1.5 h. The reaction mixture was cooled to rt, diluted with water (100 mL) and filtered through Celite. The filtrate was extracted with EtOAc (2×150 mL), the combined organic layer dried over Na₂SO₄ and evaporated to obtained a crude mixture containing an approximate 1:1 mixture of boronic ester and boronic acid (12 g). The crude material was dissolved in 1,4-dioxane (100 mL) and 2,4 dichloropyrimidine (8.4 g, 56.2 mmol) was added followed by a solution sodium carbonate (17.9 g, 168.5 mmol) in water (25 mL). The reaction mixture was deoxygenated with argon gas, Pd(PPh₃)₄ was added and again deoxygenated for 30 min. The resulting mixture was heated at 100° C. for 3 h. The reaction mixture was cooled to rt, diluted with water (100 mL), extracted with EtOAc (3×100 mL), the combined organic layer was dried (Na₂SO₄) and evaporated. The crude compound was purified by flash column chromatography (100-200 mesh silica gel), eluting with 30% EtOAc/pet ether to obtain the desired compound (6 g, 51% (over two steps)) as a white solid; R$_f$: 0.3 (40% EtOAc/pet ether); (m/z): 247[M+1]⁺; ¹H NMR (300 MHz, DMSO-d₆): δ 9.24 (1H, d, J=2.4 Hz), 8.98 (1H, d, J=2.1 Hz), 8.89 (1H, d, J=5.1 Hz), 8.21 (1H, d, J=5.1 Hz), 4.04 (3H, s). 2-Methoxy-5-[2-(6-morpholin-4-ylmethyl-pyridin-3-ylamino)-pyrimidin-4-yl]-nicotinonitrile (17)

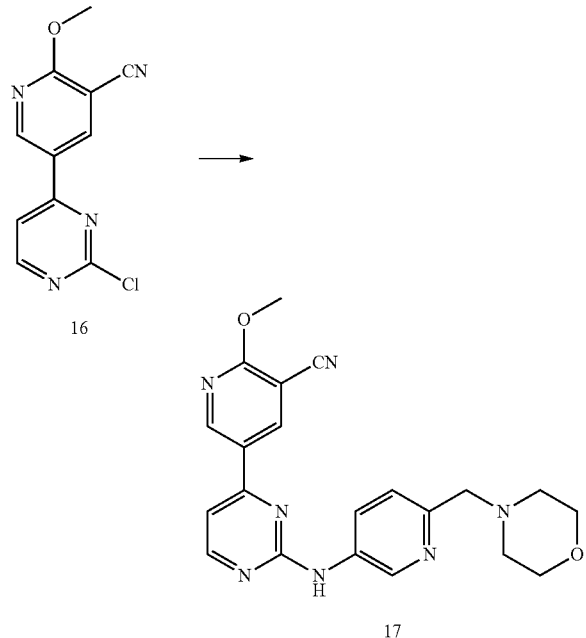

To a stirred solution of 5-(2-chloro-pyrimidin-4-yl)-2-methoxy-nicotinonitrile (2 g, 8.13 mmol) in 1,4-dioxane (50 mL) was added compound 16 (1.7 g, 8.9 mmol), caesium carbonate (5.3 g, 16.3 mmol) and DavePhos (0.31 g, 0.8 mmol), the resulting solution was deoxygenated with argon gas. Pd$_2$(dba)$_3$ (0.37 g, 0.4 mmol) was added to the above mixture, and it was again deoxygenated for another 15 min before heating at 100° C. for 5 h. The reaction mixture was cooled to rt, diluted with water (15 mL), extracted with EtOAc (3×50 mL), the combined organic layer was dried (Na$_2$SO$_4$) and evaporated. The crude compound was purified by flash column chromatography (100-200 mesh silica gel), eluting with 3% MeOH/CHCl$_3$ to obtain compound 17 (1.5 g, 46%) as a white solid. R$_f$: 0.3 (10% MeOH/CHCl$_3$); (m/z): 404 [M+1]$^+$; $^1$H NMR (400 MHz, CDCl$_3$): δ 9.04 (1H, d, J=2.4 Hz), 8.75 (1H, d, J=3.2 Hz), 8.55 (1H, d, J=2.4 Hz), 8.52 (1H, d, J=5.2 Hz), 8.20-8.17 (1H, dd, J=2.4, 8.4 Hz), 7.42 (1H, d, J=8.4 Hz), 7.23 (1H, br), 7.12 (1H, d, J=5.2 Hz), 4.15 (3H, s), 3.75 (4H, t, J=4.4 Hz), 3.65 (2H, s), 2.54-2.53 (4H, m).

2-Chloro-5-[2-(6-morpholin-4-ylmethyl-pyridin-3-ylamino)-pyrimidin-4-yl]-nicotinonitrile (18)

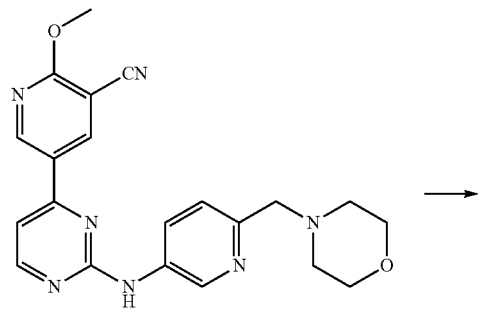

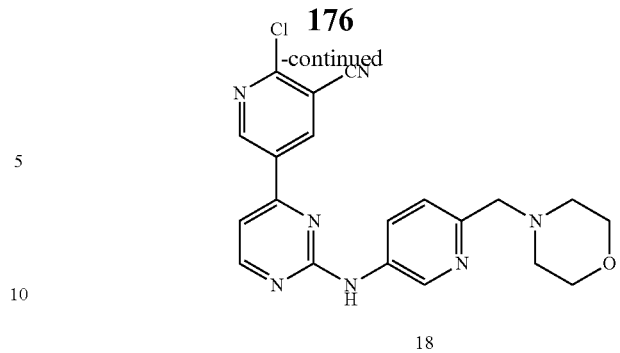

A mixture of compound 17 (1.5 g, 3.7 mmol) and phenylphosphoro dichloridate (5 mL) was heated at 130° C. for 5 h. The reaction mixture was cooled to rt, diluted with cold water (10 mL), cooled to 0° C., quenched with saturated NaHCO$_3$ solution and extracted with EtOAc (2×50 mL). The combined organic layer was washed with brine (50 mL), dried (Na$_2$SO$_4$) and evaporated. The crude compound was purified by trituration with EtOAc to obtain 18 (0.7 g, 46%) as a pale brown solid. R$_f$: 0.5 (10% MeOH/DCM); (m/z): 408 [M+1]$^+$; $^1$H NMR (400 MHz, DMSO-d$_6$): δ10.01 (1H, s), 9.40 (1H, d, J=2.4 Hz), 9.11 (1H, d, J=2.4 Hz), 8.85 (1H, d, J=2.4 Hz), 8.70 (1H, d, J=5.2 Hz), 8.21-8.18 (1H, dd, J=2.4, 8.8 Hz), 7.62 (1H, d, J=5.6 Hz), 7.40 (1H, d, J=8.4 Hz), 3.59-3.54 (6H, m), 2.46-2.41 (4H, m).

2-(1-{3-Cyano-5-[2-(6-morpholin-4-ylmethyl-pyridin-3-ylamino)-pyrimidin-4-yl]-pyridin-2-yl}-pyrrolidin-2-yl)-acetamide (DMX-130)

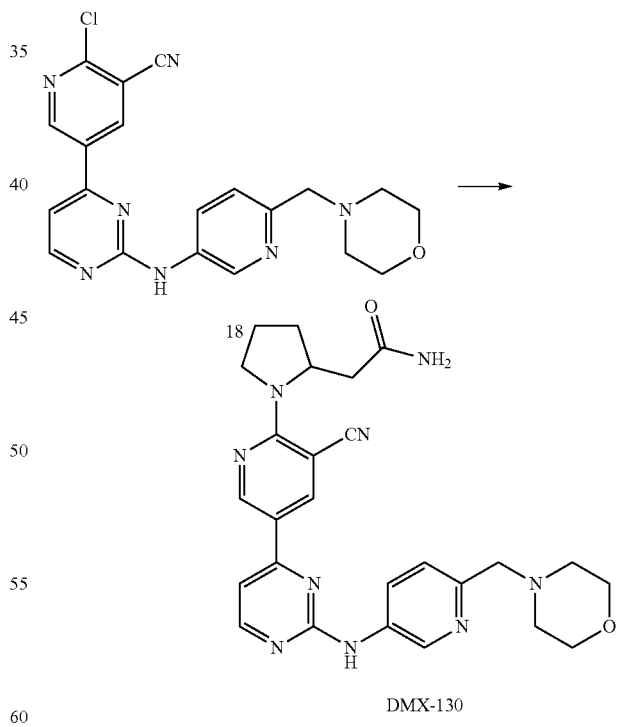

To a solution of compound 18 (100 mg, 0.24 mmol) in EtOH (5 mL) was added 2-(pyrrolidin-2-yl)acetamide-HCl (160 mg, 1.22 mmol) and DIPEA (0.22 mL, 1.22 mmol) at rt and the reaction mixture was heated at reflux for 16 h. The reaction mixture was cooled to rt, concentrated to half of its volume and triturated with n-pentane, the precipitated solid was collected by filtration to obtain DMX-130 (80 mg, 65%) as a white solid. R_f: 0.4 (10% MeOH/CHCl_3); (m/z): 499.8 [M+1]$^+$; $^1$H NMR (300 MHz, DMSO-d$_6$): δ 9.77 (1H, s), 9.13 (1H, d, J=2.4 Hz), 8.87 (1H, d, J=2.4 Hz), 8.66 (1H, d, J=1.8 Hz), 8.50 (1H, d, J=5.1 Hz), 8.16 (1H, dd, J=2.7, 9.0 Hz), 7.46 (1H, d, J=5.7 Hz), 7.38 (1H, d, J=9.0 Hz), 7.30 (1H, br), 6.84 (1H, br), 4.74 (1H, br), 3.97 (1H, br), 3.80-3.76 (1H, br), 3.59-3.53 (6H, m), 2.76-2.70 (1H, m), 2.40 (4H, br), 2.23-2.15 (1H, m), 2.10-2.98 (3H, m), 1.86-1.84 (1H, m).

The following compounds were made via this route:

TABLE V

| Structure | Ex. No. | Name | Analytical Data | Inhibition of IKKε | Inhibition of TBK1 | Salt form |
|---|---|---|---|---|---|---|
| 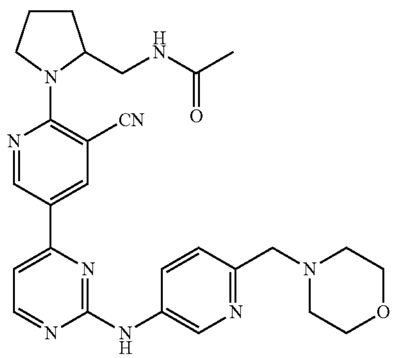 [SMILES: CC(=O)NCC1CCCN1c1ncc(-c2ccnc(Nc3ccc(CN4CCOCC4)nc3)n2)cc1C#N] | DMX-130 | N-(1-{3-Cyano-5-[2-(6-morpholin-4-ylmethyl-pyridin-3-ylamino)-pyrimidin-4-yl]-pyridin-2-yl}-pyrrolidin-2-ylmethyl)-acetamide | Method D; Rt = 5.39 min; m/z 514 (MH$^+$); yellow solid | <1 μM | <1 μM | None |
| 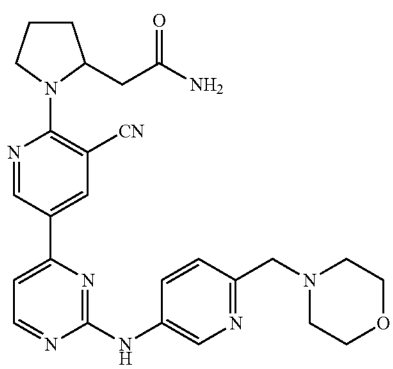 [SMILES: N#Cc1cc(-c2ccnc(Nc3ccc(CN4CCOCC4)nc3)n2)cnc1N1CCCC1CC(N)=O] | DMX-131 | 2-(1-{3-Cyano-5-[2-(6-morpholin-4-ylmethyl-pyridin-3-ylamino)-pyrimidin-4-yl]-pyridin-2-yl}-pyrrolidin-2-yl)-acetamide | Method D; Rt = 5.24 min; m/z 500 (MH$^+$); cream solid | <30 nM | <30 nM | None |
| 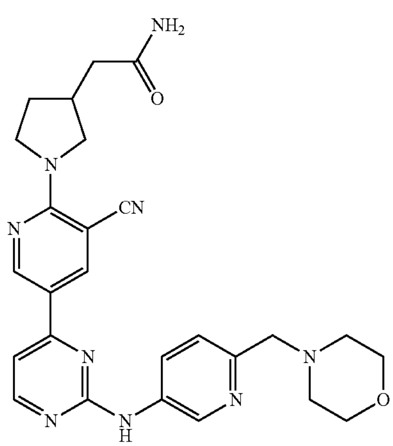 [SMILES: N#Cc1cc(-c2ccnc(Nc3ccc(CN4CCOCC4)nc3)n2)cnc1N1CCC(CC(N)=O)C1] | DMX-158 | 2-(1-{3-Cyano-5-[2-(6-morpholin-4-ylmethyl-pyridin-3-ylamino)-pyrimidin-4-yl]-pyridin-2-yl}-pyrrolidin-3-yl)-acetamide | Method D; Rt = 5.17 min; m/z 500 (MH$^+$); cream solid | <100 nM | <100 nM | None |

TABLE V-continued

| Structure | Ex. No. | Name | Analytical Data | Inhibition of IKKε | Inhibition of TBK1 | Salt form |
|---|---|---|---|---|---|---|
| 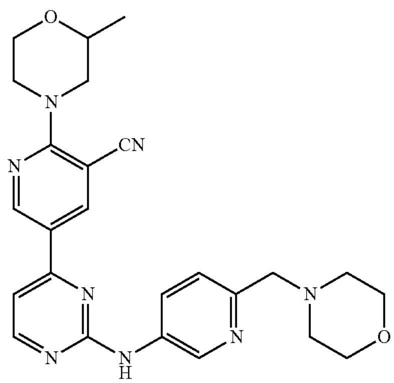 [SMILES: CC1CN(c2ncc(-c3ccnc(Nc4ccc(CN5CCOCC5)nc4)n3)cc2C#N)CCO1] | DMX-159 | 2-(2-Methyl-morpholin-4-yl)-5-[2-(6-morpholin-4-ylmethyl-pyridin-3-ylamino)-pyrimidin-4-yl]-nicotinonitrile | Method D; Rt = 5.75 min; m/z 473 (MH+); cream solid | <1 μM | <1 μM | None |
| 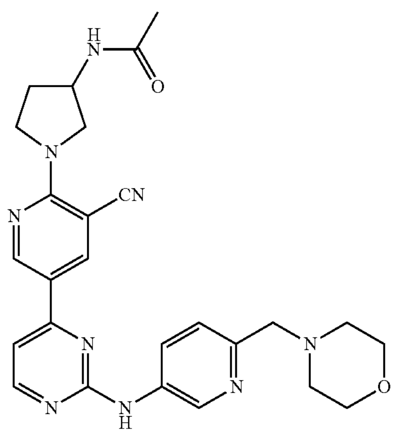 [SMILES: CC(=O)NC1CCN(c2ncc(-c3ccnc(Nc4ccc(CN5CCOCC5)nc4)n3)cc2C#N)C1] | DMX-132 | N-(1-{3-Cyano-5-[2-(6-morpholin-4-ylmethyl-pyridin-3-ylamino)-pyrimidin-4-yl]-pyridin-2-yl}-pyrrolidin-3-yl)-acetamide | Method D; Rt = 5.03 min; m/z 499 (MH+); cream solid | <1 μM | <1 μM | None |
| 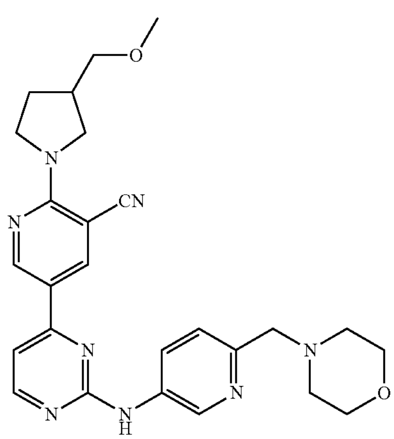 [SMILES: COCC1CCN(c2ncc(-c3ccnc(Nc4ccc(CN5CCOCC5)nc4)n3)cc2C#N)C1] | DMX-160 | 2-(3-Methoxymethyl-pyrrolidin-1-yl)-5-[2-(6-morpholin-4-ylmethyl-pyridin-3-ylamino)-pyrimidin-4-yl]-nicotinonitrile | Method D; Rt = 5.89 min; m/z 487 (MH+); cream solid | <100 nM | <1 μM | None |

TABLE V-continued

| Structure | Ex. No. | Name | Analytical Data | Inhibition of IKKε | Inhibition of TBK1 | Salt form |
|---|---|---|---|---|---|---|
| 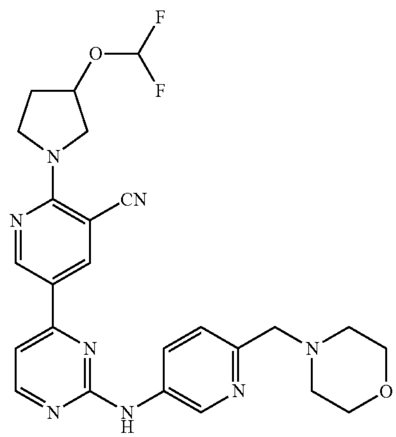 [SMILES: N#Cc1cc(-c2ccnc(Nc3ccc(CN4CCOCC4)nc3)n2)cnc1N1CCC(OC(F)F)C1] | DMX-161 | 2-(3-Difluoromethoxy-pyrrolidin-1-yl)-5-[2-(6-morpholin-4-ylmethyl-pyridin-3-ylamino)-pyrimidin-4-yl]-nicotinonitrile | Method D; Rt = 5.90 min; m/z 509 (MH$^+$); cream solid | <30 nM | <100 nM | None |
| 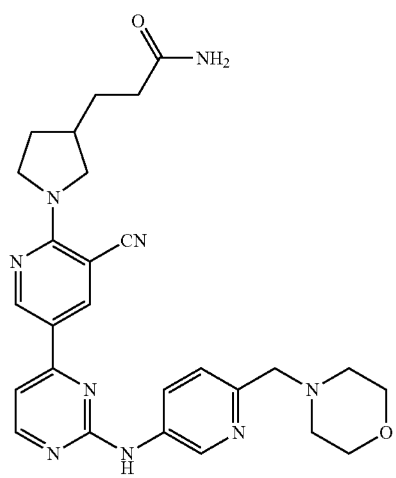 [SMILES: N#Cc1cc(-c2ccnc(Nc3ccc(CN4CCOCC4)nc3)n2)cnc1N1CCC(CCC(N)=O)C1] | DMX-162 | 3-(1-{3-Cyano-5-[2-(6-morpholin-4-ylmethyl-pyridin-3-ylamino)-pyrimidin-4-yl]-pyridin-2-yl}-pyrrolidin-3-yl)-propionamide | Method D; Rt = 5.41 min; m/z 514 (MH$^+$); cream solid | <30 nM | <100 nM | None |
| 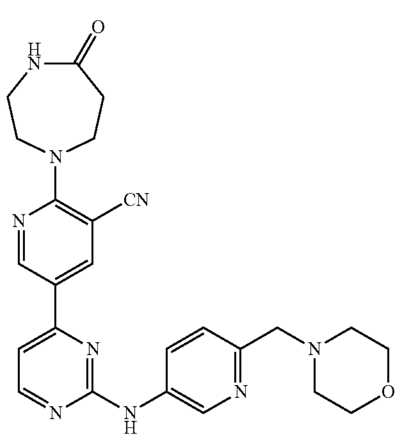 [SMILES: N#Cc1cc(-c2ccnc(Nc3ccc(CN4CCOCC4)nc3)n2)cnc1N1CCNC(=O)CC1] | DMX-133 | 5-[2-(6-Morpholin-4-ylmethyl-pyridin-3-ylamino)-pyrimidin-4-yl]-2-(5-oxo-[1,4]diazepan-1-yl)-nicotinonitrile | Method D; Rt = 4.91 min; m/z 486 (MH$^+$); cream solid | <1 μM | <1 μM | None |

TABLE V-continued

| Structure | Ex. No. | Name | Analytical Data | Inhibition of IKKε | Inhibition of TBK1 | Salt form |
|---|---|---|---|---|---|---|
| 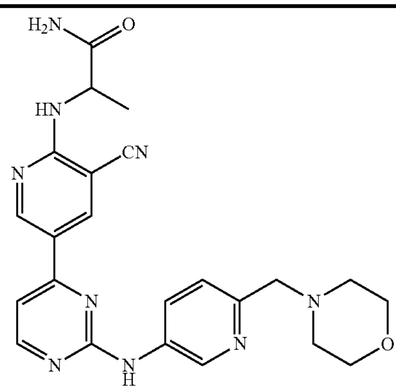 | DMX-134 | 2-{3-Cyano-5-[2-(6-morpholin-4-ylmethyl-pyridin-3-ylamino)-pyrimidin-4-yl]-pyridin-2-ylamino}-propionamide | Method D; Rt = 4.73 min; m/z 460 (MH+); cream solid | <100 nM | <100 nM | None |
| 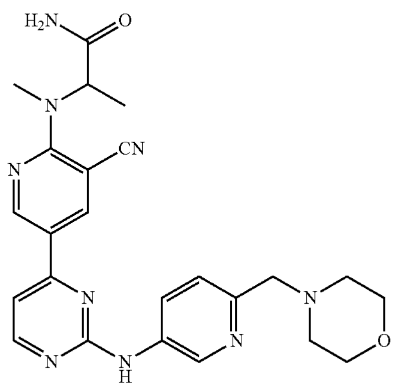 [SMILES: CC(C(N)=O)N(C)c1ncc(-c2ccnc(Nc3ccc(CN4CCOCC4)nc3)n2)cc1C#N] | DMX-135 | 2-({3-Cyano-5-[2-(6-morpholin-4-ylmethyl-pyridin-3-ylamino)-pyrimidin-4-yl]-pyridin-2-yl}-methyl-amino)-propionamide | Method D; Rt = 5.02 min; m/z 474 (MH+); yellow solid | <100 nM | <100 nM | None |
| 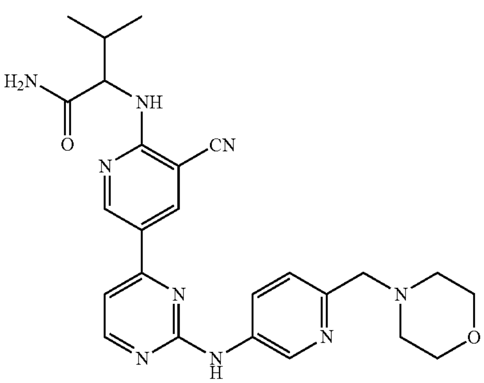 [SMILES: CC(C)C(Nc1ncc(-c2ccnc(Nc3ccc(CN4CCOCC4)nc3)n2)cc1C#N)C(N)=O] | DMX-136 | 2-{3-Cyano-5-[2-(6-morpholin-4-ylmethyl-pyridin-3-ylamino)-pyrimidin-4-yl]-pyridin-2-ylamino}-3-methyl-butyramide | Method D; Rt = 5.41 min; m/z 488 (MH+); brown solid | <15 nM | <15 nM | None |
| 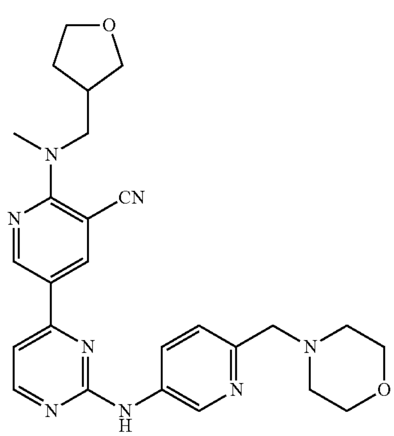 [SMILES: CN(CC1CCOC1)c1ncc(-c2ccnc(Nc3ccc(CN4CCOCC4)nc3)n2)cc1C#N] | DMX-137 | 2-[Methyl-(tetrahydro-furan-3-ylmethyl)-amino]-5-[2-(6-morpholin-4-ylmethyl-pyridin-3-ylamino)-pyrimidin-4-yl]-nicotinonitrile | Method D; Rt = 5.65 min; m/z 487 (MH+); brown solid | <1 μM | <1 μM | None |

TABLE V-continued

| Structure | Ex. No. | Name | Analytical Data | Inhibition of IKKε | Inhibition of TBK1 | Salt form |
|---|---|---|---|---|---|---|
| 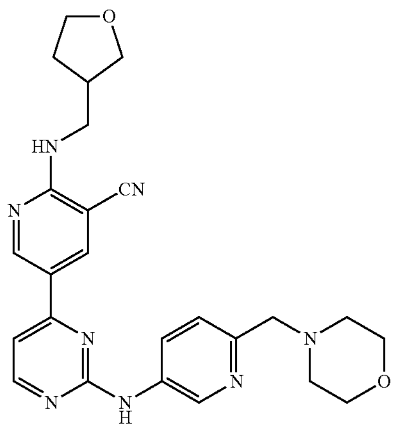 [SMILES: N#Cc1cc(-c2ccnc(Nc3ccc(CN4CCOCC4)nc3)n2)cnc1NCC1CCOC1] | DMX-138 | 5-[2-(6-Morpholin-4-ylmethyl-pyridin-3-ylamino)-pyrimidin-4-yl]-2-[(tetrahydro-furan-3-ylmethyl)-amino]-nicotinonitrile | Method D; Rt = 5.30 min; m/z 473 (MH+); cream solid | <1 μM | <100 nM | None |
| 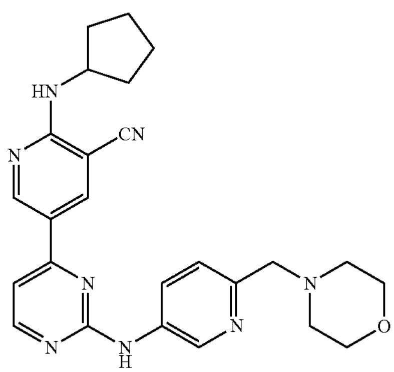 [SMILES: N#Cc1cc(-c2ccnc(Nc3ccc(CN4CCOCC4)nc3)n2)cnc1NC1CCCC1] | DMX-139 | 2-Cyclopentylamino-5-[2-(6-morpholin-4-ylmethyl-pyridin-3-ylamino)-pyrimidin-4-yl]-nicotinonitrile | Method D; Rt = 6.17 min; m/z 457 (MH+); brown solid | <100 nM | <100 nM | None |
| 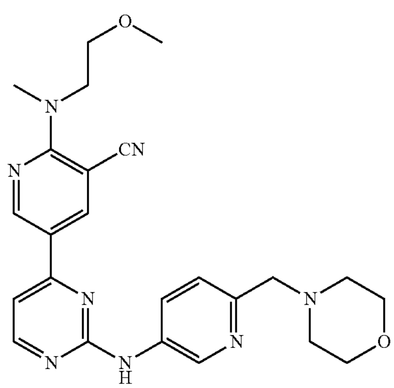 [SMILES: COCCN(C)c1ncc(-c2ccnc(Nc3ccc(CN4CCOCC4)nc3)n2)cc1C#N] | DMX-140 | 2-[(2-Methoxy-ethyl)-methyl-amino]-5-[2-(6-morpholin-4-ylmethyl-pyridin-3-ylamino)-pyrimidin-4-yl]-nicotinonitrile | Method D; Rt = 5.50 min; m/z 461 (MH+); brown solid | <1 μM | <1 μM | None |
| 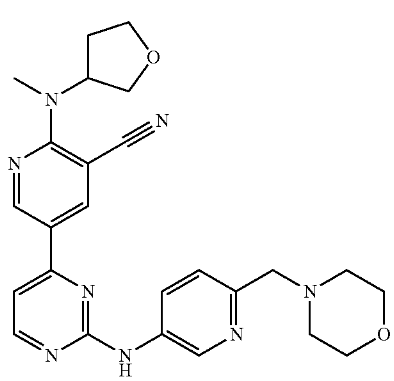 [SMILES: CN(c1ncc(-c2ccnc(Nc3ccc(CN4CCOCC4)nc3)n2)cc1C#N)C1CCOC1] | DMX-163 | 2-[Methyl-(tetrahydro-furan-3-yl)-amino]-5-[2-(6-morpholin-4-ylmethyl-pyridin-3-ylamino)-pyrimidin-4-yl]-nicotinonitrile | Method D; Rt = 5.51 min; m/z 473 (MH+); brown solid | <100 nM | <100 nM | None |

A number of the requisite amines utilised for either Buchwald or S$_N$Ar type reactions required synthesising from commercially available starting materials.

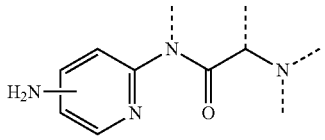

A1

Amines of formula A1 where the dashed line represents an optional bond to a carbon atom were made via the following routes:

Example

N-(5-Amino-pyridin-2-yl)-2-piperidin-1-yl-acetamide (A1-1)

2-Chloro-N-(5-nitro-pyridin-2-yl)-acetamide (20)

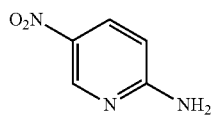

19

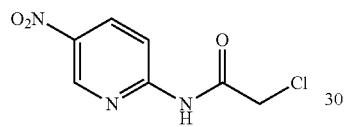

20

2-Amino-5-nitropyridine (19) (4.0 g, 28.8 mmol) was dissolved in THF (300 mL). TEA (12.0 mL, 86.1 mmol) was added and the stirred mixture cooled to 0° C. Chloroacetyl chloride (7.0 mL, 87.9 mmol) was added dropwise. The stirred solution was allowed to warm to rt then stirred at this temperature for 1 hour. The mixture was heated at reflux for 1 hour. The solvent was evaporated in vacuo and the residue partitioned between DCM (100 mL) and saturated aqueous sodium bicarbonate solution (50 mL). The layers were separated and the organic phase washed with saturated brine solution (50 mL), then separated, dried over MgSO4, filtered and concentrated in vacuo. Approximately half the crude product was purified by column chromatography (Biotage SP1) eluting with isohexane→30% EtOAc-isohexane, combining the crude material with this purified product. The combined material was triturated with EtOAc-isohexane to provide the title compound as a brown solid (3.6 g, 58%); Rf: 0.45 (3:1 isohexane-EtOAc).

N-(5-Amino-pyridin-2-yl)-2-piperidin-1-yl-acetamide (A1-1)

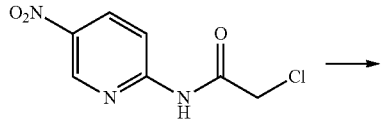

Compound 20 (3.0 g, 13.9 mmol), was dissolved in THF (100 mL). Morpholine (20 mL, 229 mmol) was added and the mixture stirred at reflux for 1 hour. DCM (200 mL) and saturated aqueous sodium bicarbonate solution (200 mL) were added and the layers separated. The organic phase was dried (MgSO$_4$), filtered and the solvent evaporated in vacuo. The residue was dissolved in EtOH (200 mL) and 10% Pd/C (wet, ~300 mg) followed by ammonium formate (880 mg, 14.0 mmol) added. The mixture was stirred at reflux for 1 hour. The mixture was cooled to rt, filtered through celite, washing the precipitate with EtOAc. The collected filtrate was diluted with saturated ammonium bicarbonate solution (100 mL) and the layers separated. The organic phase was dried (MgSO$_4$), filtered and the solvent evaporated in vacuo. The residue was triturated with EtOAc-isohexane to afford the title compound as an off-white solid (2.1 g, 63%); (m/z): 237 [MH]$^+$.

The following amines were made using this approach:

| Structure | Ex. No |
|---|---|
| 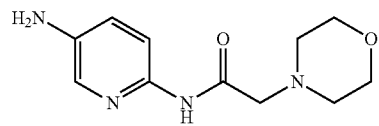 [SMILES: Nc1ccc(NC(=O)CN2CCOCC2)nc1] | A1-1 |
| 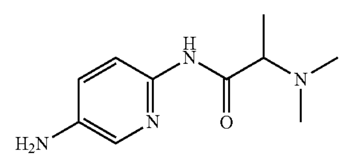 | A1-2 |
| 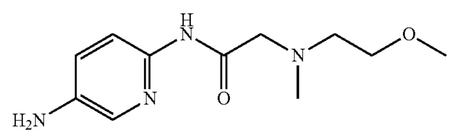 [SMILES: COCCN(C)CC(=O)Nc1ccc(N)cn1] | A1-3 |
| 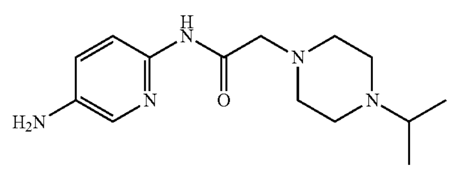 [SMILES: CC(C)N1CCN(CC(=O)Nc2ccc(N)cn2)CC1] | A1-4 |
| 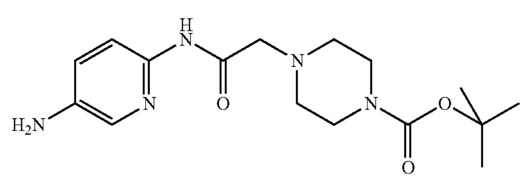 [SMILES: CC(C)(C)OC(=O)N1CCN(CC(=O)Nc2ccc(N)cn2)CC1] | A1-5 |
| 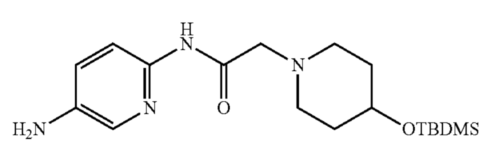 [SMILES: CC(C)(C)[Si](C)(C)OC1CCN(CC(=O)Nc2ccc(N)cn2)CC1] | A1-6 |
| 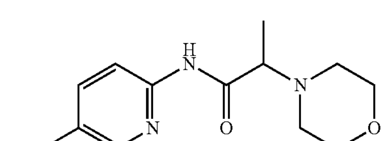 | A1-7 |

| Structure | Ex. No |
|---|---|
| 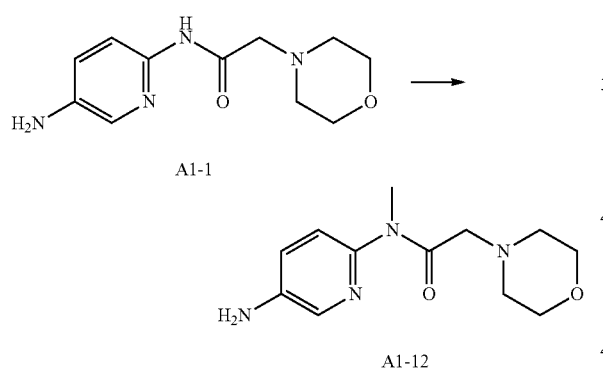 (shown in table) | A1-8 |
| 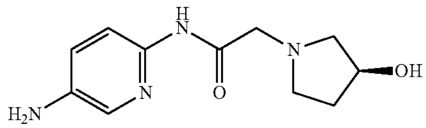 [SMILES: Nc1ccc(NC(=O)CN2CC[C@H](O)C2)nc1] | A1-9 |
| 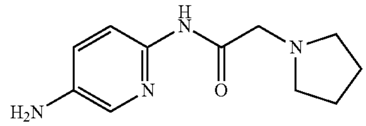 [SMILES: Nc1ccc(NC(=O)CN2CCCC2)nc1] | A1-10 |
| 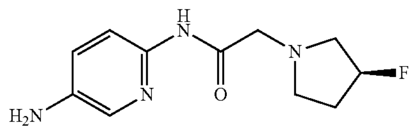 [SMILES: Nc1ccc(NC(=O)CN2CC[C@H](F)C2)nc1] | A1-11 |

Amine A1-1 was also used to synthesise amine A1-12

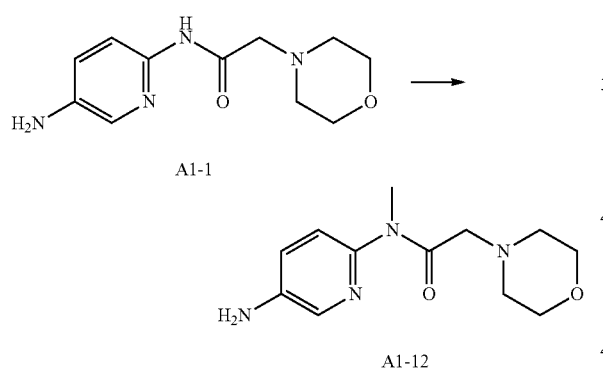

N-(5-Amino-pyridin-2-yl)-N-methyl-2-morpholin-4-yl-acetamide (A1-12)

To a solution of A1-1 (150 mg, 0.64 mmol) in dry THF (5 mL) was added methyl iodide (50 µL, 0.80 mmol) and potassium tert-butoxide (100 mg, 0.89 mmol) and the reaction mixture stirred at room temperature for 1 h. After which time a further amount of methyl iodide (50 µL, 0.80 mmol) was added and the reaction mixture stirred at room temperature for 16 h. After which time the reaction mixture was evaporated and the crude residue portioned between ethyl acetate (20 mL) and water (10 mL). The organic layer was separated, dried over MgSO4, filtered and evaporated to dryness to give the title compound (87 mg, 55%); LCMS, Rt=1.47 min (MeOH-FA method), m/z 251 (MH$^+$).

Other amines containing the general formula A1 that were made using alternative chemistry include:

Example A1-13

[1-(5-Amino-pyridin-2-ylcarbamoyl)-1-methyl-ethyl]-carbamic acid tert-butyl ester

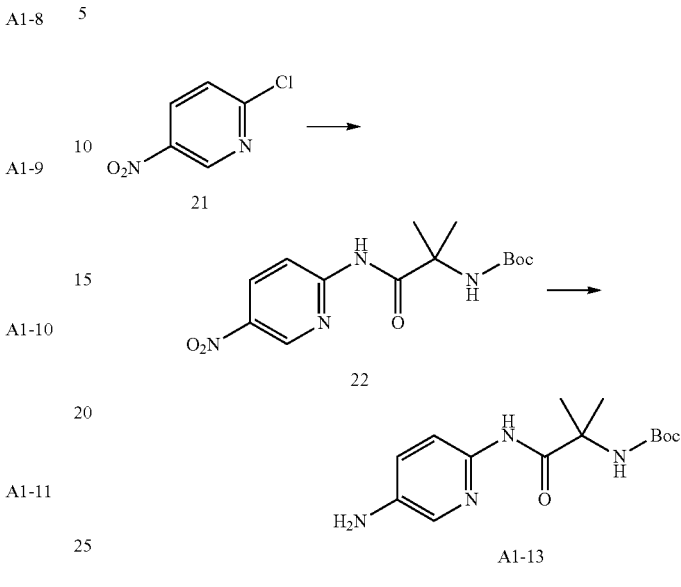

2-Chloro-5-nitropyridine (21) (100 mg, 0.63 mmol), Pd$_2$(dba)$_3$ (29 mg, 0.03 mmol), Dave-Phos (25 mg, 0.06 mmol), 1-carbamoyl-1-methyl-ethyl)-carbamic acid tert-butyl ester (141 mg, 0.70 mmol) and sodium tert-butoxide (91 mg, 0.95 mmol) in 1,4 dioxane (4 mL) was deoxygenated for 10 mins by bubbling nitrogen through the mixture. The mixture was then heated in the microwave at 120° C. for 20 min. This procedure was repeated for a second time with a further 100 mg of 2-chloro-5-nitropyridine. The reaction mixtures were combined, evaporated and purified by flash chromatography on silica eluting with 0-40% ethyl acetate/isohexane. The fractions containing 22 were combined and evaporated and added to Pd/C (10 mg) in ethanol (5 mL) followed by ammonium formate (99 mg, 1.58 mmol). The reaction mixture was heated at reflux for 2 h, then filtered through celite, washing with ethanol to remove the Pd/C residues. The filtrate was evaporated to give A1-13 as a pale yellow oil (80 mg, 21%); LCMS, Rt=1.80 min (MeOH-FA method), m/z 294 (MH$^+$).

Example A1-14

(S)-2-(5-Amino-pyridin-2-ylcarbamoyl)-pyrrolidine-1-carboxylic acid tert-butyl ester

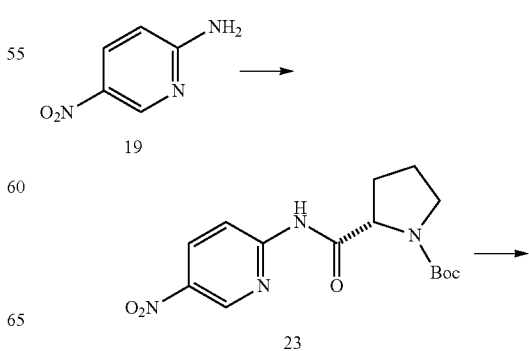

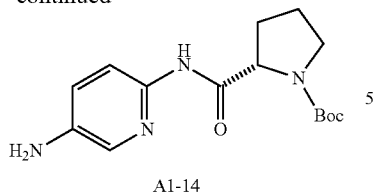

A1-14

To a solution of Boc protected proline (1 g, 4.7 mmol) in THF (20 mL) was added triethyl amine (0.63 mL, 4.7 mmol) and the reaction mixture was cooled to 0° C. and ethylchloroformate (0.45 mL, 4.65 mmol) added slowly at 0° C. and stirred for 30 min. 2-Amino-5-nitropyridine (646 mg, 4.7 mmol) was then added to the reaction mixture at 0° C. and stirred for 1 h and then allowed to warm to rt and stirred for 20 h. After this time the reaction was heated 70° C. and stirred for 3 h. After completion of the reaction monitored by TLC the reaction mixture was cooled and diluted with EtOAc (50 mL) and filtered, The filtrate was washed with NH$_4$Cl solution (50 mL), brine solution (50 mL) and dried over anhydrous Na$_2$SO$_4$, filtered and evaporated under vacuum. The crude residue was purified on flash column chromatography using EtOAc: Hexane (1:9) to give A1-14 (300 mg, 20%); m/z 307 (MH$^+$).

Example A1-15

N-(5-Amino-pyridin-3-yl)-2-morpholin-4-yl-acetamide

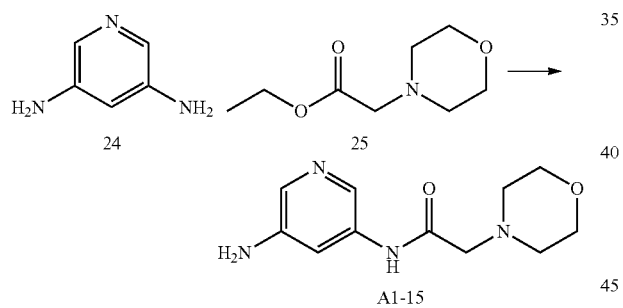

A1-15

To a stirred solution of pyridine-3,5-diamine (24) (1.5 g, 17.4 mmol) and morpholin-4-yl-acetic acid ethyl ester (25) (1.5 g, 8.6 mmol) in toluene (30 mL) was added 2M solution of tri-methyl aluminum in toluene (17.4 mL, 34.8 mmol) at 0° C. The resulting reaction mixture was stirred at room temperature for 1 h. The reaction mixture was concentrated; the residue was dissolved in water and extracted with 10% MeOH/CHCl$_3$ (3×50 mL). The combined organic layer was washed with brine, dried over Na$_2$SO$_4$ and concentrated. The crude compound was purified by silica gel column-chromatography (100-200 mesh, eluted with 5% MeOH/CHCl$_3$) to give A1-15 (600 mg, 40%) as a solid, the compound contains di-amide impurity and was used as such for the next step. 50 mg of the above compound was further purified by preparative HPLC for analytical purposes and 10 mg of compound A1-15 was obtained as a white solid. R$_f$: 0.4 (10% MeOH/CHCl$_3$); (m/z): 237 [M+H]$^+$; $^1$H NMR (400 MHz, CDCl$_3$): δ 9.05 (1H, br s), 7.84 (2H, m), 7.78-7.77 (1H, m), 3.78 (4H, t, J=4.4 Hz), 3.74 (2H, br s), 3.14 (2H, s), 2.62 (4H, t, J=4.4 Hz).

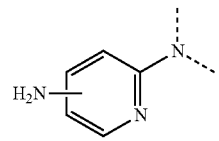

A2

Amines of formula A2 where the dashed line represents an optional bond to a carbon atom were made via the following routes:

Example A2-1

4-(5-Amino-pyridin-2-yl)-piperazine-1-carboxylic acid tert-butyl ester 4-(5-Nitro-pyridin-2-yl)-piperazine-1-carboxylic acid tert-butyl ester (26)

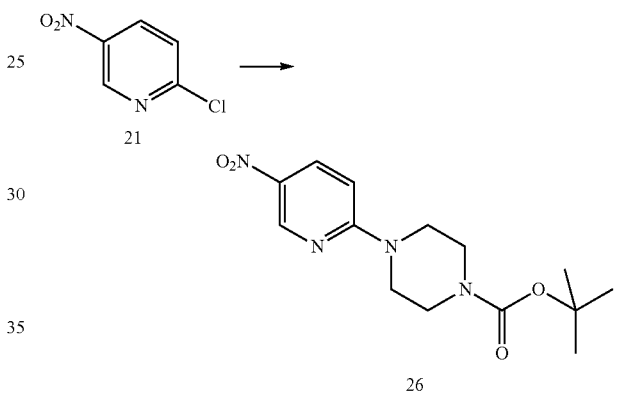

5-Nitro-2-chloropyridine (21) (350 mg, 2.21 mmol) and 1-Boc-piperazine (430 mg, 2.31 mmol) were dissolved in MeCN (3.6 mL). TEA (400 µL, 2.87 mmol) was added and the mixture heated at 140° C. in the microwave (250 W, stirring) for 30 minutes. The solvent was evaporated in vacuo and the residue dissolved in DCM (75 mL). The solution was washed with 0.5N HCl (2×20 mL) and the organic phase washed with saturated brine solution (40 mL), then dried (MgSO$_4$), filtered and the solvent evaporated in vacuo to afford the title compound as a yellow solid (646 mg, 95%); LCMS, Rt=2.97 min (MeOH-FA method), m/z 309 (MH$^+$).

4-(5-Amino-pyridin-2-yl)-piperazine-1-carboxylic acid tert-butyl ester (A2-1)

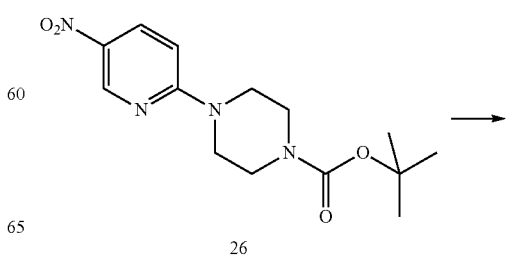

26

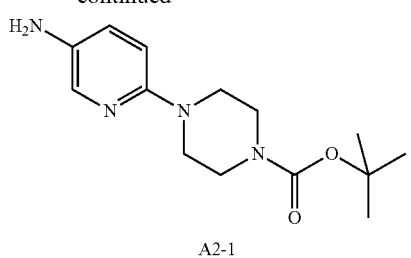

A2-1

Compound 26 (646 mg, 2.10 mmol) and ammonium formate (661 mg, 10.5 mmol) were dissolved in EtOH (20 mL). 10% Pd/C (22 mg, 0.207 mmol) was added and the mixture stirred at reflux for 1 hour. The mixture was filtered through celite, washing the precipitate with EtOAc. The filtrate was evaporated in vacuo and the residue dissolved in EtOAc (50 mL). The solution was washed with 0.5N HCl (2×20 mL), saturated brine solution (20 mL), then dried (MgSO$_4$), filtered and the solvent evaporated in vacuo to afford A2-1 as a purple solid (458 mg, 79%); LCMS, Rt=1.51 min (MeOH-FA method), m/z 279 (MH$^+$).

The following amines were made using this approach:

| Structure | Ex. No. |
|---|---|
| 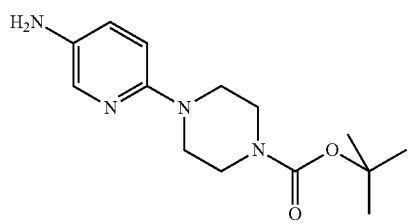 [SMILES: CC(C)(C)OC(=O)N1CCN(c2ccc(N)cn2)CC1] | A2-1 |
| 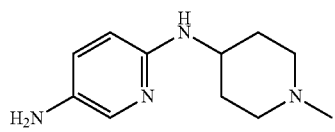 | A2-2 |
| 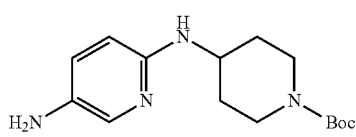 | A2-3 |
| 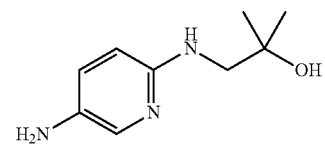 | A2-4 |
| 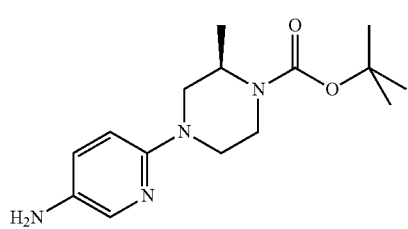 [SMILES: C[C@@H]1CN(c2ccc(N)cn2)CCN1C(=O)OC(C)(C)C] | A2-5 |
| 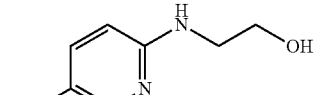 | A2-6 |
| 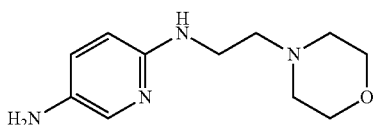 | A2-7 |
| 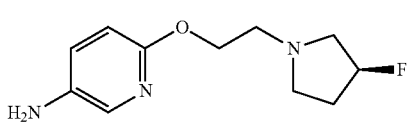 [SMILES: Nc1ccc(OCCN2CC[C@H](F)C2)nc1] | A2-8† |
| 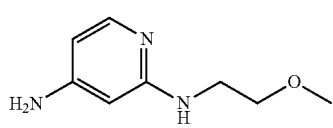 | A2-9 |
| 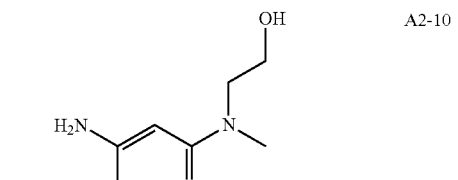 | A2-10 |

†displacement with alcohol was carried out using sodium hydride in THF.

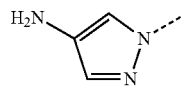

A3

Amines of formula A3 where the dashed line represents a bond to a carbon atom were made via the following routes:

Example A3-1

3-(4-Amino-pyrazol-1-yl)-propan-1-ol 3-(4-Nitro-pyrazol-1-yl)-propan-1-ol (28)

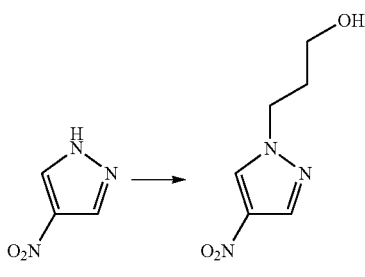

To a stirred solution of 4-nitro-1H-pyrazole (27) (1.0 g, 8.9 mmol) in MeCN (15 mL) was added K$_2$CO$_3$ (1.8 g, 13.2 mmol) and 3-bromo-propanol (880 µL, 9.7 mmol). The mixture was stirred at 75° C. for 6 hours. The solvent was evaporated in vacuo and the residue partitioned between H₂O (15 mL) and EtOAc (15 mL). The layers were separated and the aqueous phase extracted with EtOAc (2×15 mL). The combined organics were dried (MgSO₄), filtered and the solvent evaporated in vacuo to afford the title compound as a pale yellow oil (1.41 g, 93%); LCMS, Rt=1.31 min (MeOH-FA method), m/z 172 (MH⁺).

3-(4-Amino-pyrazol-1-yl)-propan-1-ol (A3-1)

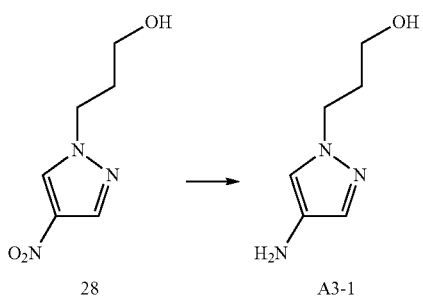 [SMILES: O=[N+]([O-])c1cnn(CCCO)c1 ; Nc1cnn(CCCO)c1]

3-(4-Nitro-pyrazol-1-yl)-propan-1-ol (1.41 g, 8.23 mmol) was dissolved in MeOH (15 mL). Pd/C (0.532 g, 0.82 mmol) was added and the mixture was stirred under H₂ at rt for 16 hours. The reaction mixture was filtered and the solvent evaporated in vacuo to afford the title compound as a red/brown oil (1.18 g, 100%); LCMS, Rt=0.31 min (MeOH-FA method), m/z 142 (MH⁺).

Example A3-2

(S)-3-(4-Amino-pyrazol-1-yl)-propane-1,2-diol (S)-3-(4-Nitro-pyrazol-1-yl)-propane-1,2-diol (29)

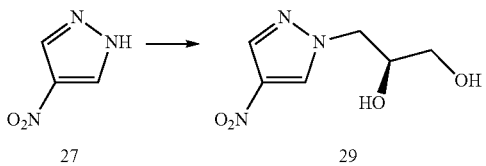 [SMILES: O=[N+]([O-])c1cn[nH]c1 ; O=[N+]([O-])c1cnn(C[C@H](O)CO)c1]

3-Nitro-1-H-pyrazole (27) (600 mg, 5.3 mmol), (S)-glycidol (702 µL, 10.6 mmol) and K₂CO₃ (1.1 g, 8.0 mmol) in acetonitrile (7 mL) were heated in the microwave at 100° C. for 1 h. The solvent was evaporated in vacuo and the residue dissolved in ethyl acetate (20 mL) and water (20 mL). The organic layer was separated and the aqueous layer further extracted with ethyl acetate (10×20 mL). The organics were combined, dried over MgSO₄, filtered and evaporated to give a crude oil. This was purified by flash chromatography on silica eluting with a gradient of 70% ethyl acetate/isohexane to ethyl acetate, to give the desired compound as a white solid (180 mg, 18%); LCMS, Rt=0.98 min (MeOH-FA method), m/z 188 (MH⁺).

(S)-3-(4-Amino-pyrazol-1-yl)-propane-1,2-diol

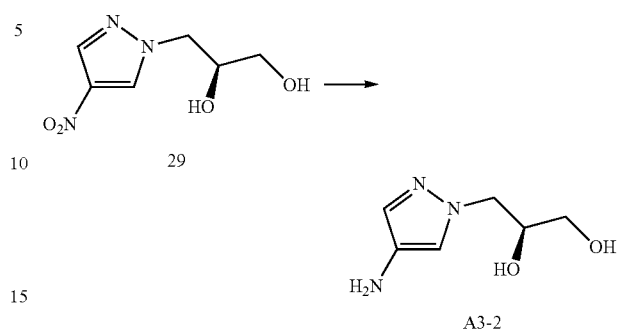

(S)-3-(4-Nitro-pyrazol-1-yl)-propane-1,2-diol (29) (180 mg, 10 mmol), and 10% Pd/C (116 mg) in methanol (20 mL) were stirred under hydrogen for at atmospheric pressure and room temperature for 48 h. The reaction mixture was subsequently filtered through celite and concentrated to give A3-2 (160 mg, 100%); LCMS, Rt=0.28 min (MeOH-FA method), m/z 158 (MH⁺).

The following amines were made via this route:

| Structure | Ex. No. |
|---|---|
| H₂N—[pyrazole]—CH₂CH(OH)CH₂OH | A3-2 |
| H₂N—[pyrazole]—CH₂CH(OH)CH₂OH | A3-3 |

A4

Amines of formula A4 where the dashed line represents an optional bond to a carbon atom and Q is CH or N were made via the following routes:

Example A4-1

6-((S)-3-Methoxy-pyrrolidin-1-ylmethyl)-pyridin-3-ylamine

5-Nitro-pyridine-2-carbaldehyde (31)

To a stirred solution of compound 2-methyl-5-nitropyridine (30) (10 g, 72.5 mmol) in 1,4-dioxane (150 mL) was added SeO$_2$ (9.5 g, 87.0 mmol) at room temperature. The resulting reaction mixture was stirred at 80° C. for 16 h. The reaction mixture was evaporated, the residue was diluted with water (100 mL), the resulting precipitate was separated by filtration and the filtrate was extracted with ethyl acetate (3×100 mL). The combined organic layer was washed with water (100 mL), brine (100 mL), the organic layer was dried over Na$_2$SO$_4$ and concentrated to give 31 (6.4 g, 58%) as a brown solid. R$_f$: 0.7 (30% EtOAc/pet-ether); $^1$H NMR (400 MHz, CDCl$_3$): δ 10.18 (1H, s), 9.59 (1H, d, J=2.0 Hz), 8.68-8.65 (1H, m), 8.16 (1H, d, J=8.4 Hz)

2-((S)-3-Methoxy-pyrrolidin-1-ylmethyl)-5-nitro-pyridine (32)

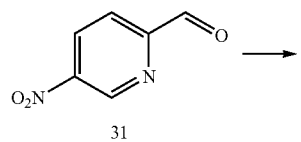

To a stirred solution of 31 (0.4 g, 2.6 mmol) and (S)-3-methoxy-pyrrolidine (0.4 g, 3.2 mmol) in dichloromethane (10 mL) was added acetic acid (0.01 mL, 0.25 mmol). After 30 minutes, sodium triacetoxyborohydride (1.1 g, 5.3 mmol) was added to the above mixture and stirred at rt for 15 minutes. The reaction mixture was diluted with water (10 mL), treated with saturated NaHCO$_3$ solution to get pH~8 and extracted with dichloromethane (2×20 mL). The combined organic layers were washed with brine (50 mL), dried (Na$_2$SO$_4$) and evaporated. The crude compound was purified by silica gel flash chromatography, eluting with 2% MeOH/DCM to afford 32 (0.25 g, 40%) as a liquid. R$_f$: 0.3 (5% MeOH/DCM); (m/z): 238 [MH]$^+$; $^1$H NMR (400 MHz, DMSO-d$_6$): δ 9.28 (1H, d, J=2.8 Hz), 8.59-8.56 (1H, m), 7.71 (1H, d, J=8.8 Hz), 3.93-3.80 (3H, m), 3.16 (3H, s), 2.73-2.62 (2H, m), 2.56-2.53 (1H, m), 2.50-2.47 (1H, m), 2.06-2.02 (1H, m), 1.72-1.65 (1H, m).

6-((S)-3-Methoxy-pyrrolidin-1-ylmethyl)-pyridin-3-ylamine (A4-1)

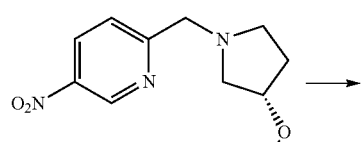

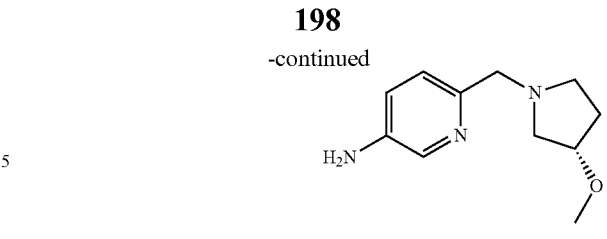

A solution of 32 (0.25 g, 1.05 mmol) in MeOH (6 mL) was hydrogenated using 10% Pd/C (50 mg) under a hydrogen atmosphere (balloon pressure) at rt for 1 h. The reaction mixture was filtered through a Celite bed and the filtrate was evaporated to give the desired amine (0.2 g, 82%) as brown liquid. R$_f$: 0.1 (10% MeOH/DCM); m/z): 208 [MH]$^+$; $^1$H NMR (400 MHz, DMSO-d$_6$): δ 7.82 (1H, d, J=2.4 Hz), 7.01-6.99 (1H, m), 6.88-6.86 (1H, m), 5.16 (2H, br s), 3.93-3.80 (3H, m), 3.21-3.13 (5H, m), 2.65-2.61 (1H, m), 2.42-2.34 (2H, m), 1.99-1.92 (1H, m).

The following amines were made via this route:

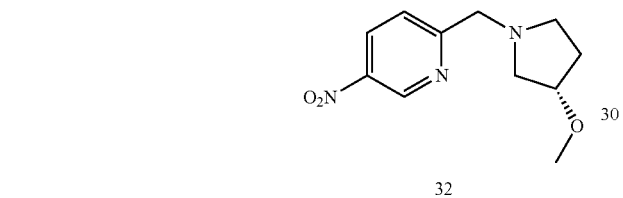

| Structure | Ex. No. |
|---|---|
| 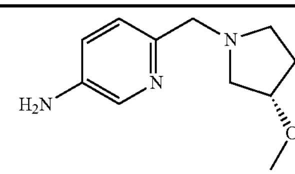 | A4-1 |
| 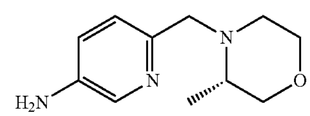 | A4-2 |
| 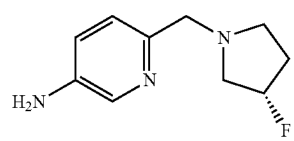 [SMILES: Nc1ccc(CN2CC[C@H](F)C2)nc1] | A4-3 |
| 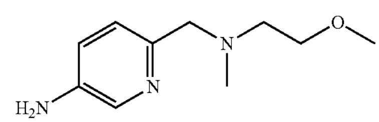 | A4-4 |
| 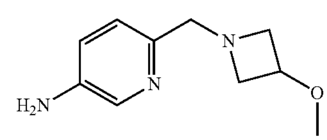 | A4-5 |
| 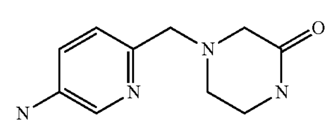 [SMILES: Nc1ccc(CN2CCNC(=O)C2)nc1] | A4-6 |
| 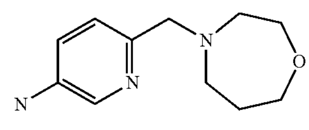 [SMILES: Nc1ccc(CN2CCCOCC2)nc1] | A4-7 |
| 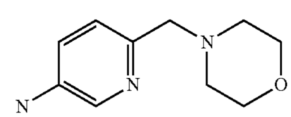 [SMILES: Nc1ccc(CN2CCOCC2)nc1] | A4-8 |

In a few cases an additional step was required in order to protect a secondary amine before carrying out the Buchwald step

Example A4-9

(5-Amino-pyridin-2-ylmethyl)-(2-methanesulfonyl-ethyl)-carbamic acid tert-butyl ester (2-Methanesulfonyl-ethyl)-(5-nitro-pyridin-2-ylmethyl)-amine (33)

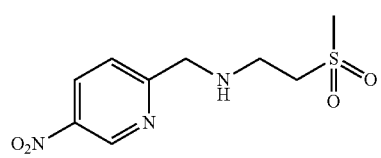

33

Synthesised as described above for compound 32.

(2-Methanesulfonyl-ethyl)-(5-nitro-pyridin-2-ylmethyl)-carbamic acid tert-butyl ester (34)

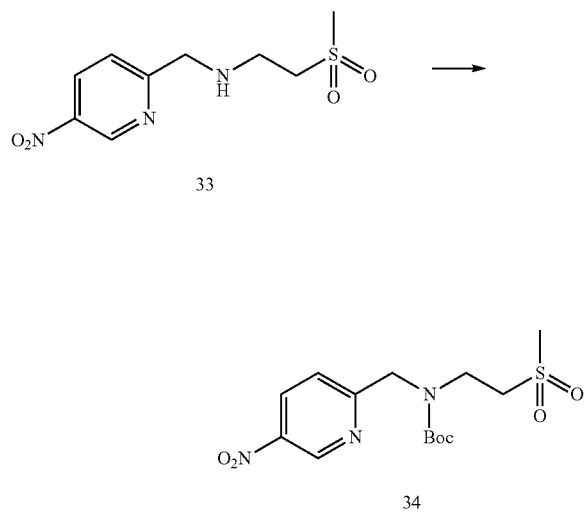

To a solution of 32 (0.30 g, 1.2 mmol) in acetonitrile (10 mL) was added TEA (0.32 mL, 2.3 mmol) and Boc$_2$O (0.30 g, 1.4 mmol) and the reaction mixture stirred at room temperature for 6 h. The reaction mixture was evaporated, the residue was diluted with water and extracted with 10% MeOH in CHCl$_3$ (2×20 mL). The combined organic layer was washed with brine (50 mL), dried (Na$_2$SO$_4$) and evaporated. The crude compound was purified by silica gel column chromatography (100-200 mesh, eluted by 50% EtOAc/pet ether) to give compound 34 (0.16 g, 35%) as a brown gummy liquid. R$_f$: 0.7 (10% MeOH/CHCl$_3$); (m/z): 360 [MH]$^+$; $^1$H NMR (400 MHz, CDCl$_3$): δ 8.01 (1H, s), 6.99-6.95 (2H, m), 4.44 (2H, br s), 3.74-3.67 (2H, m), 3.31 (2H, m), 2.95 (3H, s), 1.44 (9H, s).

(5-Amino-pyridin-2-ylmethyl)-(2-methanesulfonyl-ethyl)-carbamic acid tert-butyl ester (A4-9)

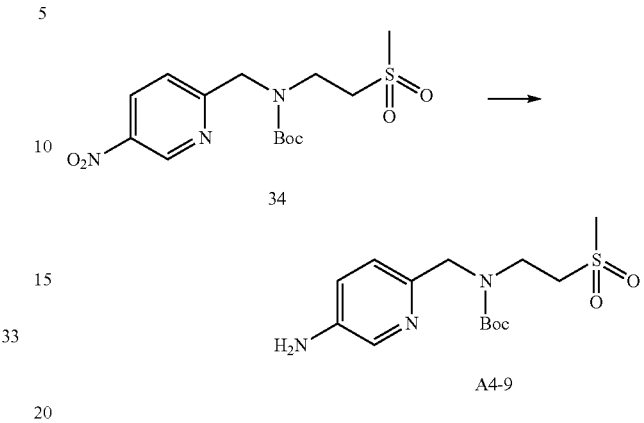

To a stirred solution of 34 (0.35 g 1.0 mmol) in MeOH (6 mL) was added 10% Pd/C and hydrogenated under balloon pressure at rt for 2 h. The reaction mixture was filtered through Celite and the filtrate was evaporated to give the desired amine A4-9 (0.25 g, 78%) as a liquid. R$_f$: 0.1 (10% MeOH/CHCl$_3$); (m/z): 330 [M+1]$^+$; $^1$H NMR (400 MHz, CDCl$_3$): δ 8.01 (1H, s), 7.07-6.94 (2H, m), 4.44 (2H, br s), 3.74-3.72 (2H, m), 3.33-3.31 (2H, m), 2.95-2.86 (3H, m), 2.06-2.01 (2H, m), 1.39 (9H, m).

The following amines were made using this approach:

| Structure | Ex. No. |
|---|---|
| H$_2$N-pyridine-CH$_2$-N(Boc)-CH$_2$CH$_2$-SO$_2$Me | A4-9 |
| H$_2$N-pyridine-CH$_2$-N(Boc)-CH$_2$CH$_2$-OMe | A4-10 |
| H$_2$N-pyridine-CH$_2$-N(Boc)-oxetanyl | A4-20 |

Example A4-11

6-(1-Morpholin-4-yl-ethyl)-pyridin-3-ylamine

A4-11 was made using a variation of the above approach from methylketone 35. The methylketone was synthesised from 2-chloro-5-nitropyridine (21).

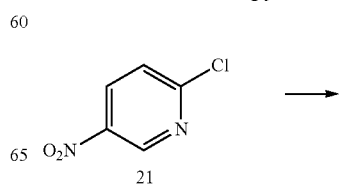

21

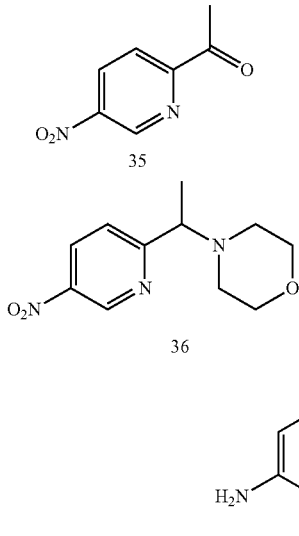

4-[1-(5-Nitro-pyridin-2-yl)-ethyl]-morpholine (36)

2-chloro-5-nitropyridine (21) (1.0 g, 6.3 mmol), copper (I) iodide (181 mg, 1.0 mmol), bis-(triphenylphosphine) palladium dichloride (218 mg, 0.3 mmol), ethoxyvinyl tributyl tin (2.3 mL, 6.9 mmol) were combined in acetonitrile (10 mL) and heated to reflux for 1 h under nitrogen. After which time the reaction had not gone to completion so a further amount of ethoxyvinyl tributyl tin (1 mL, 3.0 mmol) and bis-(triphenylphosphine) palladium dichloride (100 mg, 0.1 mmol) was added and the reaction mixture heated at reflux for a further 1 h. After which time the solvent was removed and the residue partitioned between ethyl acetate (50 mL) and water (50 mL). The organic layer was separated, dried over MgSO$_4$, filtered and evaporated. The crude residue was purified by flash chromatography on silica, eluting with 0-20% ethyl acetate/isohexane to isolate the vinyl ether intermediate. This was dissolved in acetone (10 mL) and p-toluene sulfonic acid (570 mg, 1.9 mmol) was added. The reaction mixture was stirred at room temperature for 18 h. The solvent was evaporated, the residue dissolved in dichloromethane (50 mL) and washed with water (50 mL). The organic phase was passed through a hydrophobic frit and the solvent evaporated. The crude residue was purified by flash chromatography on silica, eluting with 0-30% ethyl acetate/isohexane to give ketone 35 as a white solid (717 mg), m/z 167 (MH$^+$); Ketone 35 (360 mg, 2.2 mmol) was dissolved in 1,2 dichloroethane and morpholine (1.9 mL, 22.0 mmol), tri-acetoxyborohydride (2.3 g, 11.0 mmol) and acetic acid (0.25 mL, 4.4 mmol) were added. The reaction mixture was heated in the microwave at 100° C. for 2 h. Saturated NaHCO$_3$ (aq) (20 mL) was added followed by dichlormethane (20 mL). The organic layer was separated and the aqueous phase further extracted with dichloromethane (1×20 mL). The organic layers were combined, dried over MgSO$_4$, filtered and evaporated. The crude residue was purified by flash chromatography, eluting with 0-50% ethyl acetate/isohexane to give the desired compound 36 as a red oil (178 mg, 23% from 21); LCMS, Rt=0.39 min (MeOH-FA), m/z 238 (MH$^+$).

6-(1-Morpholin-4-yl-ethyl)-pyridin-3-ylamine (A4-11)

Compound 36 (178 mg, 0.75 mmol) was added to Pd/C (20 mg) in ethanol (5 mL), followed by ammonium formate (237 mg, 3.76 mmol) and the reaction mixture heated to reflux for 1 h. The reaction mixture was filtered through celite and the filtrate evaporated. The residue was dissolved in dichloromethane (20 mL) and washed with saturated sodium bicarbonate (20 mL). The organic phase was passed through a hydrophobic frit and evaporated to give the title compound as a yellow oil (155 mg, quant.; LCMS, Rt=0.32 min (MeOH-FA method), m/z 208 (MH$^+$).

Example A4-12

2-[(5-Amino-pyridin-2-ylmethyl)-methyl-amino]-ethanol

A4-12 was made in 4 steps from 5-amino-pyridine-2-carbonitrile (37)

5-Dibenzylamino-pyridine-2-carbonitrile (38)

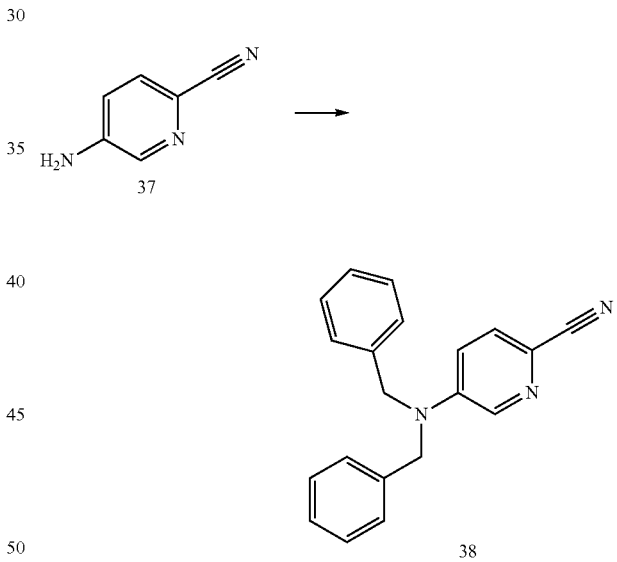

To a solution of 5-amino-pyridine-2-carbonitrile (37) (800 mg, 6.72 mmol) in DMF (8 mL) was added NaH (60%) (806 mg, 20.2 mmol) portion wise at 0° C. Benzyl bromide (2.3 mL, 20.2 mmol) was subsequently added and the mixture allowed to stir at rt for 3 h. The reaction mixture was diluted with water (20 mL), extracted with EtOAc (2×50 mL), the combined organic layers were washed with brine (20 mL), dried (Na$_2$SO$_4$) and evaporated. The crude compound was purified by silica gel column chromatography (100-200 mesh, eluted with 30% EtOAc/pet-ether) to obtain compound 38 (1.3 g, 65%) as a pale yellow solid. R$_f$: 0.7 (10% MeOH/CHCl$_3$); (m/z): 300 [MH]$^+$; $^1$H NMR (400 MHz, DMSO-d$_6$): δ 8.14 (1H, d, J=2.8 Hz), 7.65 (1H, d, J=9.2 Hz), 7.37-7.25 (10H, m), 7.08 (1H, dd, J=3.6, 9.6 Hz), δ 4.88 (4H, s).

5-Dibenzylamino-pyridine-2-carbaldehyde (39)

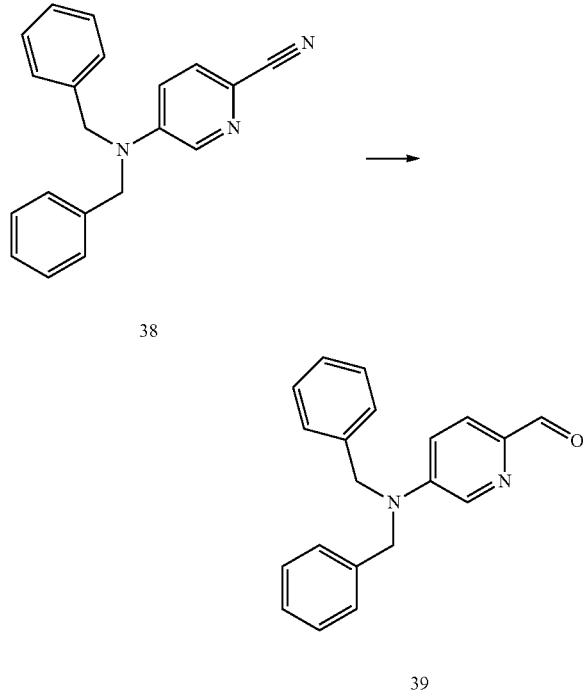

To a solution of 38 (500 mg, 1.7 mmol) in THF (25 mL) was added 1.6M DIBALH in toluene (3.1 mL, 5.01 mmol) at −78° C. and stirred for 3 h at the same temperature. The reaction mixture was quenched with water (20 mL), extracted with EtOAc (2×50 mL), the combined organic layers were washed with brine (20 mL), dried (Na$_2$SO$_4$) and evaporated. The crude compound was purified by silica gel column chromatography (100-200 mesh, eluted with 20% EtOAc/pet-ether) to obtain compound 39 (350 mg, 69%) as a brown solid. R$_f$: 0.5 (40% EtOAc/pet-ether); (m/z): 303 [MH]$^+$; $^1$H NMR (400 MHz, CDCl$_3$): δ 9.85 (1H, S), 8.27 (1H, d, J=2.8 Hz), 7.79 (1H, d, J=8.8 Hz), 7.38-7.20 (10H, m), 7.03 (1H, dd, J=3.2, 8.8 Hz), δ 4.77 (4H, s).

2-[(5-Dibenzylamino-pyridin-2-ylmethyl)-methyl-amino]-ethanol (40)

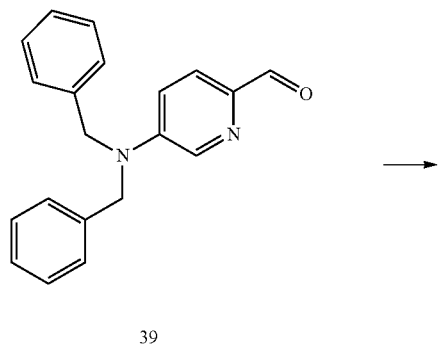

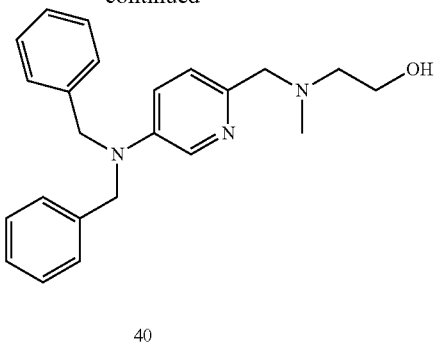

To a solution of 39 (600 mg, 2.0 mmol) in THF (25 mL) was added 2-(methyl amino) ethanol (224 mg, 3.0 mmol) and a catalytic amount of acetic acid (0.1 mL) and cooled to 0° C. Na(OAc)$_3$BH (1 g, 5.0 mmol) was added portion wise and the reaction mixture allowed to warm and stired at rt for 3 h. The reaction mixture was neutralized by using NaHCO$_3$ (aq), diluted with water (25 mL, 1:3 dilution), extracted with EtOAc (2×100 mL), the combined organic layers were washed with brine (20 mL), dried (Na$_2$SO$_4$) and evaporated. The crude compound was purified by column chromatography (neutral alumina, eluted with 5% MeOH/CHCl$_3$) to obtain compound 40 (400 mg, 55%) as a brown solid. R$_f$: 0.3 (10% MeOH/CHCl$_3$); (m/z): 362 [MH]$^+$; $^1$H NMR (400 MHz, DMSO-d$_6$) δ 7.91 (1H, d, J=2.8 Hz), 7.35-7.22 (10H, m), 7.12 (1H, d, J=8.8 Hz), 7.02 (1H, dd, J=2.8, 8.8 Hz), 4.72 (4H, s), 4.37 (1H, br s), 3.46-3.44 (4H, m), 2.40 (2H, t, J=6.4 Hz), 2.13 (3H, S).

2-[(5-Amino-pyridin-2-ylmethyl)-methyl-amino]-ethanol (A4-12)

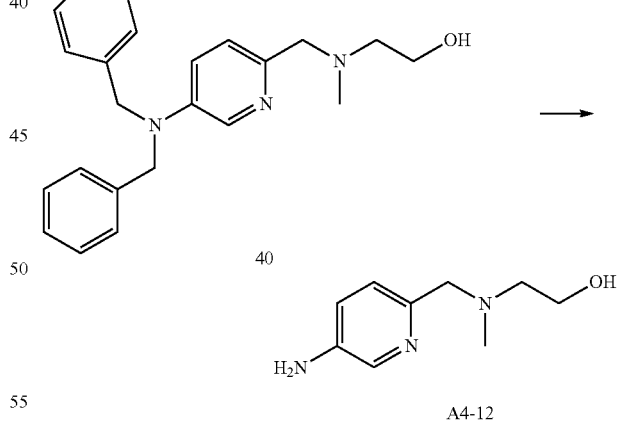

A stirred solution of 40 (400 mg, 1.1 mmol) in conc. sulfuric acid (1.3 mL) was heated at 50° C. for 3 h. The reaction mixture was cooled to 0° C., basified with 2N NaOH solution (15 mL) to pH ~9 and extracted with 10% MeOH/CHCl$_3$ (2×100 mL). The combined organic layers were washed with brine (20 mL), dried (Na$_2$SO$_4$) and evaporated to obtain the desired amine (100 mg, 50%) as a brown liquid. R$_f$: 0.4 (10% MeOH/CHCl$_3$, alumina plate); (m/z): 182 [MH]$^+$; $^1$H NMR (400 MHz, DMSO-d$_6$) δ 7.82 (1H, d, J=2.4 Hz), 7.05 (1H, d, J=8.4 Hz), 6.87 (1H, dd, J=2.8, 8.0 Hz), 5.15 (2H, s), 4.38 (1H, br s), 3.47-3.43 (4H, m), 2.42 (2H, t, J=6.4 Hz), 2.15 (3H, S).

Example A4-13

[1-(5-Amino-pyridin-2-yl)-1-methyl-ethyl]carbamic acid tert-butyl ester

A4-13 was made in 3 steps from compound 38.

[6-(1-Amino-1-methyl-ethyl)-pyridin-3-yl]-dibenzyl-amine (41)

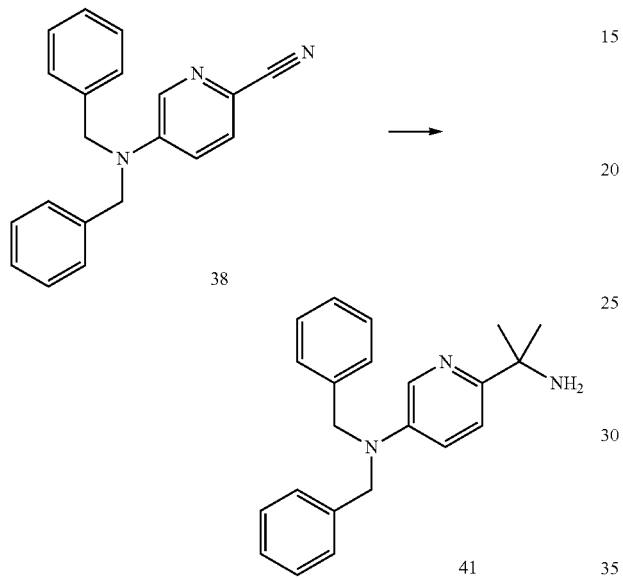

38

41

To a solution of 38 (500 mg, 1.7 mmol) in toluene (10 mL) was added CH$_3$MgBr (3M in diethyl ether) (1.7 mL, 5.0 mmol) slowly at 0° C. The reaction mixture was subsequently heated at 100° C. for 16 h. The reaction mixture was cooled to 0° C., quenched with 2N HCl (10 mL), the aqueous layer was basified with 2N NaOH solution and extracted with EtOAc (2×50 mL). The combined organic layer was washed with brine (20 mL), dried (Na$_2$SO$_4$) and evaporated. The crude compound was purified by column chromatography (neutral alumina, eluting with 3% MeOH/CHCl$_3$) to obtain the desired compound (300 mg, 54%) as a gummy liquid. R$_f$: 0.2 (10% MeOH/CHCl$_3$); (m/z): 332 [MH]$^+$; $^1$H NMR (400 MHz, DMSO-d$_6$): δ 7.92 (1H, d, J=2.8 Hz), 7.35-7.22 (11H, m), 6.97 (1H, dd, J=3.6, 8.8 Hz), 4.73 (4H, s), 1.83 (2H, br s), 1.27 (6H, s).

[1-(5-Dibenzylamino-pyridin-2-yl)-1-methyl-ethyl]carbamic acid tert-butyl ester (42)

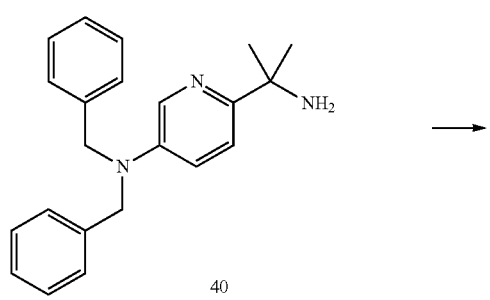

40

-continued

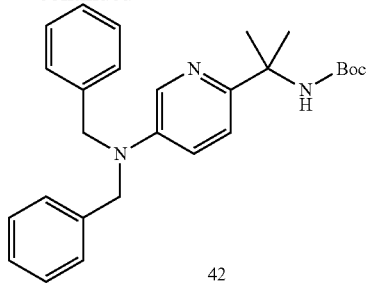

42

To a solution of 41 (700 mg, 2.1 mmol) in CH$_2$Cl$_2$ (30 mL) was added Boc$_2$O (0.47 mL, 2.1 mmol) at 0° C. and the reaction mixture allowed to stir at rt for 1 h. The reaction mixture was diluted with CH$_2$Cl$_2$ (50 mL), washed with 5% NaHCO$_3$ solution, brine (20 mL), dried (Na$_2$SO$_4$) and evaporated. The crude compound was purified by silica gel column chromatography (100-200 mesh, eluted with 10% EtOAc/pet-ether) to obtain compound 42 (400 mg, 44%) as liquid. R$_f$: 0.7 (50% EtOAc/pet. ether); (m/z): 432 [MH]$^+$; $^1$H NMR (400 MHz, DMSO-d$_6$): δ 7.88 (1H, d, J=3.2 Hz), 7.35-7.22 (10H, m), 7.12 (1H, d, J=8.8 Hz), 7.02 (1H, dd, J=2.8, 8.8 Hz), 4.72 (4H, s), 1.42 (6H, s), 1.32 (9H, s).

[1-(5-Amino-pyridin-2-yl)-1-methyl-ethyl]carbamic acid tert-butyl ester (A4-13)

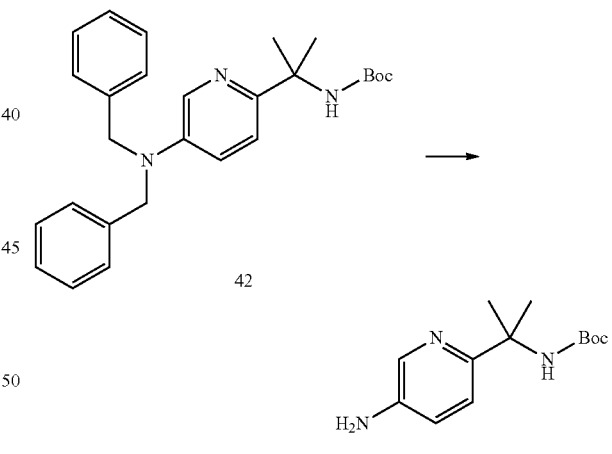

42

A4-13

To a solution of 42 (700 mg, 1.6 mmol) in methanol (30 mL) was added 20% Pd(OH)$_2$ (1.25 g) and hydrogenated at 50 psi for 16 h. The reaction mixture was filtered through a pad of Celite and the filtrate was evaporated. The crude compound was purified by silica gel column chromatography (100-200 mesh, eluting with 5% MeOH/CHCl$_3$) to obtain A4-13 (250 mg, 61%) as a white solid. R$_f$: 0.3 (10% MeOH/CHCl$_3$), (m/z): 252 [MH]$^+$; $^1$H NMR (400 MHz, DMSO-d$_6$): δ 7.81 (1H, d, J=2.8 Hz), 7.08 (1H, d, J=8.4 Hz), 6.99 (1H, br s), 6.89 (1H, dd, J=2.4, 8.4 Hz), 5.11 (2H, br s), 1.45 (6H, s), 1.34 (9H, s).

Example A4-14

2-Morpholin-4-ylmethyl-pyridin-4-ylamine

A4-14 was made in 3 steps from compound 43.

[2-(Morpholine-4-carbonyl)-pyridin-4-yl]-carbamic acid tert-butyl ester (44)

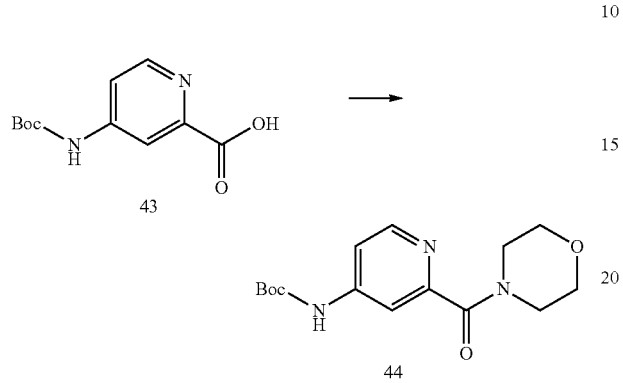

To a solution of 4-tert-butoxycarbonylamino-pyridine-2-carboxylic acid (43) (800 mg, 3.2 mmol) in CHCl$_3$ was added morpholine (0.4 mL, 3.8 mmol), HOBT (857 mg, 6.3 mmol), EDC.HCl (1.2 g, 6.3 mmol) and DIPEA (0.8 mL, 4.8 mmol), and stirred at rt for 16 h. The reaction mixture was diluted with water and extracted with 10% MeOH/CHCl$_3$. The organic layer was washed with water, dried over Na$_2$SO$_4$ and evaporated to give compound 44 (920 mg, 92%) as a white solid; (m/z): 308 [MH]$^+$; $^1$H NMR (400 MHz, CDCl$_3$): δ 8.40 (1H, d, J=5.6 Hz), 7.57 (1H, d, J=2.0 Hz), 7.54 (1H, d, J=5.6 Hz), 6.98 (1H, br s), 3.79 (4H, m), 3.67-3.66 (4H, m), 1.53 (9H, s).

(2-Morpholin-4-ylmethyl-pyridin-4-yl)-carbamic acid tert-butyl ester (45)

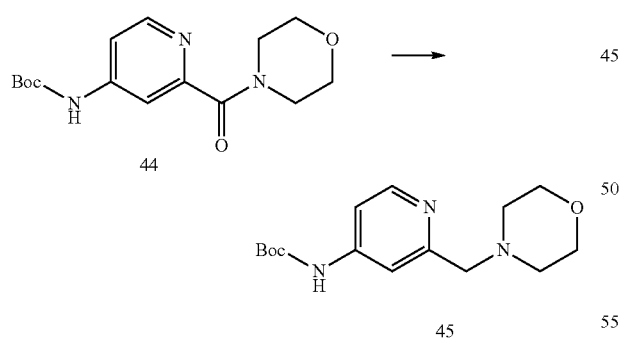

A solution of 44 (1 g, 3.25 mmol) in toluene was heated to 50° C. and Red-Al (2.2 mL, 8.14 mmol) was introduced at 50° C. After the addition was complete, the reaction mixture was heated at 90° C. for 2 h. The reaction mixture was cooled to rt, basified with 1N aq. NaOH solution and extracted with 10% MeOH/CHCl$_3$. The combined organic layer was dried over Na$_2$SO$_4$, concentrated and the obtained crude compound was purified by silica gel chromatography (100-200 mesh, eluted with 2% MeOH/DCM) to get compound 45 (300 mg, 33%) as gummy liquid; (m/z): 294 [MH]$^+$; $^1$H NMR (400 MHz, DMSO-d$_6$) δ 9.76 (1H, s), 8.24 (1H, d, J=5.6 Hz), 7.53 (1H, d, J=1.2 Hz), 7.30 (1H, d, J=2.0, 5.6 Hz), 3.58 (4H, t, J=4.6 Hz), 3.48 (2H, s), 2.40-2.38 (4H, m), 1.49 (9H, s).

2-Morpholin-4-ylmethyl-pyridin-4-ylamine (A4-14)

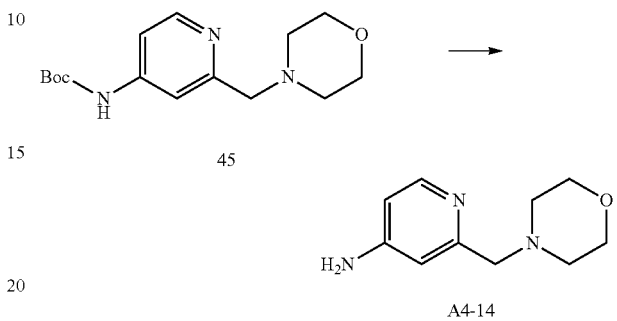

To a stirred solution of 45 (150 mg, 0.513 mmol) in DCM (5 mL) was added TFA (1 mL) at 0° C. and allowed to stir at rt for 2 h. The reaction mixture was concentrated, the residue was dissolved in MeOH and treated with Ambersep-900-OH resin to basify the solution, then filtered to separate the resin and concentrated the filtrate to obtain the desired amine (90 mg, 88%) as a gummy liquid. (m/z): 194 [MH]$^+$; $^1$H NMR (400 MHz, DMSO-d$_6$) δ 7.87 (1H, d, J=5.6 Hz), 6.57 (1H, d, J=2.4 Hz), 6.33 (1H, dd, J=5.2, 2.4 Hz), 5.90 (2H, br s), 3.58-3.56 (4H, m), 3.34 (2H, s), 2.38-2.36 (4H, m).

The following amines were made using this approach:

| Structure | Ex. No. |
|---|---|
| ![structure] 2-morpholinylmethyl-4-aminopyridine | A4-14 |
| ![structure] 3-morpholinylmethyl-5-aminopyridine | A4-15 |

Example A4-16

2-((S)-3-Methyl-morpholin-4-ylmethyl)-pyridin-4-ylamine

A4-16 was made in 3 steps from 4-aminopyrdine-2-carboxylic acid methy ester (46)

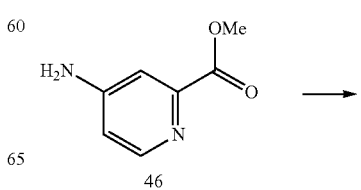

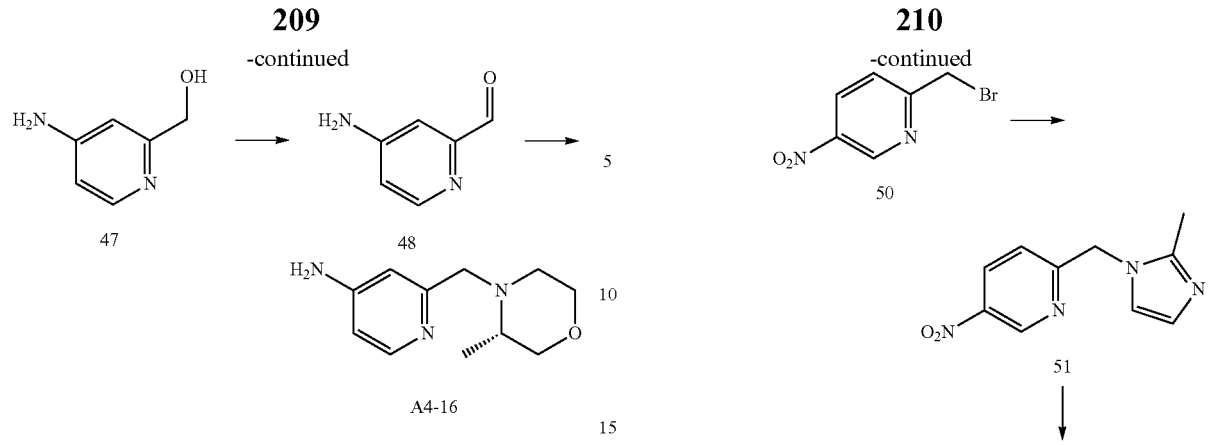

To a solution of 4-amino-pyridine-2-carboxylic acid methyl ester (46) (950 mg, 6.2 mmol) in THF (14 mL) was added 1 M LiAlH$_4$ in THF (15.6 mL, 15.6 mmol) dropwise and the reaction mixture subsequently stirred at room temperature for 16 h. A small amount of starting material remained so a further amount of 1 M LiAlH$_4$ in THF (2 mL, 20 mmol) was added and the reaction mixture warmed to 50° C. for 30 min KOH (250 mg) in water (2 mL) was then added carefully to the reaction mixture at 50° C. and the reaction mixture stirred for 5-10 min. The organic layer was carefully decanted, dried over MgSO$_4$, filtered and evaporated to obtain 47 as a pale yellow solid (519 mg, 57%). 47 (330 mg, 2.7 mmol) was dissolved in acetonitrile (30 mL) and manganese dioxide (1.2 g, 14.1 mmol) was added. The reaction mixture was heated at reflux for 2 h then filtered through celite to give after evaporation of the filtrate the desired aldehde as a brown solid (277 mg, 85%). The crude aldheyde was used as is for the synthesis of A4-16. To a solution of aldehyde 48 (138 mg, 1.1 mmol) in dichloromethane (4 mL) was added DMF (~1 mL) until soluble. 3(S)-methylmorpholine (229 mg, 2.3 mmol), acetic acid (129 µL, 2.3 mmol) and sodium tri-acetoxy borohydride (479 mg, 2.3 mmol) were added and the reaction mixture stirred at room temperature for 2 h. Saturated NaHCO$_3$ (aq) (5 mL) was added and the mixture extracted with dichlormethane (2×15 mL). The organic layers were combined, dried over MgSO$_4$, filtered and evaporated. The crude residue was purified by flash chromatography on silica, eluting with 0-10% methanol/dichloromethane followed by 20% 2M NH$_3$ in methanol/dichloromethane to give the desired amine (38 mg, 16%); m/z 208 (MH$^+$).

Example A4-17

5-Methyl-2-(2-methyl-imidazol-1-ylmethyl)-pyridine

A4-17 was made in 4 steps from aldehyde 31.

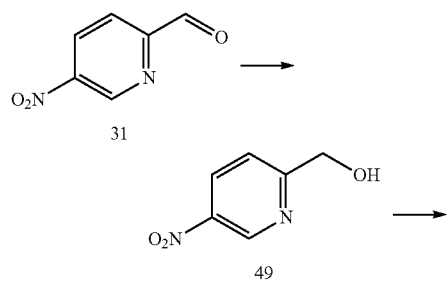

2-(2-Methyl-imidazol-1-ylmethyl)-5-nitro-pyridine (51)

Aldehyde 31 (500 mg, 3.3 mmol) was dissolved in dry methanol (15 mL) and sodium borohydride (150 mg, 4.0 mmol) was added and the reaction mixture stirred at room temperature for 18 h. The solvent was evaporated and the residue partitioned between ethylacetate (50 mL) and saturated ammonium chloride (aq) (25 mL). The organic phase was separated, washed with brine (20 mL), dried over Mg504, filtered and evaporated to give 49 as a yellow solid (301 mg, 59%). This was used as is in the next step. To a solution of alcohol 49 (237 mg, 1.5 mmol) in dichloromethane (15 mL) was added phosphorus tribromide (90 µL, 1.0 mmol) and the reaction mixture stirred at room temperature for 16 h. The reaction mixture was diluted with saturated NaHCO$_3$ (aq) (20 mL) and dichloromethane (20 mL). The organic phase was separated, washed with brine (20 mL), dried over MgSO$_4$, filtered and evaporated to give the corresponding alkyl bromide 50 as a red oil (262 mg, 79%). This was used as is in the next step. To a solution of 50 (250 mg, 1.2 mmol) in dry methanol (8 mL) was added 2-methylimidazole (300 mg, 3.7 mmol) and the mixture stirred at 80° C. in the microwave for 2 h. The solvent was evaporated and the crude residue redissolved in methanol (5 mL). The solution was poured onto a SCX-2 (Biotage) ion-exchange cartridge and the cartridge washed with 4 column volumes of methanol. The desired compound was then extracted from the cartridge by washing with 4 column volumes of 0.5 M NH$_3$ in methanol. The solvent was evaporated and the crude residue further purified by flash chromatography on silica, eluting with 0-10% methanol/ethyl acetate to give 51 as a white solid (227 mg, 87%); LCMS, Rt=1.97 min (MeOH-FA method), m/z 219 (MH$^+$).

5-Methyl-2-(2-methyl-imidazol-1-ylmethyl)-pyridine (A4-17)

51 (227 mg, 1.0 mmol) was added to Pd/C (30 mg) in ethanol (10 mL) followed by ammonium formate (330 mg, 5.2 mmol) and the reaction mixture heated to reflux for 1 h. The reaction mixture was filtered through celite and the filtrate evaporated. The crude residue was dissolved in methanol poured onto a SCX-2 (Biotage) ion-exchange cartridge and the cartridge washed with 4 column volumes of methanol. The desired compound was then extracted from the cartridge by washing with 4 column volumes of 0.5 M NH$_3$ in methanol. The solvent was evaporated in vacuo to give A4-17 as a tan solid (117 mg, 60%);

LCMS, Rt=0.27 min (MeOH-FA method), m/z 189 (MH$^+$).

Example A4-18

1-(5-Amino-pyridin-2-ylmethyl)-3-methyl-azetidin-3-ol

A4-18 was made in 3 steps from alcohol 49.

Methanesulfonic acid 5-nitro-pyridin-2-ylmethyl ester (52)

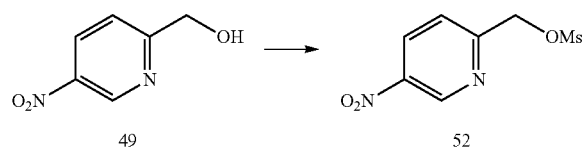 [SMILES: O=[N+]([O-])c1ccc(CO)nc1 ; CS(=O)(=O)OCc1ccc([N+](=O)[O-])cn1]

To a stirred solution of (5-Nitro-pyridin-2-yl)-methanol (49) (0.5 g, 3.2 mmol) and triethylamine (1.0 mL, 6.5 mmol) in THF (10 mL) was added mesyl anhydride (1.1 g, 6.5 mmol) 0° C. and stirred for 30 minutes at the same temperature The reaction mixture was quenched with NaHCO$_3$ solution and extracted with ethyl acetate (2×50 mL). The combined organic layer was dried over Na$_2$SO$_4$, filtered and evaporated. to give crude compound 52 (0.6 g, LCMS purity 83%) as a brown liquid. The crude material was used in the next step. R$_f$: 0.6 (50% EtOAc/pet ether); (m/z): 232.9 [MH]$^+$; $^1$H NMR (400 MHz, DMSO-d$_6$) δ 9.38 (1H, d, J=2.4 Hz), 8.69 (1H, dd, J=8.8, 2.4 Hz), 7.80 (1H, d, J=8.8 Hz), 5.48 (2H, s), 3.34 (3H, s).

3-Methyl-1-(5-nitro-pyridin-2-ylmethyl)azetidin-3-ol (53)

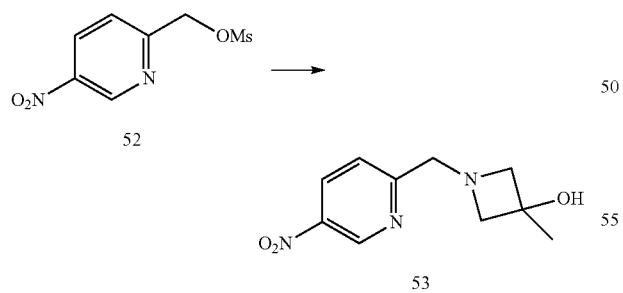

To a solution of 52 (0.5 g, 2.2 mmol) in MeOH (25 mL) was added Ambersep-900 OH resin (50 g) filtered to separate the resin and concentrated to obtain the free base. The free base was dissolved in MeOH-THF (10 mL, 1:1) and cooled to 0° C. 3-methyl-azetidin-3-ol (0.53 g, 4.3 mmol) and triethylamine (0.7 mL, 4.3 mmol) were added and the reaction mixture warmed to rt and stirred for 16 h. The reaction mixture was concentrated and the crude compound was purified by silica gel column chromatography (100-200 mesh), eluting with 3% MeOH/CHCl$_3$ to give the desired compound (0.35 g, 48%, over two steps) as a pale yellow liquid. R$_f$: 0.3 (10% MeOH/DCM); (m/z): 224 [MH]$^+$; $^1$H NMR (400 MHz, DMSO-d$_6$): δ 9.27 (1H, d, J=2.4 Hz), 8.56 (1H, dd, J=8.8, 2.8 Hz), 7.64 (1H, d, J=8.8 Hz), 5.22 (1H, s), 3.85 (2H, s), 3.36-3.26 (2H, m), 3.02-3.00 (2H, m), 1.38 (3H, s).

1-(5-Amino-pyridin-2-ylmethyl)-3-methyl-azetidin-3-ol (A4-18)

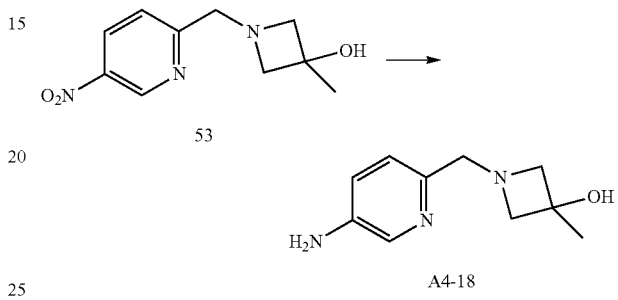

To a stirred solution of 53 (0.35 g, 2.2 mmol) in MeOH (6 mL) was added 10% Pd/C (50 mg) and hydrogenated using a balloon for 2 h at rt. The reaction mixture was filtered through a pad of Celite and concentrated to give the desired amine A4-18 (0.3 g, 69%) as a gummy liquid. R$_f$: 0.1 (10% MeOH/DCM); (m/z): 194 [MH]$^+$; $^1$H NMR (400 MHz, DMSO-d$_6$): δ 7.82 (1H, d, J=2.8 Hz), 6.95 (1H, d, J=8.4 Hz), 6.86 (1H, dd, J=8.4, 2.4 Hz), 5.12-5.10 (2H, m), 4.08 (1H, br s), 3.48 (2H, s), 3.16-3.14 (4H, m), 1.33 (3H, s).

Example A4-19

5-[(2-Methoxy-ethylamino)-methyl]-pyridin-3-ylamine

A4-19 was synthesised in 3 steps from (5-hydroxymethyl-pyridin-3-yl)-carbamic acid tert-butyl ester (54)

Methanesulfonic acid 5-tert-butoxycarbonylamino-pyridin-3-ylmethyl ester (56)

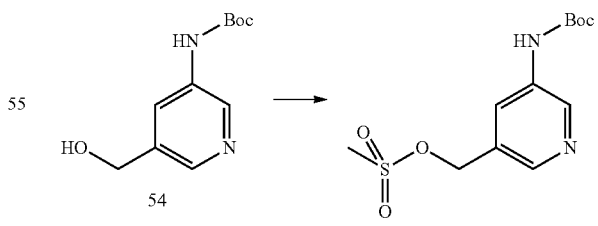

To a solution of 54 (0.35 g, 1.6 mmol) in THF (3.5 mL) was added triethylamine (2.27 g, 16.8 mmol) and methanesulphonic anhydride (3.22 g, 16.8 mmol) at 0° C. and stirred for 5 min. The reaction mixture was diluted with DCM (10 mL) and washed with saturated NaHCO$_3$ solution (2×10 mL). The organic layer was dried (Na$_2$SO$_4$) and concentrated to obtained the desired compound (0.4 g, 84%) as a yellow gummy liquid. R$_f$: 0.6 (50% EtOAc/pet ether); (m/z): 303 [MH]$^+$; $^1$H NMR (400 MHz, DMSO-d$_6$): δ 9.58 (1H, br s), 8.44 (1H, s), 8.15 (1H, s), 7.97-7.93 (1H, m), 3.79 (2H, s), 3.25 (3H, s), 1.48 (9H, s).

{5-[(2-Methoxy-ethylamino)-methyl]-pyridin-3-yl}-carbamic acid tert-butyl ester (56)

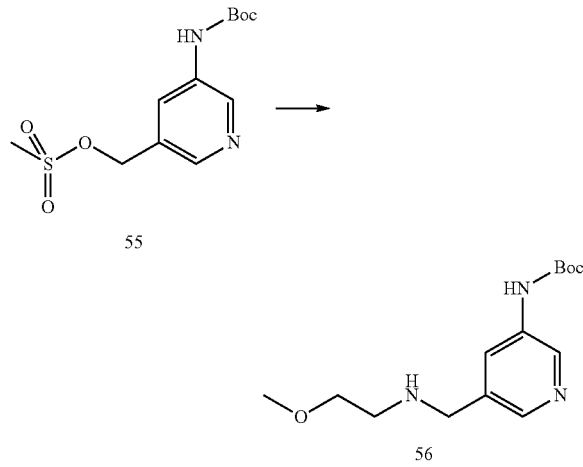

To a solution of 55 (0.4 g, 1.3 mmol) in THF (5 mL) was added 2-methoxyethanamine (0.22 mL, 75.1 mmol) and stirred at rt for 16 h. The reaction mixture was diluted with DCM (10 mL) and washed with water (2×20 mL). The organic layer was dried (Na$_2$SO$_4$) and concentrated to obtain compound 56 (0.11 g, 28%) as a brown liquid. R$_f$: 0.3 (20% MeOH/CHCl$_3$); (m/z): 282 [MH]$^+$; $^1$H NMR (400 MHz, CDCl$_3$) δ 8.33 (1H, d, J=2.4 Hz), 8.24 (1H, s), 7.95 (1H, s), 6.53 (1H, br s), 3.81 (2H, s), 3.52-3.49 (3H, m), 3.35 (3H, s), 2.81-2.78 (2H, m), 1.52 (9H, s).

5-[(2-Methoxy-ethylamino)-methyl]-pyridin-3-ylamine (A4-19)

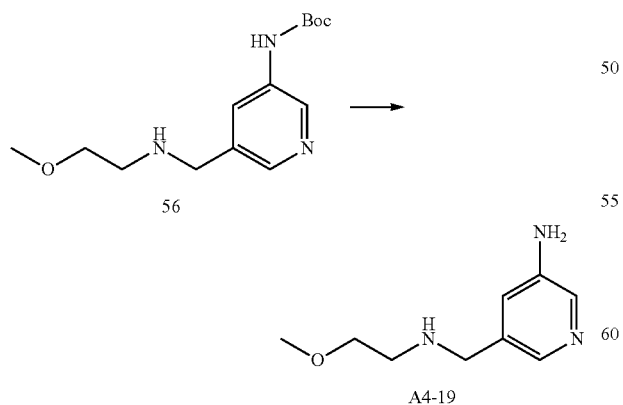

To a stirred solution of 56 (0.4 g, 1.42 mmol) in DCM (3 mL) was added TFA (3 mL) at 0° C. and stirred at rt for 3 h. The reaction mixture was concentrated, the residue was dissolved in MeOH, basified with Ambersep 900-OH resin, filtered to separate the resin and the filtrate concentrated to obtain the desired amine (90 mg, 88%) as a brown color viscous liquid. R$_f$: 0.1 (10% MeOH/CHCl$_3$); (m/z):182 [M+1]$^+$; $^1$H NMR (400 MHz, DMSO-d$_6$) δ 7.77 (1H, d, J=2.4 Hz), 7.66 (1H, d, J=1.6 Hz), 6.86 (1H, d, J=2 Hz), 5.19 (2H, m), 3.66 (2H, s), 3.39-3.36 (3H, m), 3.22 (3H, s), 2.62-2.59 (2H, m), 1.93-1.92 (1H, br s).

Example A4-20

3-Amino-5,7-dihydro-pyrrolo[3,4-b]pyridine-6-carboxylic acid tert-butyl ester

A4-20 was made in 4 steps from (5-bromo-2-hydroxymethyl-pyridin-3-yl)-methanol (57).

Methanesulfonic acid 5-bromo-3-methanesulfonyloxymethyl-pyridin-2-ylmethyl ester (58)

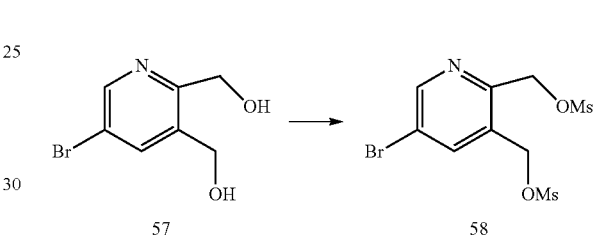

To a stirred suspension of 57 (1.4 g, 6.5 mmol) in THF (80 mL) was added TEA (5.4 mL, 38.7 mmol) at 0° C. Methanesulfonic anhydride (4.49 g, 25.8 mmol) was added portion wise to the above solution to keep the temperature below 5° C. and stirred at 0° C. for 1 h. The reaction mixture was diluted with EtOAc (100 mL), washed with 10% NaHCO$_3$ solution (2×20 mL), the organic layer was dried (Na$_2$SO$_4$) and evaporated to give the desired compound (1 g, crude,) as a brown liquid. R$_f$: 0.7 (40% EtOAc/pet-ether). Crude compound was taken as such for the next step without further purification; (m/z): 374, 376 [MH]$^+$.

3-Bromo-6,7-dihydro-5H-pyrrolo[3,4-b]pyridine (59)

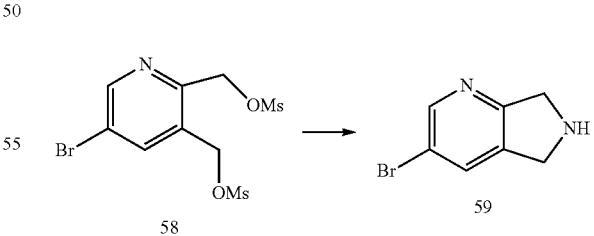

To a solution of 58 (1 g, crude) in MeOH (5 mL) was added MeOH—NH$_3$ (5 mL) at 0° C. and stirred at rt for overnight. The reaction mixture was evaporated to obtain the desired compound (600 mg, crude) as a brown liquid. R$_f$: 0.2 (10% MeOH/CHCl$_3$). The crude compound was used in the next step without further purification; (m/z): 199, 201 [MH]$^+$.

3-Bromo-5,7-dihydro-pyrrolo[3,4-b]pyridine-6-carboxylic acid tert-butyl ester

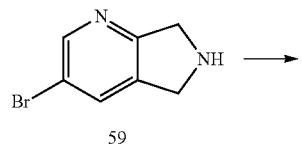

59

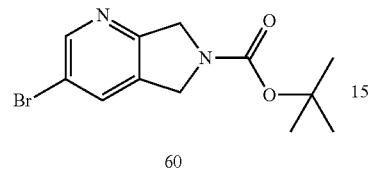

60

To a solution of 59 (600 mg, crude) in MeOH (10 mL) was added Et$_3$N (1.27 mL, 9.1 mmol) and Boc$_2$O (1 mL, 4.5 mmol) at 0° C. and stirred at rt for 16 h. The reaction mixture was concentrated and the crude compound was purified by silica gel column chromatography (100-200 mesh, eluting with 6% EtOAc/pet-ether) to obtain compound 60 (200 mg, 9% (over 3 steps)) as a white solid. R$_f$: 0.6 (20% EtOAc/pet-ether); (m/z): 299, 301 [MH]$^+$; $^1$H NMR (400 MHz, DMSO-d$_6$): δ 8.57 (1H, d, J=1.2 Hz), 8.05 (1H, d, J=7.6 Hz), 4.61 (2H, d, J=11.6 Hz), 4.51 (2H, d, J=10.0 Hz), 1.45 (9H, s).

3-Amino-5,7-dihydro-pyrrolo[3,4-b]pyridine-6-carboxylic acid tert-butyl ester (A4-20)

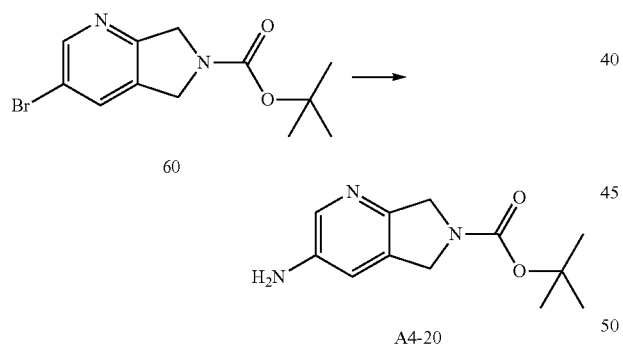

NH$_4$OH (1.5 mL) was added to a suspension of 60 (250 mg, 0.83 mmol), CuI (32 mg, 0.16 mmol), L-proline (38.6 mg, 0.33 mmol) and K$_2$CO$_3$ (173 mg, 1.25 mmol) in DMSO (1 mL) at rt. The reaction mixture was sealed, irradiated in a microwave reactor at 90° C. for 1 h. The reaction mixture was cooled to rt, diluted with ethyl acetate (50 mL), washed with water (2×20 mL), the organic layer was dried (Na$_2$SO$_4$) and evaporated. The crude compound was purified by silica gel column chromatography (100-200 mesh, eluted with 3% MeOH/CHCl$_3$) to obtain the desired amine A4-20 (100 mg, 50%) as a white solid. R$_f$: 0.4 (5% MeOH/CHCl$_3$); (m/z): 236 [MH]$^+$; $^1$H NMR (400 MHz, DMSO-d$_6$): δ7.8 (1H, d, J=2.8 Hz), 6.85 (1H, d, J=4.4 Hz), 5.28 (2H, s), 4.47 (2H, d, J=13.2 Hz), 4.34 (2H, d, J=10.4 Hz), 1.45 (9H, s).

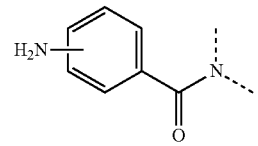

A5

Amines of formula A5 where the dashed line represents an optional bond to a carbon atom were made via the following routes:

Example A5-1

3-Amino-N-(1-methyl-piperidin-4-yl)-benzamide

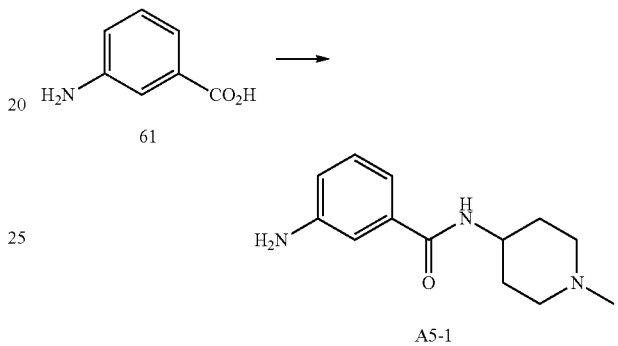

3-Aminobenzoic acid (61) (0.50 g, 3.7 mmol), TBTU (1.3 g, 4.0 mmol) and 1-methylpiperidine-4-amine (0.62 g, 5.4 mmol) were dissolved in dry DCM (5 mL). DIPEA (0.95 mL, 5.5 mmol) was added and the reaction mixture was stirred at room temperature for 18 hours. The solvent was evaporated in vacuo and the residue dissolved in DMSO (5 mL). The crude product was purified by reversed phase preparative LC-MS. Fractions containing the desired product were combined and the solvent evaporated in vacuo. Toluene (10 mL) was added and the solvent evaporated in vacuo. The product was obtained as a white solid (808 mg, 95%); LCMS, Rt=1.05 min (MeOH-FA method), m/z 234 (MH$^+$).

The following amines were made using this approach:

| Structure | Ex. No. |
|---|---|
| 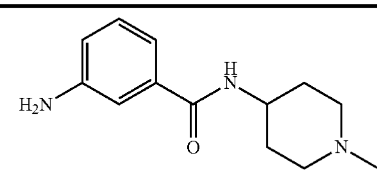 | A5-1 |
| 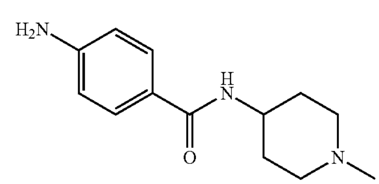 [SMILES: CN1CCC(NC(=O)c2ccc(N)cc2)CC1] | A5-2 |

Alternatively amines of formula A5 could be made from the corresponding nitro-acid by amide coupling followed by reduction of the nitro group, using standard conditions familiar to those skilled in the art. The following amines were made using this approach:

| Structure | Ex. No |
|---|---|
| 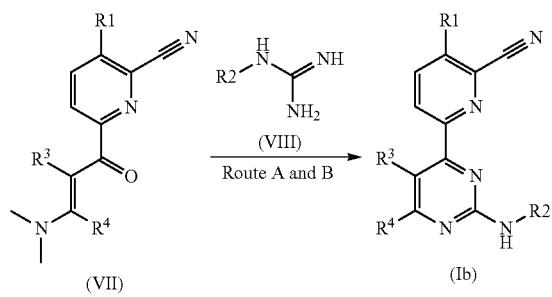 | A5-3 |
| 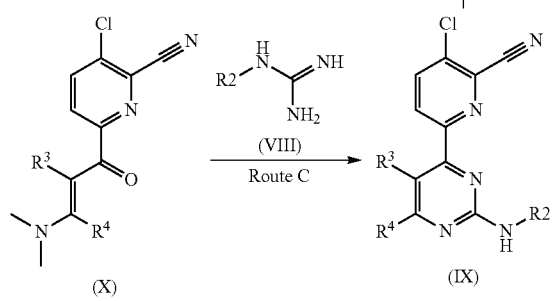 | A5-4 |

A number of examples of formula Ib were synthesised by a condensation reaction to form the pyrimidine ring.

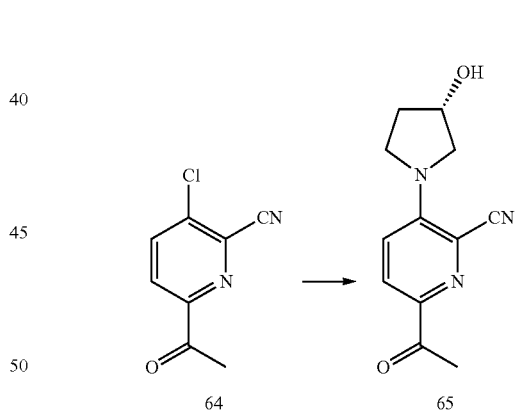

Route A

Example DMX-57

Synthesis of 3-((S)-3-Hydroxy-pyrrolidin-1-yl)-6-[2-(4-morpholin-4-yl-phenylamino)-pyrimidin-4-yl]-pyridine-2-carbonitrile 6-Acetyl-3-chloro-pyridine-2-carbonitrile (64)

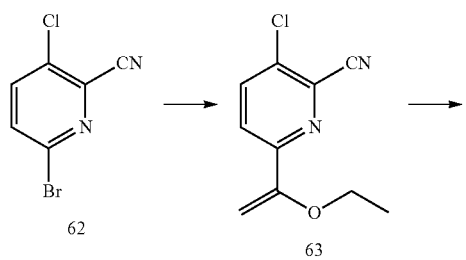

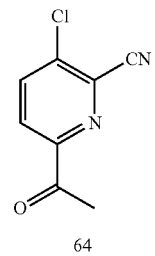

To a stirred suspension of 6-bromo-3-chloro-2-cyanopyridine (62) (2.34 g, 10.8 mmol) in MeCN (15 mL) under $N_2$ was added copper (I) iodide (307 mg, 1.6 mmol), bis(triphenylphosphine)palladium chloride (378 mg, 0.54 mmol) and ethoxyvinyltributyl tin (4.0 mL, 11.8 mmol) and the reaction mixture was stirred at reflux for 1 hour. The mixture was filtered washing the precipitate with EtOAc (20 mL).

The solvent was evaporated in vacuo and the residue dissolved in acetone (15 mL). p-Toluenesulfonic acid.$H_2O$ (614 mg, 3.2 mmol) was added and the mixture was stirred at rt for 1 hour. The solvent was evaporated in vacuo and the residue dissolved in EtOAc (60 mL). The solution was washed with saturated brine solution (40 mL), dried ($MgSO_4$), filtered and the solvent evaporated in vacuo. The crude product was purified by flash chromatography (Biotage SP1, 50 g SNAP cartridge) eluting with 8:2 isohexane-EtOAc to yield the title compound as an orange crystalline solid (1.91 g, 98%); LCMS, Rt=2.30 min (MeOH-FA method), m/z 181 (MH$^+$).

6-Acetyl-3-((S)-3-hydroxy-pyrrolidin-1-yl)-pyridine-2-carbonitrile (65)

6-Acetyl-3-chloro-pyridine-2-carbonitrile (64) (1.80 g, 9.97 mmol) was dissolved in MeCN (19 mL). (S)-3-Pyrrolidinol (884 µL, 10.9 mmol) and TEA (4.16 mL, 29.8 mmol) were added and the mixture stirred at 100° C. in the microwave for 20 minutes. The solvent was evaporated in vacuo and the crude material dissolved in EtOAc (100 mL). The solution was washed with 1:1 saturated brine solution-$H_2O$ (100 mL), saturated brine solution (100 mL), then dried ($MgSO_4$), filtered and the solvent evaporated in vacuo. The crude product was purified by flash chromatography (Biotage SP1, 50 g SNAP cartridge) eluting with 6:4 isohexane-EtOAc→8:2 EtOAc-isohexane to yield the title compound as a yellow solid (1.32 g, 64%); LCMS, Rt=2.04 min (MeOH-FA method), m/z 232 (MH$^+$).

6-((E)-3-Dimethylamino-acryloyl)-3-((S)-3-hydroxy-pyrrolidin-1-yl)-pyridine-2-carbonitrile (66)

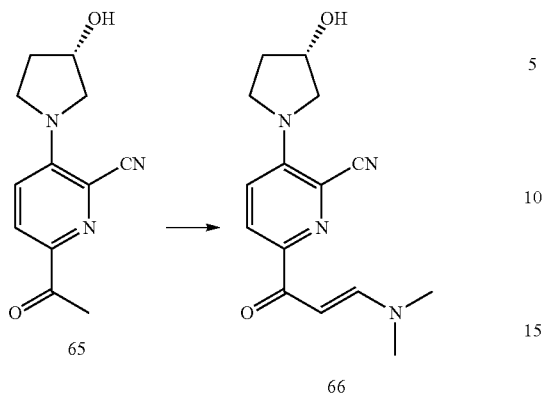

6-Acetyl-3-((S)-3-hydroxy-pyrrolidin-1-yl)-pyridine-2-carbonitrile (65) (1.32 g, 5.71 mmol) was dissolved in dry toluene (30 mL). N,N-dimethylformamide dimethyl acetal (2.3 mL, 17.3 mmol) was added and the mixture was stirred at reflux for 5 hours. N,N-Dimethylformamide dimethyl acetal (5.0 mL, 37.6 mmol) was added and the mixture was stirred at reflux for 4 hours. The solution was cooled to rt and the solution left to stand at rt for 16 hours. The solvent was carefully decanted and the remaining reside triturated with Et$_2$O (50 mL) followed by EtOAc (50 mL). The residual solvent was evaporated in vacuo. The title compound 66 was afforded as an orange solid (1.11 g, 68%); LCMS, Rt=1.98 min (MeOH-FA method), m/z 287 (MH$^+$).

3-((S)-3-Hydroxy-pyrrolidin-1-yl)-6-[2-(4-morpholin-4-yl-phenylamino)-pyrimidin-4-yl]-pyridine-2-carbonitrile (DMX-57)

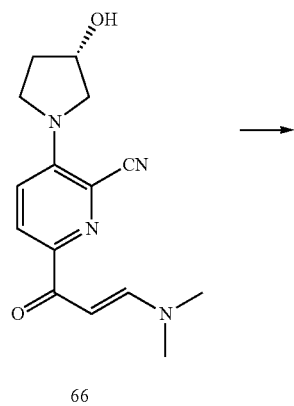

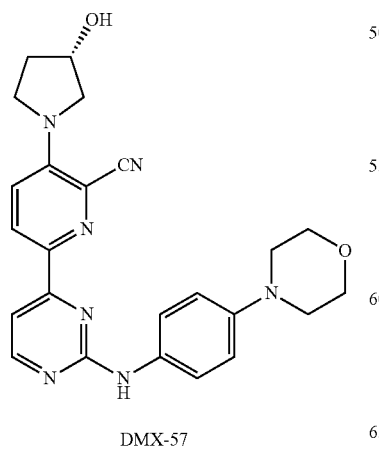

Compound 66 (150 mg, 0.524 mmol) and N-(4-morpholin-4-yl-phenyl)-guanidine were dissolved in EtOH (4 mL). The mixture was then stirred at 180° C. in the microwave for 30 minutes. The solvent was evaporated in vacuo and the residue diluted with MeOH (50 mL). The solution was heated to 60° C. on a rotary evaporator with swirling. The solution was cooled to rt and the solvent carefully decanted. The process was repeated twice more. The residual solvent was then evaporated in vacuo. The title compound was afforded as a yellow solid (110 mg, 47%); LCMS, Rt=2.58 min (MeOH-FA method), m/z 444 (MH$^+$).

Route B

Example DMX-58

6-[2-(4-Morpholin-4-yl-phenylamino)-pyrimidin-4-yl]-3-pyrrolidin-1-yl-pyridine-2-carbonitrile

3-Chloro-6-(–3-dimethylamino-acryloyl)-pyridine-2-carbonitrile (67)

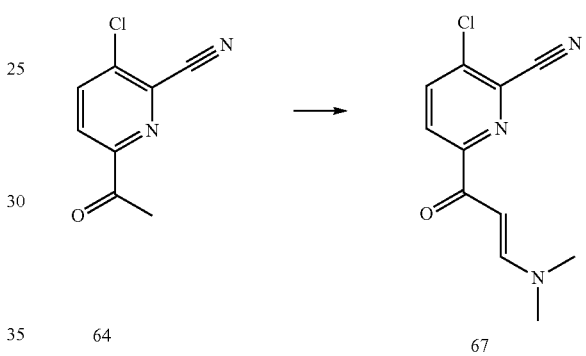

Compound 64 (633 mg, 2.7 mmol) and N,N-dimethylformamide dimethyl acetal (1.1 mL, 8.1 mmol) in toluene was heated to reflux for 5 h. After which time the solvent was evaporated and the crude product triturated with isoxane/diethylether to give compound 67 as an orange solid (222 mg, 35%); LCMS Rt=2.35 min (MeOH-FA method), m/z 236 (MH$^+$).

3-Pyrrolidin-1-yl-6-(3-pyrrolidin-1-yl-acryloyl)-pyridine-2-carbonitrile (68) and 6-(3-Dimethylamino-acryloyl)-3-pyrrolidin-1-yl-pyridine-2-carbonitrile (69)

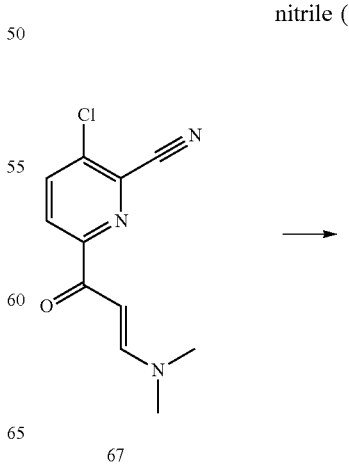

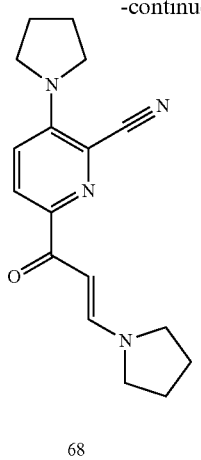
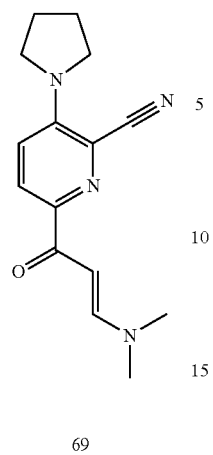

68      69

Compound 67 (159 mg, 0.7 mmol) and pyrrolidine (278 μL, 3.4 mmol) in 1,4-dioxane (3 mL) were heated at 60° C. for 18 h. The reaction mixture was allowed to cool to rt and a precipitate formed. Diethylether (2 mL) was added to encourage further precipitation. The precipitate was collected by filtration, washed with a 1:1 mixture of isohexane and diethylether (5 mL) and dried to yield a mixture of compounds 68 and 69 as a cream solid (110 mg, 55%). LCMS shows 94% 68, Rt 2.58 min (MeOH-FA method), m/z 297 (MH⁺) and 5% 69, Rt 2.34 min (MeOH-FA method), m/z 271 (MH⁺).

6-[2-(4-Morpholin-4-yl-phenylamino)-pyrimidin-4-yl]-3-pyrrolidin-1-yl-pyridine-2-carbonitrile (DMX-58)

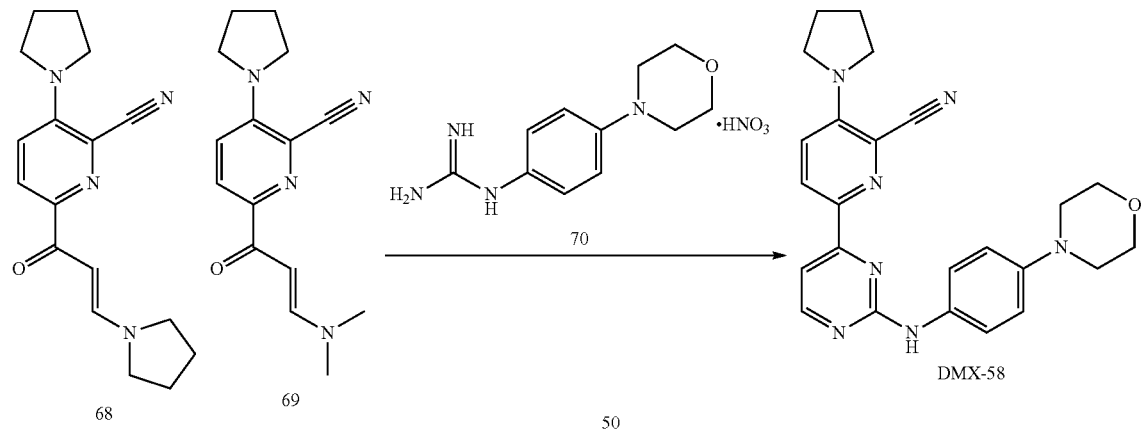

A mixture of 68 and 69 (100 mg, 0.4 mmol) and 70 (158 mg, 0.6 mmol) in ethanol (4 mL) was heated in the microwave at 180° C. for 4.5 h. After which time the solvent was evaporated and the crude material dissolved in DMSO and purified by reversed phase preparative LC-MS. Fractions containing desired product were combined and the MeOH evaporated in vacuo. The aqueous solution was frozen (−78° C.) and the solvent evaporated in vacuo (freeze dried). The title compound was obtained as a green/brown white solid (68 mg, 38%); LCMS, Rt=8.23 min (Method C), m/z 428 (MH⁺).

Route C

Example DMX-59

3-((S)-3-Hydroxy-pyrrolidin-1-yl)-6-[2-(1-methyl-M-pyrazol-4-ylamino)-pyrimidin-4-yl]-pyridine-2-carbonitrile

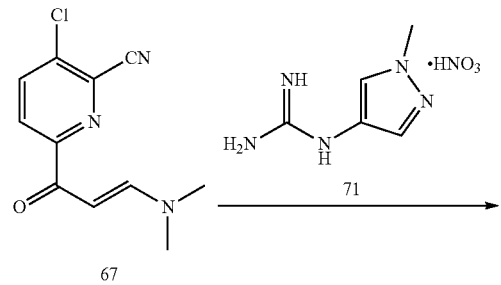

-continued

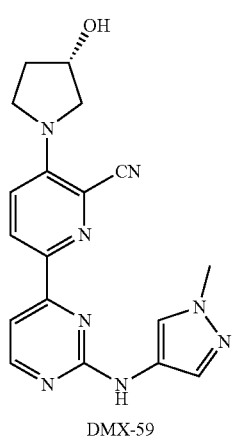

DMX-59

Compound 67 (115 mg, 0.49 mmol) and compound 71 (100 mg, 0.49 mmol) in ethanol (2 mL) were heated at 180° C. in the microwave for 1.5 h after which time the solvent was evaporated. Acetonitrile (2 mL) and (S)-pyrrolidin-3-ol (44 µL, 0.52 mmol) were added and the reaction mixture heated at 140° C. for 30 mins. The solvent was evaporated and the residue dissolved in methanol and loaded onto a SCX-2 (Biotage) catridge. The cartridge was washed with 5 column volumes of methanol, then the product eluted with 0.5M NH3/MeOH (5 column volumes). The solvent was evaporated, the crude material dissolved in DMSO and purified by reversed phase preparative LC-MS. Fractions containing desired product were combined and the MeOH evaporated in vacuo. The aqueous solution was frozen (−78° C.) and the solvent evaporated in vacuo (freeze dried). The title compound was obtained as a yellow solid (4 mg, 2%); LCMS, Rt=6.81 min (Method C), m/z 363 (MH$^+$).

Compounds prepared via these routes are as follows:

TABLE VI

| Structure | Ex. No. | Name | Route | Analytical Data | Inhibition of IKKε | Inhibition of TBK1 | Salt Form |
|---|---|---|---|---|---|---|---|
| 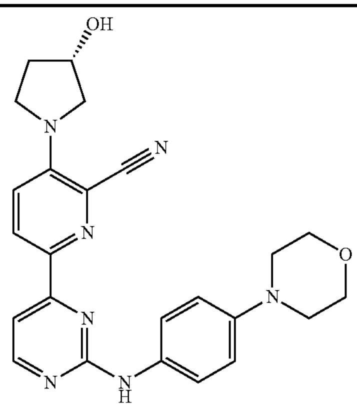 | DMX-57 | 3-((S)-3-Hydroxy-pyrrolidin-1-yl)-6-[2-(4-morpholin-4-yl-phenylamino)-pyrimidin-4-yl]-pyridine-2-carbonitrile | A | MeOH—FA; Rt = 2.58 min; m/z 444 (MH$^+$); yellow solid | <30 nM | <15 nM | None |
| 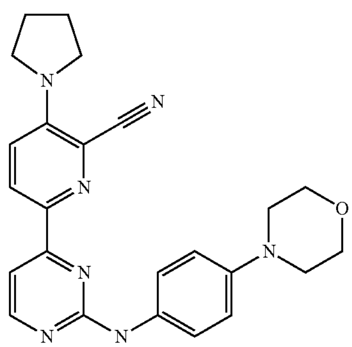 [SMILES: N#Cc1nc(-c2ccnc(Nc3ccc(N4CCOCC4)cc3)n2)ccc1N1CCCC1] | DMX-58 | 6-[2-(4-Morpholin-4-yl-phenylamino)-pyrimidin-4-yl]-3-pyrrolidin-1-yl-pyridine-2-carbonitrile | B | Method C; Rt = 8.23 min; m/z 428 (MH$^+$); green/brown solid | <15 nM | <15 nM | None |
| 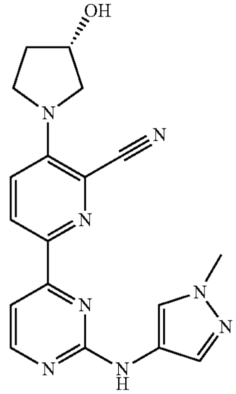 [SMILES: Cn1cc(Nc2nccc(-c3ccc(N4CC[C@H](O)C4)c(C#N)n3)n2)cn1] | DMX-59 | 3-((S)-3-Hydroxy-pyrrolidin-1-yl)-6-[2-(1-methyl-1H-pyrazol-4-ylamino)-pyrimidin-4-yl]-pyridine-2-carbonitrile | C | Method C; Rt = 6.81min; m/z 363 (MH$^+$); pale yellow solid | <100 nM | <100 nM | None |

TABLE VI-continued

| Structure | Ex. No. | Name | Route | Analytical Data | Inhibition of IKKε | Inhibition of TBK1 | Salt Form |
|---|---|---|---|---|---|---|---|
| 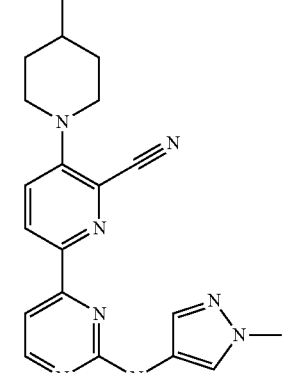 | DMX-60 | 2'-Cyano-6'-[2-(1-methyl-1H-pyrazol-4-ylamino)-pyrimidin-4-yl]-3,4,5,6-tetrahydro-2H-[1,3']bipyridinyl-4-carboxylic acid amide | B | Method C; Rt = 6.82 min; m/z 404 (MH+); brown solid | <100 nM | <100 nM | None |
| 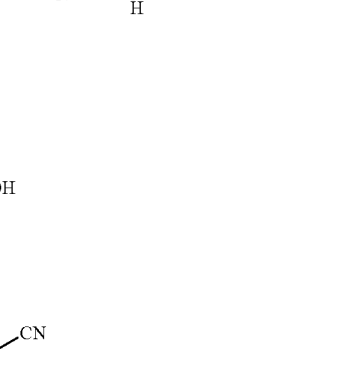 | DMX-141 | N-(5-{4-[6-Cyano-5-((S)-3-hydroxy-pyrrolidin-1-yl)-pyridin-2-yl]-pyrimidin-2-ylamino}-pyridin-2-yl)-2-morpholin-4-yl-acetamide | A | Method D; Rt = 5.40 min; m/z 502 (MH+); yellow solid | <100 nM | <100 nM | None |
| 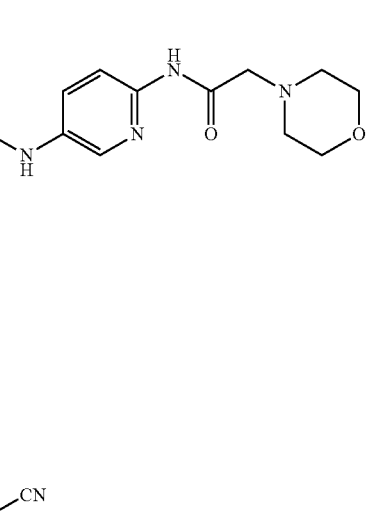 | DMX-142 | N-(5-{4-[6-Cyano-5-((S)-3-fluoro-pyrrolidin-1-yl)-pyridin-2-yl]-pyrimidin-2-ylamino}-pyridin-2-yl])-2-morpholin-4-yl-acetamide | A | Method D; Rt = 5.98 min; m/z 504 (MH+); brown solid | <15 nM | <15 nM | None |

TABLE VI-continued

| Structure | Ex. No. | Name | Route | Analytical Data | Inhibition of IKKε | Inhibition of TBK1 | Salt Form |
|---|---|---|---|---|---|---|---|
| 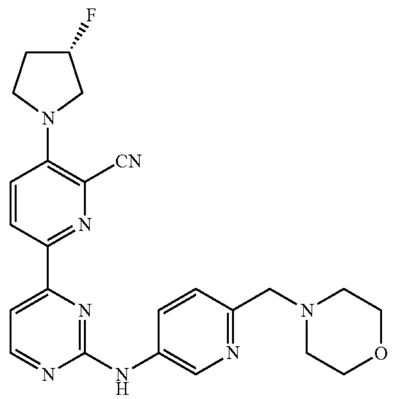 [SMILES: N#Cc1nc(-c2ccnc(Nc3ccc(CN4CCOCC4)nc3)n2)ccc1N1CC[C@H](F)C1] | DMX-143 | 3-((S)-3-Fluoro-pyrrolidin-1-yl)-6-[2-(6-morpholin-4-ylmethyl-pyridin-3-ylamino)-pyrimidin-4-yl]-pyridine-2-carbonitrile | A | Method D; Rt = 5.44 min; m/z 461 (MH$^+$); yellow solid | <15 nM | <15 nM | FA |
| 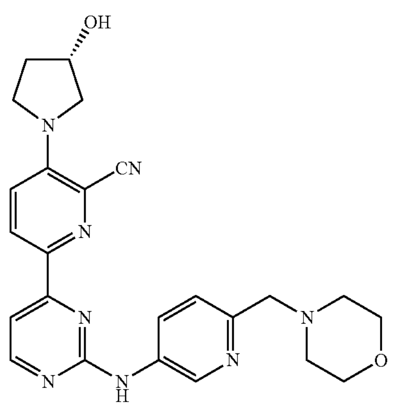 [SMILES: N#Cc1nc(-c2ccnc(Nc3ccc(CN4CCOCC4)nc3)n2)ccc1N1CC[C@H](O)C1] | DMX-144 | 3-((S)-3-Hydroxy-pyrrolidin-1-yl)-6-[2-(6-morpholin-4-ylmethyl-pyridin-3-ylamino)-pyrimidin-4-yl]-pyridine-2-carbonitrile | A | Method D; Rt = 4.97 min; m/z 459 (MH$^+$); orange solid | <30 nM | <30 nM | FA |
| 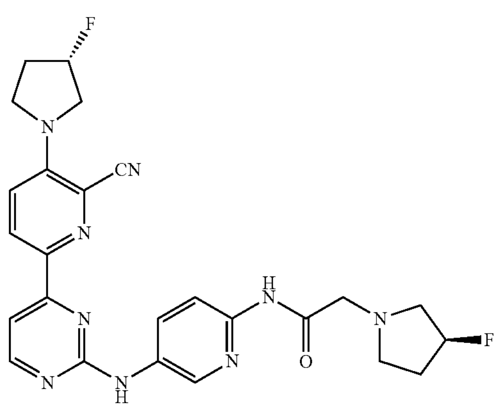 [SMILES: N#Cc1nc(-c2ccnc(Nc3ccc(NC(=O)CN4CC[C@H](F)C4)nc3)n2)ccc1N1CC[C@H](F)C1] | DMX-145 | N-(5-{4-[6-Cyano-5-((S)-3-fluoro-pyrrolidin-1-yl)-pyridin-2-yl]-pyrimidin-2-ylamino}-pyridin-2-yl)-2-((S)-3-fluoro-pyrrolidin-1-yl)-acetamide | A | Method D; Rt = 5.56 min; m/z 506 (MH$^+$); orange solid | <30 nM | <30 nM | FA |

TABLE VI-continued

| Structure | Ex. No. | Name | Route | Analytical Data | Inhibition of IKKε | Inhibition of TBK1 | Salt Form |
|---|---|---|---|---|---|---|---|
| 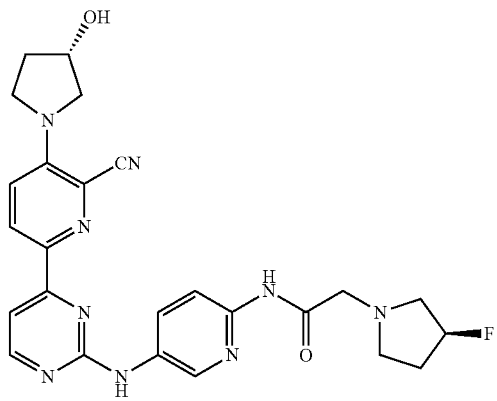 [SMILES: N#Cc1nc(-c2ccnc(Nc3ccc(NC(=O)CN4CC[C@H](F)C4)nc3)n2)ccc1N1CC[C@H](O)C1] | DMX-146 | N-(5-{4-[6-Cyano-5-((S)-3-hydroxy-pyrrolidin-1-yl)-pyridin-2-yl]-pyrimidin-2 ylamino}-pyridin-2-yl)-2-((S)-3-fluoro-pyrrolidin-1-yl)-acetamide | A | Method D; Rt = 5.13 min; m/z 504 (MH⁺); yellow solid | <100 nM | <30 nM | FA |
| 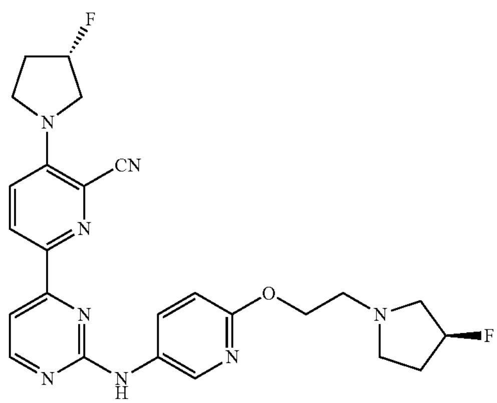 [SMILES: N#Cc1nc(-c2ccnc(Nc3ccc(OCCN4CC[C@H](F)C4)nc3)n2)ccc1N1CC[C@H](F)C1] | DMX-147 | 3-((S)-3-Fluoro-pyrrolidin-1-yl)-6-(2-{6-[2-((S)-3-fluoro-pyrrolidin-1-yl)-ethoxy]-pyridin-3-ylamino}-pyrimidin-4-yl)-pyridine-2-carbonitrile | A | Method D; Rt = 5.54 min; m/z 493 (MH⁺); yellow solid | <100 nM | <30 nM | FA |
| 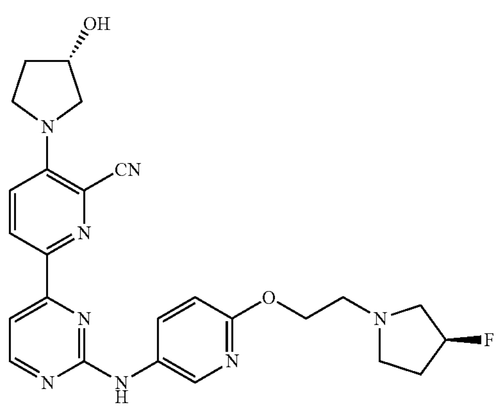 [SMILES: N#Cc1nc(-c2ccnc(Nc3ccc(OCCN4CC[C@H](F)C4)nc3)n2)ccc1N1CC[C@H](O)C1] | DMX-148 | 6-(2-{6-[2-((S)-3-Fluoro-pyrrolidin-1-yl)-ethoxy]-pyridin-3-ylamino}-pyrimidin-4-yl)-3-((S)-3-hydroxy-pyrrolidin-1-yl)-pyridine-2-carbonitrile | A | Method D; Rt = 5.13 min; m/z 491 (MH⁺); yellow solid | <100 nM | <100 nM | FA |

TABLE VI-continued

| Structure | Ex. No. | Name | Route | Analytical Data | Inhibition of IKKε | Inhibition of TBK1 | Salt Form |
|---|---|---|---|---|---|---|---|
| 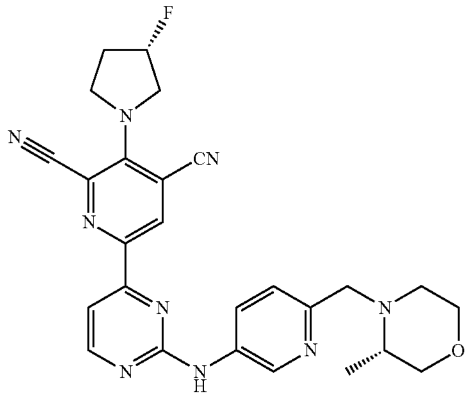 | DMX-149 | 3-((S)-3-Fluoro-pyrrolidin-1-yl)-6-{2-[6-((S)-3-methyl-morpholin-4-ylmethyl)-pyridin-3-ylamino]-pyrimidin-4-yl}-pyridine-2-carbonitrile | A | Method D; Rt = 5.53 min; m/z 475 (MH+); brown solid | <15 nM | <15 nM | None |
| 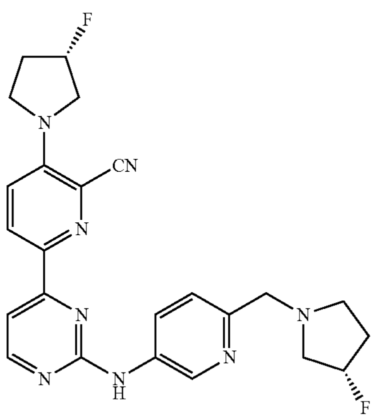 [SMILES: N#Cc1nc(-c2ccnc(Nc3ccc(CN4CC[C@H](F)C4)nc3)n2)ccc1N1CC[C@H](F)C1] | DMX-150 | 3-((S)-3-Fluoro-pyrrolidin-1-yl)-6-{2-[6-((S)-3-fluoro-pyrrolidin-1-ylmethyl)-pyridin-3-ylamino]-pyrimidin-4-yl}-pyridine-2-carbonitrile | A | Method D; Rt = 5.42 min; m/z 463 (MH+); white solid | <15 nM | <15 nM | None |
| 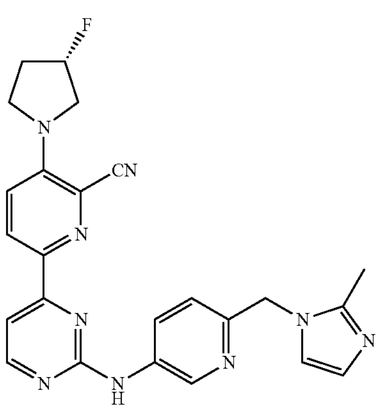 [SMILES: Cc1nccn1Cc1ccc(Nc2nccc(-c3ccc(N4CC[C@H](F)C4)c(C#N)n3)n2)cn1] | DMX-151 | 3-((S)-3-Fluoro-pyrrolidin-1-yl)-6-{2-[6-(2-methyl-imidazol-1-ylmethyl)-pyridin-3-ylamino]-pyrimidin-4-yl}-pyridine-2-carbonitrile | A | Method D; Rt = 5.45 min; m/z 456 (MH+); brown solid | <30 nM | <30 nM | FA |

TABLE VI-continued

| Structure | Ex. No. | Name | Route | Analytical Data | Inhibition of IKKε | Inhibition of TBK1 | Salt Form |
|---|---|---|---|---|---|---|---|
| 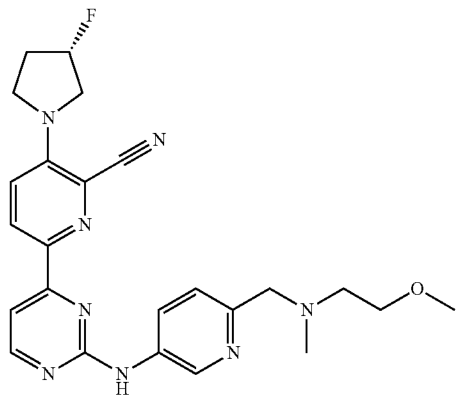 [SMILES: COCCN(C)Cc1ccc(Nc2nccc(-c3ccc(N4CC[C@H](F)C4)c(C#N)n3)n2)cn1] | DMX-152 | 3-((S)-3-Fluoro-pyrrolidin-1-yl)-6-[2-(6-{[(2-methoxy-ethyl)-methyl-amino]-methyl}-pyridin-3-ylamino)-pyrimidin-4-yl]-pyridine-2-carbonitrile | A | Method D; Rt = 5.51 min; m/z 463 (MH$^+$); white solid | <30 nM | <30 nM | None |
| 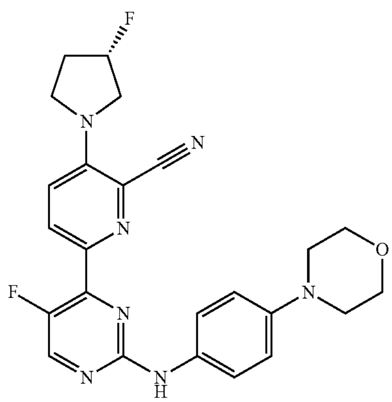 [SMILES: N#Cc1nc(-c2nc(Nc3ccc(N4CCOCC4)cc3)ncc2F)ccc1N1CC[C@H](F)C1] | DMX-153 | 6-[5-Fluoro-2-(4-morpholin-4-yl-phenylamino)-pyrimidin-4-yl]-3-((S)-3-fluoro-pyrrolidin-1-yl)-pyridine-2-carbonitrile | A* | Method D; Rt = 7.65 min; m/z 464 (MH$^+$); yellow solid | <15 nM | <15 nM | None |
| 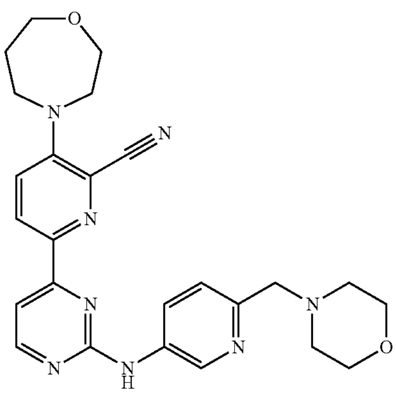 [SMILES: N#Cc1nc(-c2ccnc(Nc3ccc(CN4CCOCC4)nc3)n2)ccc1N1CCCOCC1] | DMX-164 | 6-[2-(6-Morpholin-4-ylmethyl-pyridin-3-ylamino)-pyrimidin-4-yl]-3-[1,4]oxazepan-4-yl-pyridine-2-carbonitrile | A | Method D; Rt = 5.60 min; m/z 473 (MH$^+$); yellow solid | <30 nM | <100 nM | FA |

TABLE VI-continued

| Structure | Ex. No. | Name | Route | Analytical Data | Inhibition of IKKε | Inhibition of TBK1 | Salt Form |
|---|---|---|---|---|---|---|---|
| 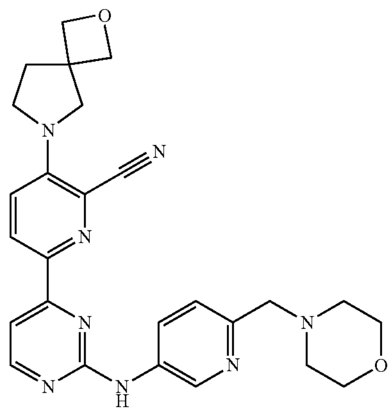 [SMILES: N#Cc1nc(-c2ccnc(Nc3ccc(CN4CCOCC4)nc3)n2)ccc1N1CCC2(COC2)C1] | DMX-165 | 6-[2-(6-Morpholin-4-ylmethyl-pyridin-3-ylamino)-pyrimidin-4-yl]-3-(2-oxa-6-aza-spiro[3.4]oct-6-yl)-pyridine-2-carbonitrile | A | Method D; Rt = 5.55 min; m/z 485 (MH+); yellow solid | <15 nM | <30 nM | FA |
| 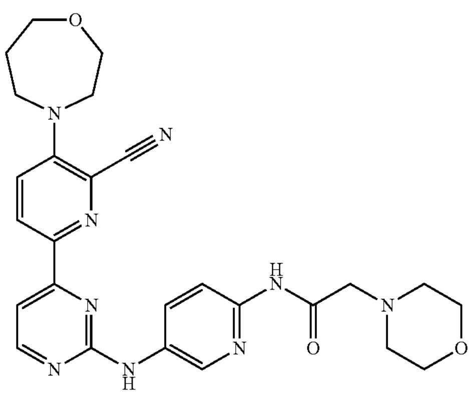 [SMILES: N#Cc1nc(-c2ccnc(Nc3ccc(NC(=O)CN4CCOCC4)nc3)n2)ccc1N1CCCOCC1] | DMX-166 | N-{5-[4-(6-Cyano-5-[1,4]oxazepan-4-yl-pyridin-2-yl)-pyrimidin-2-ylamino]-pyridin-2-yl}-2-morpholin-4-yl-acetamide | A | Method D; Rt = 6.30 min; m/z 516 (MH+); yellow solid | <100 nM | <100 nM | None |
| 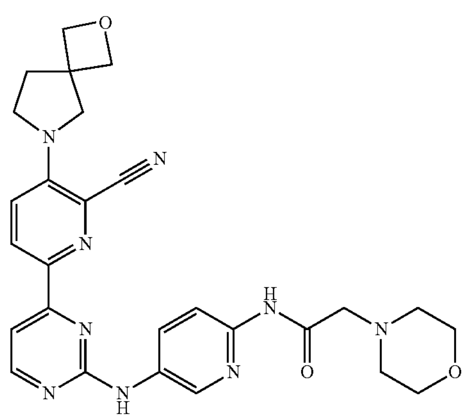 [SMILES: N#Cc1nc(-c2ccnc(Nc3ccc(NC(=O)CN4CCOCC4)nc3)n2)ccc1N1CCC2(COC2)C1] | DMX-167 | N-(5-{4-[6-Cyano-5-(2-oxa-6-aza-spiro[3.4]oct-6-yl)-pyridin-2-yl]-pyrimidin-2-ylamino}-pyridin-2-yl)-2-morpholin-4-yl-acetamide | A | MeOH—FA method; Rt = 3.07 min; m/z 528 (MH+); brown solid | <30 nM | <100 nM | None |
| 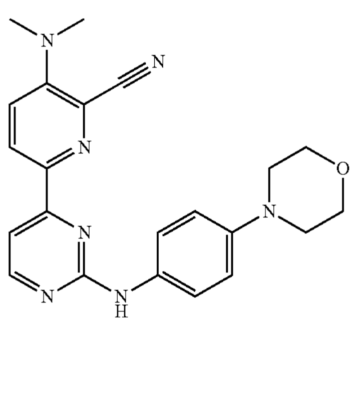 [SMILES: CN(C)c1ccc(-c2ccnc(Nc3ccc(N4CCOCC4)cc3)n2)nc1C#N] | DMX-154 | 3-[(2-Methoxy-ethyl)-methyl-amino]-6-[2-(1-methyl-1H-pyrazol-4-ylamino)-pyrimidin-4-yl]-pyridine-2-carbonitrile | C** | Method D; Rt = 7.91 min; m/z 402 (MH+); yellow solid | <100 nM | <15 nM | None |

TABLE VI-continued

| Structure | Ex. No. | Name | Route | Analytical Data | Inhibition of IKKε | Inhibition of TBK1 | Salt Form |
|---|---|---|---|---|---|---|---|
| 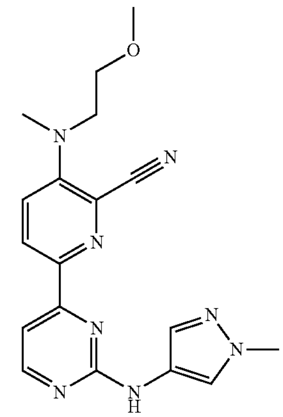 [SMILES: COCCN(C)c1ccc(-c2ccnc(Nc3cnn(C)c3)n2)nc1C#N] | DMX-155 | 3-Dimethylamino-6-[2-(4-morpholin-4-yl-phenylamino)-pyrimidin-4-yl]-pyridine-2-carbonilrile | B | Method D: Rt = 7.48 min; m/z 365 (MH+); yellow solid | <1 μM | <1 μM | None |

*For example DMX-153, the required fluorinated enone 74 was prepared from intermediate 73, which was made according to the procedures outlined in method A.

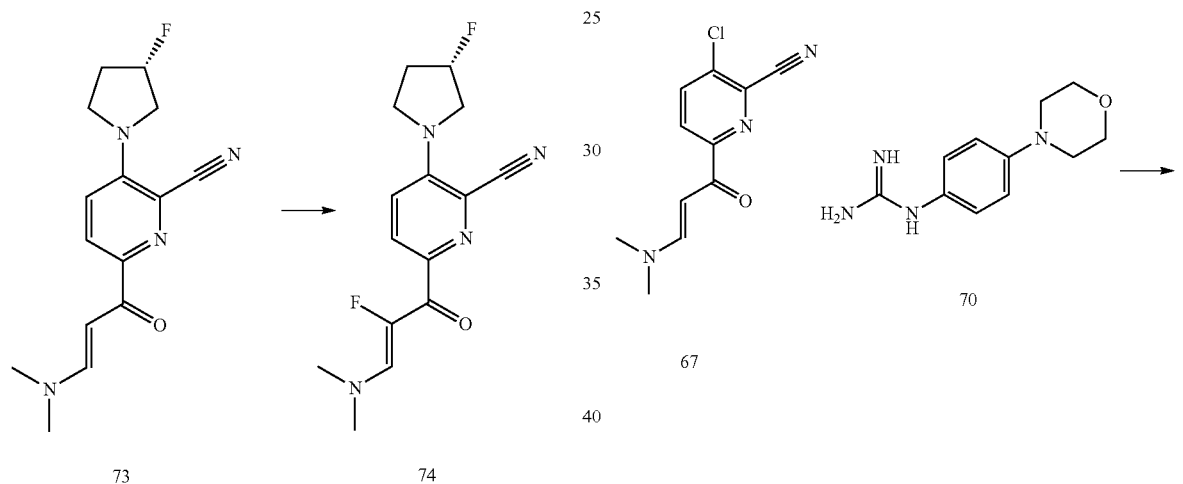

6-((Z)-3-Dimethylamino-2-fluoro-acryloyl)-3-((S)-3-fluoro-pyrrolidin-1-yl)-pyridine-2-carbonitrile (74)

Selectfluor (135 mg, 0.38 mmol) was added to a stirred solution of enone 73 (100 mg, 0.35 mmol) in MeOH (5 mL) at 0° C. The resulting mixture was stirred at 0° C. 2.5 hours. Ammonia (32% aq, 2 mL) was added and the resulting solution was extracted with DCM (3×3 mL). The combined organic phases were dried (Na$_2$SO$_4$), filtered and solvent removed in vacuo. The crude product was purified by column chromatography (Biotage SP1, 100% DCM→5% MeOH-DCM) to afford the title compound (70 mg, 66%) along with some residual starting material as an off-white solid. LCMS, Rt=2.49 min (MeOH-FA method), m/z 307 (MH+).

** Example DMX-154 was isolated as a by-product from the reaction of 67 and 70 following the procedure outlined in method C

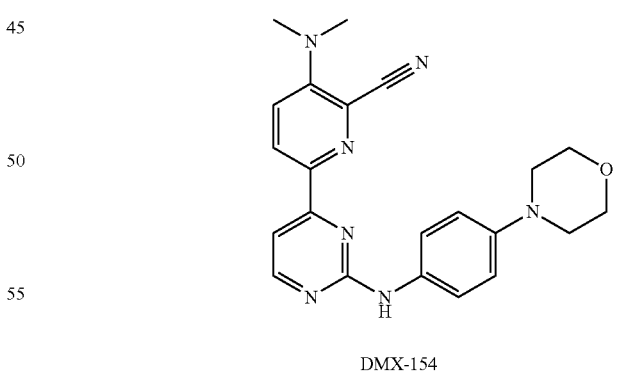

DMX-154

A number of the aryl guanidines utilised in routes A, B and C required synthesising from their requisite amines, which were either commercially available or synthesised as described previously. Aryl guanidines were generally prepared via the general route shown below.

Example

N-(5-Guanidino-pyridin-2-yl)-2-morpholin-4-yl-acetamide

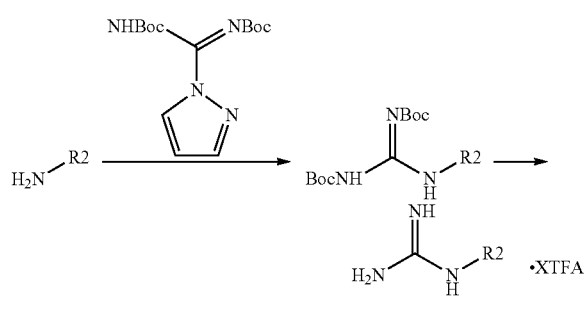

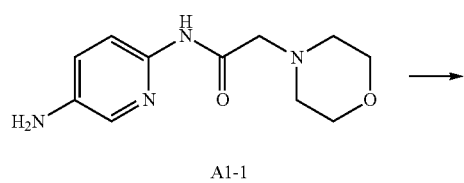

Amine A1-1 (500 mg, 2.1 mmol) and N,N-di-boc-1H-pyrazole-1-carboxamidine (700 mg, 2.3 mmol) were dissolved in MeCN (8 mL). The reaction mixture was heated in the microwave at 80° C. for 1 hour. The solvent was removed in vacuo and the crude residue purified by column chromatography (Biotage SP1, 30% EtOAc-iso-hexane→100% EtOAc) to afford compound 75 (501 mg, 50%) as an off-white solid. LCMS, Rt=2.95 min (MeOH-FA), m/z 479; Compound 75 (401 mg, 0.84 mmol) was dissolved in 9:1 DCM-TFA (20 mL). The reaction mixture was stirred at rt for 7 hours. The solvent was removed in vacuo to afford the TFA salt of the title compound 76 (520 mg, 100%) as a pale yellow gum. LCMS, Rt=0.27 min (MeOH-FA), m/z 279.

Alternatively guanidines may be made by the reaction of the corresponding amine with cyanamide in ethanol and concentrated nitric acid. This approach was used for the synthesis of DMX-58, DMX-59 and DMX-60

Example

N-(1-Methyl-1H-pyrazol-4-yl)-guanidine. nitric acid

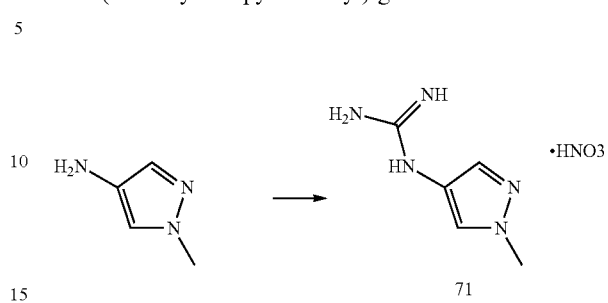

To a solution of 4-amino-1-methylpyrazole (1 g, 10 mmol) and cyanamide (650 mg, 15 mmol) in ethanol (10 mL) was added concentrated nitric acid (0.4 mL) and the reaction mixture heated to reflux for 4 h. After which time the solvent was evaporated and the crude mixture triturated with diethylether to give 71 as purple solid, m/z 140 (MH$^+$). Guanidines made by this method were used crude in the subsequent reaction to form the pyrimidine ring Other compounds of formula Ib were made from 77.

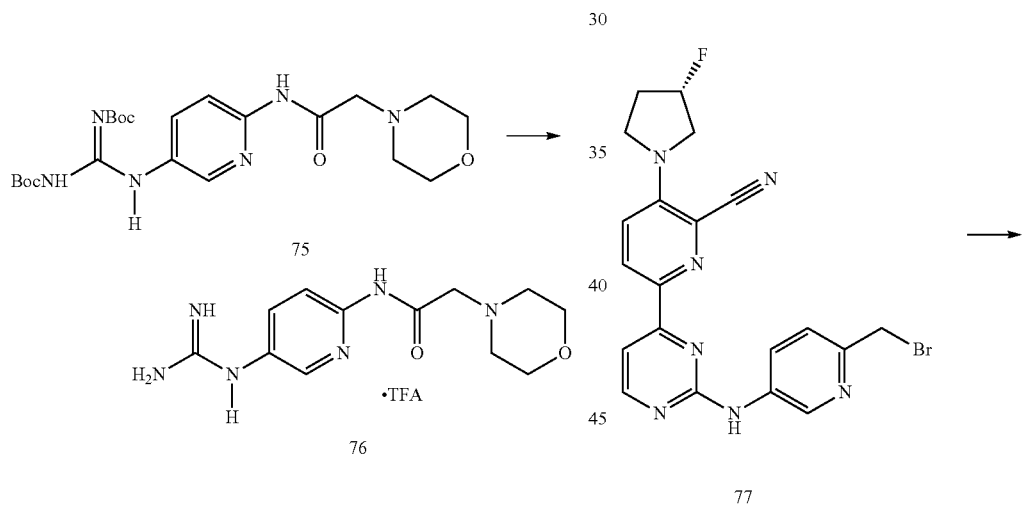

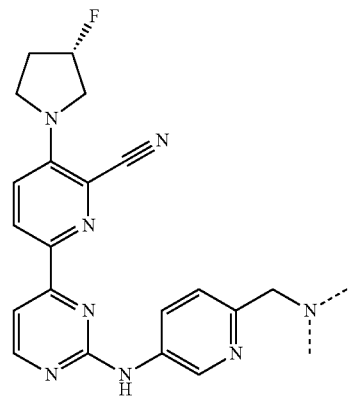

Example DMX-156

Synthesis of 3-((S)-3-Fluoro-pyrrolidin-1-yl)-6-{2-[6-(3-oxo-piperazin-1-ylmethyl)-pyridin-3-ylamino]-pyrimidin-4-yl}-pyridine-2-carbonitrile 6-(2-Amino-pyrimidin-4-yl)-3-((S)-3-fluoro-pyrrolidin-1-yl)-pyridine-2-carbonitrile (78)

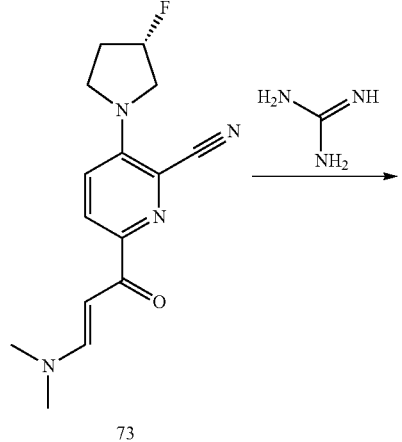

Compound 73 (1.0 g, 3.47 mmol), guanidine hydrochloride (828 mg, 8.67 mmol) and sodium methoxide (750 mg, 13.9 mmol) were dissolved in ethanol (20 mL) and heated under reflux for 29 hours. The solvent was removed in vacuo and the residue partition between DCM (2×70 mL) and sat. aq. sodium hydrogen carbonate (50 mL). The combined organic phases were concentrated in vacuo to afford the title compound (970 mg, 98%) as a pale brown solid. LCMS, Rt=2.13 min (MeOH-FA method), m/z 285.

6-(2-Chloro-pyrimidin-4-yl)-3-((S)-3-fluoro-pyrrolidin-1-yl)-pyridine-2-carbonitrile (79)

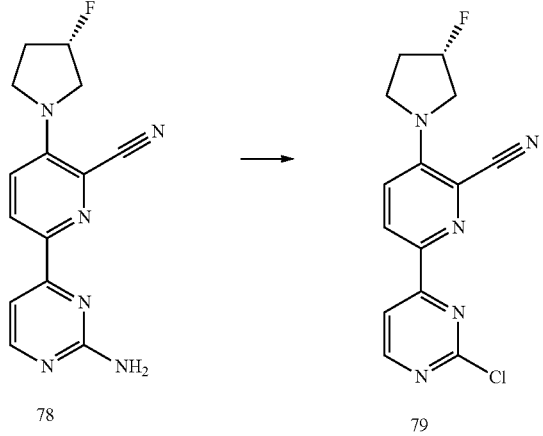 [SMILES: N#Cc1nc(-c2ccnc(N)n2)ccc1N1CC[C@H](F)C1 ; N#Cc1nc(-c2ccnc(Cl)n2)ccc1N1CC[C@H](F)C1]

Compound 78 (970 mg, 3.42 mmol) was dissolved in DCM (50 mL) and trimethyl silyl chloride (1.08 mL, 8.54 mmol) and tert-butyl nitrite (1.02 mL, 8.54 mmol) were added. The reaction mixture was stirred at rt for 60 h. The reaction was quenched with saturated aqueous sodium hydrogen carbonate (50 mL) and extracted with DCM (2×50 mL). The combined organic phases were dried (MgSO₄), filtered and solvent removed in vacuo. The crude residue was suspended in toluene (50 mL), diethyl isopropylamine (1.49 mL) and phosphorus oxychloride (5 mL) were added. The resulting mixture was heated under reflux for 3 hours and then poured into ice water with vigorous stirring. The resulting solution was neutralized with sodium hydrogen carbonate and extracted with ethanol (3×100 mL). The combined organic phases were concentrated in vacuo and the residue purified by column chromatography (Biotage SP1, 100% DCM→10% MeOH-DCM) and trituration with EtOAc to afford the title compound (270 mg, 26%) as a pale brown solid. LCMS, Rt=3.03 min (MeOH-FA), m/z 304.

6-{2-[6-(tert-Butyl-dimethyl-silanyloxymethyl)-pyridin-3-ylamino]-pyrimidin-4-yl}-3-((S)-3-fluoro-pyrrolidin-1-yl)-pyridine-2-carbonitrile (80)

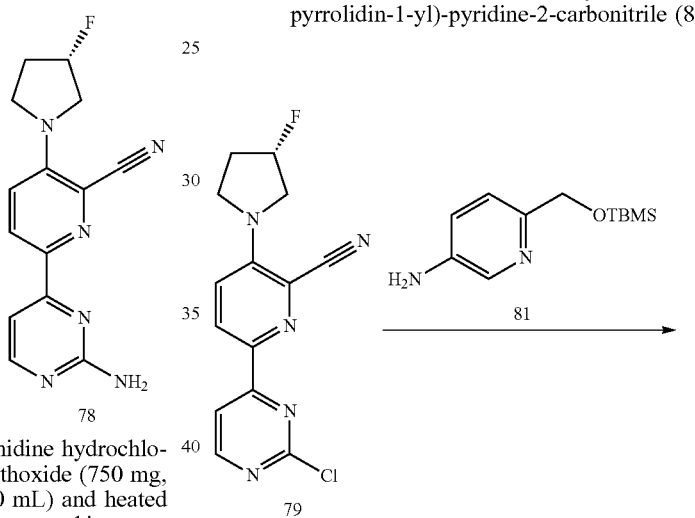

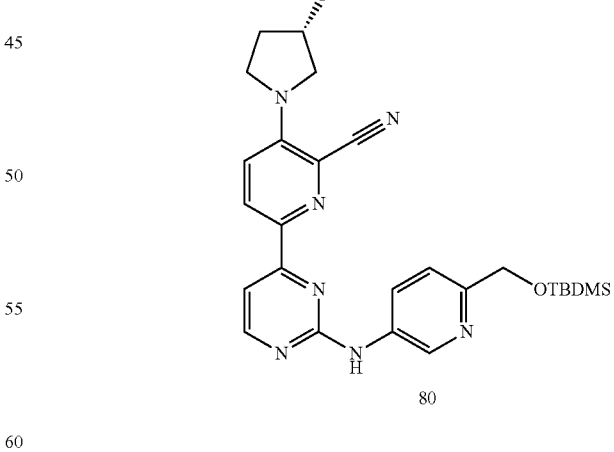

A mixture of compound 79 (120 mg, 0.40 mmol), amine 81 (122 mg, 0.5 mmol), Tris(dibenzylideneacetone)dipalladium(0) (36 mg, 0.04 mmol, 10 mol %), NaOtBu (57 mg, 0.59 mmol) and 2-dicyclohexylphosphino-2'-(N,N-dimethylamino)biphenyl (31 mg, 0.08 mmol) were dissolved in 1,4-dioxane (8 mL), deoxygenated by bubbling nitrogen for 10 mins and the mixture heated at 100° C. in the microwave (250 W, stirring) for 10 minutes. The reaction mixture was passed through a catch release cartridge (Biotage SCX-2; 5 g) washing through with MeOH (5 column volumes) and then 0.5 M ammonia-MeOH (4 column volumes). The basic fractions were combined and concentrated in vacuo to provide the title compound (202 mg, 100%) as a red oil; LCMS, Rt=3.74 min (MeOH-FA method), m/z 506 (MH⁺).

3-((S)-3-Fluoro-pyrrolidin-1-yl)-6-[2-(6-hydroxymethyl-pyridin-3-ylamino)-pyrimidin-4-yl]-pyridine-2-carbonitrile (82)

3-((S)-3-Fluoro-pyrrolidin-1-yl)-6-{2-[6-(3-oxo-piperazin-1-ylmethyl)-pyridin-3-ylamino]-pyrimidin-4-yl}-pyridine-2-carbonitrile (DMX-156)

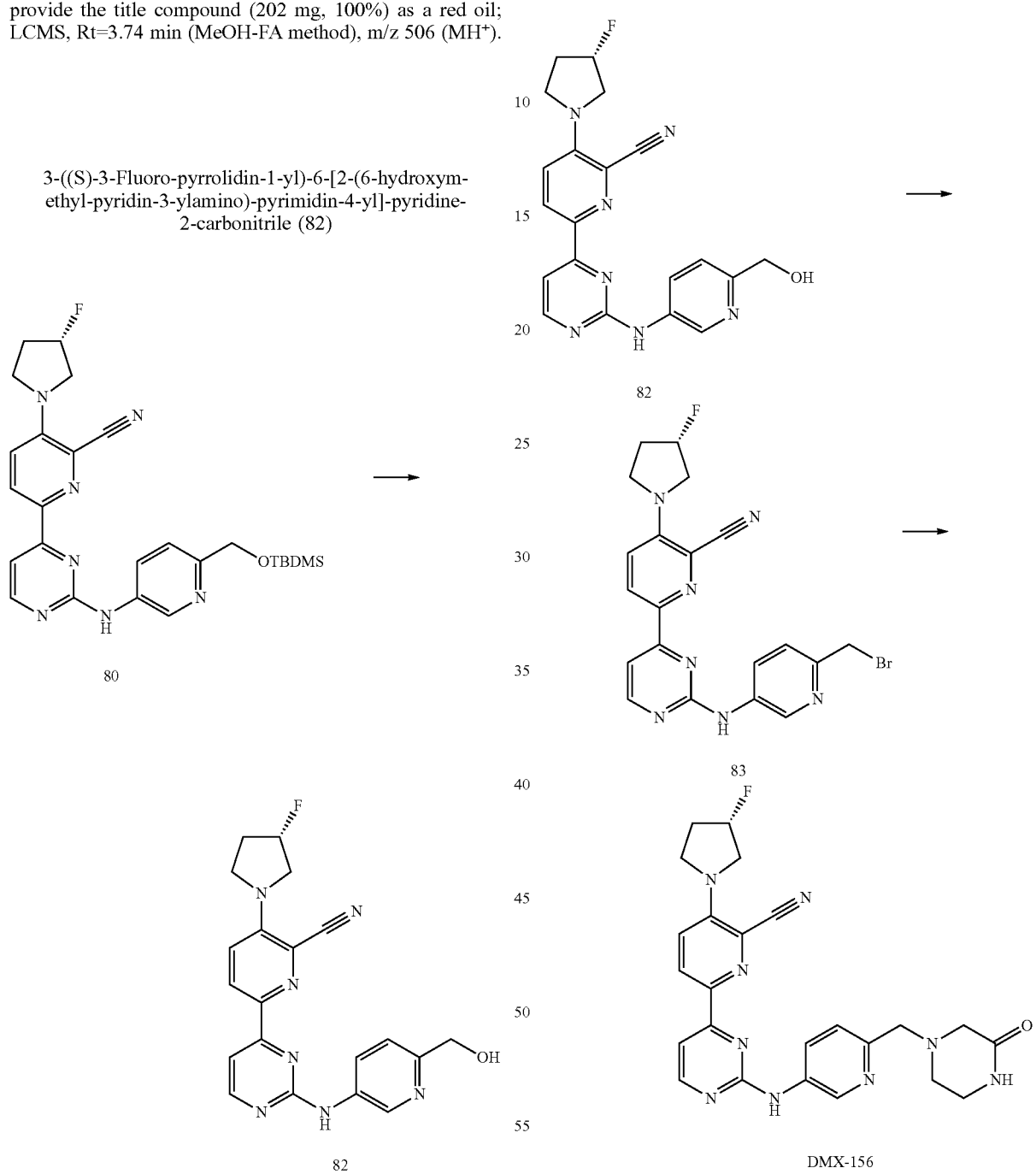

Compound 80 (252 mg, 0.5 mmol) was dissolved in 1:1 2 M HCl-MeCN and the reaction mixture stirred at rt for 5 hours. The solvent was removed in vacuo and the residue triturated with 9:1 EtOAc-MeOH to afford the title compound (152 mg, 79%) as a dark yellow solid; LCMS, Rt=2.40 min (MeOH-FA method), m/z 392 (MH⁺).

Compound 82 (40 mg, 0.10 mmol) was dissolved in MeCN (5 mL). Phosphorous tribromide (50 µL, 0.53 mmol) was added and the reaction mixture was heated under reflux for 0.5 hours. The reaction was cooled to rt and 2-oxopiperazine (100 mg, 0.99 mmol) was added and the reaction mixture stirred at rt for 16 hours. The solvent was removed in vacuo and the residue purified by reverse phase preparative LC-MS. Fractions contained the desired product were combined and the MeOH removed in vacuo. The resulting aqueous solution was frozen (−78° C.) and the solvent evaporated in vacuo (freeze dried). The title compound (3 mg, 6%) was obtained as an off-white solid. LCMS, Rt=6.15 min (MeOH-FA method), m/z 474 (MH+).

Compounds prepared via these routes are as follows:

TABLE VII

| Structure | Ex. No. | Analytical Data | Analytical Data | Inhibition of IKKε | Inhibition of TBK1 | Salt Form |
|---|---|---|---|---|---|---|
| 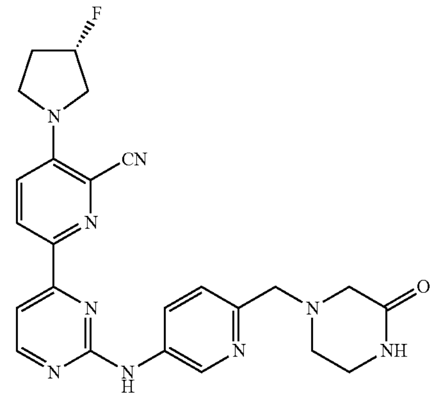 [SMILES: N#Cc1nc(-c2ccnc(Nc3ccc(CN4CCNC(=O)C4)nc3)n2)ccc1N1CC[C@H](F)C1] | DMX-156 | 3-((S)-3-Fluoro-pyrrolidin-1-yl)-6-{2-[6-(3-oxo-piperazin-1-ylmethyl)-pyridin-3-ylamino]-pyrimidin-4-yl}-pyridine-2-carbonitrile | Method D; Rt = 6.15 min; m/z 474 (MH+); white solid | <15 nM | <15 nM | FA |
| 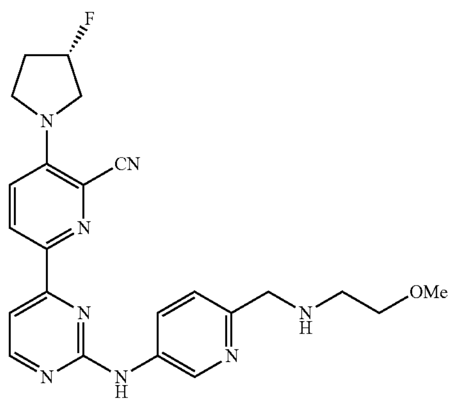 [SMILES: COCCNCc1ccc(Nc2nccc(-c3ccc(N4CC[C@H](F)C4)c(C#N)n3)n2)cn1] | DMX-157 | 3-((S)-3-Fluoro-pyrrolidin-1-yl)-6-(2-{6-[(2-methoxy-ethylamino)-methyl]-pyridin-3-ylamino}-pyrimidin-4-yl)-pyridine-2-carbonitrile | Method D; Rt = 5.47 min; m/z 449 (MH+); yellow solid | <100 nM | <30 nM | FA |

The invention claimed is:

1. A compound of the general formula I:

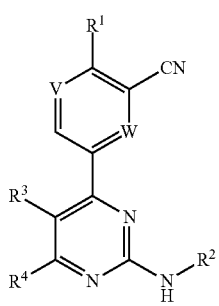

(I)

in which:
one of V and W is N, and the other of V and W is C—H;
R$^1$ represents an aliphatic heterocyclyl group having 4, 5, 6, 7, 8 or 9 ring atoms, bonded to the pyridyl group shown in formula I through a ring nitrogen atom, and optionally substituted by one or more substituents selected from halogen; OH; =O; NO$_2$; CN; NR$^a$R$^b$; (CHR$^a$)$_x$COR$^c$; O.CO.R$^c$; CO$_2$R$^a$; CONHR$^d$; (CHR$^a$)$_x$NR$^a$.COR$^c$; NR$^a$CO$_2$R$^b$; C(=NH)NH$_2$; SO$_2$R$^c$; NR$^a$SO$_2$R$^c$; CH(CF$_3$)NH$_2$; and C$_{1-4}$alkyl, C$_{1-4}$alkoxy, C$_{1-4}$alkoxyC$_{1-4}$alkyl, C$_{2-4}$alkenyl and C$_{2-4}$alkynyl groups, each optionally substituted by one or more substituents independently selected from halogen atoms, OH, S-alkyl, CONHR$^a$ and NR$^a$R$^b$ groups; or
R$^1$ represents a NR$^a$—(CHR$^a$)$_x$—C$_{3-6}$cycloalkyl group or a NR$^a$—(CHR$^a$)$_x$—C$_{3-6}$heterocycloalkyl group, said heterocycloalkyl group containing one heteroatom, wherein the heteroatom is oxygen or nitrogen, and said cycloalkyl or heterocycloalkyl being optionally substituted by one or more substituents selected from halogen; OH; =O; NO$_2$; CN; NR$^a$R$^b$; (CHR$^a$)$_x$COR$^c$; O.CO.R$^c$; CO$_2$R$^a$; CONHR$^d$; (CHR$^a$)$_x$NR$^a$.COR$^c$; NR$^a$CO$_2$R$^b$; C(=NH)NH$_2$; SO$_2$R$^c$; NR$^a$SO$_2$R$^c$; CH(CF$_3$)NH$_2$; and C$_{1-4}$alkyl, C$_{1-4}$alkoxy, C$_{1-4}$alkoxyC$_{1-4}$alkyl, C$_{2-4}$alkenyl and C$_{2-4}$alkynyl groups, each optionally substituted by one or more substituents independently selected from halogen atoms, OH, S-alkyl, CONHR$^a$ and NR$^a$R$^b$ groups; or
R$^1$ represents NR$^a$—C$_{1-6}$alkyl optionally substituted by one or more substituents independently selected from halogen; OH; =O; NO$_2$; CN; NR$^a$R$^b$; (CHR$^a$)$_x$COR$^c$; O.CO.R$^c$; CO$_2$R$^a$; CONHR$^d$; (CHR$^a$)$_x$NR$^a$.COR$^c$; NR$^a$CO$_2$R$^b$; C(=NH)NH$_2$; SO$_2$R$^c$; NR$^a$SO$_2$R$^c$; CH(CF$_3$)NH$_2$; and C$_{1-4}$alkyl, C$_{1-4}$alkoxy, $C_{1-4}$alkoxy$C_{1-4}$ alkyl, $C_{2-4}$alkenyl and $C_{2-4}$alkynyl groups, each optionally substituted by one or more substituents independently selected from halogen atoms, OH, S-alkyl, CONHR$^a$ and a NR$^a$R$^b$ group;

x is 0, 1 or 2;

R$^2$ represents

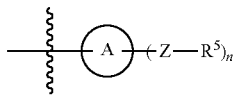

wherein A is a phenyl or 5 to 10 membered heteroaryl ring containing 1, 2 or 3 heteroatoms;

n is 0, 1, 2 or 3;

each Z is a group independently selected from —(CHR$^a$)$_p$—, —(CHR$^a$)$_p$—O—(CHR$^a$)$_r$—, —(CHR$^a$)$_p$—NR$^a$—(CHR$^a$)$_r$—, —C(=O)—, C(=O)NR$^a$— and —NR$^a$C(=O)(CHR$^a$)$_p$—, in which p is 0, 1 or 2; and r is 0, 1, 2 or 3;

and each R$^5$ is a group independently selected from:
H, halogen, OR$^b$, or NR$^a$R$^b$;
a 4 to 8 membered heterocyclyl ring containing 1, 2, or 3 heteroatoms, optionally substituted by one or more substituents independently selected from halogen atoms, OH, =O, NR$^a$R$^b$, O—C$_{1-4}$alkyl and C$_{1-4}$alkyl groups, optionally substituted with one or more halogen atoms, O—C$_{1-4}$alkyl, OH and NR$^a$R$^b$;
C$_{1-4}$alkyl, C$_{3-7}$cycloalkyl, C$_{1-4}$alkoxy, C$_{1-4}$alkoxyC$_{1-4}$ alkyl, C$_{2-4}$alkenyl or C$_{2-4}$alkynyl groups, each optionally substituted by one or more substituents independently selected from halogen, O—C$_{1-4}$alkyl, OH and NR$^a$R$^b$;
NO$_2$; CN; O.CO.R$^c$; NR$^a$.COR$^c$; NR$^a$CO$_2$R$^b$; C(=NH)NH$_2$; SO$_2$R$^c$; NR$^a$SO$_2$R$^c$; and CH(CF$_3$)NH$_2$;
or two Z—R$^5$ groups on adjacent ring atoms together with the two adjacent ring atoms form a 5-7 membered fused ring composed of the two adjacent ring atoms and —(CHR$^a$)$_r$—(CHR$^5$)—(CHR$^a$)$_r$—, wherein the —CHR$^5$— moiety can be replaced with —O— or —NR$^5$— and each r is independently 0, 1, 2, 3 or 4; or
a 5-7 membered fused ring composed of the two adjacent ring atoms and —NR$^a$.CO.(CH$_2$)$_q$—, wherein one —CH$_2$— moiety can be replaced with —O— or —NR$^a$—; and each R$^a$ independently represents a hydrogen atom or a C$_{1-4}$alkyl group;

each R$^b$ independently represents a hydrogen atom; a C$_{1-4}$alkyl group optionally substituted by one or more groups selected from OH, O—C$_{1-4}$alkyl, halogen, SO$_2$R$^c$, CONHR$^c$, NR$^a$.COR$^c$, COR$^c$, N(R$^a$)$_2$ and phenyl; or a C$_{3-8}$cycloalkyl group in which a CH$_2$ moiety may be replaced by an oxygen atom or an NR$^a$ group;

R$^c$ represents a hydrogen atom; a —NR$^a$R$^b$ group; a C$_{3-8}$cycloalkyl group, in which CH$_2$ moiety may optionally be replaced by an oxygen atom or an NR$^b$ group; or a C$_{1-4}$alkyl group optionally substituted by a OH, O—C$_{1-4}$alkyl or a NR$^a$R$^b$ group;

R$^d$ represents a 5- or 6-membered heteroaryl group containing 1 or 2 heteroatoms, optionally substituted with one or more C$_{1-4}$alkyl groups;

q represents 1, 2 or 3;

R$^3$ represents a hydrogen atom, a C$_{1-4}$alkyl group or a halogen atom; and

R$^4$ represents a hydrogen atom, a C$_{1-4}$alkyl group or a halogen atom;

or a salt thereof.

2. A compound as claimed in claim 1, in which R$^1$ represents a pyrrolidine, morpholine, piperazine, piperidine, azetidine, 2-oxa-6-azaspiro[3.4]octane, thiomorpholine, homopiperazine, homomorpholine, 8-aza-bicyclo[3.2.1]oct-8-yl group or 3-oxa-8-aza-bicyclo[3.2.1]oct-8-yl group, optionally substituted with one or two fluorine atoms; OH; CN; COR$^c$; CO$_2$R$^a$; CONHR$^d$; methoxy and C$_{1-4}$alkyl substituted with CONH$_2$ or NHCOMe.

3. A compound as claimed in claim 2, in which R$^1$ represents a pyrrolidine ring or an 8-aza-bicyclo[3.2.1]oct-8-yl group, optionally substituted with one hydroxy group or one fluorine atom.

4. A compound as claimed in claim 3, in which R$^2$ represents

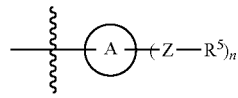

wherein A is a phenyl or 5 or 6 membered heteroaryl ring containing 1, 2 or 3 heteroatoms;

n is 1 or 2;

each Z is a group independently selected from —(CHR$^a$)$_p$—, —O—(CHR$^a$)$_r$—, —NR$^a$—(CHR$^a$)$_r$—, —C(=O)— and —NR$^a$C(=O)(CHR$^a$)$_p$—, in which p is 0, 1 or 2;

and each R$^5$ is a group independently selected from:
H, halogen, OR$^b$ or NR$^a$R$^b$;
a 4- to 6-membered heterocyclyl ring containing 1 or 2 heteroatoms, optionally substituted by one or more substituents independently selected from halogen atoms, OH, =O, NR$^a$R$^b$, O—C$_{1-4}$alkyl and C$_{1-4}$alkyl groups, optionally substituted with halogen, OMe or OH;
C$_{1-4}$alkyl or C$_{3-7}$cycloalkyl groups, each optionally substituted by one or more substituents independently selected from halogen, OMe, OH and NR$^a$R$^b$; CN, SO$_2$R$^c$ and NR$^a$SO$_2$R$^c$; or
or n=2 and two Z—R$^5$ groups on adjacent ring atoms together with the two adjacent ring atoms form a 5-7 membered fused ring composed of the two adjacent ring atoms and —(CHR$^a$)$_r$—(CHR$^5$)—(CHR$^a$)$_r$—, wherein the —CHR$^5$— moiety can be replaced with —NR$^5$— and each r is independently 1 or 2; and each R$^a$ independently represents a hydrogen atom or a C$_{1-4}$alkyl group; and each R$^b$ independently represents a hydrogen atom; a C$_{1-4}$alkyl group optionally substituted by one or more groups selected from OH, O—C$_{1-4}$alkyl, halogen and SO$_2$R$^c$; or a C$_{3-8}$cycloalkyl group in which a CH$_2$ moiety may be replaced by an oxygen atom or an NR$^a$ group; and each R$^c$ represents —NR$^a$R$^b$ or a methyl group.

5. A compound as claimed in claim 4, in which A is phenyl, pyridine or pyrazole.

6. A compound as claimed in claim 5, in which n is 1.

7. A compound as claimed in claim 6, in which R$^5$ is a group independently selected from:
H, OH, NR$^a$R$^b$ or cyclopropyl;
a 4- to 6-membered heterocyclyl ring containing 1 or 2 heteroatoms, optionally substituted by one substituent selected from F, OH, =O, O—C$_{1-4}$alkyl and C$_{1-4}$alkyl groups, optionally substituted with halogen, OMe or OH; and C$_{1-4}$alkyl optionally substituted by one or two OH groups.

8. A compound as claimed in claim 7, in which R$^5$ is a group independently selected from:

H, OH, or NR$^a$R$^b$; and a 6-membered heterocyclyl ring containing 1 or 2 heteroatoms or 5-membered heterocyclyl ring containing 1 heteroatom or 4-membered heterocycloalkyl ring containing 1 nitrogen atom, optionally substituted by one substituent selected from F, =O, C$_{1-4}$alkyl, OMe and OH groups;

C$_{1-4}$alkyl optionally substituted by one or two OH groups.

9. A compound as claimed in claim 8, in which each of R$^3$ and R$^4$ independently represents a methyl group, a hydrogen atom or a fluorine atom.

10. A compound as claimed in claim 1, selected from:

3-{4-[5-Cyano-6-((S)-3-fluoro-pyrrolidin-1-yl)-pyridin-3-yl]-pyrimidin-2-ylamino}-N-(1-methyl-piperidin-4-yl)-benzamide;

3-[4-(5-Cyano-6-pyrrolidin-1-yl-pyridin-3-yl)-pyrimidin-2-ylamino]-benzamide;

5-{2-[6-(4-Methyl-piperazin-1-yl)-pyridin-3-ylamino]-pyrimidin-4-yl}-2-pyrrolidin-1-yl-nicotinonitrile;

2-((S)-3-Fluoro-pyrrolidin-1-yl)-5-{2-[3-(piperazine-1-carbonyl)-phenylamino]-pyrimidin-4-yl}-nicotinonitrile;

5-[2-(4-Morpholin-4-yl-phenylamino)-pyrimidin-4-yl]-2-pyrrolidin-1-yl-nicotinonitrile;

2-((S)-3-Fluoro-pyrrolidin-1-yl)-5-{2-[3-(4-methyl-piperazine-1-carbonyl)-phenylamino]-pyrimidin-4-yl}-nicotinonitrile;

2-((S)-3-Fluoro-pyrrolidin-1-yl)-5-[2-(1-methyl-1H-pyrazol-4-ylamino)-pyrimidin-4-yl]-nicotinonitrile;

N-(5-{4-[5-Cyano-6-((S)-3-fluoro-pyrrolidin-1-yl)-pyridin-3-yl]-pyrimidin-2-ylamino}-pyridin-2-yl)-acetamide;

2-((S)-3-Fluoro-pyrrolidin-1-yl)-5-{2-[6-(1-methyl-piperidin-4-ylamino)-pyridin-3-ylamino]-pyrimidin-4-yl}-nicotinonitrile;

2-((S)-3-Fluoro-pyrrolidin-1-yl)-5-{2-[6-(piperidin-4-ylamino)-pyridin-3-ylamino]-pyrimidin-4-yl}-nicotinonitrile;

3-{4-[5-Cyano-6-((S)-3-fluoro-pyrrolidin-1-yl)-pyridin-3-yl]-pyrimidin-2-ylamino}-N-piperidin-4-yl-benzamide;

3-{4-[5-Cyano-6-((S)-3-hydroxy-pyrrolidin-1-yl)-pyridin-3-yl]-pyrimidin-2-ylamino}-N-(1-methyl-piperidin-4-yl)-benzamide;

2-((S)-3-Hydroxy-pyrrolidin-1-yl)-5-{2-[6-(1-methyl-piperidin-4-ylamino)-pyridin-3-ylamino]-pyrimidin-4-yl}-nicotinonitrile;

3-{4-[5-Cyano-6-(3,3-difluoro-pyrrolidin-1-yl)-pyridin-3-yl]-pyrimidin-2-ylamino}-N-(1-methyl-piperidin-4-yl)-benzamide;

2-(3,3-Difluoro-pyrrolidin-1-yl)-5-{2-[6-(1-methyl-piperidin-4-ylamino)-pyridin-3-ylamino]-pyrimidin-4-yl}-nicotinonitrile;

2-((S)-3-Hydroxy-pyrrolidin-1-yl)-5-[2-(1-methyl-1H-pyrazol-4-ylamino)-pyrimidin-4-yl]-nicotinonitrile;

N-(5-{4-[5-Cyano-6-((S)-3-fluoro-pyrrolidin-1-yl)-pyridin-3-yl]-pyrimidin-2-ylamino}-pyridin-2-yl)-2-morpholin-4-yl-acetamide;

N-(5-{4-[5-Cyano-6-((S)-3-fluoro-pyrrolidin-1-yl)-pyridin-3-yl]-pyrimidin-2-ylamino}-pyridin-2-yl)-2-dimethylamino-propionamide;

Cyclopropanecarboxylic acid (5-{4-[5-cyano-6-((S)-3-fluoro-pyrrolidin-1-yl)-pyridin-3-yl]-pyrimidin-2-ylamino}-pyridin-2-yl)-amide;

2-((S)-3-Fluoro-pyrrolidin-1-yl)-5-[2-(2-morpholin-4-yl-pyrimidin-5-ylamino)-pyrimidin-4-yl]-nicotinonitrile;

N-(5-{4-[5-Cyano-6-((S)-3-fluoro-pyrrolidin-1-yl)-pyridin-3-yl]-pyrimidin-2-ylamino}-pyridin-2-yl)-2-[(2-methoxy-ethyl)-methyl-amino]-acetamide;

2-((S)-3-Fluoro-pyrrolidin-1-yl)-5-{2-[6-(2-hydroxy-2-methyl-propylamino)-pyridin-3-ylamino]-pyrimidin-4-yl}-nicotinonitrile;

N-(5-{4-[5-Cyano-6-((S)-3-fluoro-pyrrolidin-1-yl)-pyridin-3-yl]-pyrimidin-2-ylamino}-pyridin-2-yl)-2-(4-isopropyl-piperazin-1-yl)-acetamide;

2-((S)-3-Fluoro-pyrrolidin-1-yl)-5-{2-[6-(4-methyl-piperazin-1-yl)-pyridin-3-ylamino]-pyrimidin-4-yl}-nicotinonitrile;

2-((S)-3-Fluoro-pyrrolidin-1-yl)-5-[2-(6-piperazin-1-yl-pyridin-3-ylamino)-pyrimidin-4-yl]-nicotinonitrile;

2-((S)-3-Hydroxy-pyrrolidin-1-yl)-5-{2-[6-((R)-3-methyl-piperazin-1-yl)-pyridin-3-ylamino]-pyrimidin-4-yl}-nicotinonitrile;

2-((S)-3-Fluoro-pyrrolidin-1-yl)-5-{2-[6-(2-hydroxy-ethylamino)-pyridin-3-ylamino]-pyrimidin-4-yl}-nicotinonitrile;

4-{4-[5-Cyano-6-((S)-3-fluoro-pyrrolidin-1-yl)-pyridin-3-yl]-5-fluoro-pyrimidin-2-ylamino}-N-(1-methyl-piperidin-4-yl)-benzamide;

N-(5-{4-[5-Cyano-6-((S)-3-fluoro-pyrrolidin-1-yl)-pyridin-3-yl]-pyrimidin-2-ylamino}-pyridin-2-yl)-2-(4-hydroxy-piperidin-1-yl)-acetamide;

2-((S)-3-Fluoro-pyrrolidin-1-yl)-5-[2-(4-morpholin-4-yl-methyl-phenylamino)-pyrimidin-4-yl]-nicotinonitrile;

N-(5-{4-[5-Cyano-6-((S)-3-fluoro-pyrrolidin-1-yl)-pyridin-3-yl]-pyrimidin-2-ylamino}-pyridin-2-yl)-2-piperazin-1-yl-acetamide;

N-(5-{4-[5-Cyano-6-((S)-3-fluoro-pyrrolidin-1-yl)-pyridin-3-yl]-pyrimidin-2-ylamino}-pyridin-2-yl)-2-morpholin-4-yl-propionamide;

2-((S)-3-Fluoro-pyrrolidin-1-yl)-5-{2-[1-(tetrahydro-pyran-4-yl)-1H-pyrazol-4-ylamino]-pyrimidin-4-yl}-nicotinonitrile;

N-(4-{4-[5-Cyano-6-((S)-3-fluoro-pyrrolidin-1-yl)-pyridin-3-yl]-pyrimidin-2-ylamino}-pyridin-2-yl)-2-morpholin-4-yl-acetamide;

N-(5-{4-[5-Cyano-6-((S)-3-fluoro-pyrrolidin-1-yl)-pyridin-3-yl]-pyrimidin-2-ylamino}-pyridin-2-yl)-2-((S)-3-hydroxy-pyrrolidin-1-yl)-acetamide;

2-((S)-3-Fluoro-pyrrolidin-1-yl)-5-[2-(2-morpholin-4-yl-pyridin-4-ylamino)-pyrimidin-4-yl]-nicotinonitrile;

2-Amino-N-(5-{4-[5-cyano-6-((S)-3-fluoro-pyrrolidin-1-yl)-pyridin-3-yl]-pyrimidin-2-ylamino}-pyridin-2-yl)-2-methyl-propionamide;

2-((S)-3-Fluoro-pyrrolidin-1-yl)-5-[2-(1H-pyrazol-4-ylamino)-pyrimidin-4-yl]-nicotinonitrile;

2-((S)-3-Fluoro-pyrrolidin-1-yl)-5-[2-(2H-pyrazol-3-ylamino)-pyrimidin-4-yl]-nicotinonitrile;

(S)-Pyrrolidine-2-carboxylic acid (5-{4-[5-cyano-6-((S)-3-fluoro-pyrrolidin-1-yl)-pyridin-3-yl]-pyrimidin-2-ylamino}-pyridin-2-yl)-amide;

N-(5-{4-[5-Cyano-6-((S)-3-fluoro-pyrrolidin-1-yl)-pyridin-3-yl]-pyrimidin-2-ylamino}-pyridin-2-yl)-2-pyrrolidin-1-yl-acetamide;

2-((S)-3-Fluoro-pyrrolidin-1-yl)-5-{2-[6-(2-morpholin-4-yl-ethylamino)-pyridin-3-ylamino]-pyrimidin-4-yl}-nicotinonitrile;

2-((S)-3-Fluoro-pyrrolidin-1-yl)-5-[2-(6-morpholin-4-yl-methyl-pyridin-3-ylamino)-pyrimidin-4-yl]-nicotinonitrile;

N-(5-{4-[5-Cyano-6-((S)-3-fluoro-pyrrolidin-1-yl)-pyridin-3-yl]-pyrimidin-2-ylamino}-pyridin-2-yl)-2-((S)-3-fluoro-pyrrolidin-1-yl)-acetamide;

2-((S)-3-Fluoro-pyrrolidin-1-yl)-5-(2-{6-[2-((S)-3-fluoro-pyrrolidin-1-yl)-ethoxy]-pyridin-3-ylamino}-pyrimidin-4-yl)-nicotinonitrile;

2-((S)-3-Hydroxy-pyrrolidin-1-yl)-5-[2-(2-morpholin-4-yl-pyridin-4-ylamino)-pyrimidin-4-yl]-nicotinonitrile;

2-((S)-3-Fluoro-pyrrolidin-1-yl)-5-{2-[2-(2-methoxy-ethylamino)-pyridin-4-ylamino]-pyrimidin-4-yl}-nicotinonitrile;

2-((S)-3-Fluoro-pyrrolidin-1-yl)-5-[2-(6-oxo-1,6-dihydro-pyridin-2-ylamino)-pyrimidin-4-yl]-nicotinonitrile;

N-(5-{4-[5-Cyano-6-((S)-3-fluoro-pyrrolidin-1-yl)-pyridin-3-yl]-pyrimidin-2-ylamino}-pyridin-2-yl)-N-methyl-2-morpholin-4-yl-acetamide;

N-(5-{4-[5-Cyano-6-((S)-3-hydroxy-pyrrolidin-1-yl)-pyridin-3-yl]-pyrimidin-2-ylamino}-pyridin-2-yl)-N-methyl-2-morpholin-4-yl-acetamide;

2-((S)-3-Fluoro-pyrrolidin-1-yl)-5-[2-(2-methyl-2,3-dihydro-1H-isoindol-5-ylamino)-pyrimidin-4-yl]-nicotinonitrile;

2-((S)-3-Fluoro-pyrrolidin-1-yl)-5-(2-{6-[2-(methoxy-ethylamino)-methyl]-pyridin-3-ylamino}-pyrimidin-4-yl)-nicotinonitrile;

2-((S)-3-Fluoro-pyrrolidin-1-yl)-5-{2-[2-((S)-3-methyl-morpholin-4-ylmethyl)-pyridin-4-ylamino]-pyrimidin-4-yl}-nicotinonitrile;

2-((S)-3-Fluoro-pyrrolidin-1-yl)-5-{2-[6-((S)-3-methyl-morpholin-4-ylmethyl)-pyridin-3-ylamino]-pyrimidin-4-yl}-nicotinonitrile;

2-((S)-3-Fluoro-pyrrolidin-1-yl)-5-{2-[6-((S)-3-fluoro-pyrrolidin-1-ylmethyl)-pyridin-3-ylamino]-pyrimidin-4-yl}-nicotinonitrile;

2-((S)-3-Fluoro-pyrrolidin-1-yl)-5-{2-[6-(2-methyl-imidazol-1-ylmethyl)-pyridin-3-ylamino]-pyrimidin-4-yl}-nicotinonitrile;

2-((S)-3-Fluoro-pyrrolidin-1-yl)-5-[2-(6-{[(2-methoxy-ethyl)-methyl-amino]-methyl}-pyridin-3-ylamino)-pyrimidin-4-yl]-nicotinonitrile 2-((S)-3-Fluoro-pyrrolidin-1-yl)-5-{2-[6-(3-methoxy-azetidin-1-ylmethyl)-pyridin-3-ylamino]-pyrimidin-4-yl}-nicotinonitrile;

5-[2-(6-Morpholin-4-ylmethyl-pyridin-3-ylamino)-pyrimidin-4-yl]-2-[1,4]oxazepan-4-yl-nicotinonitrile;

N-{5-[4-(5-Cyano-6-[1,4]oxazepan-4-yl-pyridin-3-yl)-pyrimidin-2-ylamino]-pyridin-2-yl}-2-morpholin-4-yl-acetamide;

N-{5-[4-(5-Cyano-6-[1,4]oxazepan-4-yl-pyridin-3-yl)-5-fluoro-pyrimidin-2-ylamino]-pyridin-2-yl}-2-morpholin-4-yl-acetamide;

5-[5-Fluoro-2-(6-morpholin-4-ylmethyl-pyridin-3-ylamino)-pyrimidin-4-yl]-2-[1,4]oxazepan-4-yl-nicotinonitrile;

N-(5-{4-[5-Cyano-6-((S)-3-fluoro-pyrrolidin-1-yl)-pyridin-3-yl]-5-fluoro-pyrimidin-2-ylamino}-pyridin-2-yl)-2-morpholin-4-yl-acetamide;

5-[5-Fluoro-2-(6-morpholin-4-ylmethyl-pyridin-3-ylamino)-pyrimidin-4-yl]-2-((S)-3-fluoro-pyrrolidin-1-yl)-nicotinonitrile;

N-(4-{4-[5-Cyano-6-((S)-3-fluoro-pyrrolidin-1-yl)-pyridin-3-yl]-5-fluoro-pyrimidin-2-ylamino}-pyridin-2-yl)-2-morpholin-4-yl-acetamide;

5-[2-(6-Morpholin-4-ylmethyl-pyridin-3-ylamino)-pyrimidin-4-yl]-2-(2-oxa-6-aza-spiro[3.4]oct-6-yl)-nicotinonitrile;

N-(4-{4-[5-Cyano-6-(2-oxa-6-aza-spiro[3.4]oct-6-yl)-pyridin-3-yl]-pyrimidin-2-ylamino}-pyridin-2-yl)-2-morpholin-4-yl-acetamide;

N-{4-[4-(5-Cyano-6-[1,4]oxazepan-4-yl-pyridin-3-yl)-5-fluoro-pyrimidin-2-ylamino]-pyridin-2-yl}-2-morpholin-4-yl-acetamide;

5-{5-Fluoro-2-[2-(2-methoxy-ethylamino)-pyridin-4-ylamino]-pyrimidin-4-yl}-2-[1,4]oxazepan-4-yl-nicotinonitrile;

2-((S)-3-Fluoro-pyrrolidin-1-yl)-5-{2-[6-(1-morpholin-4-yl-ethyl)-pyridin-3-ylamino]-pyrimidin-4-yl}-nicotinonitrile;

2-((S)-3-Fluoro-pyrrolidin-1-yl)-5-{2-[6-((S)-3-methoxy-pyrrolidin-1-ylmethyl)-pyridin-3-ylamino]-pyrimidin-4-yl}-nicotinonitrile;

2-((S)-3-Fluoro-pyrrolidin-1-yl)-5-(2-{6-[(2-methanesulfonyl-ethylamino)-methyl]-pyridin-3-ylamino}-pyrimidin-4-yl)-nicotinonitrile 2-((S)-3-Fluoro-pyrrolidin-1-yl)-5-[2-(2-morpholin-4-ylmethyl-pyridin-4-ylamino)-pyrimidin-4-yl]-nicotinonitrile;

2-((S)-3-Fluoro-pyrrolidin-1-yl)-5-[2-(5-morpholin-4-ylmethyl-pyridin-3-ylamino)-pyrimidin-4-yl]-nicotinonitrile;

2-((S)-3-Fluoro-pyrrolidin-1-yl)-5-(2-{2-[(2-hydroxy-ethyl)-methyl-amino]-pyridin-4-ylamino}-pyrimidin-4-yl)-nicotinonitrile;

2-((S)-3-Fluoro-pyrrolidin-1-yl)-5-{2-[6-(3-oxo-piperazin-1-ylmethyl)-pyridin-3-ylamino]-pyrimidin-4-yl}-nicotinonitrile;

2-((S)-3-Fluoro-pyrrolidin-1-yl)-5-[2-(6-[1,4]oxazepan-4-ylmethyl-pyridin-3-ylamino)-pyrimidin-4-yl]-nicotinonitrile;

2-((S)-3-Fluoro-pyrrolidin-1-yl)-5-[2-(6-{[(2-hydroxy-ethyl)-methyl-amino]-methyl}-pyridin-3-ylamino)-pyrimidin-4-yl]-nicotinonitrile;

2-((S)-3-Fluoro-pyrrolidin-1-yl)-5-{2-[6-(4-hydroxymethyl-2-oxo-oxazolidin-3-ylmethyl)-pyridin-3-ylamino]-pyrimidin-4-yl}-nicotinonitrile;

2-((S)-3-Fluoro-pyrrolidin-1-yl)-5-(2-{5-[(2-methoxy-ethylamino)-methyl]-pyridin-3-ylamino}-pyrimidin-4-yl)-nicotinonitrile;

5-{2-[6-(1-Amino-1-ethyl-ethyl)-pyridin-3-ylamino]-pyrimidin-4-yl}-2-((S)-3-fluoro-pyrrolidin-1-yl)-nicotinonitrile;

N-(5-{4-[5-Cyano-6-((S)-3-fluoro-pyrrolidin-1-yl)-pyridin-3-yl]-pyrimidin-2-ylamino}-pyridin-3-yl)-2-morpholin-4-yl-acetamide;

5-[2-(6,7-Dihydro-5H-pyrrolo[3,4-b]pyridin-3-ylamino)-pyrimidin-4-yl]-2-((S)-3-fluoro-pyrrolidin-1-yl)-nicotinonitrile;

2-((S)-3-Fluoro-pyrrolidin-1-yl)-5-{2-[6-(3-hydroxy-3-methyl-azetidin-1-ylmethyl)-pyridin-3-ylamino]-pyrimidin-4-yl}-nicotinonitrile;

N-(4-{4-[5-Cyano-6-((R)-3-fluoro-pyrrolidin-1-yl)-pyridin-3-yl]-pyrimidin-2-ylamino}-pyridin-2-yl)-2-morpholin-4-yl-acetamide;

N-(5-{4-[5-Cyano-6-((R)-3-fluoro-pyrrolidin-1-yl)-pyridin-3-yl]-pyrimidin-2-ylamino}-pyridin-2-yl)-2-morpholin-4-yl-acetamide;

N-[5-(4-{5-Cyano-6-[(R)-(tetrahydro-furan-3-yl)amino]-pyridin-3-yl}-pyrimidin-2-ylamino)-pyridin-2-yl]-acetamide;

5-{2-[6-(1-Methyl-piperidin-4-ylamino)-pyridin-3-ylamino]-pyrimidin-4-yl}-2-[(R)-(tetrahydro-furan-3-yl)amino]-nicotinonitrile;
3-(4-{5-Cyano-6-[(R)-(tetrahydro-furan-3-yl)amino]-pyridin-3-yl}-pyrimidin-2-ylamino)-N-(1-methyl-piperidin-4-yl)-benzamide;
5-[2-(1-Methyl-1H-pyrazol-4-ylamino)-pyrimidin-4-yl]-2-[(R)-(tetrahydro-furan-3-yl)amino]-nicotinonitrile;
3-(4-{5-Cyano-6-[(R)-(tetrahydro-furan-3-yl)amino]-pyridin-3-yl}-pyrimidin-2-ylamino)-N-piperidin-4-yl-benzamide;
2-(2-Methoxy-ethylamino)-5-{2-[6-(1-methyl-piperidin-4-ylamino)-pyridin-3-ylamino]-pyrimidin-4-yl}-nicotinonitrile;
2-Methylamino-5-{2-[6-(1-methyl-piperidin-4-ylamino)-pyridin-3-ylamino]-pyrimidin-4-yl}-nicotinonitrile;
2-(2-Hydroxy-ethylamino)-5-{2-[6-(1-methyl-piperidin-4-ylamino)-pyridin-3-ylamino]-pyrimidin-4-yl}-nicotinonitrile;
3-[4-(6-Amino-5-cyano-pyridin-3-yl)-pyrimidin-2-ylamino]-N-(1-methyl-iperidin-4-yl)-benzamide;
2-Cyclopropylamino-5-[2-(6-morpholin-4-ylmethyl-pyridin-3-ylamino)-pyrimidin-4-yl]-nicotinonitrile;
2-Cyclopropylamino-5-[5-fluoro-2-(6-morpholin-4-ylmethyl-pyridin-3-ylamino)-pyrimidin-4-yl]-nicotinonitrile;
N-{4-[4-(5-Cyano-6-cyclopropylamino-pyridin-3-yl)-5-fluoro-pyrimidin-2-ylamino]-pyridin-2-yl}-2-morpholin-4-yl-acetamide;
2-Cyclopropylamino-5-{5-fluoro-2-[2-(2-methoxy-ethylamino)-pyridin-4-ylamino]-pyrimidin-4-yl}-nicotinonitrile;
5-[2-(2,3-Dihydro-1H-isoindol-5-ylamino)-pyrimidin-4-yl]-2-((S)-3-fluoro-pyrrolidin-1-yl)-nicotinonitrile;
2-((S)-3-Fluoro-pyrrolidin-1-yl)-5-{2-[2-(2-methoxy-ethyl)-2,3-dihydro-1H-isoindol-5-ylamino]-pyrimidin-4-yl}-nicotinonitrile;
5-{2-[1-(2-Hydroxy-ethyl)-1H-pyrazol-4-ylamino]-pyrimidin-4-yl}-2-pyrrolidin-1-yl-nicotinonitrile;
4-[4-(5-Cyano-6-pyrrolidin-1-yl-pyridin-3-yl)-pyrimidin-2-ylamino]-benzamide;
5-{2-[1-((S)-2,3-Dihydroxy-propyl)-1H-pyrazol-4-ylamino]-pyrimidin-4-yl}-2-pyrrolidin-1-yl-nicotinonitrile;
5-{2-[1-((R)-2,3-Dihydroxy-propyl)-1H-pyrazol-4-ylamino]-pyrimidin-4-yl}-2-pyrrolidin-1-yl-nicotinonitrile;
(R)-1-{3-Cyano-5-[2-(1-methyl-1H-pyrazol-4-ylamino)-pyrimidin-4-yl]-pyridin-2-yl}-pyrrolidine-2-carboxylic acid;
(R)-1-{3-Cyano-5-[2-(1-methyl-1H-pyrazol-4-ylamino)-pyrimidin-4-yl]-pyridin-2-yl}-pyrrolidine-2-carboxylic acid (1-methyl-1H-pyrazol-4-yl)-amide;
2-((S)-2-Cyano-pyrrolidin-1-yl)-5-[2-(1-methyl-1H-pyrazol-4-ylamino)-pyrimidin-4-yl]-nicotinonitrile;
(R)-1-{3-Cyano-5-[2-(1-methyl-1H-pyrazol-4-ylamino)-pyrimidin-4-yl]-pyridin-2-yl}-pyrrolidine-2-carboxylic acid amide;
2-(3-Hydroxy-8-aza-bicyclo[3.2.1]oct-8-yl)-5-[2-(1-methyl-1H-pyrazol-4-ylamino)-pyrimidin-4-yl]-nicotinonitrile;
5-[2-(1-Methyl-1H-pyrazol-4-ylamino)-pyrimidin-4-yl]-2-(3-oxa-8-aza-bicyclo[3.2.1]oct-8-yl)-nicotinonitrile;
5-{2-[1-(2-Hydroxy-ethyl)-1H-pyrazol-4-ylamino]-pyrimidin-4-yl}-2-(3-oxa-8-aza-bicyclo[3.2.1]oct-8-yl)-nicotinonitrile;
5-{4-[5-Cyano-6-((S)-3-fluoro-pyrrolidin-1-yl)-pyridin-3-yl]-pyrimidin-2-ylamino}-pyridine-2-carboxylic acid amide;
4-{4-[5-Cyano-6-((S)-3-fluoro-pyrrolidin-1-yl)-pyridin-3-yl]-pyrimidin-2-ylamino}-N-(2-hydroxy-ethyl)-benzamide;
2-((S)-3-Hydroxy-pyrrolidin-1-yl)-5-[2-(4-morpholin-4-yl-phenylamino)-pyrimidin-4-yl]-nicotinonitrile;
2-((S)-3-Hydroxy-pyrrolidin-1-yl)-5-[2-(6-morpholin-4-yl-pyridin-3-ylamino)-pyrimidin-4-yl]-nicotinonitrile;
2-((S)-3-Fluoro-pyrrolidin-1-yl)-5-{2-[1-(2-hydroxy-ethyl)-1H-pyrazol-4-ylamino]-pyrimidin-4-yl}-nicotinonitrile;
2-((S)-3-Fluoro-pyrrolidin-1-yl)-5-{2-[1-(3-hydroxy-propyl)-1H-pyrazol-4-ylamino]-pyrimidin-4-yl}-nicotinonitrile;
2-((S)-3-Fluoro-pyrrolidin-1-yl)-5-{2-[1-(2-morpholin-4-yl-ethyl)-1H-pyrazol-4-ylamino]-pyrimidin-4-yl}-nicotinonitrile;
N-(5-{4-[5-Cyano-6-((S)-3-fluoro-pyrrolidin-1-yl)-pyridin-3-yl]-pyrimidin-2-ylamino}-pyridin-2-yl)-2-(2-methoxy-ethylamino)-acetamide;
2-Benzylamino-N-(5-{4-[5-cyano-6-((S)-3-fluoro-pyrrolidin-1-yl)-pyridin-3-yl]-pyrimidin-2-ylamino}-pyridin-2-yl)-propionamide;
2-Amino-N-(5-{4-[5-cyano-6-((S)-3-fluoro-pyrrolidin-1-yl)-pyridin-3-yl]-pyrimidin-2-ylamino}-pyridin-2-yl)-propionamide;
N-(5-{4-[5-Cyano-6-((S)-3-fluoro-pyrrolidin-1-yl)-pyridin-3-yl]-pyrimidin-2-ylamino}-pyridin-2-yl)-2-(2-methyl-imidazol-1-yl)-acetamide;
5-[2-(6-Amino-pyridin-3-ylamino)-pyrimidin-4-yl]-2-((S)-3-fluoro-pyrrolidin-1-yl)-nicotinonitrile;
N-(1-{3-Cyano-5-[2-(6-morpholin-4-ylmethyl-pyridin-3-ylamino)-pyrimidin-4-yl]-pyridin-2-yl}-pyrrolidin-2-ylmethyl)-acetamide;
2-(1-{3-Cyano-5-[2-(6-morpholin-4-ylmethyl-pyridin-3-ylamino)-pyrimidin-4-yl]-pyridin-2-yl}-pyrrolidin-2-yl)-acetamide;
N-(1-{3-Cyano-5-[2-(6-morpholin-4-ylmethyl-pyridin-3-ylamino)-pyrimidin-4-yl]-pyridin-2-yl}-pyrrolidin-3-yl)-acetamide;
5-[2-(6-Morpholin-4-ylmethyl-pyridin-3-ylamino)-pyrimidin-4-yl]-2-(5-oxo-[1,4]diazepan-1-yl)-nicotinonitrile;
2-{3-Cyano-5-[2-(6-morpholin-4-ylmethyl-pyridin-3-ylamino)-pyrimidin-4-yl]-pyridin-2-ylamino}-propionamide;
2-({3-Cyano-5-[2-(6-morpholin-4-ylmethyl-pyridin-3-ylamino)-pyrimidin-4-yl]-pyridin-2-yl}-methyl-amino)-propionamide;
2-{3-Cyano-5-[2-(6-morpholin-4-ylmethyl-pyridin-3-ylamino)-pyrimidin-4-yl]-pyridin-2-ylamino}-3-methyl-butyramide;
2-[Methyl-(tetrahydro-furan-3-ylmethyl)-amino]-5-[2-(6-morpholin-4-ylmethyl-pyridin-3-ylamino)-pyrimidin-4-yl]-nicotinonitrile;
5-[2-(6-Morpholin-4-ylmethyl-pyridin-3-ylamino)-pyrimidin-4-yl]-2-[(tetrahydro-furan-3-ylmethyl)-amino]-nicotinonitrile;
2-Cyclopentylamino-5-[2-(6-morpholin-4-ylmethyl-pyridin-3-ylamino)-pyrimidin-4-yl]-nicotinonitrile;
2-[(2-Methoxy-ethyl)-methyl-amino]-5-[2-(6-morpholin-4-ylmethyl-pyridin-3-ylamino)-pyrimidin-4-yl]-nicotinonitrile;

3-((S)-3-Hydroxy-pyrrolidin-1-yl)-6-[2-(4-morpholin-4-yl-phenylamino)-pyrimidin-4-yl]-pyridine-2-carbonitrile;

6-[2-(4-Morpholin-4-yl-phenylamino)-pyrimidin-4-yl]-3-pyrrolidin-1-yl-pyridine-2-carbonitrile;

3-((S)-3-Hydroxy-pyrrolidin-1-yl)-6-[2-(1-methyl-1H-pyrazol-4-ylamino)-pyrimidin-4-yl]-pyridine-2-carbonitrile;

2'-Cyano-6'-[2-(1-methyl-1H-pyrazol-4-ylamino)-pyrimidin-4-yl]-3,4,5,6-tetrahydro-2H-[1,3']bipyridinyl-4-carboxylic acid amide;

N-(5-{4-[6-Cyano-5-((S)-3-hydroxy-pyrrolidin-1-yl)-pyridin-2-yl]-pyrimidin-2-ylamino}-pyridin-2-yl)-2-morpholin-4-yl-acetamide;

N-(5-{4-[6-Cyano-5-((S)-3-fluoro-pyrrolidin-1-yl)-pyridin-2-yl]-pyrimidin-2-ylamino}-pyridin-2-yl)-2-morpholin-4-yl-acetamide;

3-((S)-3-Fluoro-pyrrolidin-1-yl)-6-[2-(6-morpholin-4-ylmethyl-pyridin-3-ylamino)-pyrimidin-4-yl]-pyridine-2-carbonitrile;

3-((S)-3-Hydroxy-pyrrolidin-1-yl)-6-[2-(6-morpholin-4-ylmethyl-pyridin-3-ylamino)-pyrimidin-4-yl]-pyridine-2-carbonitrile;

N-(5-{4-[6-Cyano-5-((S)-3-fluoro-pyrrolidin-1-yl)-pyridin-2-yl]-pyrimidin-2-ylamino}-pyridin-2-yl)-2-((S)-3-fluoro-pyrrolidin-1-yl)-acetamide;

N-(5-{4-[6-Cyano-5-((S)-3-hydroxy-pyrrolidin-1-yl)-pyridin-2-yl]-pyrimidin-2-ylamino}-pyridin-2-yl)-2-((S)-3-fluoro-pyrrolidin-1-yl)-acetamide;

3-((S)-3-Fluoro-pyrrolidin-1-yl)-6-(2-{6-[2-((S)-3-fluoro-pyrrolidin-1-yl)-ethoxy]-pyridin-3-ylamino}-pyrimidin-4-yl)-pyridine-2-carbonitrile;

6-(2-{6-[2-((S)-3-Fluoro-pyrrolidin-1-yl)-ethoxy]-pyridin-3-ylamino}-pyrimidin-4-yl)-3-((S)-3-hydroxy-pyrrolidin-1-yl)-pyridine-2-carbonitrile;

3-((S)-3-Fluoro-pyrrolidin-1-yl)-6-{2-[6-((S)-3-methyl-morpholin-4-ylmethyl)-pyridin-3-ylamino]-pyrimidin-4-yl}-pyridine-2-carbonitrile;

3-((S)-3-Fluoro-pyrrolidin-1-yl)-6-{2-[6-((S)-3-fluoro-pyrrolidin-1-ylmethyl)-pyridin-3-ylamino]-pyrimidin-4-yl}-pyridine-2-carbonitrile;

3-((S)-3-Fluoro-pyrrolidin-1-yl)-6-{2-[6-(2-methyl-imidazol-1-ylmethyl)-pyridin-3-ylamino]-pyrimidin-4-yl}-pyridine-2-carbonitrile;

3-((S)-3-Fluoro-pyrrolidin-1-yl)-6-[2-(6-{[(2-methoxy-ethyl)-methyl-amino]-methyl}-pyridin-3-ylamino)-pyrimidin-4-yl]-pyridine-2-carbonitrile;

6-[5-Fluoro-2-(4-morpholin-4-yl-phenylamino)-pyrimidin-4-yl]-3-((S)-3-fluoro-pyrrolidin-1-yl)-pyridine-2-carbonitrile;

3-[(2-Methoxy-ethyl)-methyl-amino]-6-[2-(1-methyl-1H-pyrazol-4-ylamino)-pyrimidin-4-yl]-pyridine-2-carbonitrile;

3-Dimethylamino-6-[2-(4-morpholin-4-yl-phenylamino)-pyrimidin-4-yl]-pyridine-2-carbonitrile;

3-((S)-3-Fluoro-pyrrolidin-1-yl)-6-{2-[6-(3-oxo-piperazin-1-ylmethyl)-pyridin-3-ylamino]-pyrimidin-4-yl}-pyridine-2-carbonitrile;

3-((S)-3-Fluoro-pyrrolidin-1-yl)-6-(2-{6-[(2-methoxy-ethylamino)-methyl]-pyridin-3-ylamino}-pyrimidin-4-yl)-pyridine-2-carbonitrile;

2-(1-{3-Cyano-5-[2-(6-morpholin-4-ylmethyl-pyridin-3-ylamino)-pyrimidin-4-yl]-pyridin-2-yl}-pyrrolidin-3-yl)-acetamide;

2-(2-Methyl-morpholin-4-yl)-5-[2-(6-morpholin-4-ylmethyl-pyridin-3-ylamino)-pyrimidin-4-yl]-nicotinonitrile;

2-(3-Methoxymethyl-pyrrolidin-1-yl)-5-[2-(6-morpholin-4-ylmethyl-pyridin-3-ylamino)-pyrimidin-4-yl]-nicotinonitrile;

2-(3-Difluoromethoxy-pyrrolidin-1-yl)-5-[2-(6-morpholin-4-ylmethyl-pyridin-3-ylamino)-pyrimidin-4-yl]-nicotinonitrile;

3-(1-{3-Cyano-5-[2-(6-morpholin-4-ylmethyl-pyridin-3-ylamino)-pyrimidin-4-yl]-pyridin-2-yl}-pyrrolidin-3-yl)-propionamide;

2-[Methyl-(tetrahydro-furan-3-yl)-amino]-5-[2-(6-morpholin-4-ylmethyl-pyridin-3-ylamino)-pyrimidin-4-yl]-nicotinonitrile;

6-[2-(6-Morpholin-4-ylmethyl-pyridin-3-ylamino)-pyrimidin-4-yl]-3-[1,4]oxazepan-4-yl-pyridine-2-carbonitrile;

6-[2-(6-Morpholin-4-ylmethyl-pyridin-3-ylamino)-pyrimidin-4-yl]-3-(2-oxa-6-aza-spiro[3.4]oct-6-yl)-pyridine-2-carbonitrile N-{5-[4-(6-Cyano-5-[1,4]oxazepan-4-yl-pyridin-2-yl)-pyrimidin-2-ylamino]-pyridin-2-yl}-2-morpholin-4-yl-acetamide;

N-(5-{4-[6-Cyano-5-(2-oxa-6-aza-spiro[3.4]oct-6-yl)-pyridin-2-yl]-pyrimidin-2-ylamino}-pyridin-2-yl)-2-morpholin-4-yl-acetamide Or a salt thereof.

11. A pharmaceutical composition which comprises a compound as claimed in claim 1, together with a pharmaceutically suitable carrier.

12. A composition as claimed in claim 11, which also contains an additional active ingredient.

13. A method of treating inflammation, inflammatory bowel disease, asthma, chronic obstructive pulmonary disorder (COPD), rheumatoid arthritis, osteoarthritis, psoriatic arthritis, osteoporosis, fibrotic diseases, dermatosis, psoriasis, systemic lupus erythematosus, tissue or organ rejection, Alzheimer's disease, atherosclerosis, obesity, diabetes, cancer, adult respiratory syndrome, or septic shock in a patient, the method comprising, administering to the patient a therapeutically effective amount of the compound as claimed in claim 1.

14. The method of claim 13, wherein the inflammation is associated with infection.

15. The method of claim 13, wherein the cancer is selected from the group consisting of breast cancer, lung cancer, ovarian cancer, prostate cancer, myeloma, and leukemia.

16. A compound as claimed in claim 1, in which $R^2$ represents

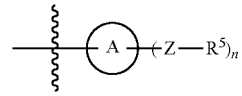

wherein A is a phenyl or 5 or 6 membered heteroaryl ring containing 1, 2 or 3 heteroatoms;

n is 1 or 2;

each Z is a group independently selected from —$(CHR^a)_p$—, —O—$(CHR^a)_r$—, —$NR^a$—$(CHR^a)_r$—, —C(=O)— and —$NR^aC(=O)(CHR^a)_p$—, in which p is 0, 1 or 2;

and each $R^5$ is a group independently selected from:
H, halogen, $OR^b$ or $NR^aR^b$;
a 4- to 6-membered heterocyclyl ring containing 1 or 2 heteroatoms, optionally substituted by one or more substituents independently selected from halogen atoms, OH, =O, $NR^aR^b$, O—$C_{1-4}$alkyl and $C_{1-4}$alkyl groups, optionally substituted with halogen, OMe or OH;

$C_{1-4}$alkyl or $C_{3-7}$cycloalkyl groups, each optionally substituted by one or more substituents independently selected from halogen, OMe, OH and $NR^aR^b$; CN, $SO_2R^c$ and $NR^aSO_2R^c$; or or n=2 and two Z—$R^5$ groups on adjacent ring atoms together with the two adjacent ring atoms form a 5-7 membered fused ring composed of the two adjacent ring atoms and —$(CHR^a)_r$—$(CHR^5)$—$(CHR^a)_r$—, wherein the —$CHR^5$— moiety can be replaced with —$NR^5$— and each r is independently 1 or 2; and each $R^a$ independently represents a hydrogen atom or a $C_{1-4}$alkyl group; and each $R^b$ independently represents a hydrogen atom; a $C_{1-4}$alkyl group optionally substituted by one or more groups selected from OH, O—$C_{1-4}$alkyl, halogen and $SO_2R^c$; or a $C_{3-8}$cycloalkyl group in which a $CH_2$ moiety may be replaced by an oxygen atom or an $NR^a$ group; and each $R^c$ represents —$NR^aR^b$ or a methyl group.

17. A compound as claimed in claim 1, in which A is phenyl, pyridine or pyrazole.

18. A compound as claimed in claim 1, in which n is 1.

19. A compound as claimed in claim 1, in which $R^5$ is a group independently selected from:
H, OH, or $NR^aR^b$; and
a 6-membered heterocyclyl ring containing 1 or 2 heteroatoms or 5-membered heterocyclyl ring containing 1 heteroatom or 4-membered heterocycloalkyl ring containing 1 nitrogen atom, optionally substituted by one substituent selected from F, =O, $C_{1-4}$alkyl, OMe and OH groups;
$C_{1-4}$alkyl optionally substituted by one or two OH groups.

20. A compound as claimed in claim 1, in which each of $R^3$ and $R^4$ independently represents a methyl group, a hydrogen atom or a fluorine atom.

21. A pharmaceutical composition which comprises a compound as claimed in claim 10, together with a pharmaceutically suitable carrier.

22. A composition as claimed in claim 21, which also contains an additional active ingredient.

* * * * *

UNITED STATES PATENT AND TRADEMARK OFFICE
CERTIFICATE OF CORRECTION

PATENT NO. : 9,433,622 B2
APPLICATION NO. : 14/769421
DATED : September 6, 2016
INVENTOR(S) : Gary Karl Newton et al.

It is certified that error appears in the above-identified patent and that said Letters Patent is hereby corrected as shown below:

On the title page of the patent, at (73), please remove --Assignee: Case Western Reserve University, Cleveland, OH (US)--

Signed and Sealed this
Sixth Day of December, 2016

Michelle K. Lee
*Director of the United States Patent and Trademark Office*